(12) United States Patent
Moola

(10) Patent No.: US 10,458,995 B2
(45) Date of Patent: Oct. 29, 2019

(54) COMBINATORIAL SYNTHESIS AND BIOMARKER DEVELOPMENT

(71) Applicant: Muralidhar Reddy Moola, Fremont, CA (US)

(72) Inventor: Muralidhar Reddy Moola, Fremont, CA (US)

(*) Notice: Subject to any disclaimer, the term of this patent is extended or adjusted under 35 U.S.C. 154(b) by 0 days.

(21) Appl. No.: 16/088,033

(22) PCT Filed: Mar. 21, 2017

(86) PCT No.: PCT/US2017/023441
§ 371 (c)(1),
(2) Date: Sep. 24, 2018

(87) PCT Pub. No.: WO2017/165438
PCT Pub. Date: Sep. 28, 2017

(65) Prior Publication Data
US 2019/0113521 A1    Apr. 18, 2019

Related U.S. Application Data

(60) Provisional application No. 62/313,580, filed on Mar. 25, 2016.

(51) Int. Cl.
*G01N 33/68* (2006.01)
*C07K 1/04* (2006.01)
*C07K 7/06* (2006.01)
*A61K 38/00* (2006.01)
*B01J 19/00* (2006.01)

(52) U.S. Cl.
CPC ...... *G01N 33/6854* (2013.01); *B01J 19/0046* (2013.01); *C07K 1/047* (2013.01); *C07K 7/06* (2013.01); *A61K 38/00* (2013.01); *B01J 2219/00648* (2013.01); *B01J 2219/00725* (2013.01); *G01N 2800/2814* (2013.01); *G01N 2800/2821* (2013.01); *G01N 2800/52* (2013.01); *G01N 2800/60* (2013.01)

(58) Field of Classification Search
None
See application file for complete search history.

(56) References Cited

U.S. PATENT DOCUMENTS

| | | |
|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |

(Continued)

FOREIGN PATENT DOCUMENTS

| | | |
|---|---|---|
| WO | WO-2012129423 A2 | 9/2012 |
| WO | WO-2013043669 A1 | 3/2013 |
| WO | WO-2014127111 A1 | 8/2014 |

OTHER PUBLICATIONS

Borman, "Combinatorial Chemistry", Chemical and Engineering News, p. 43, Feb. 24, 1997.

(Continued)

*Primary Examiner* — Adam Weidner
(74) *Attorney, Agent, or Firm* — Wilson Sonsini Goodrich & Rosati

(57) ABSTRACT

Provided herein are methods, kits, and compositions for use in the diagnosis and treatment of diseases. Peptoids recognized by Alzheimers disease specific antibodies are identified.

14 Claims, 18 Drawing Sheets

Chemical Structures of six MCI specific molecule (ErAD1-6)

(56) References Cited

U.S. PATENT DOCUMENTS

| | | | |
|---|---|---|---|
| 4,275,149 A | 6/1981 | Litman et al. | |
| 4,277,437 A | 7/1981 | Maggio et al. | |
| 4,366,241 A | 12/1982 | Tom et al. | |
| 5,143,854 A | 9/1992 | Pirrung et al. | |
| 6,344,334 B1 | 2/2002 | Ellman et al. | |
| 8,828,413 B2 | 9/2014 | Kirshenbaum et al. | |
| 2007/0003954 A1 | 1/2007 | Kodadek et al. | |
| 2010/0303805 A1 | 12/2010 | Moola et al. | |
| 2010/0303835 A1 | 12/2010 | Gocke et al. | |
| 2012/0270741 A1* | 10/2012 | Moola | C07K 1/047 506/6 |

OTHER PUBLICATIONS

Czarnik, "Encoding methods for combinatorial chemistry", Current Opinion in Chemical Biology, vol. 1, 60-66, 1997.

Fodor et al., "Light-Directed, Spatially Addressable Parallel Chemical Synthesis", Science, vol. 251, 767-773, 1991.

Klotz, "Active Surveillance for Prostate Cancer: For Whom?", Journal of Clinical Oncology, vol. 23, No. 32, 8165-8169, Nov. 10, 2005.

Kodadek et al., "Protein "fingerprinting" in complex mixtures with peptoid microarrays", Proceedings of the National Academy of Sciences vol. 102, No. 36, 12672-12677, Sep. 6, 2005.

Marani et al., "Screening of One-Bead-One-Peptide Combinatorial Library Using Red Fluorescent Dyes Presence of Positive and False Positive Beads", J. Comb. Chem., vol. 11, No. 1, 146-150, 2009.

PCT/US2017/023441 International Search Report dated Jun. 9, 2017.

Seo et al., "Peptoids: Synthesis, Characterization, and Nanostructures", Comprehensive Biomaterials, vol. 2, 53-76, 2011.

Thompson et al., "Synthesis and Applications of Small Molecule Libraries", Chem. Rev., vol. 96, 555-600, 1996.

* cited by examiner

Specificity

Alzheimer's serum
(IgA, IgM and IgG)

Phosphorylated proteins

Amyloid beta 42 peptide

Molecules bind to Alzheimer's subjects but not to normal controls

Normal Control

Alzheimer's Disease

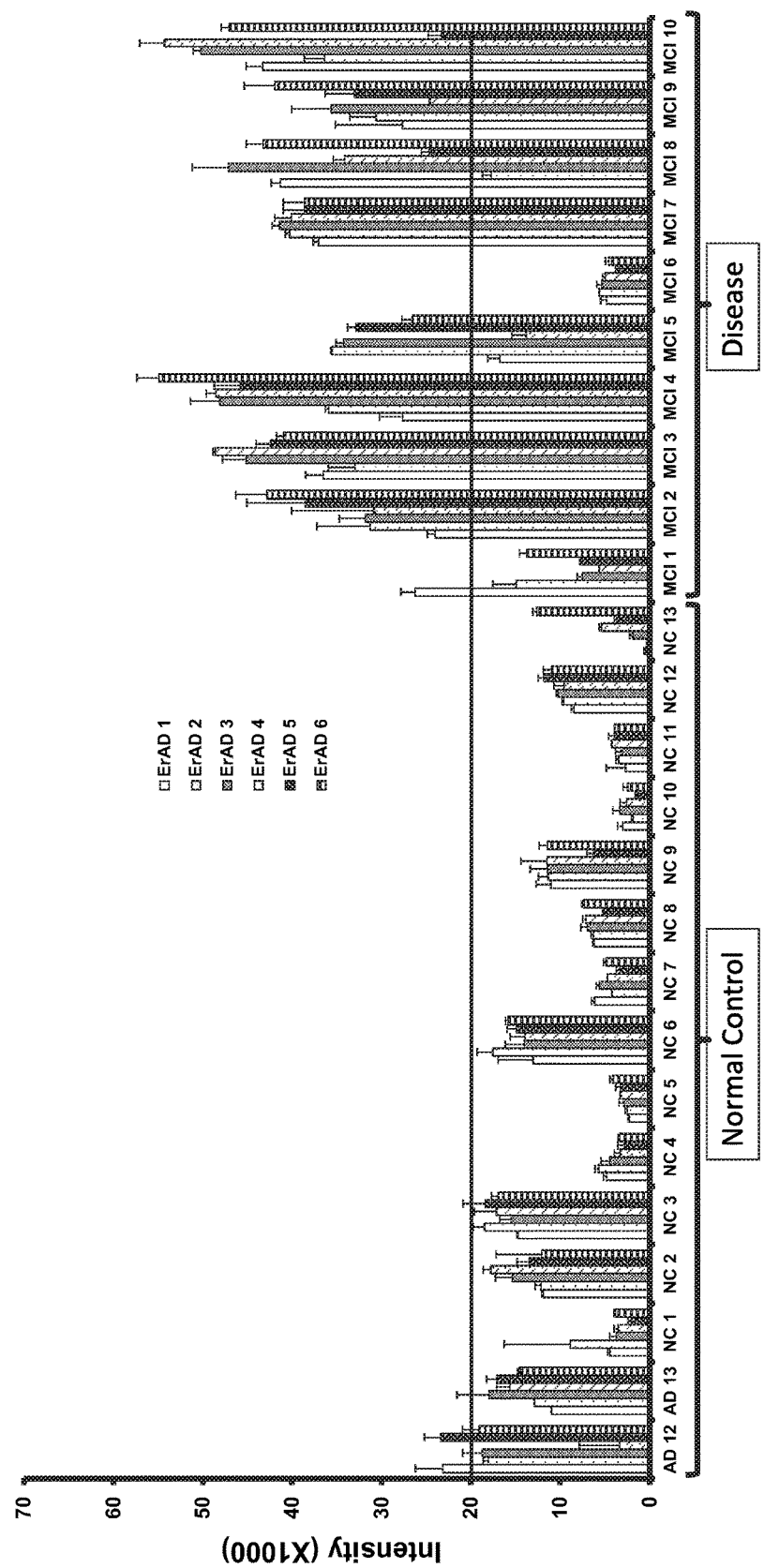
Figure 5. Blind analysis of specific molecules binding to MCI subjects

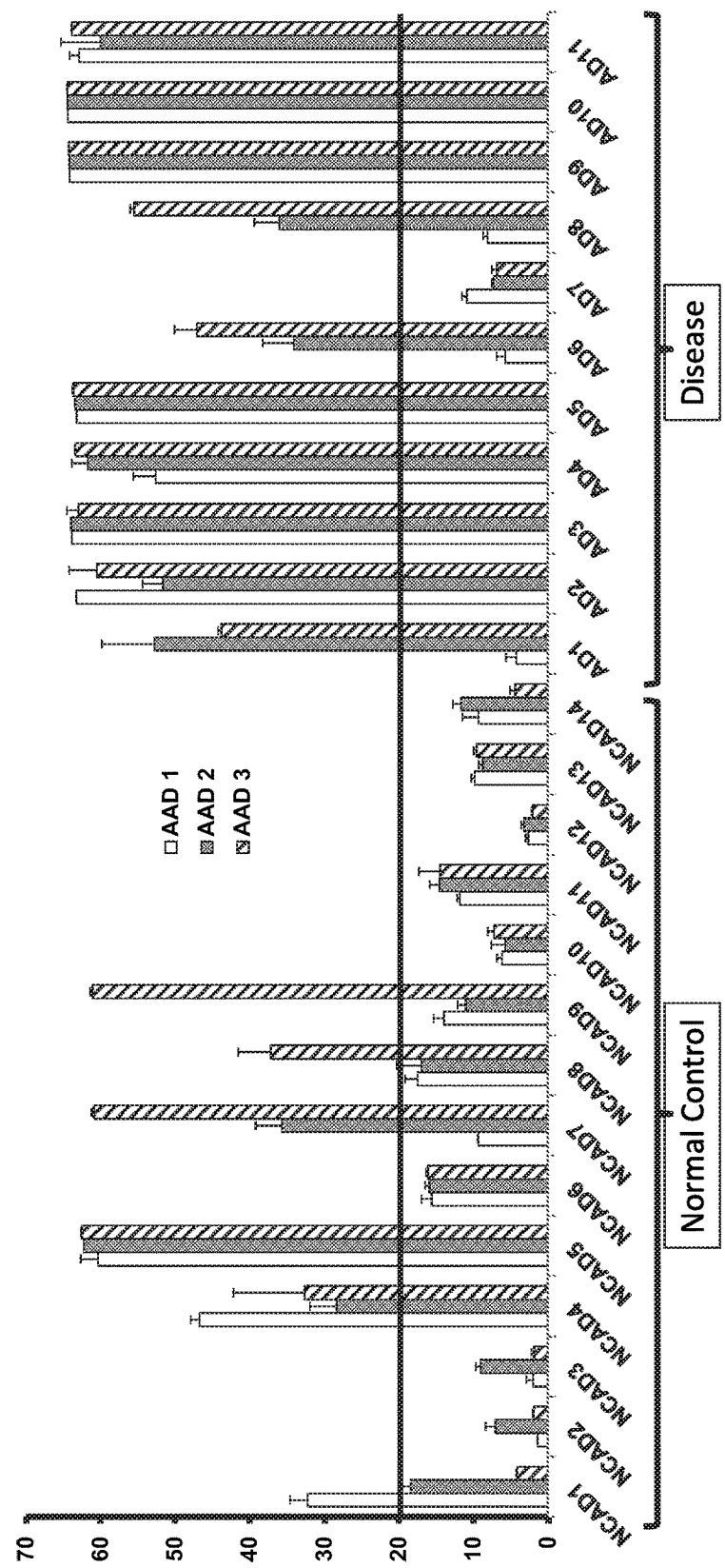
Figure 7. Blind analysis of specific molecules binding to AD subjects

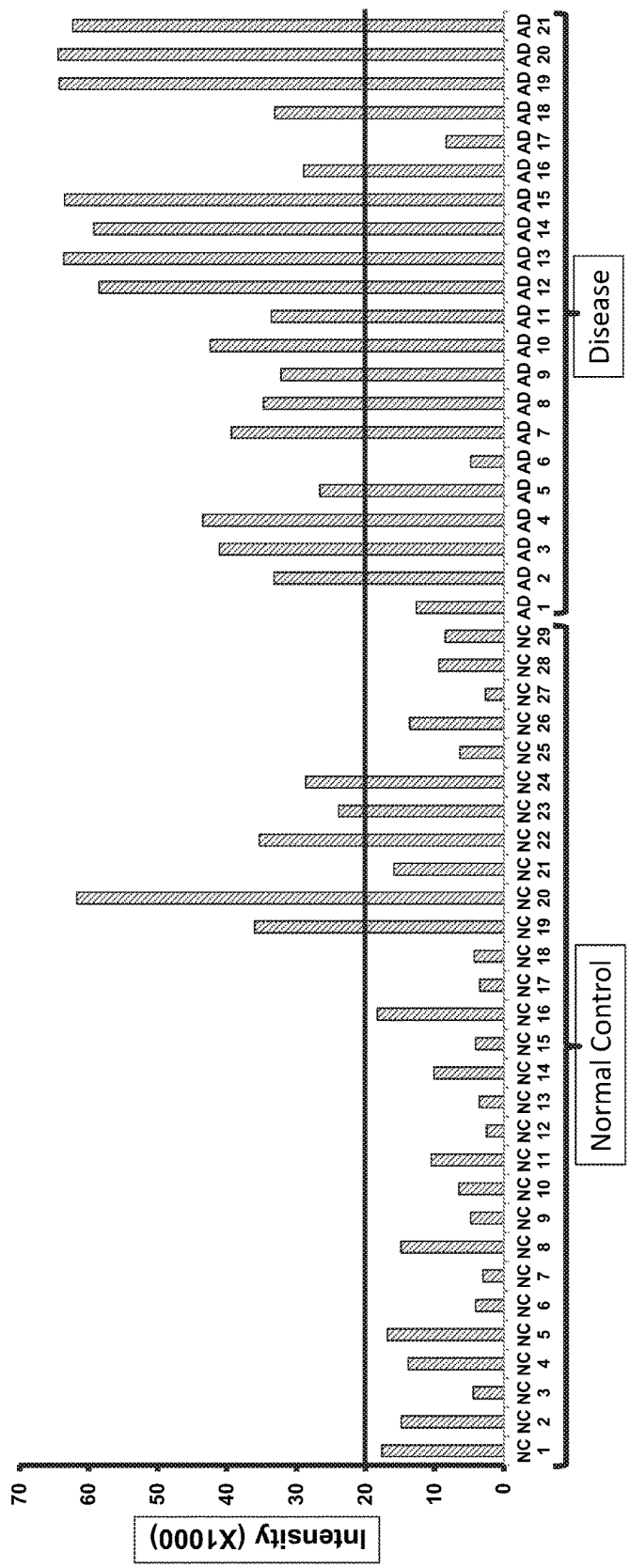
Figure 8. Quantitation of fluorescence intensity of each molecule specific to AD on the microarray that differentiates AD subjects from normal controls

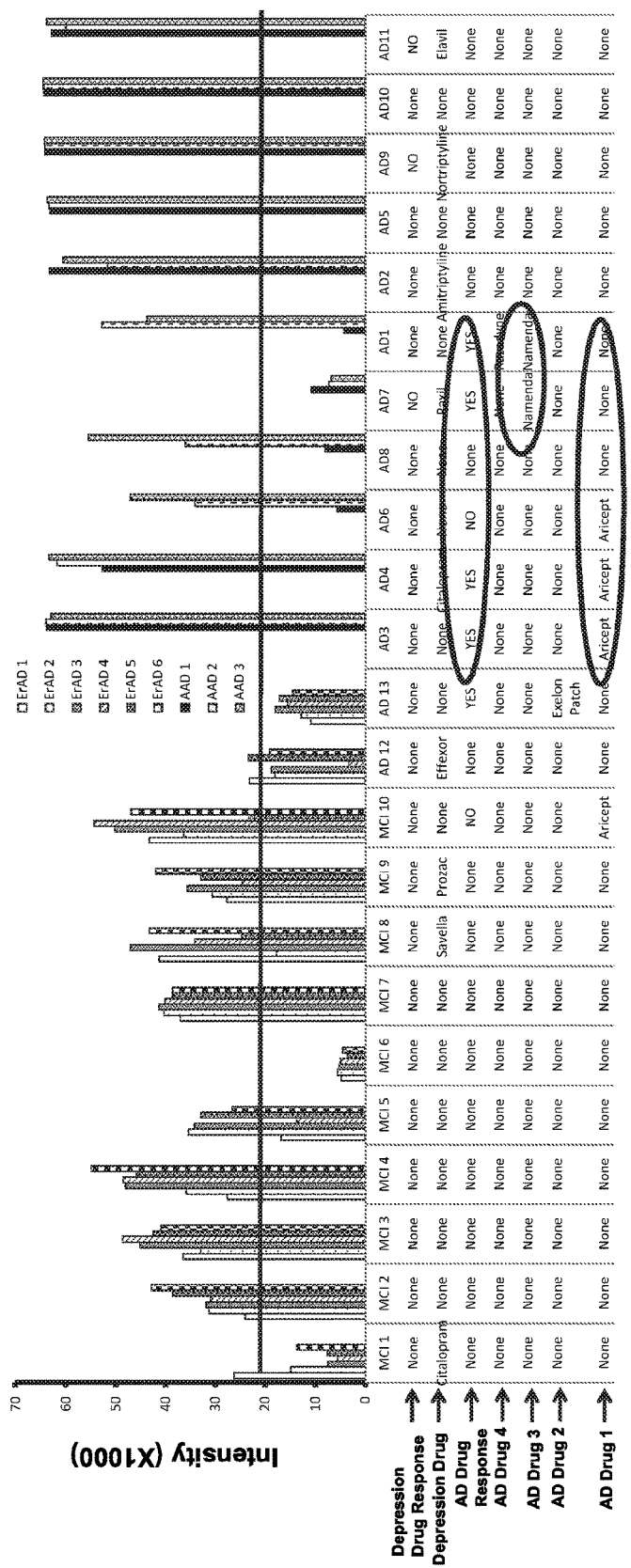
Figure 9. Alzheimer's disease specific molecules and their current drug response

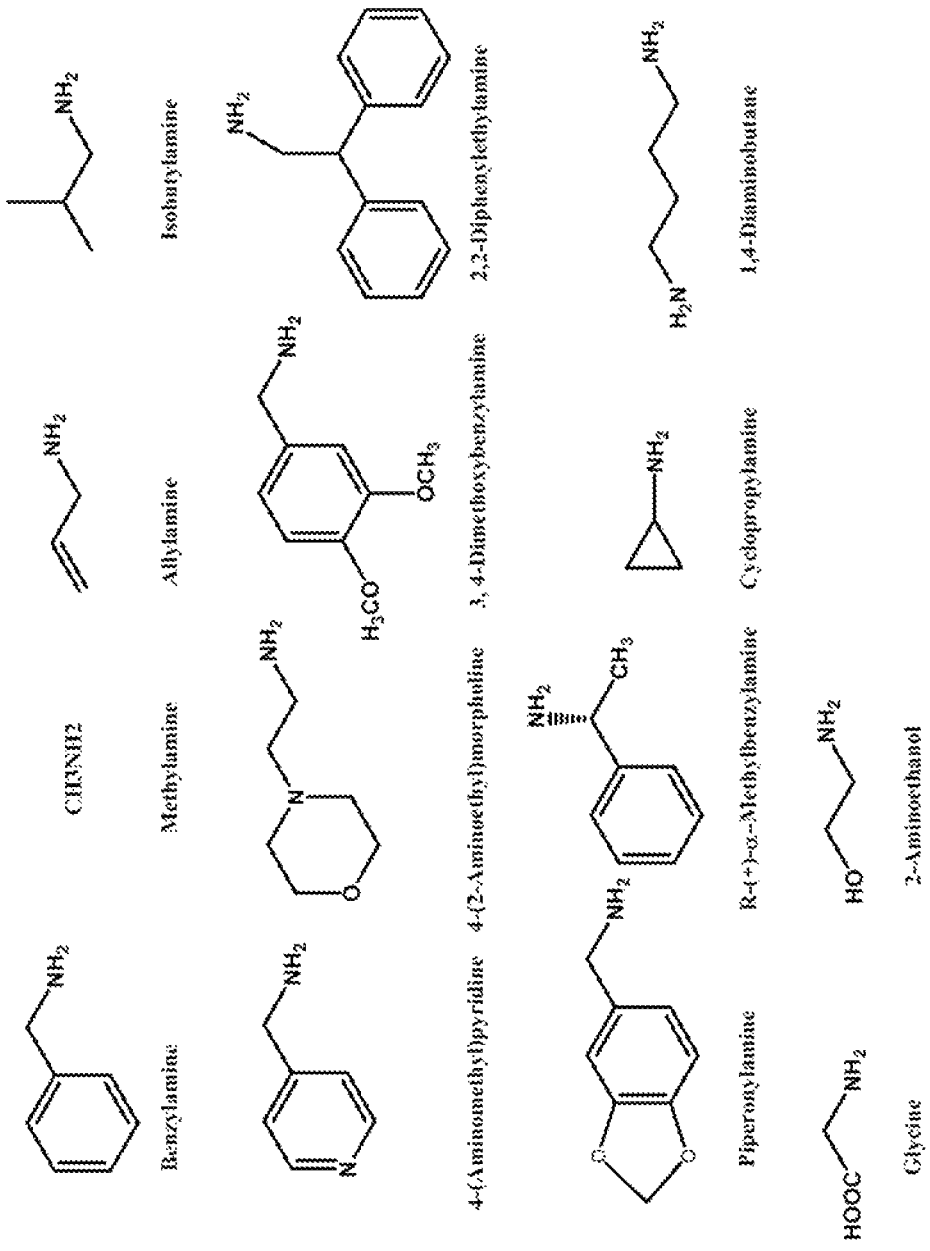
Figure 10: Building blocks

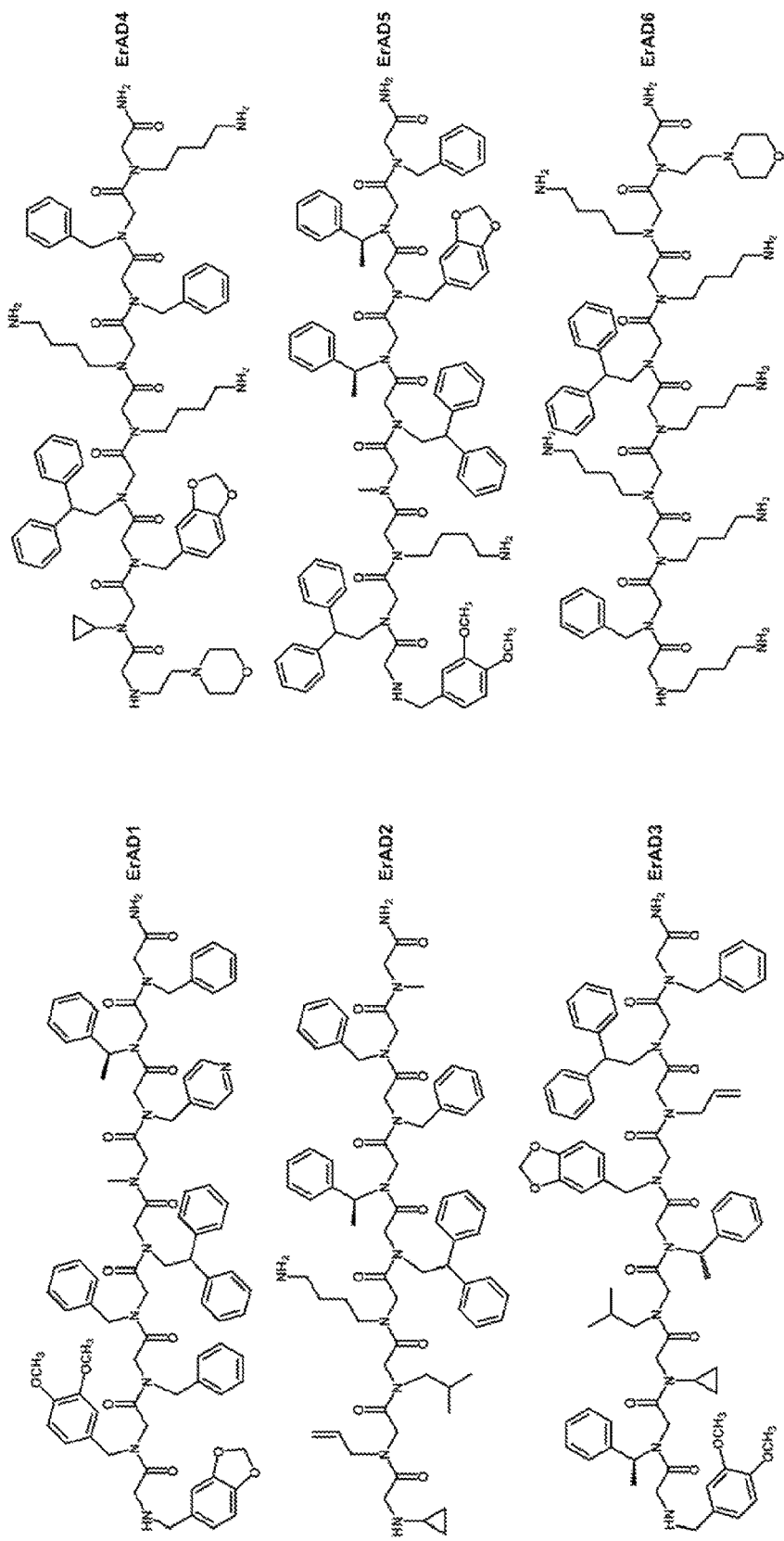
Figure 11: Chemical Structures of six MCI specific molecule (ErAD1-6)

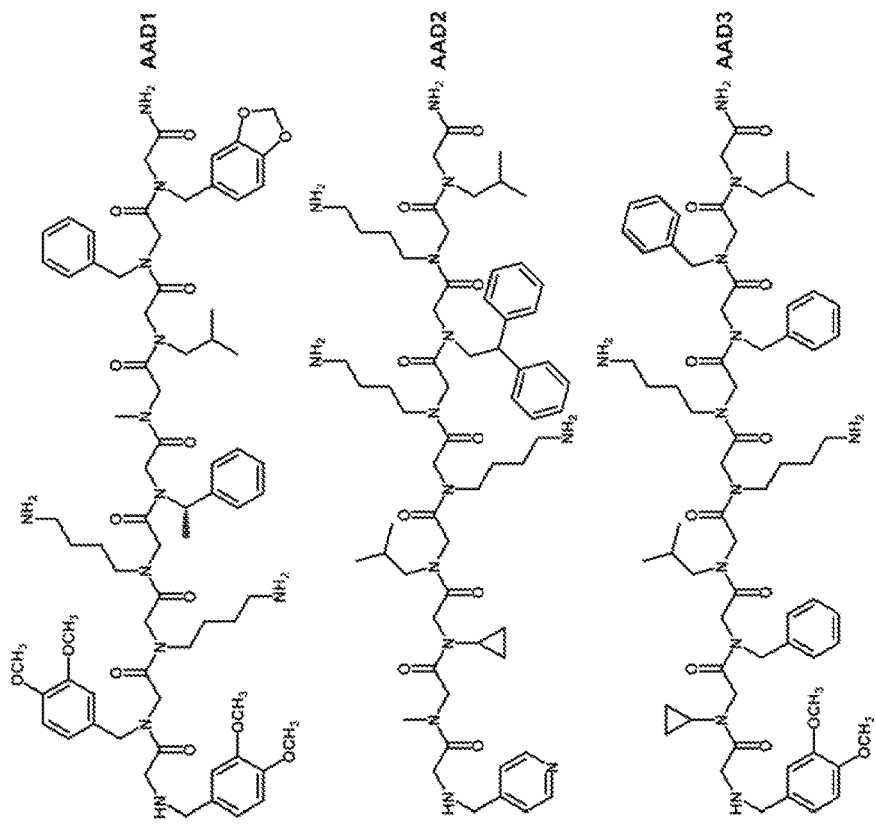
Figure 12: The Chemical Structures of three AD specific molecules (AAD1-3)

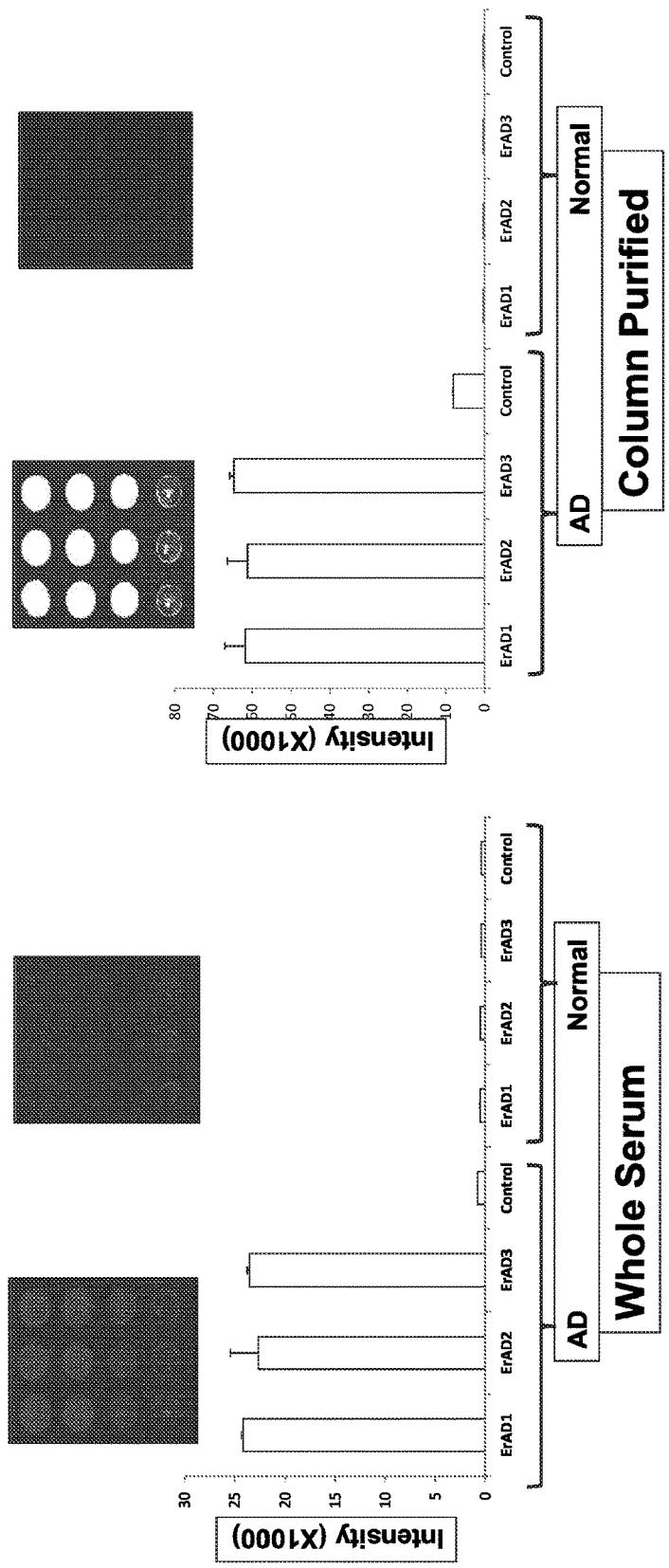
Figure 13: Purification of serum samples by AD specific molecules

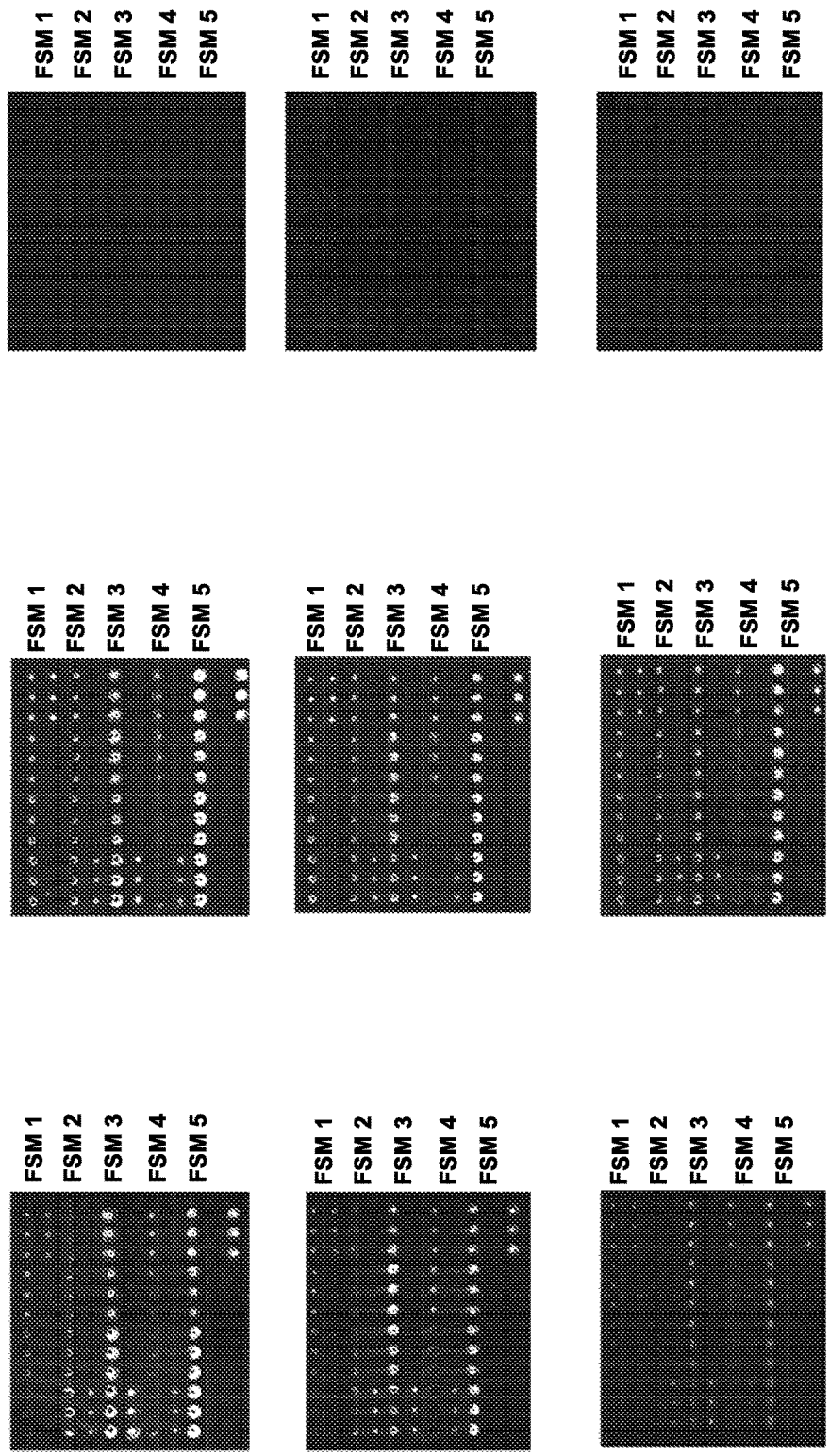
Figure 14: Tuning signal-to-background conditions

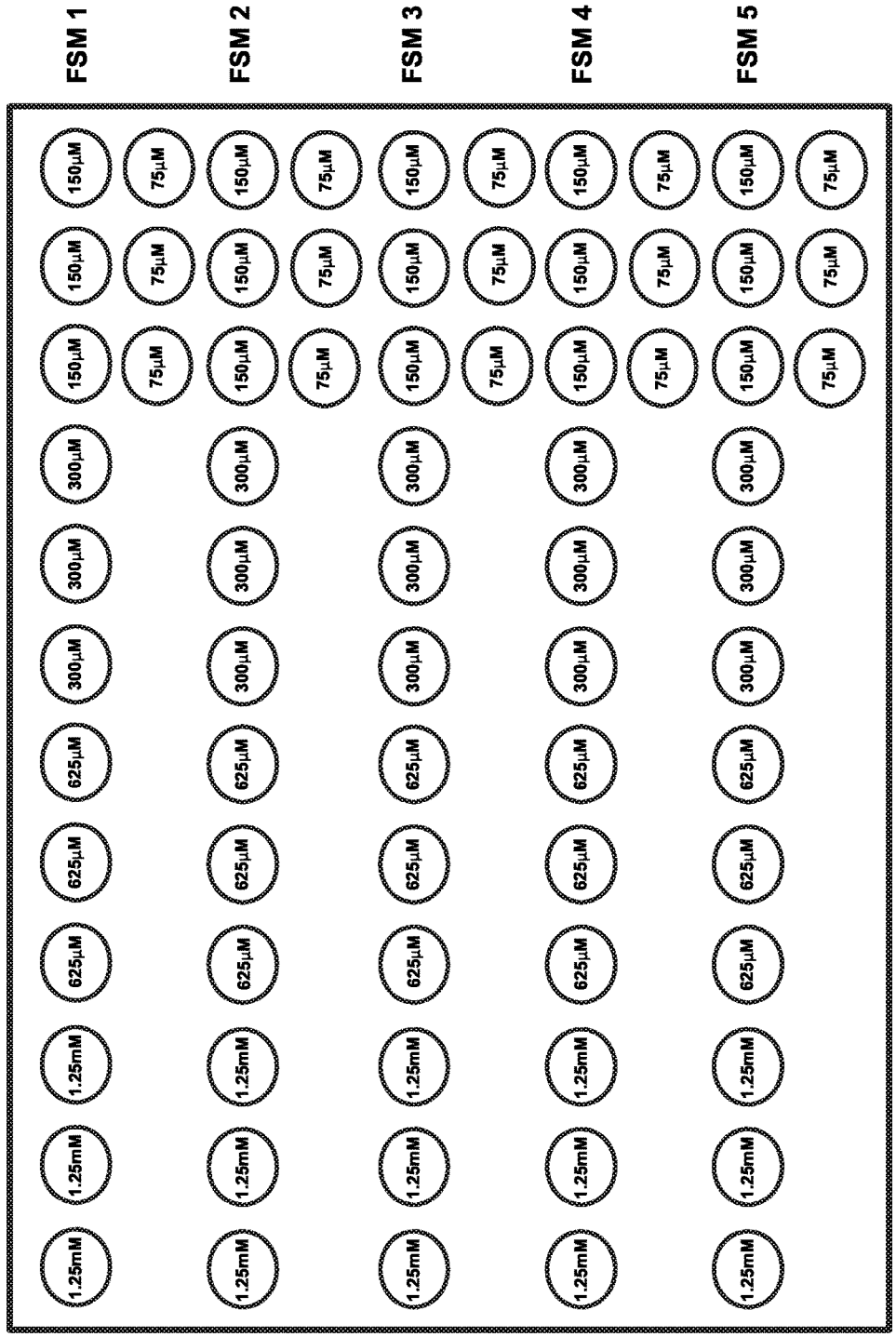
Figure 15: Tuning signal-to-background conditions

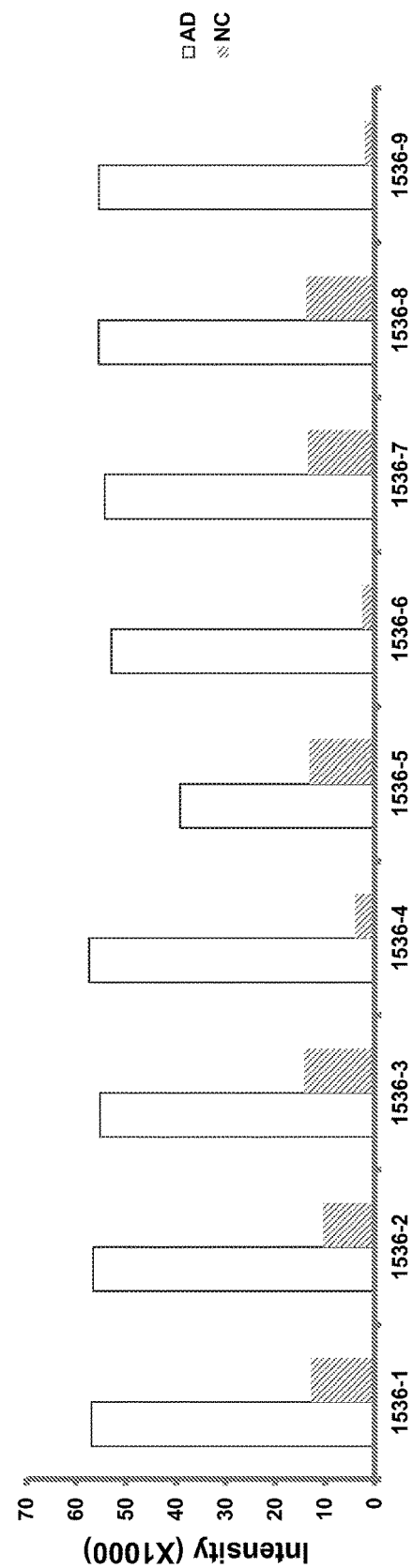
Figure 16: Response intensity

COMBINATORIAL SYNTHESIS AND BIOMARKER DEVELOPMENT

CROSS-REFERENCE

This application claims the benefit of U.S. Provisional Patent Application No. 62/313,580, filed on Mar. 25, 2016, which is herein incorporated by reference in its entirety.

BACKGROUND

Alzheimer's disease (AD) is a degenerative affliction of the nervous system that negatively impacts a person's memory, cognitive functions, and ability to perform the normal activities of daily living. AD changes tissues in the brain years before symptoms of dementia appear in a subject's behavior. Alzheimer's disease is associated with the accumulation of beta-amyloid plaques in the brain that lead to the eventual destruction of brain cells. The two key neuropathological hallmarks of AD are the presence of senile plaques predominantly comprised of aggregated beta-amyloid protein (Aβ) and neurofibrillary tangles (NFTs) formed by the accumulation of hyper phosphorylated tau protein. Researchers believe that pre-symptomatic progression of AD can begin 8 to 12 years (or longer) prior to the onset of mild dementia. Unfortunately, even when symptoms become apparent, there is no definitive test to diagnose AD. Despite efforts through decades of research, no early marker for AD has yet been discovered. Disclosed herein are molecules, methods and kits for detecting biomarkers indicative of a disease, for example AD biomarkers.

SUMMARY OF THE DISCLOSURE

Disclosed herein are methods. In some embodiments, the methods disclosed herein can detect whether or not a molecule can be bound to a peptoid or pharmaceutically acceptable salt thereof. In some embodiments, the method can comprise contacting a sample with a peptoid or pharmaceutically acceptable salt thereof. In some embodiments, the peptoid or pharmaceutically acceptable salt thereof can be capable of binding at least two antibody subtypes or fragments thereof. In some embodiments, the at least two antibody subtypes can comprise at least one of an IgG, IgM, IgD, IgE or an IgA. In some embodiments, a computer system can be used to detect whether or not a molecule is bound to said peptoid or pharmaceutically acceptable salt thereof. In some embodiments, the sample can be tissue, cell, urine, serum, whole blood, cerebrospinal fluid, sputum, saliva, or semen. In some embodiments, the sample can be serum. In some embodiments, the sample can be obtained from a mammal. In some embodiments, the mammal can be a human subject. In some embodiments, the subject can be suspected of having a disease. In some embodiments, the disease can be a neurological disease. In some embodiments, the neurological disease can be Parkinson's disease. In some embodiments, the neurological disease can be Alzheimer's disease. In some embodiments, the detecting utilizes a method comprising radio immunoassay ("RIA"), fluorescence immunoassay ("FIA"), enzyme-linked immunosorbent assay ("ELISA"), western blot, flow cytometry, Forster resonance energy transfer ("FRET"), surface plasmon resonance, or any combination thereof. In some embodiments, the method can further comprise communicating a result of whether or not the peptoid or pharmaceutically acceptable salt thereof can be bound to the molecule through a communication medium. In some embodiments, the communication medium comprises an electronic medium. In some embodiments, the electronic medium can comprises a device comprising a processor or a microprocessor. In some embodiments, the molecule can be a biomarker. In some embodiments, the method can further comprise identifying the biomarker. In some embodiments, the peptoid or pharmaceutically acceptable salt thereof has a binding affinity of at least $10^{-5}$ M ($K_D$) for the biomarker. In some embodiments, a prophylactically or therapeutically effective amount of a prophylactically or therapeutically acceptable amount of the biomarker can be administered to a patient in need thereof. In some embodiments, the biomarker can be administered for preventing, treating, ameliorating or managing a disease or condition. In some embodiments, the disease or condition can be a neurological disease, cancer, autoimmune disease or an infectious disease. In some embodiments, the disease is a neurological disease. In some embodiments, the neurological diseases can be Parkinson's disease or Alzheimer's disease. In some embodiments, the biomarker can be present in a subsect free from said disease and an absence of said biomarker is indicative of said disease. In some embodiments, the biomarker can be a peptide, a protein, a carbohydrate, a lipid, a lipoprotein, a receptor, a T cell receptor, a molecule with a molecular weight of 1000 Daltons or less, a cell, an antibody or a fragment thereof. In some embodiments, the biomarker can be an antibody or a fragment thereof. In some embodiments, the antibody can be an IgG, IgM, or an IgA, a fragment thereof or any combination thereof. In some embodiments, the antibody can be an IgM or a fragment thereof. In some embodiments, the antibody can be an IgA or a fragment thereof. In some embodiments, the peptoid or pharmaceutically acceptable salt thereof comprise integrated therein about 9, 10, 11, 12, 13 or more monomers that can be different or the same. In some embodiments, the peptoid or pharmaceutically acceptable salt thereof can be associated with a support. In some embodiments, the peptoid or pharmaceutically acceptable salt thereof can be bound to the support. In some embodiments, the peptoid or pharmaceutically acceptable salt thereof can be covalently bound to the support. In some embodiments, the peptoid or pharmaceutically acceptable salt thereof can be non-covalently bound to the support. In some embodiments, there can be a linker between the support and the peptoid or pharmaceutically acceptable salt thereof. In some embodiments, the linker can be covalently bound to the support. In some embodiments, the linker can be non-covalently bound to the support. In some embodiments, the linker can comprise a polyethylene glycol ("PEG") linker. In some embodiments, the linker can comprise integrated therein a positive amount of less than or equal to about 10 PEG monomeric units. In some embodiments, the support can be a solid support. In some embodiments, the solid support can be a glass slide, silicon surface, bead, resin or an array. In some embodiments, the solid support can be a bead. In some embodiments, the solid support can be a resin. In some embodiments, the solid support can be an array. In some embodiments, the solid support can be associated with a brush polymer. In some embodiments, the solid support can be associated with a bottle brush polymer. In some embodiments, the biomarker can indicate a subject's likelihood of having a disease. In some embodiments, the disease can be a neurological disease, cancer, autoimmune disease or an infectious disease. In some embodiments, the disease can be a neurological disease. In some embodiments, the neurological disease can be Parkinson's disease. In some embodiments, the neurological disease can be Alzheimer's disease. In some embodiments, there can be a likelihood of the disease if the biomarker can be bound to the peptoid or pharmaceutically acceptable salt thereof. In some embodiments, the likelihood of the disease can be indicated by a second test. In some embodiments, the method can further comprise diagnosing the disease if the biomarker can be bound to the peptoid or pharmaceutically acceptable salt thereof. In some embodiments, the method can further comprise diagnosing the disease if the biomarker can be bound to the peptoid or pharmaceutically acceptable salt thereof and can be above a concentration that is observed in a control non diseased subject sample. In some embodiments, the method can further comprise diagnosing the disease if the biomarker can be bound to the peptoid or pharmaceutically acceptable salt thereof and is below a concentration that can be observed in a control non diseased subject sample. In some embodiments, the method can further comprise administering a treatment for the disease. In some embodiments, the method can further comprise repeating contacting a sample with a peptoid or pharmaceutically acceptable salt thereof and detecting whether or not a molecule is bound to the peptoid or pharmaceutically acceptable salt thereof at different time points to monitor a disease. In some embodiments, the different time points can be within 1 week, 2 weeks, 1 month, 2 months, 3 months, 6 months, 8 months or 1 year. In some embodiments, the method can further comprise repeating contacting a sample with a peptoid or pharmaceutically acceptable salt thereof and detecting whether or not a molecule is bound to the peptoid or pharmaceutically acceptable salt thereof at different time points can be performed following the administration of a treatment to a subject. In some embodiments, the detecting of the biomarker can be determinative of the subject's response to the treatment. In some embodiments, the detecting of the biomarker can be determinative at least in part for whether a subject can be eligible for a clinical trial. In some embodiments, the biomarker can determine a likelihood of a subject having an adverse reaction to a drug. In some embodiments, the peptoid or pharmaceutically acceptable salt thereof can be selected from a group comprising a formula:

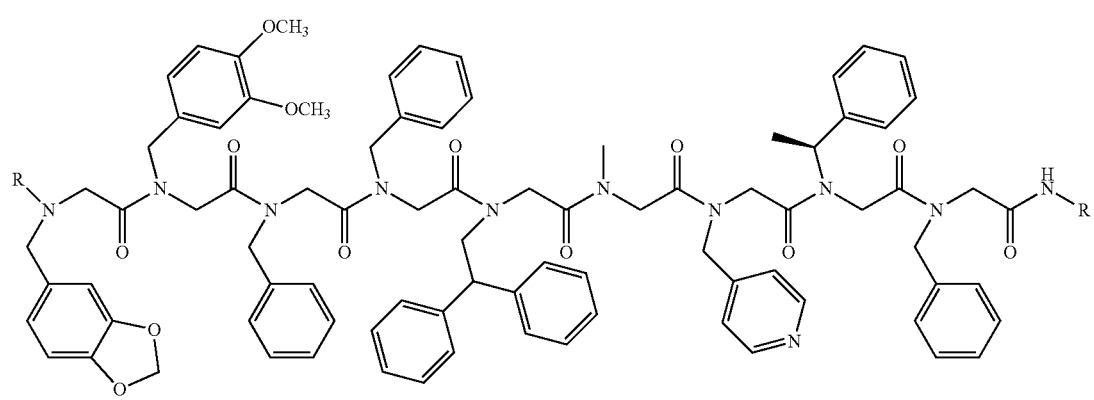

ErAD1

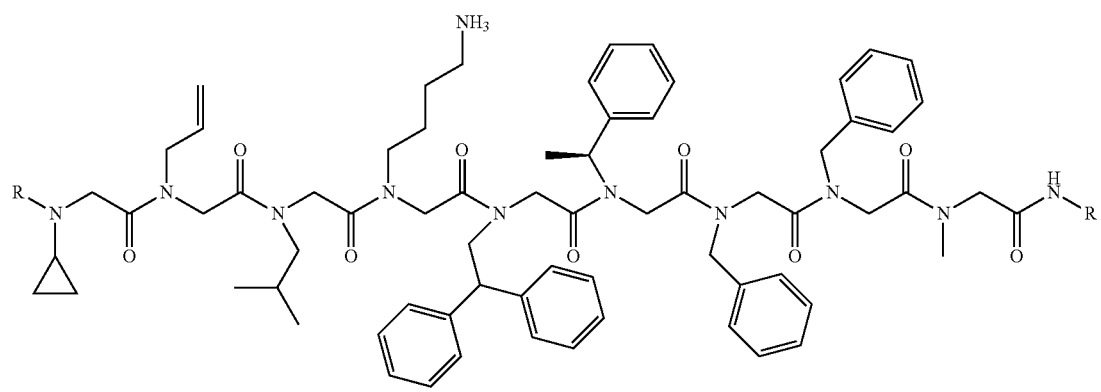

ErAD2

ErAD3
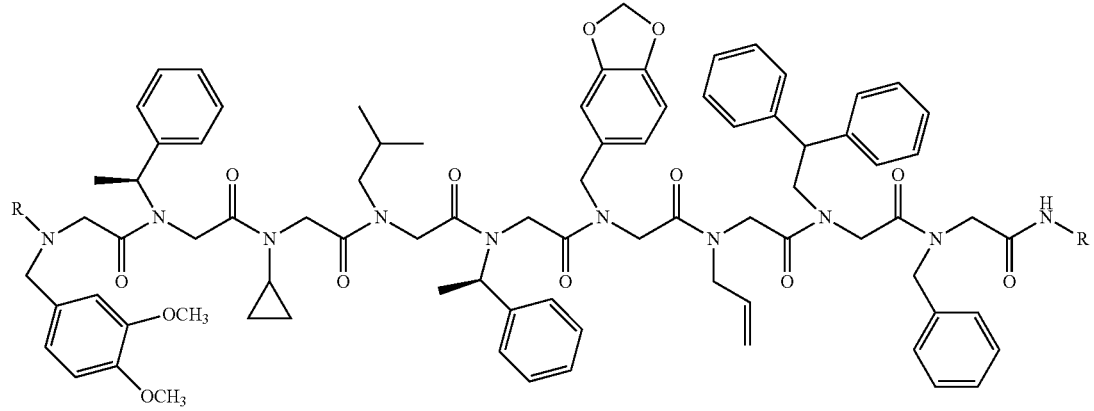
ErAD4
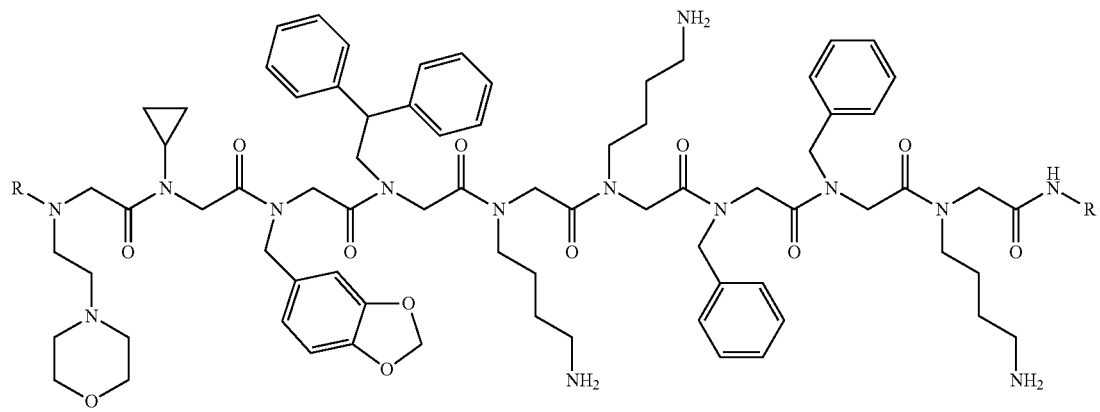
ErAD5
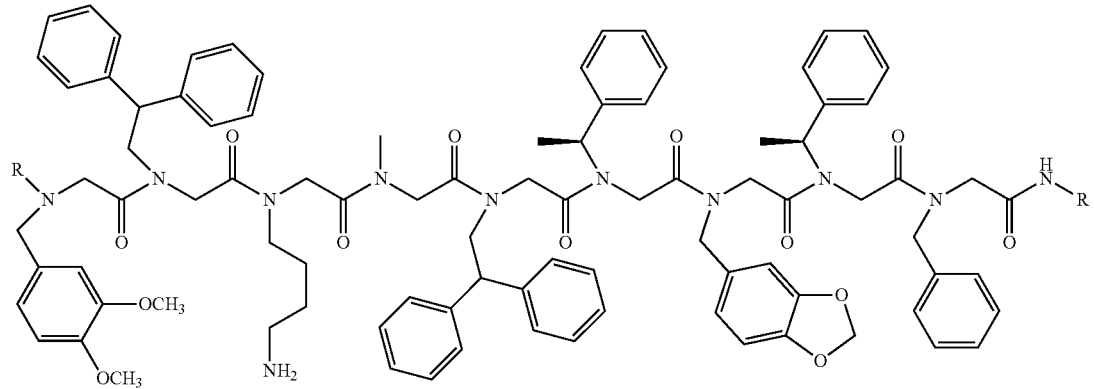
ErAD6
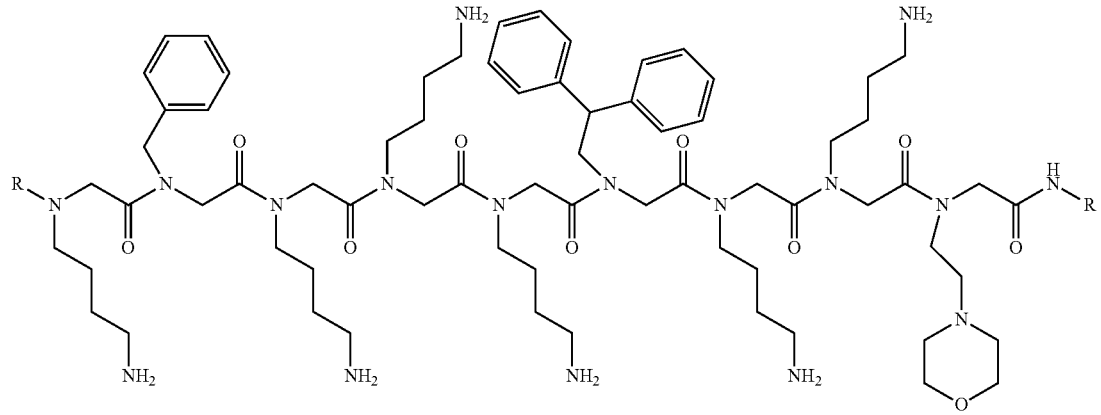

-continued

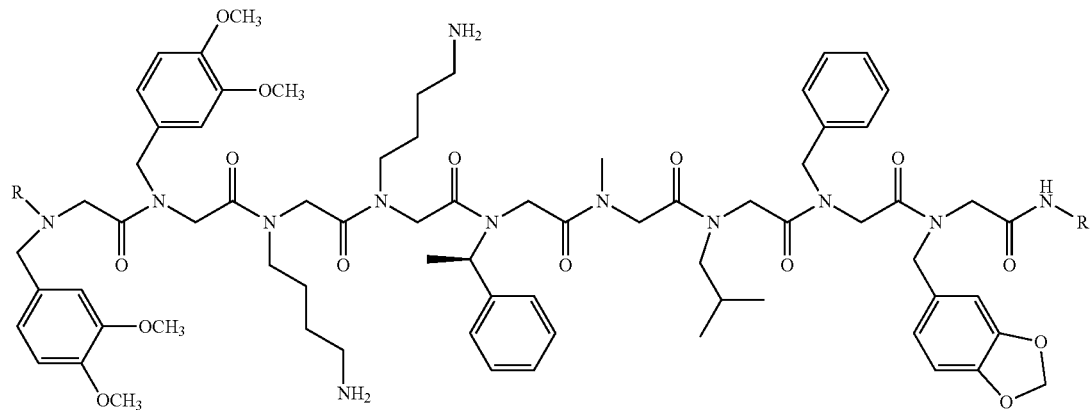

AAD1

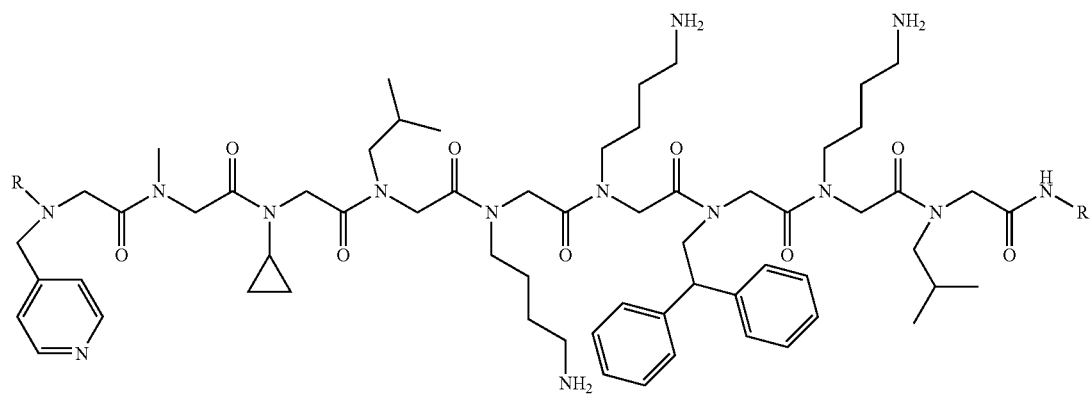

AAD2

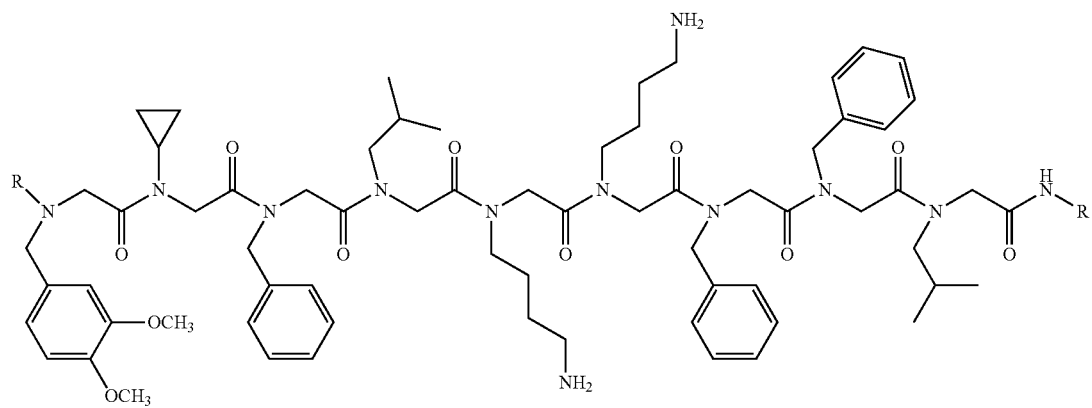

AAD3 or any combination thereof. In some embodiments, R can independently be selected from a group consisting of a coupling group capable of coupling to a linker, a substrate, or a label; hydrogen; deuterium; $C_{1-6}$ alkyl; $C_{2-6}$ alkenyl; $C_{2-6}$ alkynyl, $C_{3-8}$cycloalkyl; heteroaryl, cycloalkyl; $C_{1-6}$alkylheteroaryl; $C_{1-6}$alkylaryl; and alkylcycloalkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof.

Disclosed herein are peptoids or pharmaceutically acceptable salt thereof. In some embodiments, the method can comprise contacting a sample with a peptoid or pharmaceutically acceptable salt thereof. In some embodiments, the peptoid or pharmaceutically acceptable salt thereof can comprise a compound of formula I:

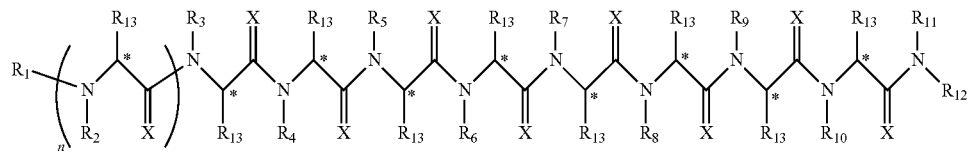

In some embodiments, $R_1$ can be independently selected from a group consisting of a coupling group capable of coupling to a linker, a substrate, or a label; hydrogen; deuterium; $C_{1-6}$ alkyl; $C_{2-6}$ alkenyl; $C_{2-6}$ alkynyl, $C_{3-8}$cycloalkyl; heteroaryl, cycloalkyl; $C_{1-6}$alkylheteroaryl; $C_{1-6}$alkylaryl; and alkylcycloalkyl, each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_2$ can be independently selected from a group consisting of hydrogen; deuterium; $(CY_2)_n$-aryl; $(CY_2)_n$-alkoxyaryl; cycloalkyl; $(CY_2)_n$-heteroaryl; and $(CY_2)_n$-alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_3$ can be independently selected from a group consisting of hydrogen; deuterium; $(CY_2)_n$-aryl; $(CY_2)_n$-alkoxyaryl; alkenyl; alkylaryl; cycloalkyl; alkyldiaryl; and alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_4$ can be independently selected from a group consisting of hydrogen; deuterium; $(CY_2)_n$-aryl; alkyl; cycloalkyl; and $(CY_2)_n$-alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_5$ can be independently selected from a group consisting of hydrogen; deuterium; $(CY_2)_n$-aryl; $(CY_2)_n$-alkyl; alkyl; and alkyldiaryl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_6$ can be independently selected from a group consisting of hydrogen; deuterium; alkyldiaryl; alkylaryl; and $(CY_2)_n$-alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_7$ can be independently selected from a group consisting of hydrogen; deuterium; alkyl; alkylaryl; $(CY_2)_n$-aryl; $(CY_2)_n$-alkyl; and alkyldiaryl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_8$ can be independently selected from a group consisting of hydrogen; deuterium; $(CY_2)_n$-heteroaryl; $(CY_2)_n$-aryl; alkenyl; $(CY_2)_n$-alkyl; alkyl; and alkyldiaryl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_9$ can be independently selected from a group consisting of hydrogen; deuterium; alkylaryl; $(CY_2)_n$-aryl; alkyldiaryl; and $(CY_2)_n$-alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_{10}$ can be independently selected from a group consisting of hydrogen; deuterium; $(CY_2)_n$-aryl; alkyl; $(CY_2)_n$-alkyl; and $(CY_2)_n$-heteroaryl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_{11}$ can be independently selected from a group consisting of hydrogen; deuterium; $C_{1-6}$ alkyl; $C_{2-6}$ alkenyl; $C_{2-6}$ alkynyl, $C_{3-8}$cycloalkyl; heteroaryl, cycloalkyl; $C_{1-6}$alkylheteroaryl; $C_{1-6}$alkylaryl; and alkylcycloalkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_{12}$ can be independently selected from a group consisting of a coupling group capable of coupling to a linker, a substrate, or a label; hydrogen; deuterium; $C_{1-6}$ alkyl; $C_{2-6}$ alkenyl; $C_{2-6}$ alkynyl, $C_{3-8}$cycloalkyl; heteroaryl, cycloalkyl; $C_{1-6}$alkylheteroaryl; $C_{1-6}$alkylaryl; and alkylcycloalkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_{13}$ can be individually and independently selected from a group consisting of hydrogen; deuterium; a halogen; ethyl; and methyl. In some embodiments, when $R_{13}$ can be not hydrogen each carbon denoted with an * can independent be R or S. In some embodiments, X can be independently selected from oxygen or sulfur. In some embodiments, Y can be independently selected from deuterium or hydrogen. In some embodiments, A can be hydrogen, deuterium, aryl, or heteroaryl. In some embodiments, n can be 1-10. In some embodiments, $R_3$ is not hydrogen or deuterium. In some embodiments, $R_4$ is not hydrogen or deuterium. In some embodiments, $R_5$ is not hydrogen or deuterium. In some embodiments, $R_6$ is not hydrogen or deuterium. In some embodiments, $R_7$ is not hydrogen or deuterium. In some embodiments, $R_8$ is not hydrogen or deuterium. In some embodiments, $R_9$ is not hydrogen or deuterium. In some embodiments, $R_{10}$ is not hydrogen or deuterium. In some embodiments, the peptoid or pharmaceutically acceptable salt thereof of formula I, $R_1$ can be selected from the group consisting of deuterium and hydrogen. In some embodiments, the peptoid or pharmaceutically acceptable salt thereof of formula I, $R_2$ can be selected from the group consisting of piperonyl; cyclopropyl; dimethoxybenzyl; morpholyl; aminobutyl; and pyridyl. In some embodiments, the peptoid or pharmaceutically acceptable salt thereof of formula I, $R_3$ can be selected from the group consisting of allyl; methylbenzyl; cyclopropyl; diphenylethyl; benzyl; dimethoxybenzyl; and methyl. In some embodiments, the peptoid or pharmaceutically acceptable salt thereof of formula I, $R_4$ can be selected from the group consisting of benzyl; can be isobutyl; cyclopropyl; piperonyl; and aminobutyl. In some embodiments, the peptoid or pharmaceutically acceptable salt thereof of formula I, $R_5$ can be selected from the group consisting of benzyl; aminobutyl; can isobutyl; diphenylethyl; and methyl. In some embodiments, the peptoid or pharmaceutically acceptable salt thereof of formula I, $R_6$ can be selected from the group consisting of diphenylethyl; aminobutyl; or methylbenzyl. In some embodiments, the peptoid or pharmaceutically acceptable salt thereof of formula I, $R_7$ can be selected from the group consisting of methyl; methylbenzyl; piperonyl; diphenylethyl; aminobutyl. In some embodiments, the peptoid or pharmaceutically acceptable salt thereof of formula I, $R_8$ can be selected from the group consisting of pyridyl; allyl; piperonyl; aminobutyl; can isobutyl; diphenylethyl; or benzyl. In some embodiments, the peptoid or pharmaceutically acceptable salt thereof of formula I, $R_9$ can be selected from the group consisting of methylbenzyl; benzyl; diphenylethyl; aminobutyl. In some embodiments, the peptoid or pharmaceutically acceptable salt thereof of formula I, $R_{10}$ can be selected from the group consisting of methyl; aminobutyl; benzyl; piperonyl; can isobutyl. In some embodiments, the peptoid or pharmaceutically acceptable salt thereof of formula I, $R_{11}$ can be selected from the group consisting of hydrogen and deuterium. In some embodiments, the peptoid or pharmaceutically acceptable salt thereof of formula I, $R_{12}$ can be selected from the group consisting of hydrogen and deuterium. In some embodiments, the peptoid or pharmaceutically acceptable salt thereof of formula I, $R_{13}$ can be selected from the group consisting of hydrogen and deuterium. In some embodiments, the peptoid or pharmaceutically acceptable salt thereof of formula I, $R_1$ can be hydrogen or deuterium; $R_2$ can be piperonyl; $R_3$ can be dimethoxybenzyl; $R_4$ can be benzyl; $R_5$ can be benzyl; $R_6$ can be diphenylethyl; $R_7$ can be methyl; $R_8$ can be pyridyl; $R_9$ can be methylbenzyl; $R_{10}$ can be benzyl; $R_{11}$, $R_{12}$ and $R_{13}$ can be each independently selected from hydrogen or deuterium. In some embodiments, the peptoid or pharmaceutically acceptable salt thereof of formula I, $R_1$ can be hydrogen or deuterium; $R_2$ can be cyclopropyl; $R_3$ can be allyl; $R_4$ can be can isobutyl; $R_5$ can be aminobutyl; $R_6$ can be diphenylethyl; $R_7$ can be methylbenzyl; $R_8$ can be benzyl; $R_9$ can be benzyl; $R_{10}$ can be methyl; $R_{11}$, $R_{12}$ and $R_{13}$ can be each independently selected from hydrogen or deuterium. In some embodiments, the peptoid or pharmaceutically acceptable salt thereof of formula I, $R_1$ can be hydrogen or deuterium; $R_2$ can be dimethoxybenzyl; $R_3$ can be methylbenzyl; $R_4$ can be cyclopropyl; $R_5$ can be can isobutyl; $R_6$ can be methylbenzyl; $R_7$ can be piperonyl; $R_8$ can be allyl; $R_9$ can be diphenylethyl; $R_{10}$ can be benzyl; $R_{11}$, $R_{12}$ and $R_{13}$ can be each independently selected from hydrogen or deuterium. In some embodiments, the peptoid or pharmaceutically acceptable salt thereof of formula I, $R_1$ can be hydrogen or deuterium; $R_2$ can be morpholyl; $R_3$ can be cyclopropyl; $R_4$ can be piperonyl; $R_5$ can be diphenylethyl; $R_6$ can be aminobutyl; $R_7$ can be aminobutyl; $R_8$ can be benzyl; $R_9$ can be benzyl; $R_{10}$ can be aminobutyl; $R_{11}$, $R_{12}$ and $R_{13}$ can be each independently selected from hydrogen or deuterium. In some embodiments, the peptoid or pharmaceutically acceptable salt thereof of formula I, $R_1$ can be hydrogen or deuterium; $R_2$ can be dimethoxybenzyl; $R_3$ can be diphenylethyl; $R_4$ can be aminobutyl; $R_5$ can be methyl; $R_6$ can be diphenylethyl; $R_7$ can be methylbenzyl; $R_8$ can be piperonyl; $R_9$ can be methylbenzyl; $R_{10}$ can be benzyl; $R_{11}$, $R_{12}$ and $R_{13}$ can be each independently selected from hydrogen or deuterium. In some embodiments, the peptoid or pharmaceutically acceptable salt thereof of formula I, $R_1$ can be hydrogen or deuterium; $R_2$ can be aminobutyl; $R_3$ can be benzyl; $R_4$ can be aminobutyl; $R_5$ can be aminobutyl; $R_6$ can be aminobutyl; $R_7$ can be diphenylethyl; $R_8$ can be aminobutyl; $R_9$ can be aminobutyl; $R_{10}$ can be morpholyl; $R_{11}$, $R_{12}$ and $R_{13}$ can be each independently selected from hydrogen or deuterium. In some embodiments, the peptoid or pharmaceutically acceptable salt thereof of formula I, $R_1$ can be hydrogen or deuterium; $R_2$ can be dimethoxybenzyl; $R_3$ can be dimethoxybenzyl; $R_4$ can be aminobutyl; $R_5$ can be aminobutyl; $R_6$ can be methylbenzyl; $R_7$ can be methyl; $R_8$ can be can isobutyl; $R_9$ can be benzyl; $R_{10}$ can be piperonyl; $R_{11}$, $R_{12}$ and $R_{13}$ can be each independently selected from hydrogen or deuterium. In some embodiments, the peptoid or pharmaceutically acceptable salt thereof of formula I, $R_1$ can be hydrogen or deuterium; $R_2$ can be pyridyl; $R_3$ can be methyl; $R_4$ can be cyclopropyl; $R_5$ can be can isobutyl; $R_6$ can be aminobutyl; $R_7$ can be aminobutyl; $R_8$ can be diphenylethyl; $R_9$ can be aminobutyl; $R_{10}$ can be can isobutyl; $R_{11}$, $R_{12}$ and $R_{13}$ can be each independently selected from hydrogen or deuterium. In some embodiments, the peptoid or pharmaceutically acceptable salt thereof of formula I, $R_1$ can be hydrogen or deuterium; $R_2$ can be dimethoxybenzyl; $R_3$ can be cyclopropyl; $R_4$ can be benzyl; $R_5$ can be can isobutyl; $R_6$ can be aminobutyl; $R_7$ can be aminobutyl; $R_8$ can be benzyl; $R_9$ can be benzyl; $R_{10}$ can be can isobutyl; $R_{11}$, $R_{12}$ and $R_{13}$ can be each independently selected from hydrogen or deuterium. In some embodiments, the sample can be tissue, cell, urine, serum, whole blood, cerebrospinal fluid, sputum, saliva, or semen. In some embodiments, the sample can be serum. In some embodiments, the sample can be obtained from a mammal. In some embodiments, the mammal can be a human subject. In some embodiments, the subject can be suspected of having a disease. In some embodiments, the disease can be a neurological disease. In some embodiments, the neurological disease can be Parkinson's disease. In some embodiments, the neurological disease can be Alzheimer's disease. In some embodiments, the detecting utilizes a method comprising radio immunoassay ("RIA"), fluorescence immunoassay ("FIA"), enzyme-linked immunosorbent assay ("ELISA"), western blot, flow cytometry, Forster resonance energy transfer ("FRET"), surface plasmon resonance, or any combination thereof. In some embodiments, the method can further comprise communicating a result of whether or not the peptoid or pharmaceutically acceptable salt thereof can be bound to the molecule through a communication medium. In some embodiments, the communication medium comprises an electronic medium. In some embodiments, the electronic medium comprises a device comprising a processor or a microprocessor. In some embodiments, the molecule can be a biomarker. In some embodiments, the method can further comprise identifying the biomarker. In some embodiments, the peptoid or pharmaceutically acceptable salt thereof has a binding affinity of at least $10^{-5}$ M ($K_D$) for the biomarker.

In some embodiments, a prophylactically or therapeutically effective amount of a prophylactically or therapeutically acceptable amount of the biomarker can be administered to a patient in need thereof. In some embodiments, the biomarker can be administered for preventing, treating, ameliorating or managing a disease or condition. In some embodiments, the disease or condition can be a neurological disease, cancer, autoimmune disease or an infectious disease. In some embodiments, the disease is a neurological disease. In some embodiments, the neurological diseases can be Parkinson's disease or Alzheimer's disease. In some embodiments, the biomarker can be present in a subsect free from said disease and an absence of said biomarker is indicative of said disease. In some embodiments, the biomarker can be a peptide, a protein, a carbohydrate, a lipid, a lipoprotein, a receptor, a T cell receptor, a molecule with a molecular weight of 1000 Daltons or less, a cell, an antibody or a fragment thereof. In some embodiments, the biomarker can be an antibody or a fragment thereof. In some embodiments, the antibody can be an IgG, IgM, or an IgA, a fragment thereof or any combination thereof. In some embodiments, the antibody can be an IgM or a fragment thereof. In some embodiments, the antibody can be an IgA or a fragment thereof. In some embodiments, the peptoid or pharmaceutically acceptable salt thereof comprise integrated therein about 9, 10, 11, 12, 13 or more monomers that can be different or the same. In some embodiments, the peptoid or pharmaceutically acceptable salt thereof can be associated with a support. In some embodiments, the peptoid or pharmaceutically acceptable salt thereof can be bound to the support. In some embodiments, the peptoid or pharmaceutically acceptable salt thereof can be covalently bound to the support. In some embodiments, the peptoid or pharmaceutically acceptable salt thereof can be non-covalently bound to the support. In some embodiments, there can be a linker between the support and the peptoid or pharmaceutically acceptable salt thereof. In some embodiments, the linker can be covalently bound to the support. In some embodiments, the linker can be non-covalently bound to the support. In some embodiments, the linker can comprise a polyethylene glycol ("PEG") linker. In some embodiments, the linker can comprise integrated therein a positive amount of less than or equal to about 10 PEG monomeric units. In some embodiments, the support can be a solid support. In some embodiments, the solid support can be a glass slide, silicon surface, bead, resin or an array. In some embodiments, the solid support can be a bead. In some embodiments, the solid support can be a resin. In some embodiments, the solid support can be an array. In some embodiments, the solid support can be associated with a brush polymer. In some embodiments, the solid support can be associated with a bottle brush polymer. In some embodiments, the biomarker can indicate a subject's likelihood of having a disease. In some embodiments, the disease can be a neurological disease, cancer, autoimmune disease or an infectious disease. In some embodiments, the disease can be a neurological disease. In some embodiments, the neurological disease can be Parkinson's disease. In some embodiments, the neurological disease can be Alzheimer's disease. In some embodiments, there can be a likelihood of the disease if the biomarker can be bound to the peptoid or pharmaceutically acceptable salt thereof. In some embodiments, the likelihood of the disease can be indicated by a second test. In some embodiments, the method can further comprise diagnosing the disease if the biomarker can be bound to the peptoid or pharmaceutically acceptable salt thereof. In some embodiments, the method can further comprise diagnosing the disease if the biomarker can be bound to the peptoid or pharmaceutically acceptable salt thereof and can be above a concentration that is observed in a control non diseased subject sample. In some embodiments, the method can further comprise diagnosing the disease if the biomarker can be bound to the peptoid or pharmaceutically acceptable salt thereof and is below a concentration that can be observed in a control non diseased subject sample. In some embodiments, the method can further comprise administering a treatment for the disease. In some embodiments, the method can further comprise repeating contacting a sample with a peptoid or pharmaceutically acceptable salt thereof and detecting whether or not a molecule is bound to the peptoid or pharmaceutically acceptable salt thereof at different time points to monitor a disease. In some embodiments, the different time points can be within 1 week, 2 weeks, 1 month, 2 months, 3 months, 6 months, 8 months or 1 year. In some embodiments, the method can further comprise repeating contacting a sample with a peptoid or pharmaceutically acceptable salt thereof and detecting whether or not a molecule is bound to the peptoid or pharmaceutically acceptable salt thereof at different time points can be performed following the administration of a treatment to a subject. In some embodiments, the detecting of the biomarker can be determinative of the subject's response to the treatment. In some embodiments, the detecting of the biomarker can be determinative at least in part for whether a subject can be eligible for a clinical trial. In some embodiments, the biomarker can determine a likelihood of a subject having an adverse reaction to a drug. In some embodiments, the peptoid or pharmaceutically acceptable salt thereof can be selected from a group comprising a formula:

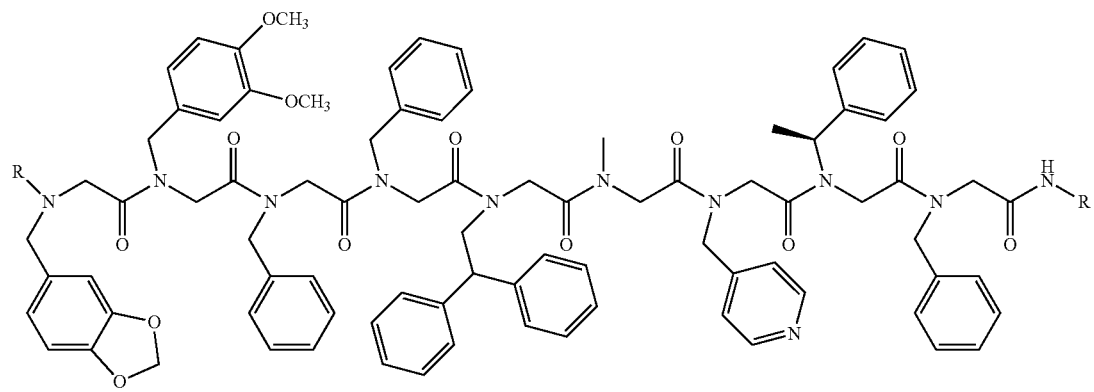

ErAD1

-continued
ErAD2
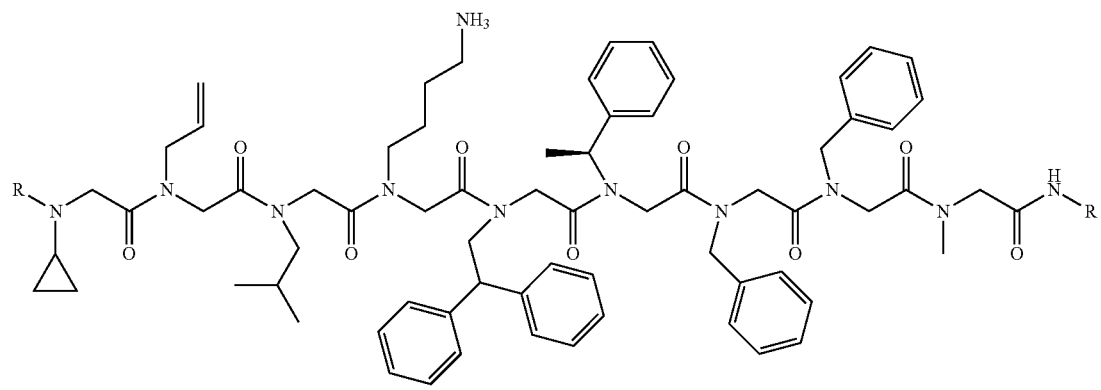
ErAD3
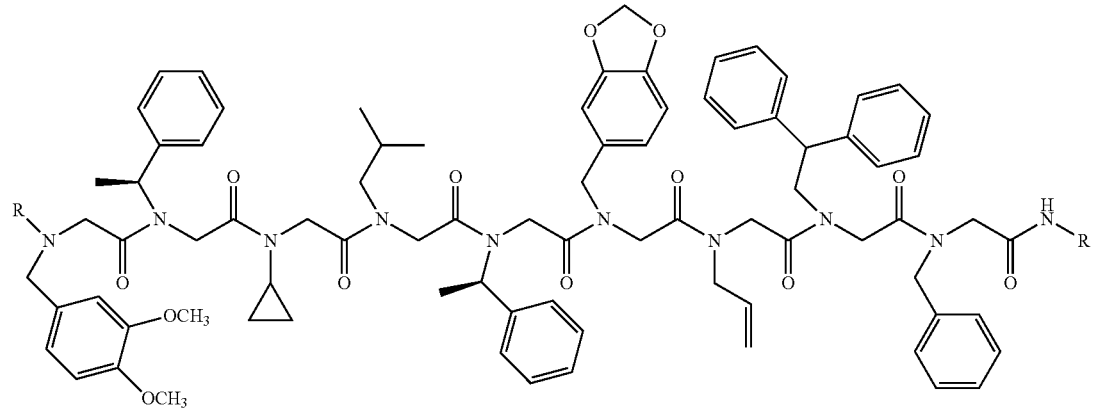
ErAD4
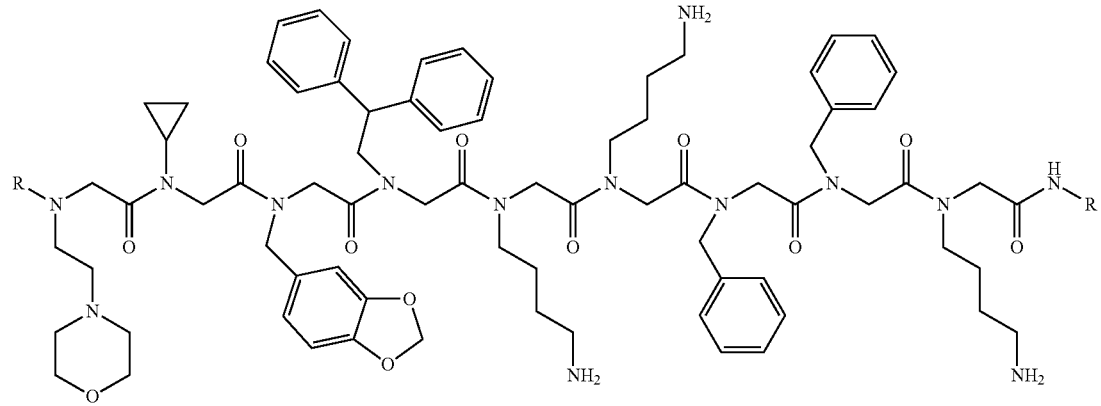
ErAD5
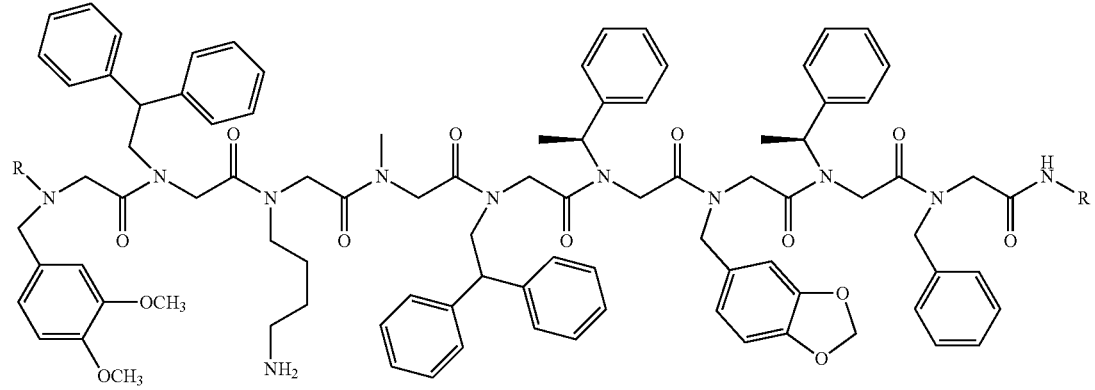

ErAD6
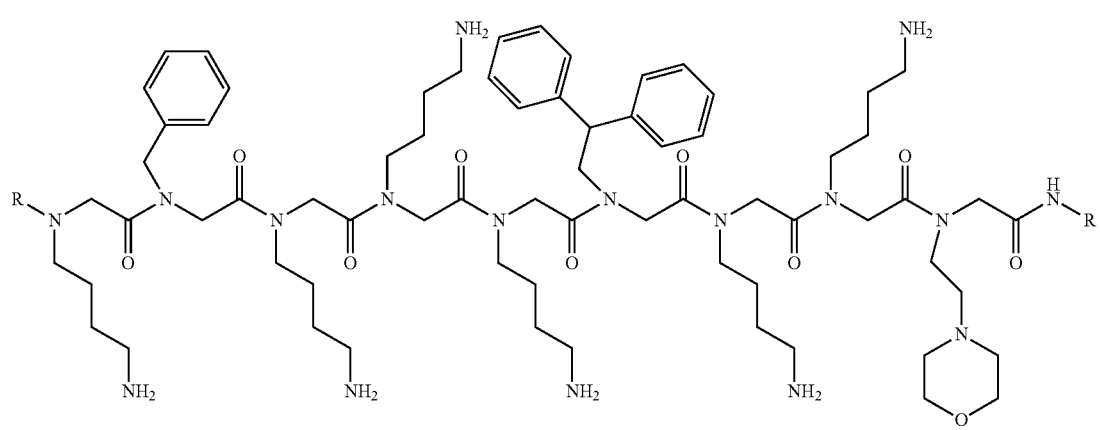
AAD1
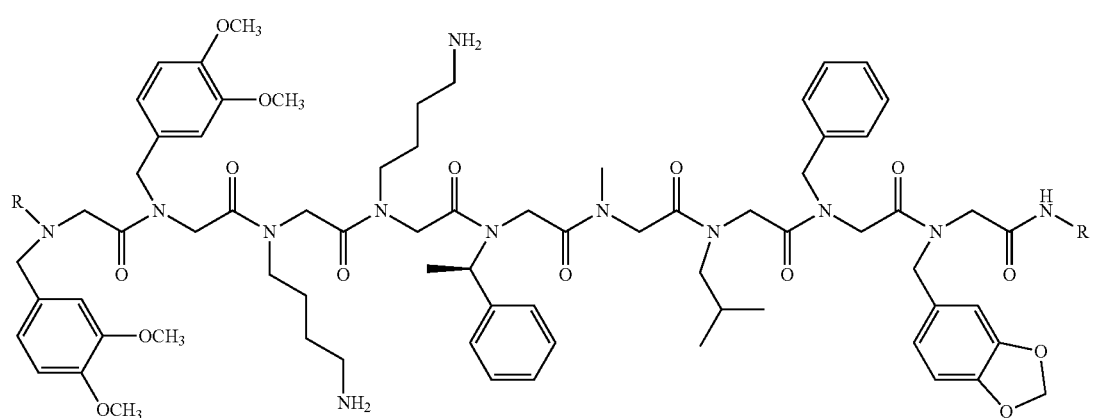
AAD2
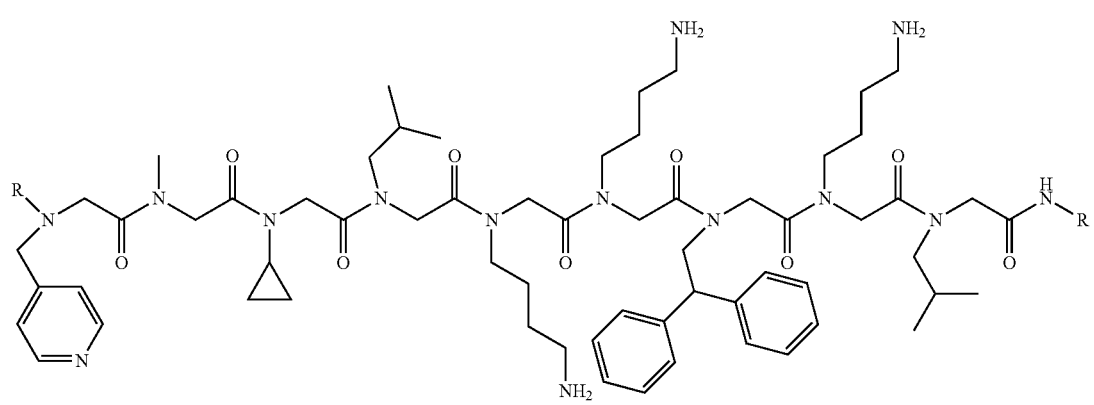
AAD3
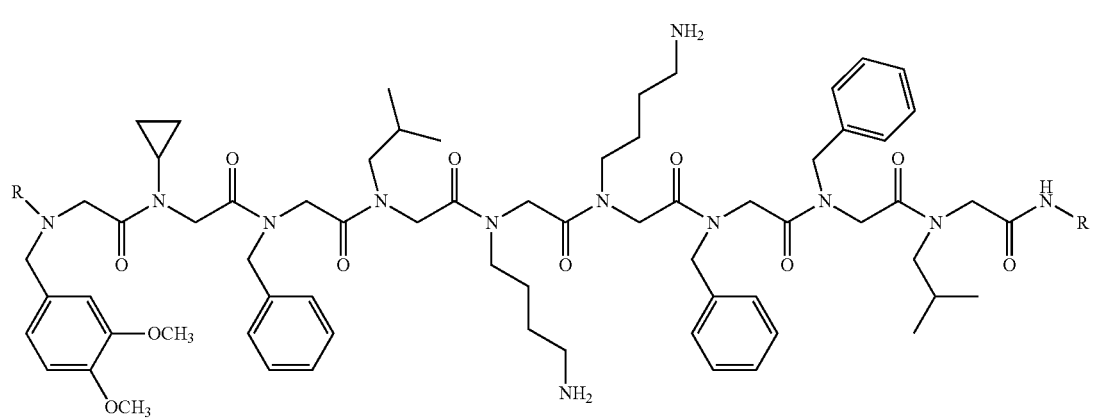

or any combination thereof. In some embodiments, R can be independently selected from a group consisting of a coupling group capable of coupling to a linker, a substrate, or a label; hydrogen; deuterium; $C_{1-6}$ alkyl; $C_{2-6}$ alkenyl; $C_{2-6}$ alkynyl, $C_{3-8}$cycloalkyl; heteroaryl, cycloalkyl; $C_{1-6}$alkylheteroaryl; $C_{1-6}$alkylaryl; and alkylcycloalkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof.

Disclosed herein are methods. In some embodiments, the method can comprise contacting a sample with a non-random peptoid library. In some embodiments, the non-random peptoid library can comprise a peptoid or pharmaceutically acceptable salt thereof having an affinity to an antibody. In some embodiments, the antibody can comprise an IgA or a fragment thereof, or an IgM or a fragment thereof. In some embodiments, the method can further comprise detecting whether the antibody is bound to the peptoid or pharmaceutically acceptable salt thereof. In some embodiments, the peptoid or pharmaceutically acceptable salt thereof can be selected from a group comprising a formula:

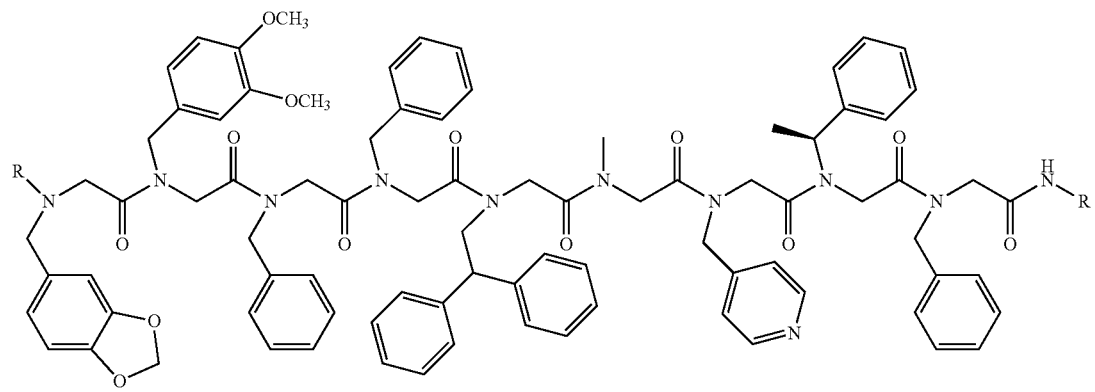

ErAD1

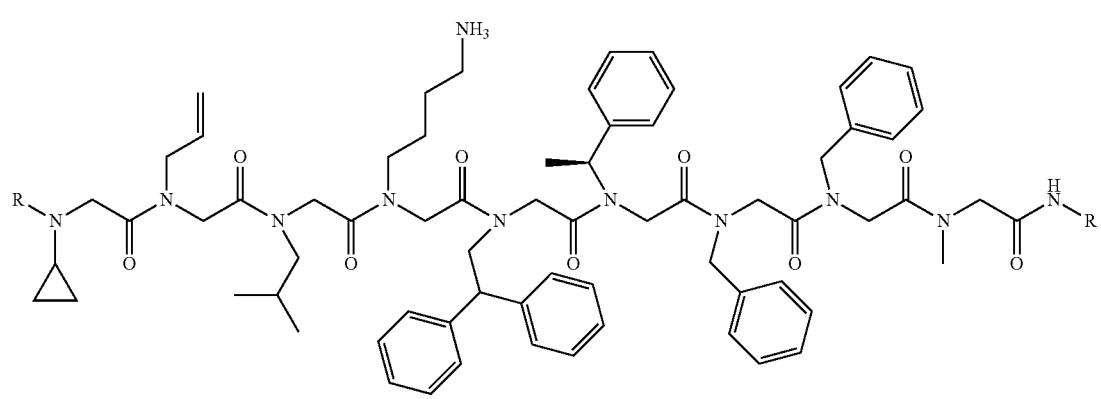

ErAD2

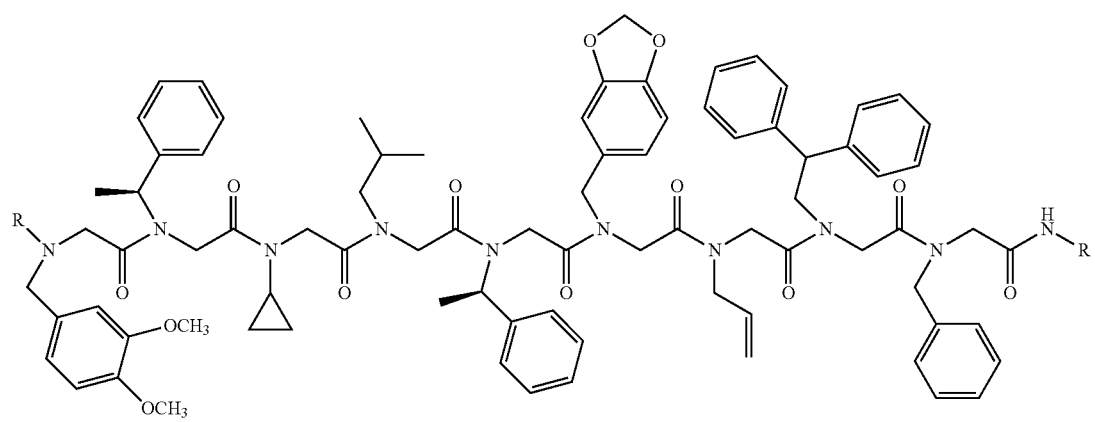

ErAD3

-continued
ErAD4
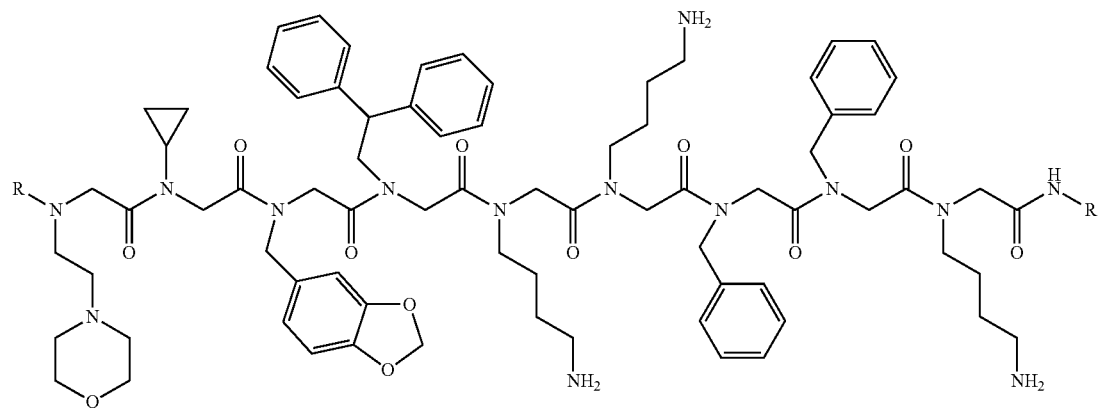
ErAD5
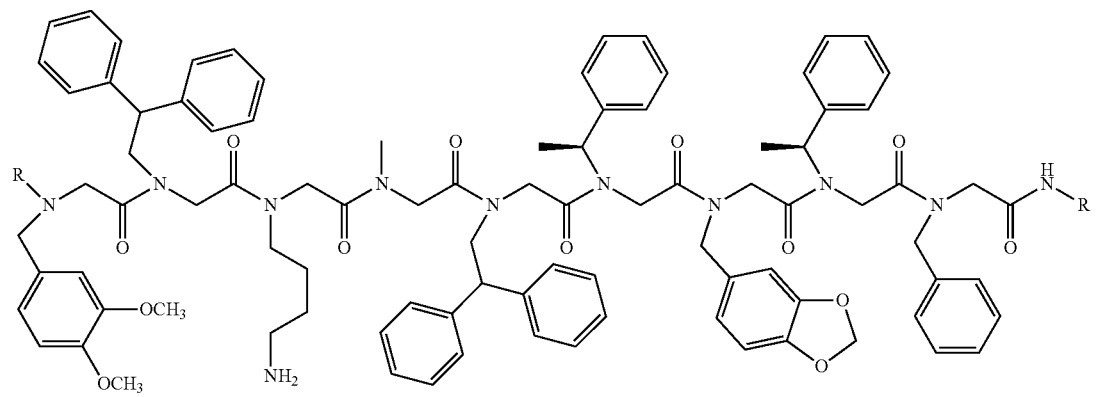
ErAD6
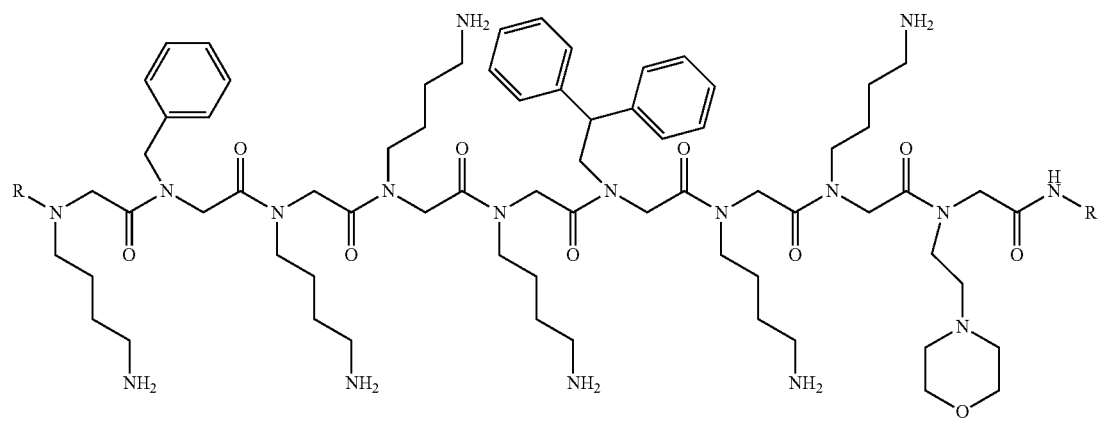
AAD1
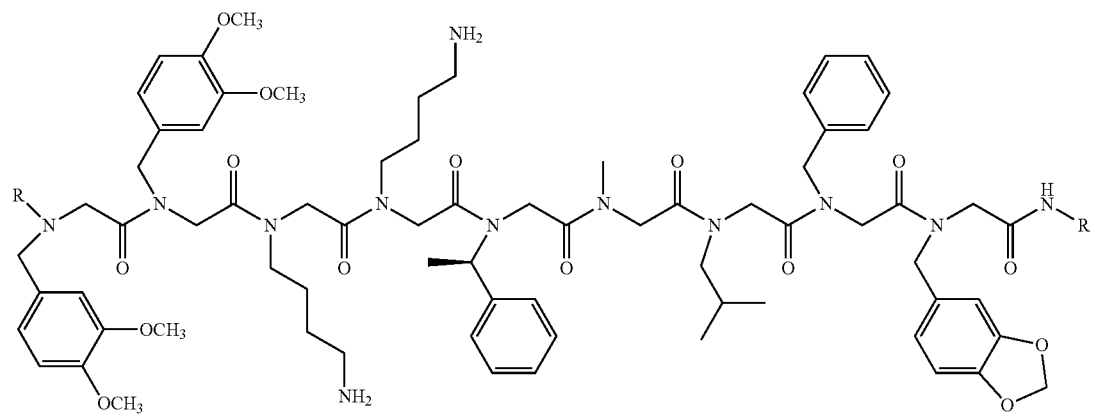

-continued

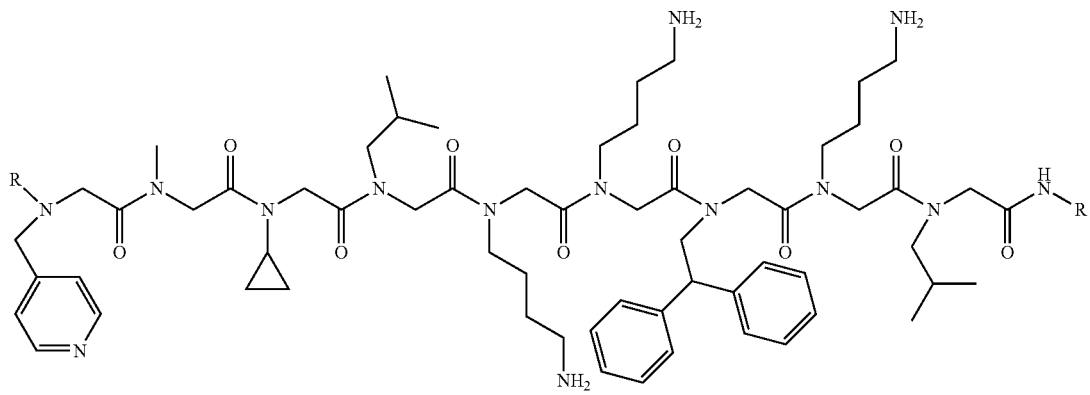

AAD2

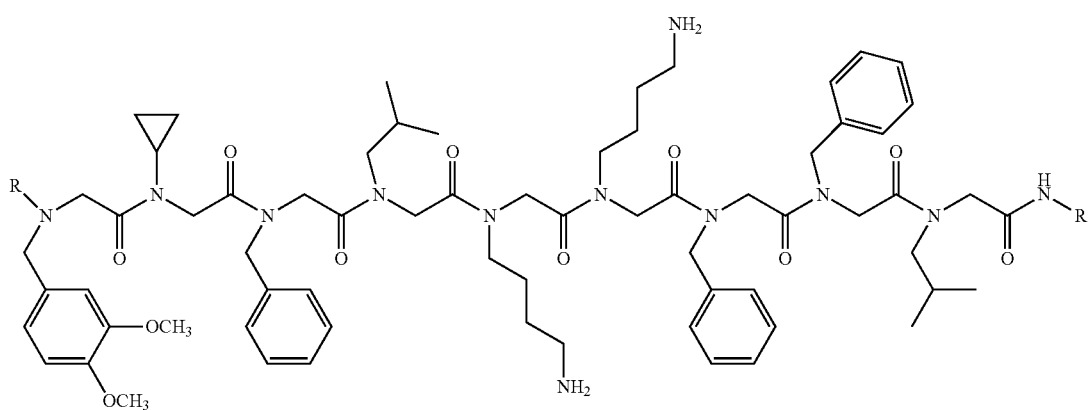

AAD3 or any combination thereof. In some embodiments, R can be independently selected from a group consisting of a coupling group capable of coupling to a linker, a substrate, or a label; hydrogen; deuterium; $C_{1-6}$ alkyl; $C_{2-6}$ alkenyl; $C_{2-6}$ alkynyl, $C_{3-8}$cycloalkyl; heteroaryl, cycloalkyl; $C_{1-6}$alkylheteroaryl; $C_{1-6}$alkylaryl; and alkylcycloalkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, X can be independently selected from oxygen or sulfur. In some embodiments, Y can be independently selected from deuterium or hydrogen. In some embodiments, A can be hydrogen, deuterium, aryl, or heteroaryl.

Disclosed herein are methods. In some embodiments, the method can comprise screening for a biomarker. In some embodiments, the method can comprise contacting a control sample with a support. In some embodiments, the support can have at least one peptoid or pharmaceutically acceptable salt thereof associated with the support. In some embodiments, the peptoid or pharmaceutically acceptable salt thereof can have a formula:

In some embodiments, $R_1$ can be independently selected from a group consisting of a coupling group capable of coupling to a linker, a substrate, or a label; hydrogen; deuterium; $C_{1-6}$ alkyl; $C_{2-6}$ alkenyl; $C_{2-6}$ alkynyl, $C_{3-8}$cycloalkyl; heteroaryl, cycloalkyl; $C_{1-6}$alkylheteroaryl; $C_{1-6}$alkylaryl; and alkylcycloalkyl, each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_2$ can be independently selected from a group consisting of hydrogen; deuterium; $(CY_2)_n$-aryl; $(CY_2)_n$-alkoxyaryl; cycloalkyl; $(CY_2)_n$-heteroaryl; and $(CY_2)_n$-alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_3$ can be independently selected from a group consisting of hydrogen; deuterium; $(CY_2)_n$-aryl; $(CY_2)_n$-alkoxyaryl; alkenyl; alkylaryl; cycloalkyl; alkyldiaryl; and alkyl; each of which except hydrogen and deuterium may be individually and indepen-

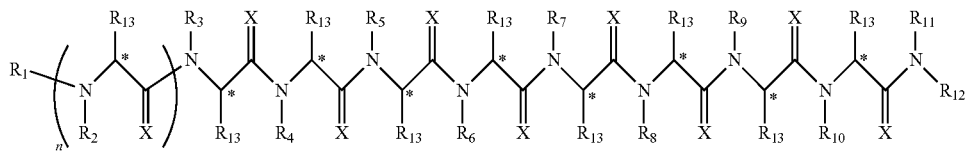

dently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_4$ can be independently selected from a group consisting of hydrogen; deuterium; $(CY_2)_n$-aryl; alkyl; cycloalkyl; and $(CY_2)_n$-alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_5$ can be independently selected from a group consisting of hydrogen; deuterium; $(CY_2)_n$-aryl; $(CY_2)_n$-alkyl; alkyl; and alkyldiaryl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_6$ can be independently selected from a group consisting of hydrogen; deuterium; alkyldiaryl; alkylaryl; and $(CY_2)_n$-alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_7$ can be independently selected from a group consisting of hydrogen; deuterium; alkyl; alkylaryl; $(CY_2)_n$-aryl; $(CY_2)_n$-alkyl; and alkyldiaryl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_8$ can be independently selected from a group consisting of hydrogen; deuterium; $(CY_2)_n$-heteroaryl; $(CY_2)_n$-aryl; alkenyl; $(CY_2)_n$-alkyl; alkyl; and alkyldiaryl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_9$ can be independently selected from a group consisting of hydrogen; deuterium; alkylaryl; $(CY_2)_n$-aryl; alkyldiaryl; and $(CY_2)_n$-alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_{10}$ can be independently selected from a group consisting of hydrogen; deuterium; $(CY_2)_n$-aryl; alkyl; $(CY_2)_n$-alkyl; and $(CY_2)_n$-heteroaryl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_{11}$ can be independently selected from a group consisting of hydrogen; deuterium; $C_{1-6}$ alkyl; $C_{2-6}$ alkenyl; $C_{2-6}$ alkynyl, $C_{3-8}$cycloalkyl; heteroaryl, cycloalkyl; $C_{1-6}$alkylheteroaryl; $C_{1-6}$alkylaryl; and alkylcycloalkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_{12}$ can be independently selected from a group consisting of a coupling group capable of coupling to a linker, a substrate, or a label; hydrogen; deuterium; $C_{1-6}$ alkyl; $C_{2-6}$ alkenyl; $C_{2-6}$ alkynyl, $C_{3-8}$cycloalkyl; heteroaryl, cycloalkyl; $C_{1-6}$alkylheteroaryl; $C_{1-6}$alkylaryl; and alkylcycloalkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_{13}$ can be individually and independently selected from a group consisting of hydrogen; deuterium; a halogen; ethyl; and methyl. In some embodiments, when $R_{13}$ can be not hydrogen each carbon denoted with an * can independent be R or S. In some embodiments, X can be independently selected from oxygen or sulfur. In some embodiments, Y can be independently selected from deuterium or hydrogen. In some embodiments, A can be hydrogen, deuterium, aryl, or heteroaryl. In some embodiments, n can be 1-10. In some embodiments, $R_3$ is not hydrogen or deuterium. In some embodiments, $R_4$ is not hydrogen or deuterium. In some embodiments, $R_5$ is not hydrogen or deuterium. In some embodiments, $R_6$ is not hydrogen or deuterium. In some embodiments, $R_7$ is not hydrogen or deuterium. In some embodiments, $R_8$ is not hydrogen or deuterium. In some embodiments, $R_9$ is not hydrogen or deuterium. In some embodiments, $R_{10}$ is not hydrogen or deuterium. In some embodiments, the method can comprise contacting the support with a disease sample. In some embodiments, the method can further comprise detecting the biomarker. In some embodiments, the biomarker can be bound to the peptoid or pharmaceutically acceptable salt thereof. In some embodiments, the biomarker is not present in the control sample. In some embodiments, the biomarker is in lower quantities in a control sample when compared to a disease sample. In some embodiments, the biomarker is in higher quantities in a control sample when compared to a disease sample. In some embodiments, a prophylactically or therapeutically effective amount of a prophylactically or therapeutically acceptable amount of the biomarker can be administered to a patient in need thereof. In some embodiments, the biomarker can be administered for preventing, treating, ameliorating or managing a disease or condition. In some embodiments, the disease or condition can be a neurological disease, cancer, autoimmune disease or an infectious disease. In some embodiments, the disease is a neurological disease. In some embodiments, the neurological diseases can be Parkinson's disease or Alzheimer's disease. In some embodiments, the biomarker can be present in a subsect free from said disease and an absence of said biomarker is indicative of said disease. In some embodiments, the peptoid or pharmaceutically acceptable salt thereof does not bind to the biomarker in the control sample. In some embodiments, the peptoid or pharmaceutically acceptable salt thereof can be selected from a group comprising a formula:

ErAD1
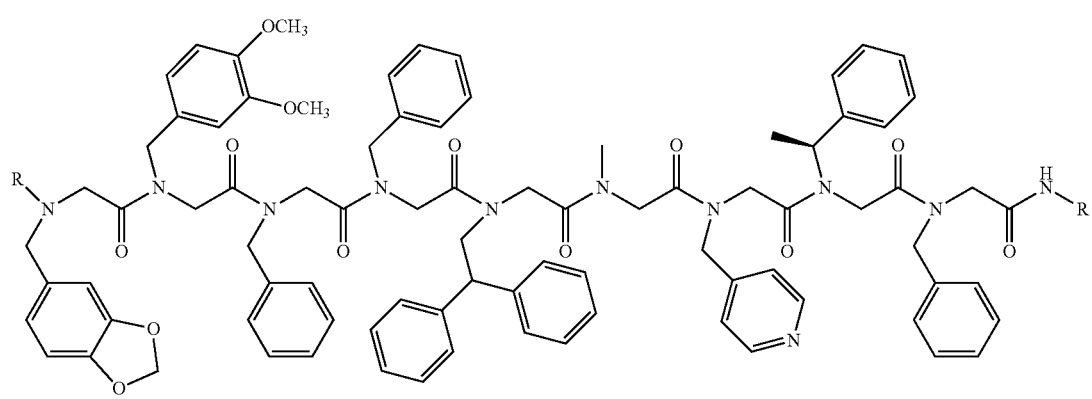
ErAD2
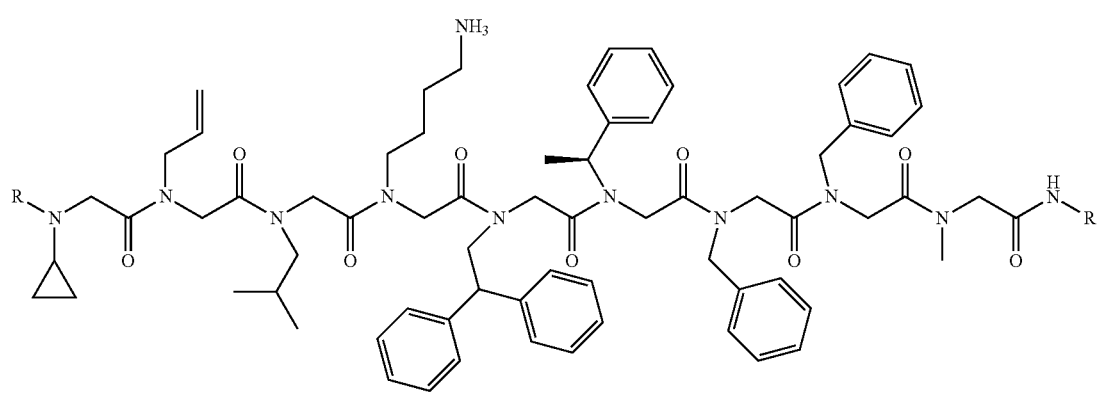
ErAD3
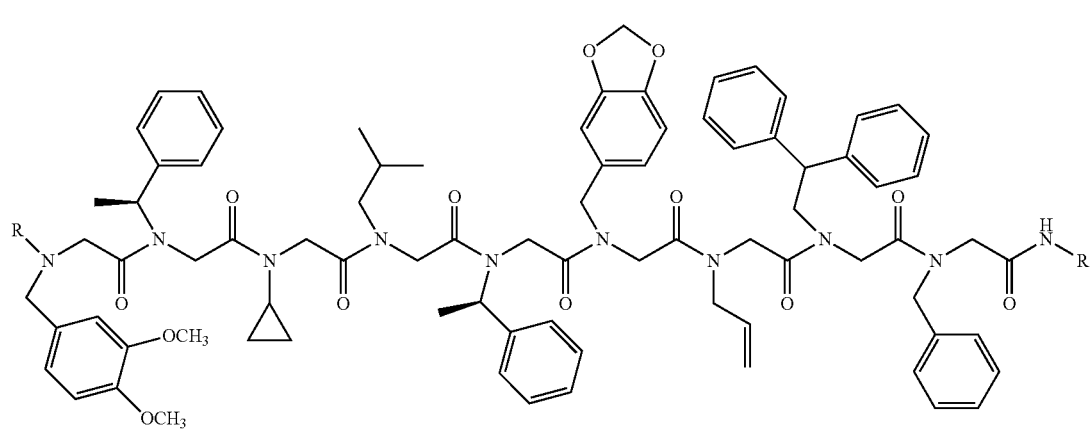
ErAD4
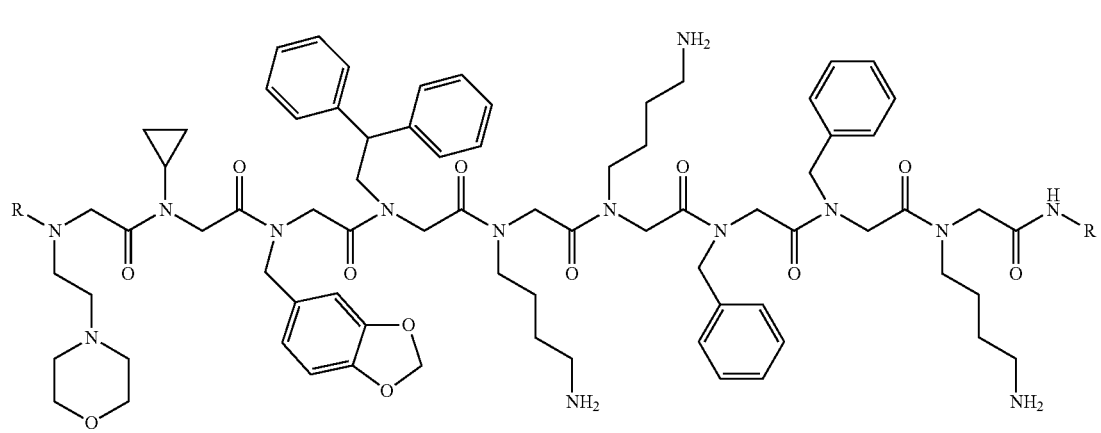

-continued
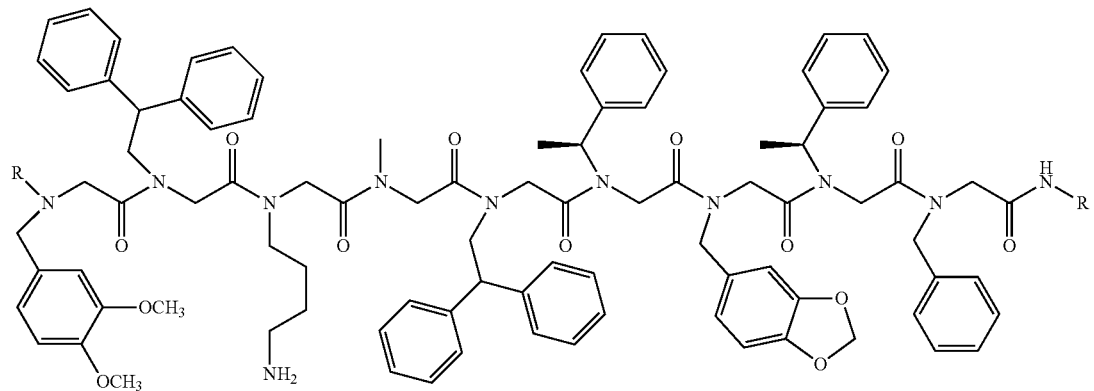
ErAD5
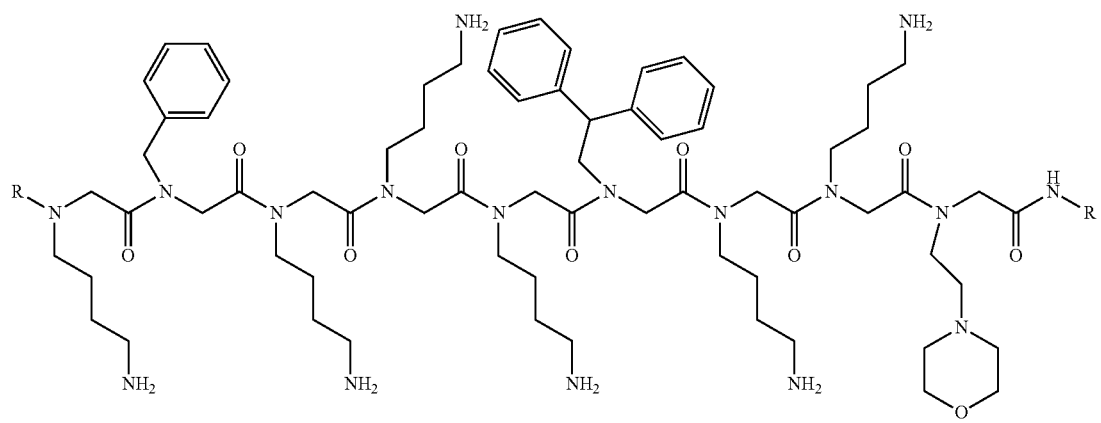
ErAD6
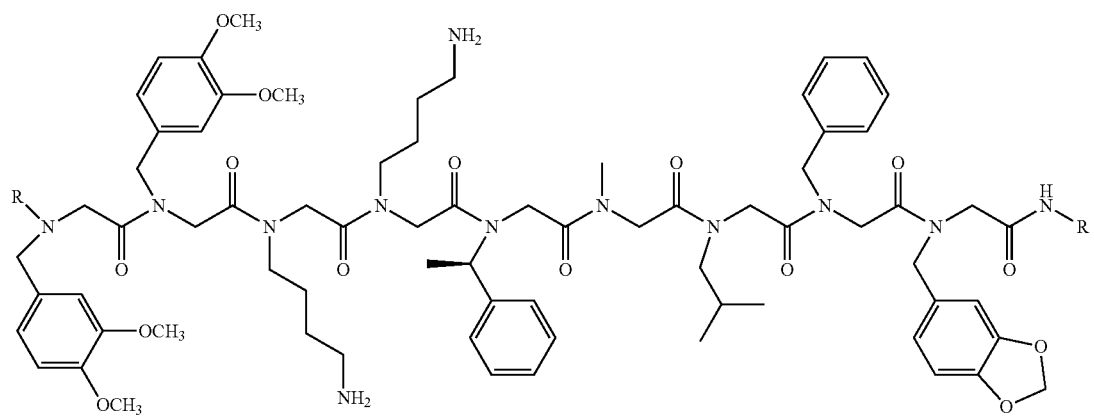
AAD1
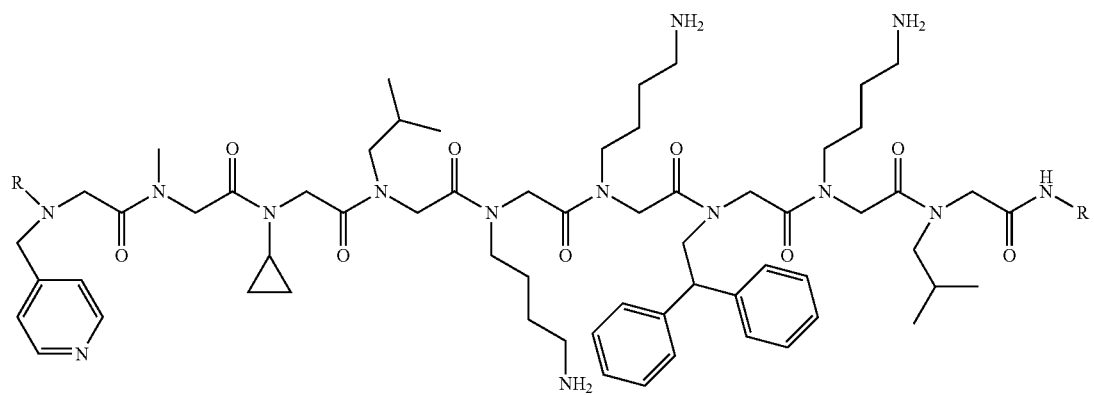
AAD2

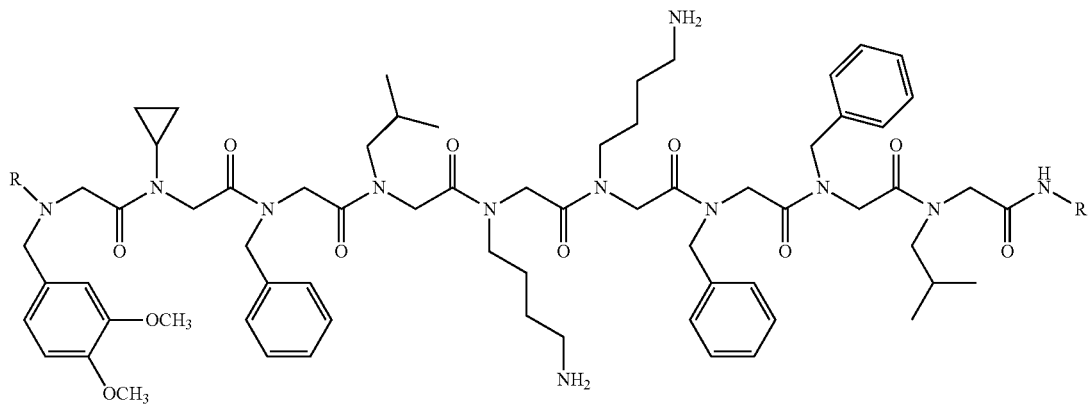

AAD3 or any combination thereof. In some embodiments, R can be independently selected from a group consisting of a coupling group capable of coupling to a linker, a substrate, or a label; hydrogen; deuterium; $C_{1-6}$ alkyl; $C_{2-6}$ alkenyl; $C_{2-6}$ alkynyl, $C_{3-8}$cycloalkyl; heteroaryl, cycloalkyl; $C_{1-6}$alkylheteroaryl; $C_{1-6}$alkylaryl; and alkylcycloalkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof.

Disclosed herein are methods. In some embodiments, the method can comprise contacting a peptoid or pharmaceutically acceptable salt thereof with a support. In some embodiments, the support can have at least one biomarker associated with the support. In some embodiment, the peptoid or pharmaceutically acceptable salt thereof can have the formula:

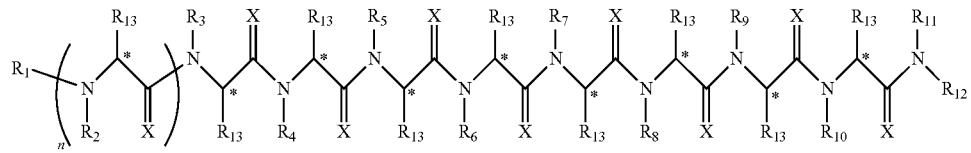

In some embodiments, $R_1$ can be independently selected from a group consisting of a coupling group capable of coupling to a linker, a substrate, or a label; hydrogen; deuterium; $C_{1-6}$ alkyl; $C_{2-6}$ alkenyl; $C_{2-6}$ alkynyl, $C_{3-8}$cycloalkyl; heteroaryl, cycloalkyl; $C_{1-6}$alkylheteroaryl; $C_{1-6}$alkylaryl; and alkylcycloalkyl, each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_2$ can be independently selected from a group consisting of hydrogen; deuterium; $(CY_2)_n$-aryl; $(CY_2)_n$-alkoxyaryl; cycloalkyl; $(CY_2)_n$-heteroaryl; and $(CY_2)_n$-alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_3$ can be independently selected from a group consisting of hydrogen; deuterium; $(CY_2)_n$-aryl; $(CY_2)_n$-alkoxyaryl; alkenyl; alkylaryl; cycloalkyl; alkyldiaryl; and alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_4$ can be independently selected from a group consisting of hydrogen; deuterium; $(CY_2)_n$-aryl; alkyl; cycloalkyl; and $(CY_2)_n$-alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_5$ can be independently selected from a group consisting of hydrogen; deuterium; $(CY_2)_n$-aryl; $(CY_2)_n$-alkyl; alkyl; and alkyldiaryl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_6$ can be independently selected from a group consisting of hydrogen; deuterium; alkyldiaryl; alkylaryl; and $(CY_2)_n$-alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_7$ can be independently selected from a group consisting of hydrogen; deuterium; alkyl; alkylaryl; $(CY_2)_n$-aryl; $(CY_2)_n$-alkyl; and alkyldiaryl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_8$ can be independently selected from a group consisting of hydrogen; deuterium; $(CY_2)_n$-heteroaryl; $(CY_2)_n$-aryl; alkenyl; $(CY_2)_n$-alkyl; alkyl; and alkyldiaryl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_9$ can be independently selected from a group consisting of hydrogen; deuterium; alkylaryl; $(CY_2)_n$-aryl; alkyldiaryl; and $(CY_2)_n$-alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_{10}$ can be independently selected from a group consisting of hydrogen; deuterium; $(CY_2)_n$-aryl; alkyl; $(CY_2)_n$-alkyl; and $(CY_2)_n$-heteroaryl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_{11}$ can be independently selected from a group consisting of hydrogen; deuterium; $C_{1-6}$ alkyl; $C_{2-6}$ alkenyl; $C_{2-6}$ alkynyl, $C_{3-8}$cycloalkyl; heteroaryl, cycloalkyl; $C_{1-6}$alkylheteroaryl; $C_{1-6}$alkylaryl; and alkylcycloalkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_{12}$ can be independently selected from a group consisting of a coupling group capable of coupling to a linker, a substrate, or a label; hydrogen; deuterium; $C_{1-6}$ alkyl; $C_{2-6}$ alkenyl; $C_{2-6}$ alkynyl, $C_{3-8}$cycloalkyl; heteroaryl, cycloalkyl; $C_{1-6}$alkylheteroaryl; $C_{1-6}$alkylaryl; and alkylcycloalkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_{13}$ can be individually and independently selected from a group consisting of hydrogen; deuterium; a halogen; ethyl; and methyl. In some embodiments, when $R_{13}$ can be not hydrogen each carbon denoted with an * can independent be R or S. In some embodiments, X can be independently selected from oxygen or sulfur. In some embodiments, Y can be independently selected from deuterium or hydrogen. In some embodiments, A can be hydrogen, deuterium, aryl, or heteroaryl. In some embodiments, n can be 1-10. In some embodiments, $R_3$ is not hydrogen or deuterium. In some embodiments, $R_4$ is not hydrogen or deuterium. In some embodiments, $R_5$ is not hydrogen or deuterium. In some embodiments, $R_6$ is not hydrogen or deuterium. In some embodiments, $R_7$ is not hydrogen or deuterium. In some embodiments, $R_8$ is not hydrogen or deuterium. In some embodiments, $R_9$ is not hydrogen or deuterium. In some embodiments, $R_0$ is not hydrogen or deuterium. In some embodiments, the method can further comprise detecting the biomarker having said peptoid or pharmaceutically acceptable salt thereof bound thereto. In some embodiments, the peptoid or pharmaceutically acceptable salt thereof is selected from a group comprising a formula:

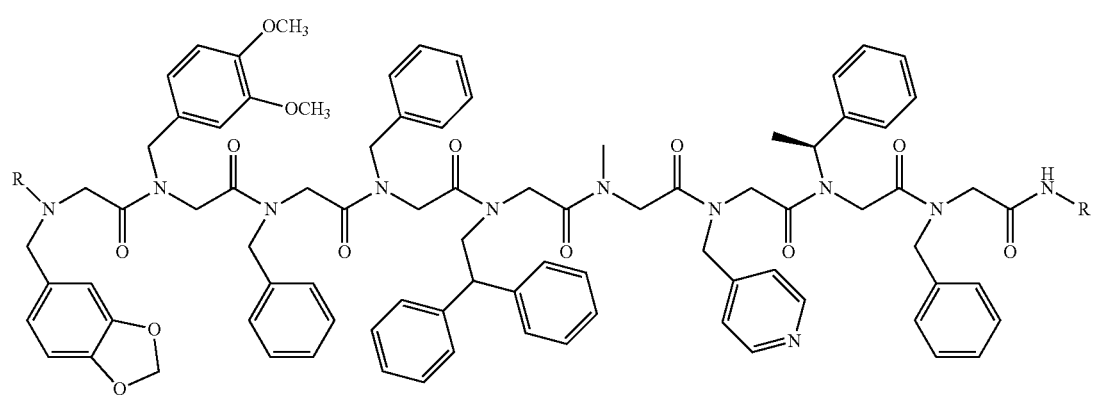

ErAD1

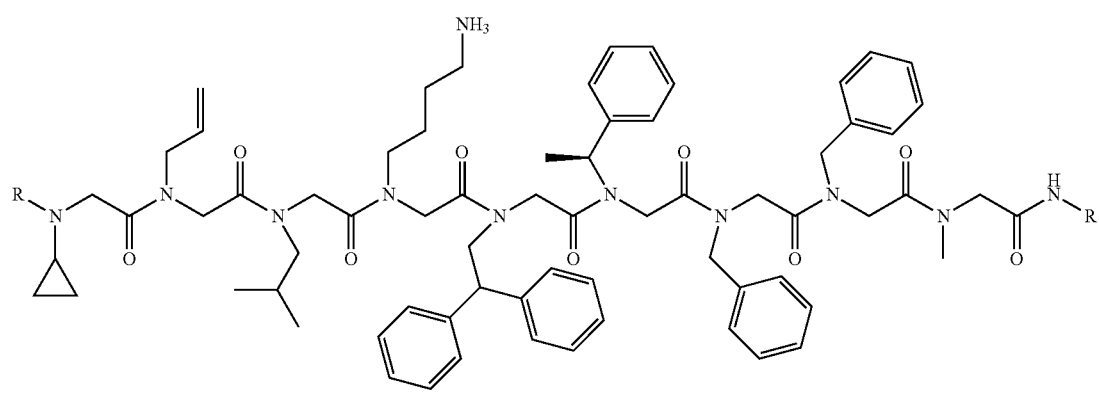

ErAD2

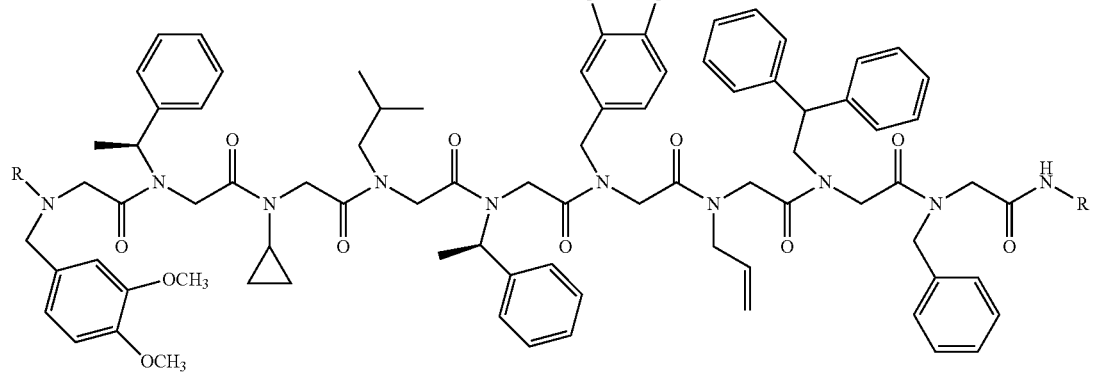
ErAD3
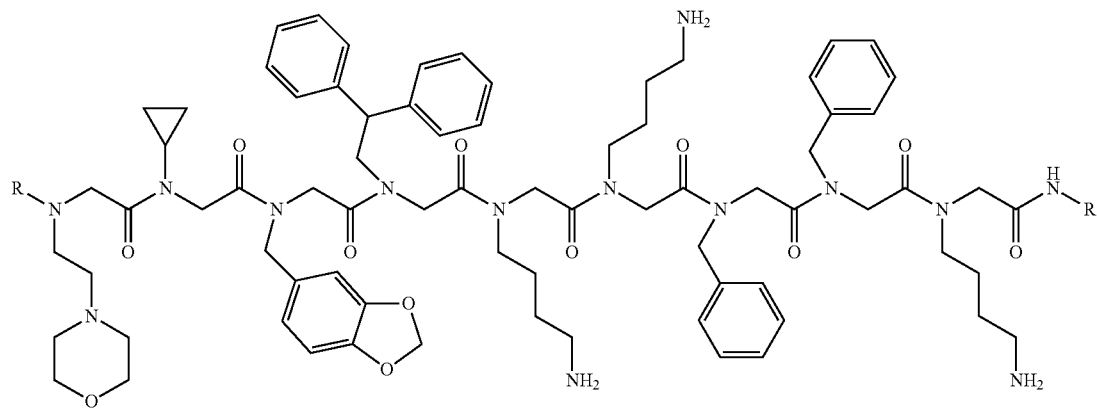
ErAD4
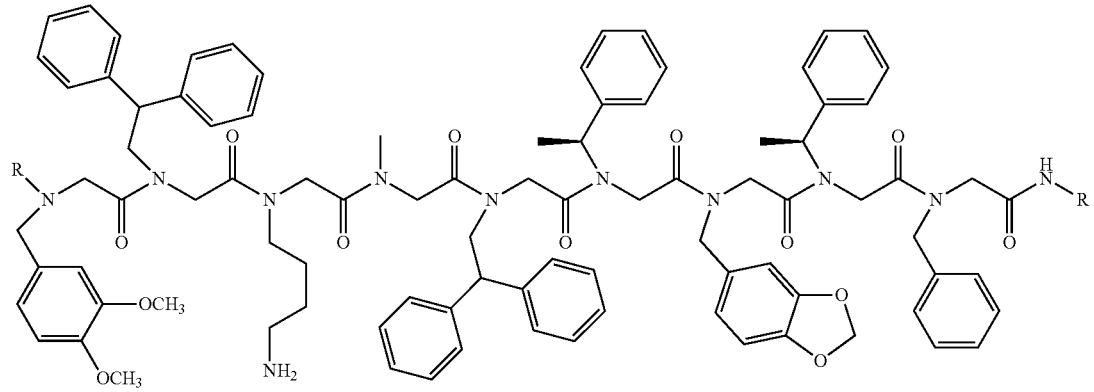
ErAD5
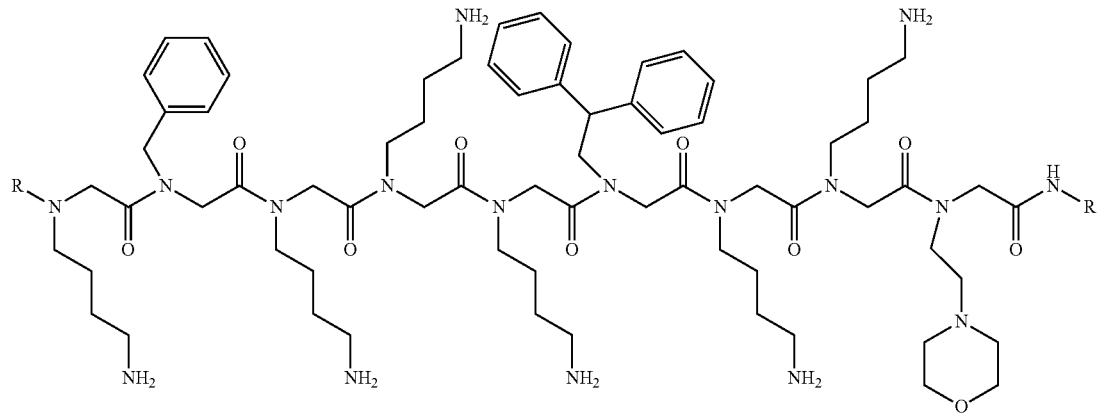
ErAD6

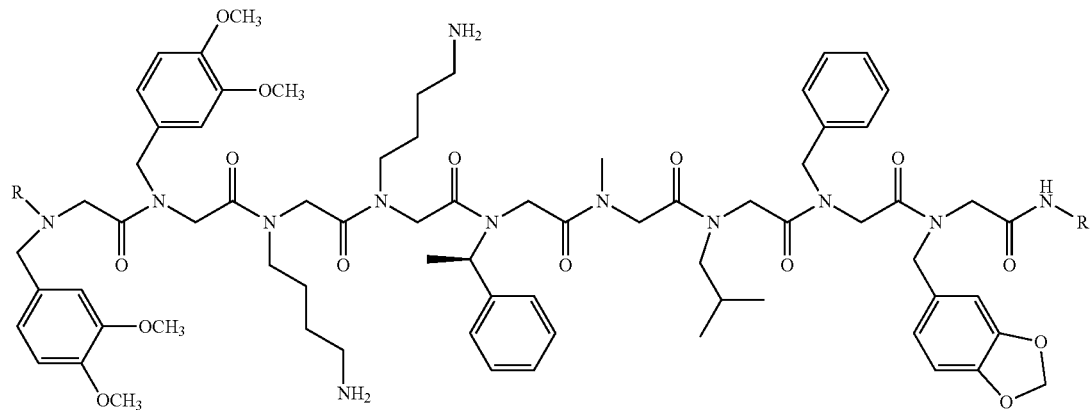

AAD1

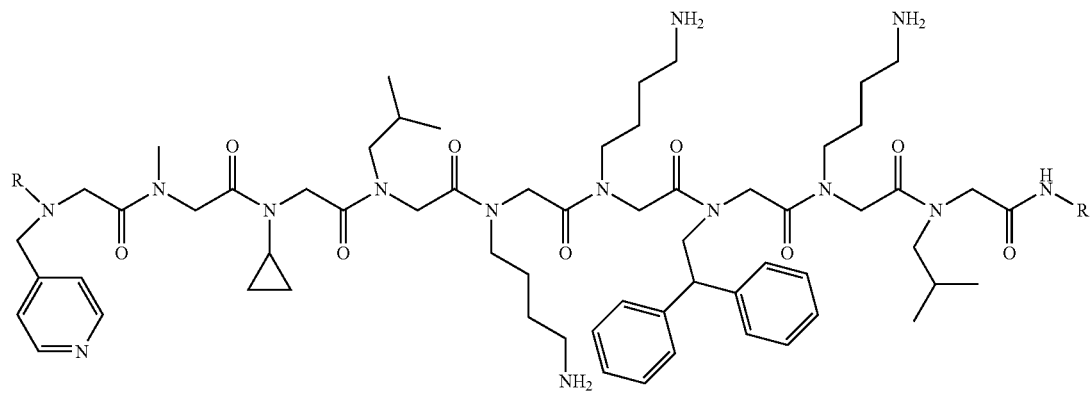

AAD2

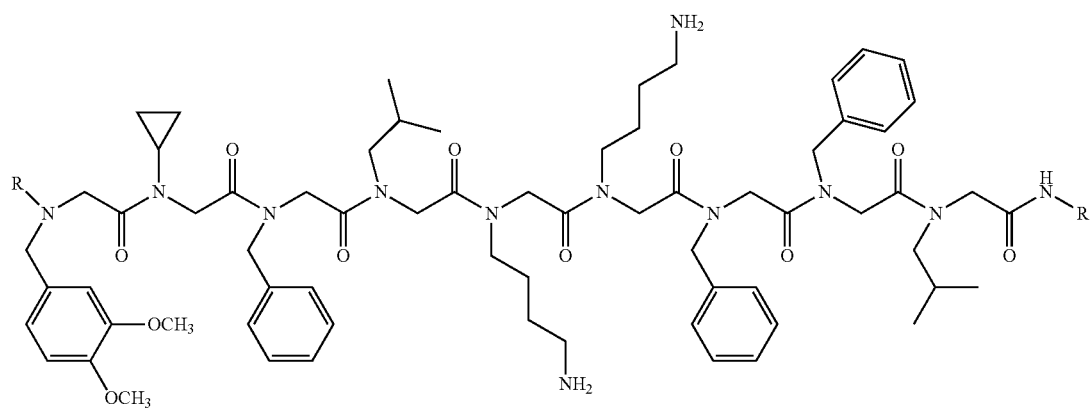

AAD3 or any combination thereof. In some embodiments, R can be independently selected from a group consisting of a coupling group capable of coupling to a linker, a substrate, or a label; hydrogen; deuterium; $C_{1-6}$ alkyl; $C_{2-6}$ alkenyl; $C_{2-6}$ alkynyl, $C_{3-8}$cycloalkyl; heteroaryl, cycloalkyl; $C_{1-6}$alkylheteroaryl; $C_{1-6}$alkylaryl; and alkylcycloalkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof.

Disclosed herein are peptoids or pharmaceutically acceptable salt thereof. A peptoid or pharmaceutically acceptable salt thereof can comprise a compound of formula:

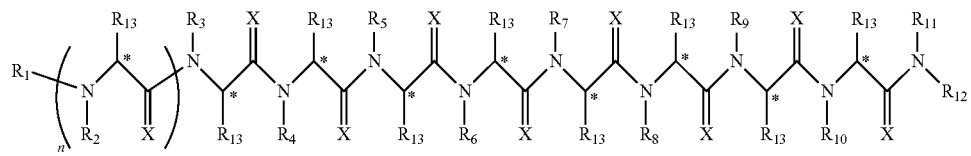

In some embodiments, $R_1$ can be independently selected from a group consisting of a coupling group capable of coupling to a linker, a substrate, or a label; hydrogen; deuterium; $C_{1-6}$ alkyl; $C_{2-6}$ alkenyl; $C_{2-6}$ alkynyl, $C_{3-8}$cycloalkyl; heteroaryl, cycloalkyl; $C_{1-6}$alkylheteroaryl; $C_{1-6}$alkylaryl; and alkylcycloalkyl, each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; $=$X; $XCY_2X$ or any combinations thereof. In some embodiments, $R_2$ can be independently selected from a group consisting of hydrogen; deuterium; $(CY_2)_n$-aryl; $(CY_2)_n$-alkoxyaryl; cycloalkyl; $(CY_2)_n$-heteroaryl; and $(CY_2)_n$-alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; $=$X; $XCY_2X$ or any combinations thereof. In some embodiments, $R_3$ can be independently selected from a group consisting of hydrogen; deuterium; $(CY_2)_n$-aryl; $(CY_2)_n$-alkoxyaryl; alkenyl; alkylaryl; cycloalkyl; alkyldiaryl; and alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; $=$X; $XCY_2X$ or any combinations thereof. In some embodiments, $R_4$ can be independently selected from a group consisting of hydrogen; deuterium; $(CY_2)_n$-aryl; alkyl; cycloalkyl; and $(CY_2)_n$-alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; $=$X; $XCY_2X$ or any combinations thereof. In some embodiments, $R_5$ can be independently selected from a group consisting of hydrogen; deuterium; $(CY_2)_n$-aryl; $(CY_2)_n$-alkyl; alkyl; and alkyldiaryl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; $=$X; $XCY_2X$ or any combinations thereof. In some embodiments, $R_6$ can be independently selected from a group consisting of hydrogen; deuterium; alkyldiaryl; alkylaryl; and $(CY_2)$-alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; $=$X; $XCY_2X$ or any combinations thereof. In some embodiments, $R_7$ can be independently selected from a group consisting of hydrogen; deuterium; alkyl; alkylaryl; $(CY_2)_n$-aryl; $(CY_2)_n$-alkyl; and alkyldiaryl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; $=$X; $XCY_2X$ or any combinations thereof. In some embodiments, $R_8$ can be independently selected from a group consisting of hydrogen; deuterium; $(CY_2)_n$-heteroaryl; $(CY_2)_n$-aryl; alkenyl; $(CY_2)_n$-alkyl; alkyl; and alkyldiaryl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; $=$X; $XCY_2X$ or any combinations thereof. In some embodiments, $R_9$ can be independently selected from a group consisting of hydrogen; deuterium; alkylaryl; $(CY_2)_n$-aryl; alkyldiaryl; and $(CY_2)_n$-alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; $=$X; $XCY_2X$ or any combinations thereof. In some embodiments, $R_{10}$ can be independently selected from a group consisting of hydrogen; deuterium; $(CY_2)_n$-aryl; alkyl; $(CY_2)_n$-alkyl; and $(CY_2)_n$-heteroaryl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; $=$X; $XCY_2X$ or any combinations thereof. In some embodiments, $R_{11}$ can be independently selected from a group consisting of hydrogen; deuterium; $C_{1-6}$ alkyl; $C_{2-6}$ alkenyl; $C_{2-6}$ alkynyl, $C_{3-8}$cycloalkyl; heteroaryl, cycloalkyl; $C_{1-6}$alkylheteroaryl; $C_{1-6}$alkylaryl; and alkylcycloalkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; $=$X; $XCY_2X$ or any combinations thereof. In some embodiments, $R_{12}$ can be independently selected from a group consisting of a coupling group capable of coupling to a linker, a substrate, or a label; hydrogen; deuterium; $C_{1-6}$ alkyl; $C_{2-6}$ alkenyl; $C_{2-6}$ alkynyl, $C_{3-8}$cycloalkyl; heteroaryl, cycloalkyl; $C_{1-6}$alkylheteroaryl; $C_{1-6}$alkylaryl; and alkylcycloalkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; $=$X; $XCY_2X$ or any combinations thereof. In some embodiments, $R_{13}$ can be individually and independently selected from a group consisting of hydrogen; deuterium; a halogen; ethyl; and methyl. In some embodiments, when $R_{13}$ can be not hydrogen each carbon denoted with an * can independent be R or S. In some embodiments, X can be independently selected from oxygen or sulfur. In some embodiments, Y can be independently selected from deuterium or hydrogen. In some embodiments, A can be hydrogen, deuterium, aryl, or heteroaryl. In some embodiments, n can be 1-10. In some embodiments, $R_3$ is not hydrogen or deuterium. In some embodiments, $R_4$ is not hydrogen or deuterium. In some embodiments, $R_5$ is not hydrogen or deuterium. In some embodiments, $R_6$ is not hydrogen or deuterium. In some embodiments, $R_7$ is not hydrogen or deuterium. In some embodiments, $R_8$ is not hydrogen or deuterium. In some embodiments, $R_9$ is not hydrogen or deuterium. In some embodiments, $R_{10}$ is not hydrogen or deuterium. In some embodiments, the peptoid or pharmaceutically acceptable salt thereof can be selected from a group comprising a formula:

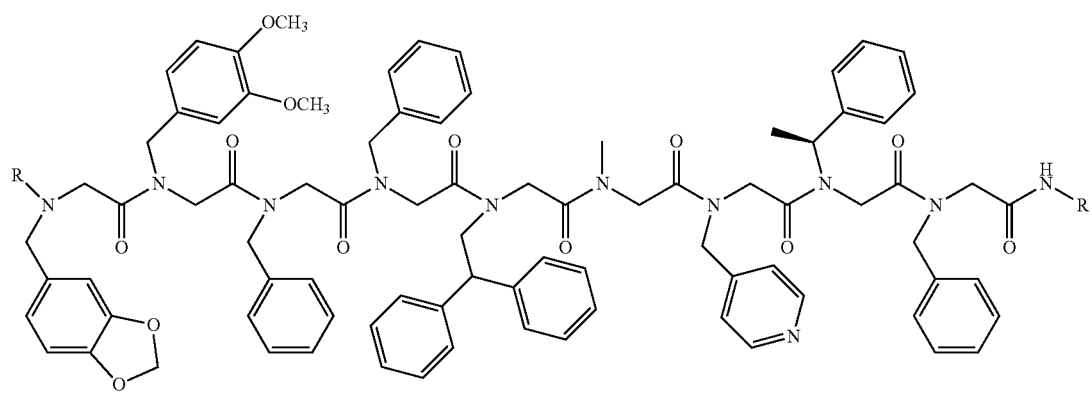
ErAD1
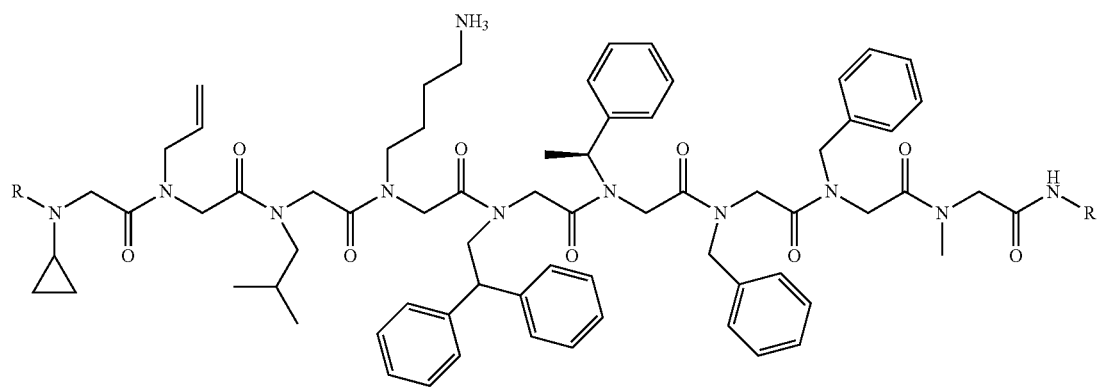
ErAD2
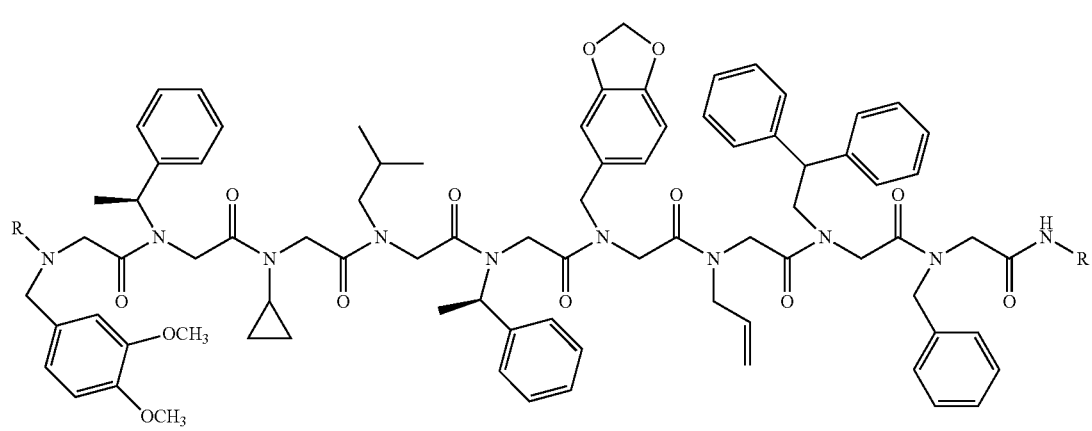
ErAD3
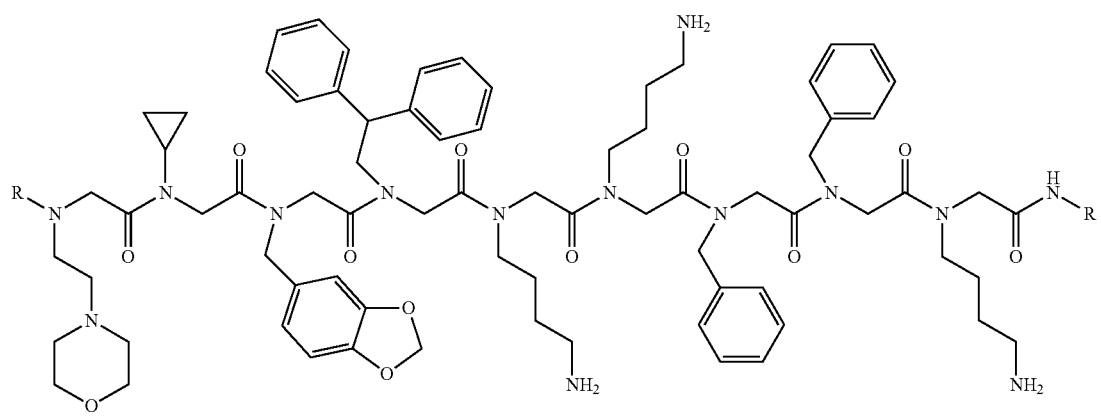
ErAD4

-continued
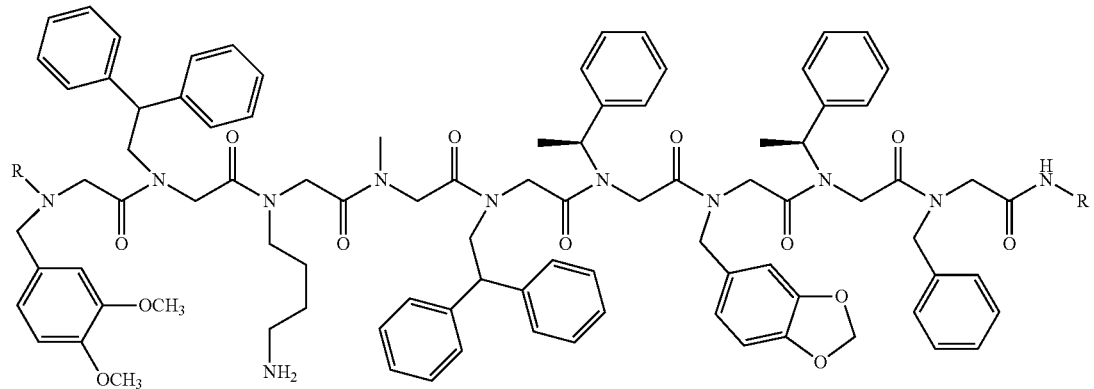
ErAD5
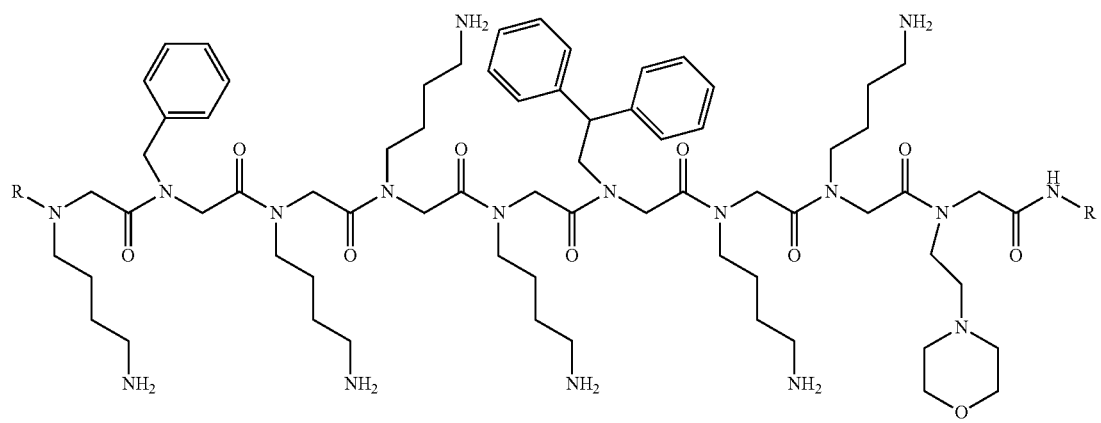
ErAD6
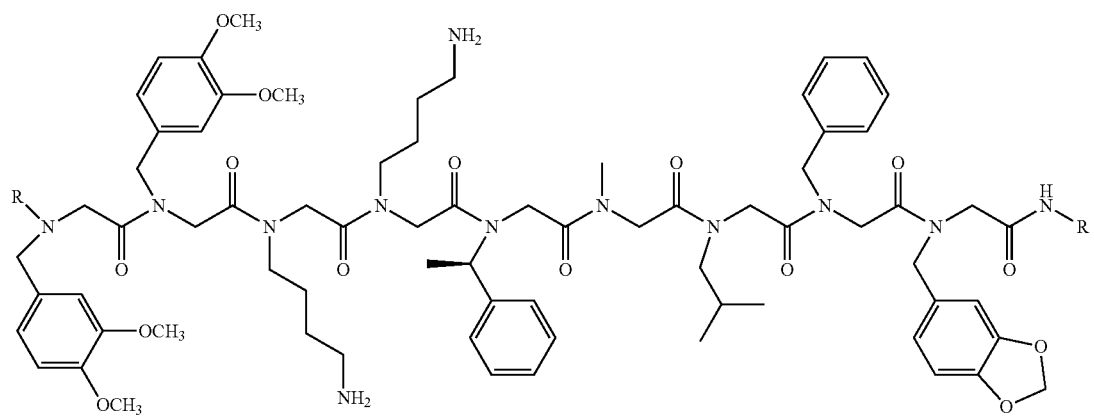
AAD1
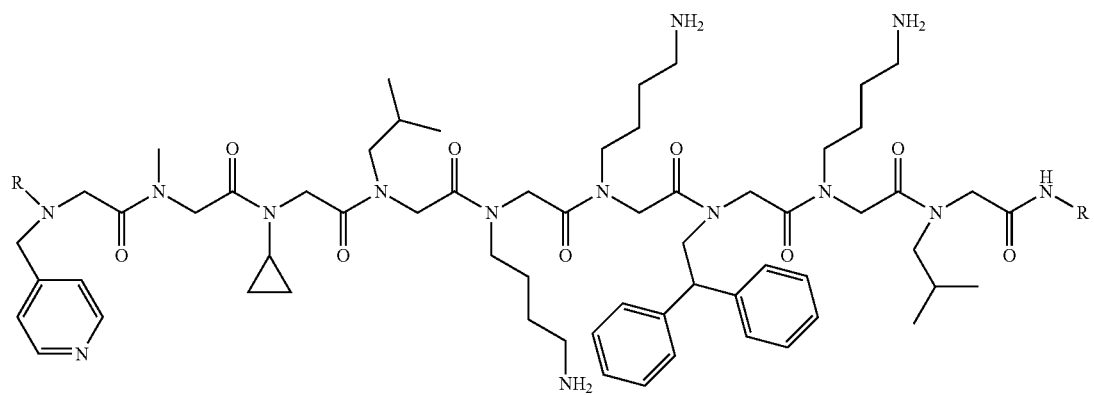
AAD2

-continued

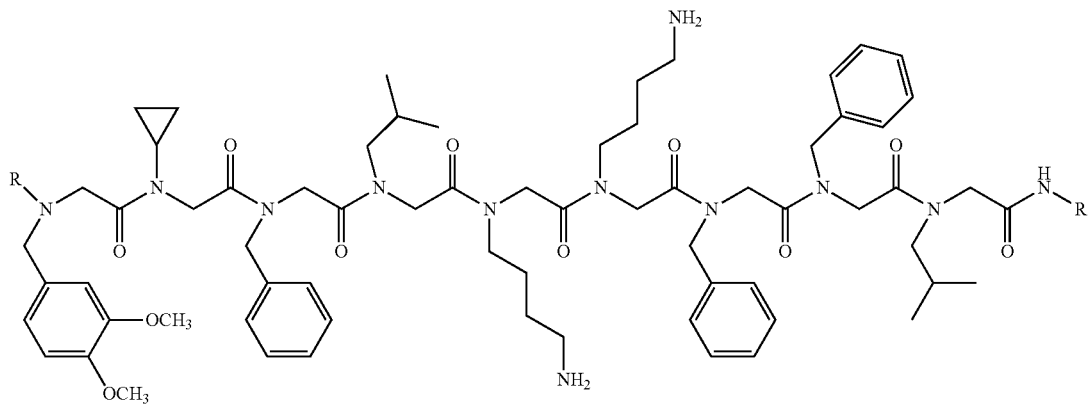

AAD3 or any combination thereof. In some embodiments, R can be independently selected from a group consisting of a coupling group capable of coupling to a linker, a substrate, or a label; hydrogen; deuterium; $C_{1-6}$ alkyl; $C_{2-6}$ alkenyl; $C_{2-6}$ alkynyl; $C_{3-8}$cycloalkyl; heteroaryl, cycloalkyl; $C_{1-6}$alkyl-heteroaryl; $C_{1-6}$alkylaryl; and alkylcycloalkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, the peptoid or pharmaceutically acceptable salt thereof can comprise a structure

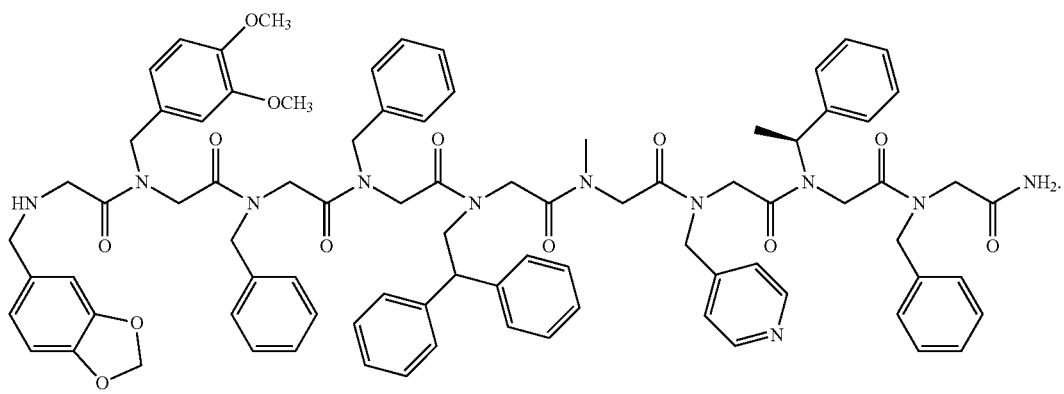 [SMILES: COc1ccc(CN(CC(=O)N(CC(=O)N(CC(=O)N(CC(=O)N(C)CC(=O)N(CC(=O)N(CC(=O)N(CC(N)=O)Cc2ccccc2)[C@@H](C)c2ccccc2)Cc2ccncc2)CC(c2ccccc2)c2ccccc2)Cc2ccccc2)Cc2ccccc2)C(=O)CNCc2ccc3c(c2)OCO3)cc1OC]

In some embodiments, the peptoid or pharmaceutically acceptable salt thereof can comprise a structure

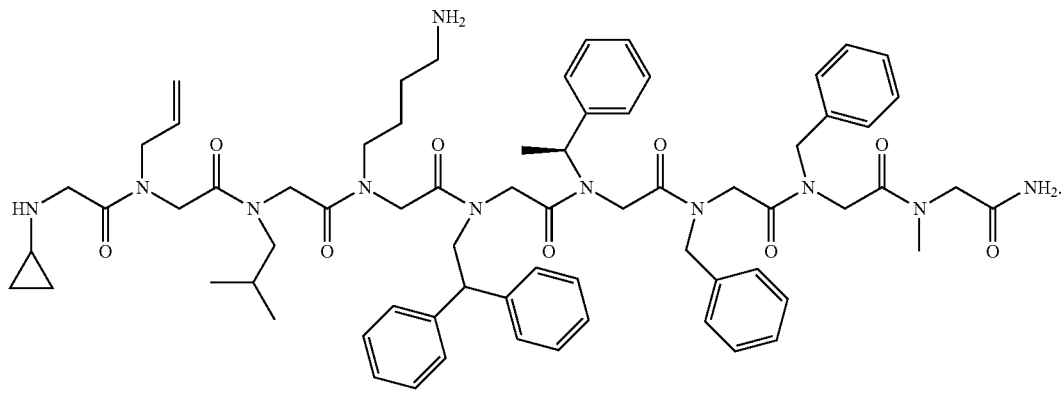 [SMILES: C=CCN(CC(=O)N(CC(=O)N(CCCCN)CC(=O)N(CC(=O)N(CC(=O)N(CC(=O)N(CC(=O)N(C)CC(N)=O)Cc1ccccc1)Cc1ccccc1)[C@@H](C)c1ccccc1)CC(c1ccccc1)c1ccccc1)CC(C)C)C(=O)CNC1CC1]

In some embodiments, the peptoid or pharmaceutically acceptable salt thereof can comprise a structure
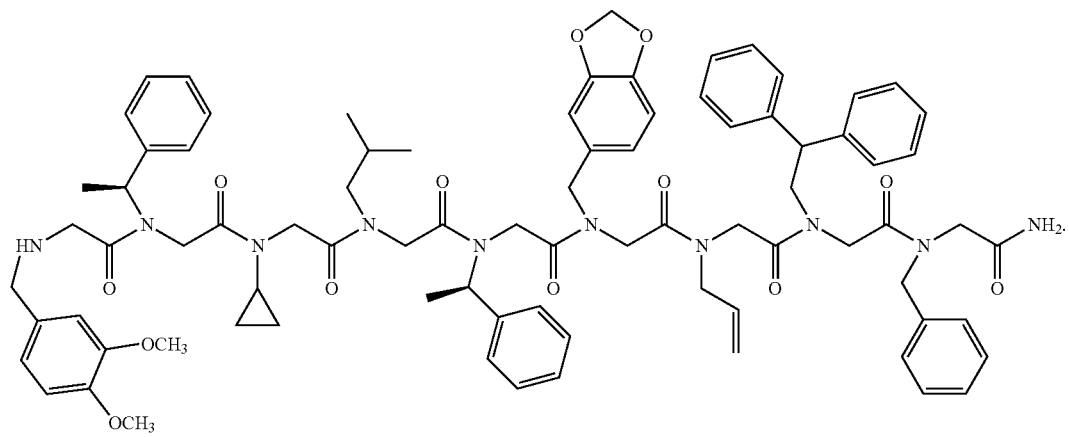 [SMILES: C=CCN(CC(=O)N(CC(=O)N(CC(N)=O)Cc1ccccc1)CC(c1ccccc1)c1ccccc1)C(=O)CN(Cc1ccc2c(c1)OCO2)C(=O)CN(C(=O)CN(CC(C)C)C(=O)CN(C(=O)CN(C(=O)CNCc1ccc(OC)c(OC)c1)[C@@H](C)c1ccccc1)C1CC1)[C@H](C)c1ccccc1]
In some embodiments, the peptoid or pharmaceutically acceptable salt thereof can comprise a structure
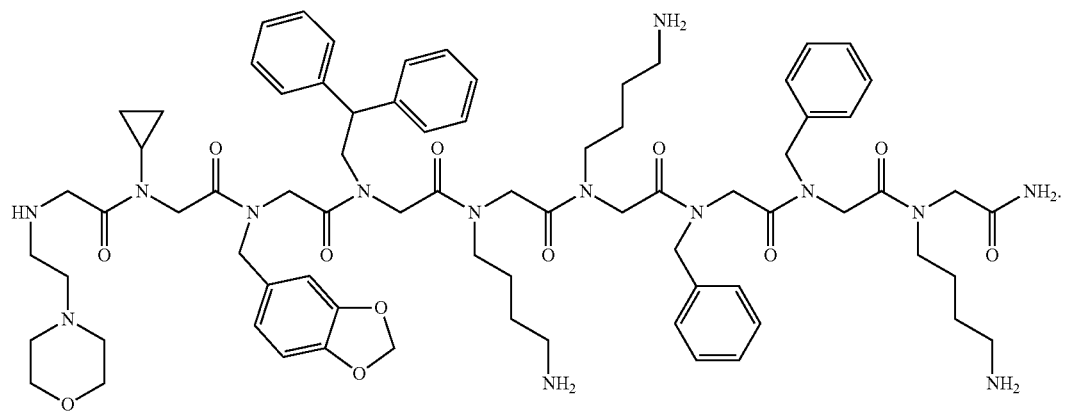 [SMILES: NCCCCN(CC(N)=O)C(=O)CN(Cc1ccccc1)C(=O)CN(Cc1ccccc1)C(=O)CN(CCCCN)C(=O)CN(CCCCN)C(=O)CN(CC(c1ccccc1)c1ccccc1)C(=O)CN(Cc1ccc2c(c1)OCO2)C(=O)CN(C(=O)CNCCN1CCOCC1)C1CC1]
In some embodiments, the peptoid or pharmaceutically acceptable salt thereof can comprise a structure
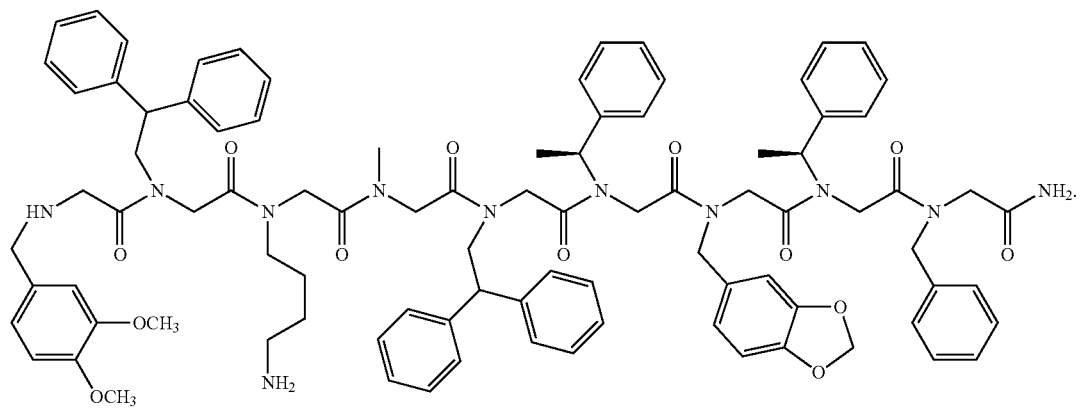 [SMILES: COc1ccc(CNCC(=O)N(CC(=O)N(CCCCN)CC(=O)N(C)CC(=O)N(CC(=O)N(CC(=O)N(CC(=O)N(CC(=O)N(CC(N)=O)Cc2ccccc2)[C@@H](C)c2ccccc2)Cc2ccc3c(c2)OCO3)[C@@H](C)c2ccccc2)CC(c2ccccc2)c2ccccc2)CC(c2ccccc2)c2ccccc2)cc1OC]

In some embodiments, the peptoid or pharmaceutically acceptable salt thereof can comprise a structure
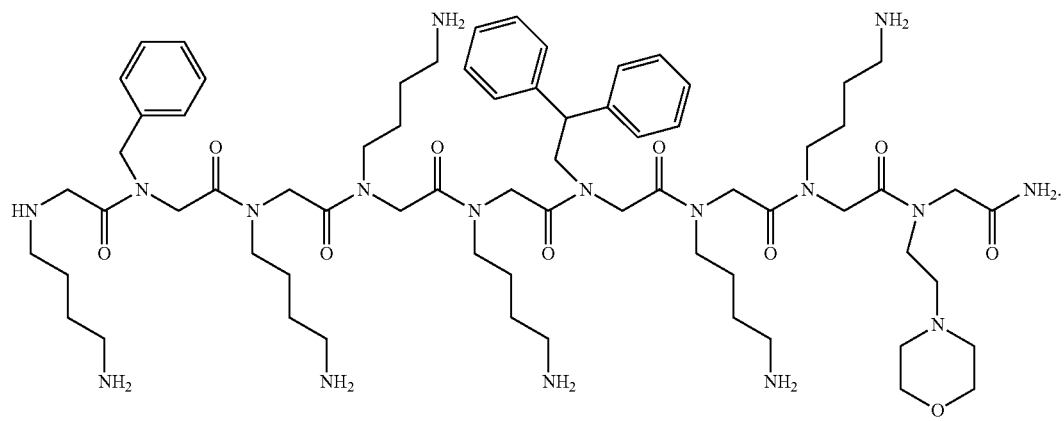 [SMILES: NCCCCNCC(=O)N(CC(=O)N(CCCCN)CC(=O)N(CCCCN)CC(=O)N(CCCCN)CC(=O)N(CC(=O)N(CCCCN)CC(=O)N(CCCCN)CC(=O)N(CCN1CCOCC1)CC(N)=O)CC(c1ccccc1)c1ccccc1)Cc1ccccc1]
In some embodiments, the peptoid or pharmaceutically acceptable salt thereof can comprise a structure
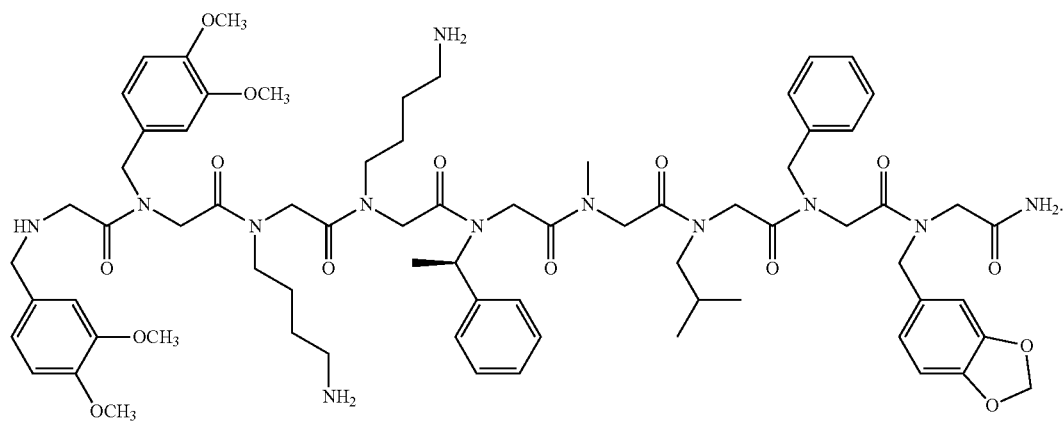 [SMILES: COc1ccc(CNCC(=O)N(CC(=O)N(CCCCN)CC(=O)N(CCCCN)CC(=O)N(CC(=O)N(C)CC(=O)N(CC(=O)N(CC(=O)N(CC(N)=O)Cc2ccc3c(c2)OCO3)Cc2ccccc2)CC(C)C)[C@H](C)c2ccccc2)Cc2ccc(OC)c(OC)c2)cc1OC]
In some embodiments, the peptoid or pharmaceutically acceptable salt thereof can comprise a structure
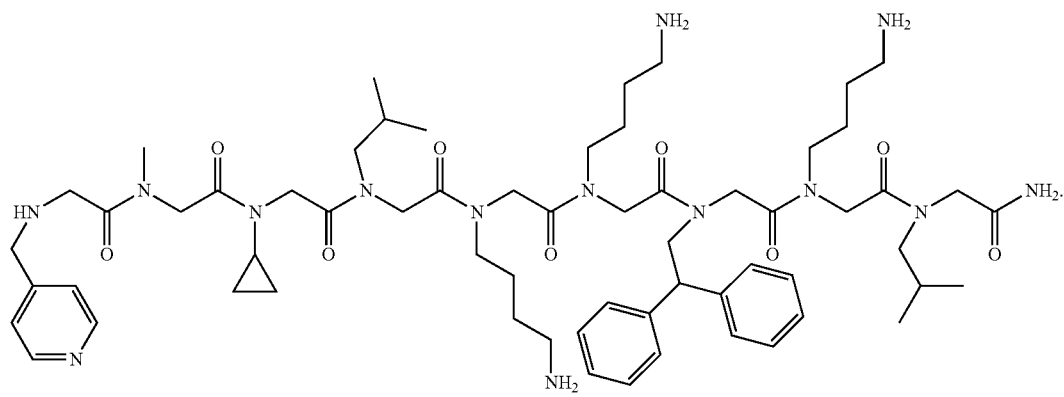 [SMILES: CC(C)CN(CC(N)=O)C(=O)CN(CCCCN)C(=O)CN(CC(c1ccccc1)c1ccccc1)C(=O)CN(CCCCN)C(=O)CN(CCCCN)C(=O)CN(CC(C)C)C(=O)CN(C(=O)CN(C)C(=O)CNCc1ccncc1)C1CC1]

In some embodiments, the peptoid or pharmaceutically acceptable salt thereof can comprise a structure

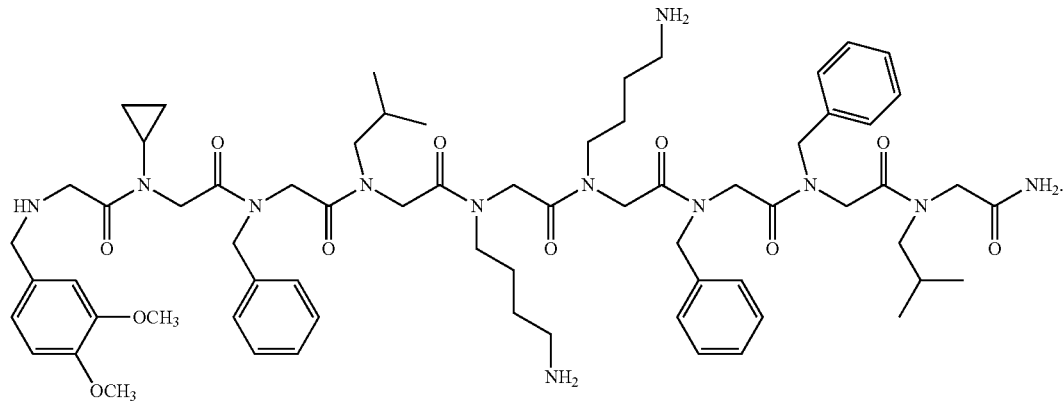 [SMILES: COc1ccc(CNCC(=O)N(CC(=O)N(CC(=O)N(CC(=O)N(CCCCN)CC(=O)N(CCCCN)CC(=O)N(CC(=O)N(CC(=O)N(CC(N)=O)CC(C)C)Cc2ccccc2)Cc2ccccc2)CC(C)C)Cc2ccccc2)C2CC2)cc1OC]

In some embodiments, a prophylactically or therapeutically effective amount of a prophylactically or therapeutically acceptable amount of the peptoid or pharmaceutically acceptable salt thereof can be administered to a patient in need thereof. In some embodiments, the peptoid or pharmaceutically acceptable salt thereof can be administered for preventing, treating, ameliorating or managing a disease or condition. In some embodiments, the disease or condition can be a neurological disease, cancer, autoimmune disease or an infectious disease. In some embodiments, the disease is a neurological disease. In some embodiments, the neurological diseases can be Parkinson's disease or Alzheimer's disease.

Disclosed herein are methods of making an array. In some embodiments, the method making an array can comprise associating a peptoid or pharmaceutically acceptable salt thereof with a support. In some embodiments, the peptoid can have the formula:

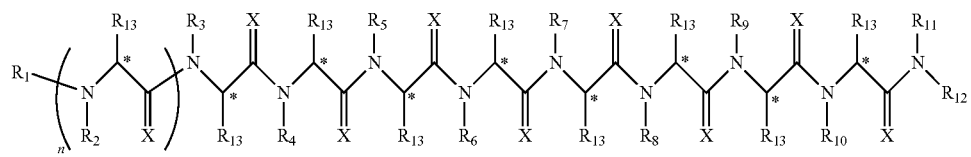

In some embodiments, $R_1$ can be independently selected from a group consisting of a coupling group capable of coupling to a linker, a substrate, or a label; hydrogen; deuterium; $C_{1-6}$ alkyl; $C_{2-6}$ alkenyl; $C_{2-6}$ alkynyl, $C_{3-8}$cycloalkyl; heteroaryl, cycloalkyl; $C_{1-6}$alkylheteroaryl; $C_{1-6}$alkylaryl; and alkylcycloalkyl, each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; $=X$; $XCY_2X$ or any combinations thereof. In some embodiments, $R_2$ can be independently selected from a group consisting of hydrogen; deuterium; $(CY_2)_n$-aryl; $(CY_2)$-alkoxyaryl; cycloalkyl; $(CY_2)$-heteroaryl; and $(CY_2)_n$-alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; $=X$; $XCY_2X$ or any combinations thereof. In some embodiments, $R_3$ can be independently selected from a group consisting of hydrogen; deuterium; $(CY_2)_n$-aryl; $(CY_2)_n$-alkoxyaryl; alkenyl; alkylaryl; cycloalkyl; alkyldiaryl; and alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; $=X$; $XCY_2X$ or any combinations thereof. In some embodiments, $R_4$ can be independently selected from a group consisting of hydrogen; deuterium; $(CY_2)_n$-aryl; alkyl; cycloalkyl; and $(CY_2)_n$-alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; $=X$; $XCY_2X$ or any combinations thereof. In some embodiments, $R_5$ can be independently selected from a group consisting of hydrogen; deuterium; $(CY_2)_n$-aryl; $(CY_2)_n$-alkyl; alkyl; and alkyldiaryl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; $=X$; $XCY_2X$ or any combinations thereof. In some embodiments, $R_6$ can be independently selected from a group consisting of hydrogen; deuterium; alkyldiaryl; alkylaryl; and $(CY_2)_n$-alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; $=X$; $XCY_2X$ or any combinations thereof. In some embodiments, $R_7$ can be independently selected from a group consisting of hydrogen; deuterium; alkyl; alkylaryl; $(CY_2)_n$-aryl; $(CY_2)_n$-alkyl; and alkyldiaryl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; $=X$; $XCY_2X$ or any combinations thereof. In some embodiments, $R_8$ can be independently selected from a group consisting of hydrogen; deuterium; $(CY_2)_n$-heteroaryl; $(CY_2)_n$-aryl; alkenyl; $(CY_2)_n$-alkyl; alkyl; and alkyldiaryl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_9$ can be independently selected from a group consisting of hydrogen; deuterium; alkylaryl; $(CY_2)_n$-aryl; alkyldiaryl; and $(CY_2)_n$-alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_{10}$ can be independently selected from a group consisting of hydrogen; deuterium; $(CY_2)_n$-aryl; alkyl; $(CY_2)_n$-alkyl; and $(CY_2)_n$-heteroaryl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_{11}$ can be independently selected from a group consisting of hydrogen; deuterium; $C_{1-6}$ alkyl; $C_{2-6}$ alkenyl; $C_{2-6}$ alkynyl, $C_{3-8}$cycloalkyl; heteroaryl, cycloalkyl; $C_{1-6}$alkylheteroaryl; $C_{1-6}$alkylaryl; and alkylcycloalkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_{12}$ can be independently selected from a group consisting of a coupling group capable of coupling to a linker, a substrate, or a label; hydrogen; deuterium; $C_{1-6}$ alkyl; $C_{2-6}$ alkenyl; $C_{2-6}$ alkynyl, $C_{3-8}$cycloalkyl; heteroaryl, cycloalkyl; $C_{1-6}$alkylheteroaryl; $C_{1-6}$alkylaryl; and alkylcycloalkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_{13}$ can be individually and independently selected from a group consisting of hydrogen; deuterium; a halogen; ethyl; and methyl. In some embodiments, when $R_{13}$ can be not hydrogen each carbon denoted with an * can independent be R or S. In some embodiments, X can be independently selected from oxygen or sulfur. In some embodiments, Y can be independently selected from deuterium or hydrogen. In some embodiments, A can be hydrogen, deuterium, aryl, or heteroaryl. In some embodiments, n can be 1-10. In some embodiments, $R_3$ is not hydrogen or deuterium. In some embodiments, $R_4$ is not hydrogen or deuterium. In some embodiments, $R_5$ is not hydrogen or deuterium. In some embodiments, $R_6$ is not hydrogen or deuterium. In some embodiments, $R_7$ is not hydrogen or deuterium. In some embodiments, $R_8$ is not hydrogen or deuterium. In some embodiments, $R_9$ is not hydrogen or deuterium. In some embodiments, $R_{10}$ is not hydrogen or deuterium.

Disclosed herein are methods of synthesizing a peptoid or pharmaceutically acceptable salt thereof in association with a support. In some embodiments, the peptoid can have the formula:

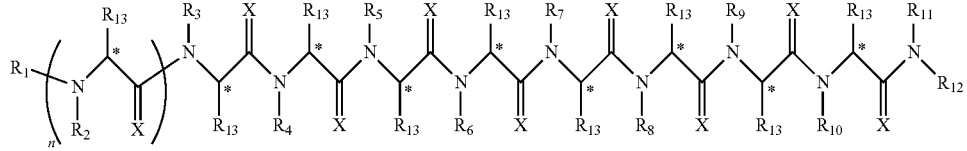

In some embodiments, $R_1$ can be independently selected from a group consisting of a coupling group capable of coupling to a linker, a substrate, or a label; hydrogen; deuterium; $C_{1-6}$ alkyl; $C_{2-6}$ alkenyl; $C_{2-6}$ alkynyl, $C_{3-8}$cycloalkyl; heteroaryl, cycloalkyl; $C_{1-6}$alkylheteroaryl; $C_{1-6}$alkylaryl; and alkylcycloalkyl, each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_2$ can be independently selected from a group consisting of hydrogen; deuterium; $(CY_2)_n$-aryl; $(CY_2)_n$-alkoxyaryl; cycloalkyl; $(CY_2)_n$-heteroaryl; and $(CY_2)_n$-alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_3$ can be independently selected from a group consisting of hydrogen; deuterium; $(CY_2)_n$-aryl; $(CY_2)_n$-alkoxyaryl; alkenyl; alkylaryl; cycloalkyl; alkyldiaryl; and alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_4$ can be independently selected from a group consisting of hydrogen; deuterium; $(CY_2)_n$-aryl; alkyl; cycloalkyl; and $(CY_2)_n$-alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_5$ can be independently selected from a group consisting of hydrogen; deuterium; $(CY_2)_n$-aryl; $(CY_2)_n$-alkyl; alkyl; and alkyldiaryl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_6$ can be independently selected from a group consisting of hydrogen; deuterium; alkyldiaryl; alkylaryl; and $(CY_2)_n$-alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_7$ can be independently selected from a group consisting of hydrogen; deuterium; alkyl; alkylaryl; $(CY_2)_n$-aryl; $(CY_2)_n$-alkyl; and alkyldiaryl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_8$ can be independently selected from a group consisting of hydrogen; deuterium; $(CY_2)_n$-heteroaryl; $(CY_2)_n$-aryl; alkenyl; $(CY_2)_n$-alkyl; alkyl; and alkyldiaryl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_9$ can be independently selected from a group consisting of hydrogen; deuterium; alkylaryl; $(CY_2)_n$-aryl; alkyldiaryl; and $(CY_2)_n$-alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_{10}$ can be independently selected from a group consisting of hydrogen; deuterium; $(CY_2)_n$-aryl; alkyl; $(CY_2)_n$-alkyl; and $(CY_2)_n$-heteroaryl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_{11}$ can be independently selected from a group consisting of hydrogen; deuterium; $C_{1-6}$ alkyl; $C_{2-6}$ alkenyl; $C_{2-6}$ alkynyl, $C_{3-8}$cycloalkyl; heteroaryl, cycloalkyl; $C_{1-6}$alkylheteroaryl; $C_{1-6}$alkylaryl; and alkylcycloalkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_{12}$ can be independently selected from a group consisting of a coupling group capable of coupling to a linker, a substrate, or a label; hydrogen; deuterium; $C_{1-6}$ alkyl; $C_{2-6}$ alkenyl; $C_{2-6}$ alkynyl, $C_{3-8}$cycloalkyl; heteroaryl, cycloalkyl; $C_{1-6}$alkylheteroaryl; $C_{1-6}$alkylaryl; and alkylcycloalkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_{13}$ can be individually and independently selected from a group consisting of hydrogen; deuterium; a halogen; ethyl; and methyl. In some embodiments, when $R_{13}$ can be not hydrogen each carbon denoted with an * can independent be R or S. In some embodiments, X can be independently selected from oxygen or sulfur. In some embodiments, Y can be independently selected from deuterium or hydrogen. In some embodiments, A can be hydrogen, deuterium, aryl, or heteroaryl. In some embodiments, n can be 1-10. In some embodiments, $R_3$ is not hydrogen or deuterium. In some embodiments, $R_4$ is not hydrogen or deuterium. In some embodiments, $R_5$ is not hydrogen or deuterium. In some embodiments, $R_6$ is not hydrogen or deuterium. In some embodiments, $R_7$ is not hydrogen or deuterium. In some embodiments, $R_8$ is not hydrogen or deuterium. In some embodiments, $R_9$ is not hydrogen or deuterium. In some embodiments, $R_{10}$ is not hydrogen or deuterium.

Disclosed herein are methods of making a peptoid or pharmaceutically acceptable salt thereof. In some embodiments, the method of making the peptoid or pharmaceutically acceptable salt thereof can comprise coupling one or more monomers to form the peptoid or pharmaceutically acceptable salt thereof. In some embodiments, the peptoid or pharmaceutically acceptable salt thereof can have the formula:

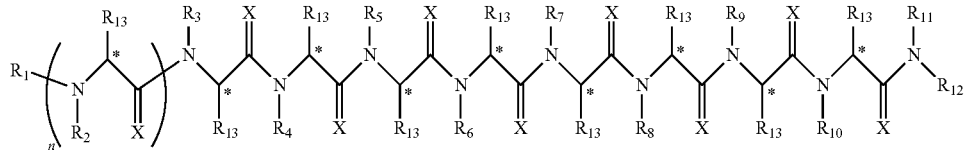

In some embodiments, $R_1$ can be independently selected from a group consisting of a coupling group capable of coupling to a linker, a substrate, or a label; hydrogen; deuterium; $C_{1-6}$ alkyl; $C_{2-6}$ alkenyl; $C_{2-6}$ alkynyl, $C_{3-8}$cycloalkyl; heteroaryl, cycloalkyl; $C_{1-6}$alkylheteroaryl; $C_{1-6}$alkylaryl; and alkylcycloalkyl, each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_2$ can be independently selected from a group consisting of hydrogen; deuterium; $(CY_2)_n$-aryl; $(CY_2)_n$-alkoxyaryl; cycloalkyl; $(CY_2)_n$-heteroaryl; and $(CY_2)_n$-alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_3$ can be independently selected from a group consisting of hydrogen; deuterium; $(CY_2)_n$-aryl; $(CY_2)_n$-alkoxyaryl; alkenyl; alkylaryl; cycloalkyl; alkyldiaryl; and alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_4$ can be independently selected from a group consisting of hydrogen; deuterium; $(CY_2)_n$-aryl; alkyl; cycloalkyl; and $(CY_2)_n$-alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_5$ can be independently selected from a group consisting of hydrogen; deuterium; $(CY_2)_n$-aryl; $(CY_2)_n$-alkyl; alkyl; and alkyldiaryl; each of which except hydrogen and deuterium may be individually and independently substituted one or more times with XA; halogen; $NY_2$; CXXY;

XCY$_3$; alkyl; hydrogen; deuterium; carboxylic acid; ether; amine; XX$_2$NY$_2$; =X; XCY$_2$X or any combinations thereof. In some embodiments, R$_6$ can be independently selected from a group consisting of hydrogen; deuterium; alkyldiaryl; alkylaryl; and (CY$_2$)$_n$-alkyl; each of which except hydrogen and deuterium may be individually and independently substituted one or more times with XA; halogen; NY$_2$; CXXY; XCY$_3$; alkyl; hydrogen; deuterium; carboxylic acid; ether; amine; XX$_2$NY$_2$; =X; XCY$_2$X or any combinations thereof. In some embodiments, R$_7$ can be independently selected from a group consisting of hydrogen; deuterium; alkyl; alkylaryl; (CY$_2$)$_n$-aryl; (CY$_2$)$_n$-alkyl; and alkyldiaryl; each of which except hydrogen and deuterium may be individually and independently substituted one or more times with XA; halogen; NY$_2$; CXXY; XCY$_3$; alkyl; hydrogen; deuterium; carboxylic acid; ether; amine; XX$_2$NY$_2$; =X; XCY$_2$X or any combinations thereof. In some embodiments, R$_8$ can be independently selected from a group consisting of hydrogen; deuterium; (CY$_2$)$_n$-heteroaryl; (CY$_2$)$_n$-aryl; alkenyl; (CY$_2$)$_n$-alkyl; alkyl; and alkyldiaryl; each of which except hydrogen and deuterium may be individually and independently substituted one or more times with XA; halogen; NY$_2$; CXXY; XCY$_3$; alkyl; hydrogen; deuterium; carboxylic acid; ether; amine; XX$_2$NY$_2$; =X; XCY$_2$X or any combinations thereof. In some embodiments, R$_9$ can be independently selected from a group consisting of hydrogen; deuterium; alkylaryl; (CY$_2$)$_n$-aryl; alkyldiaryl; and (CY$_2$)$_n$-alkyl; each of which except hydrogen and deuterium may be individually and independently substituted one or more times with XA; halogen; NY$_2$; CXXY; XCY$_3$; alkyl; hydrogen; deuterium; carboxylic acid; ether; amine; XX$_2$NY$_2$; =X; XCY$_2$X or any combinations thereof. In some embodiments, R$_{10}$ can be independently selected from a group consisting of hydrogen; deuterium; (CY$_2$)$_n$-aryl; alkyl; (CY$_2$)$_n$-alkyl; and (CY$_2$)$_n$-heteroaryl; each of which except hydrogen and deuterium may be individually and independently substituted one or more times with XA; halogen; NY$_2$; CXXY; XCY$_3$; alkyl; hydrogen; deuterium; carboxylic acid; ether; amine; XX$_2$NY$_2$; =X; XCY$_2$X or any combinations thereof. In some embodiments, R$_{11}$ can be independently selected from a group consisting of hydrogen; deuterium; C$_{1-6}$ alkyl; C$_{2-6}$ alkenyl; C$_{2-6}$ alkynyl, C$_{3-8}$cycloalkyl; heteroaryl, cycloalkyl; C$_{1-6}$alkylheteroaryl; C$_{1-6}$alkylaryl; and alkylcycloalkyl; each of which except hydrogen and deuterium may be individually and independently substituted one or more times with XA; halogen; NY$_2$; CXXY; XCY$_3$; alkyl; hydrogen; deuterium; carboxylic acid; ether; amine; XX$_2$NY$_2$; =X; XCY$_2$X or any combinations thereof. In some embodiments, R$_{12}$ can be independently selected from a group consisting of a coupling group capable of coupling to a linker, a substrate, or a label; hydrogen; deuterium; C$_{1-6}$ alkyl; C$_{2-6}$ alkenyl; C$_{2-6}$ alkynyl, C$_{3-8}$cycloalkyl; heteroaryl, cycloalkyl; C$_{1-6}$alkylheteroaryl; C$_{1-6}$alkylaryl; and alkylcycloalkyl; each of which except hydrogen and deuterium may be individually and independently substituted one or more times with XA; halogen; NY$_2$; CXXY; XCY$_3$; alkyl; hydrogen; deuterium; carboxylic acid; ether; amine; XX$_2$NY$_2$; =X; XCY$_2$X or any combinations thereof. In some embodiments, R$_{13}$ can be individually and independently selected from a group consisting of hydrogen; deuterium; a halogen; ethyl; and methyl. In some embodiments, when R$_{13}$ can be not hydrogen each carbon denoted with an * can independent be R or S. In some embodiments, X can be independently selected from oxygen or sulfur. In some embodiments, Y can be independently selected from deuterium or hydrogen. In some embodiments, A can be hydrogen, deuterium, aryl, or heteroaryl. In some embodiments, n can be 1-10. In some embodiments, R$_3$ is not hydrogen or deuterium. In some embodiments, R$_4$ is not hydrogen or deuterium. In some embodiments, R$_5$ is not hydrogen or deuterium. In some embodiments, R$_6$ is not hydrogen or deuterium. In some embodiments, R$_7$ is not hydrogen or deuterium. In some embodiments, R$_8$ is not hydrogen or deuterium. In some embodiments, R$_9$ is not hydrogen or deuterium. In some embodiments, R$_0$ is not hydrogen or deuterium. In some embodiments, each of said one or monomers can be independently selected from one of a Benzylamine, Methylamine, Allylamine, Isobutulamine, 4-(Aminomethyl)pyridine, 4-(2-Aminoethyl)morpholine, 3,4-Dimethoxybenzylamine, 2,2-Diphenylethylamine, Piperonylamine, R-(+)-α-Methylbenzylamine, Cyclopropylamine, 1,4-Diaminobutane, or Glycine, or 2-Aminoethanol.

Disclosed herein are kits. In some embodiments, the kits disclosed herein can comprise a peptoid or pharmaceutically acceptable salt thereof. In some embodiments, the peptoid or pharmaceutically acceptable salt can comprise the formula:

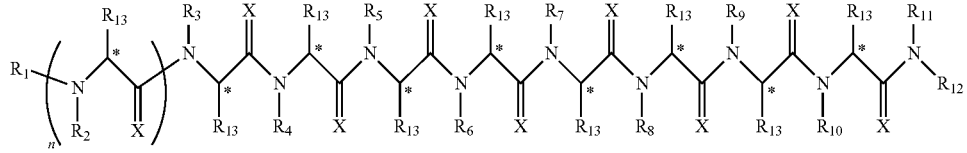

In some embodiments, R$_1$ can be independently selected from a group consisting of a coupling group capable of coupling to a linker, a substrate, or a label; hydrogen; deuterium; C$_{1-6}$ alkyl; C$_{2-6}$ alkenyl; C$_{2-6}$ alkynyl, C$_{3-8}$cycloalkyl; heteroaryl, cycloalkyl; C$_{1-6}$alkylheteroaryl; C$_{1-6}$alkylaryl; and alkylcycloalkyl, each of which except hydrogen and deuterium may be individually and independently substituted one or more times with XA; halogen; NY$_2$; CXXY; XCY$_3$; alkyl; hydrogen; deuterium; carboxylic acid; ether; amine; XX$_2$NY$_2$; =X; XCY$_2$X or any combinations thereof. In some embodiments, R$_2$ can be independently selected from a group consisting of hydrogen; deuterium; (CY$_2$)$_n$-aryl; (CY$_2$)$_n$-alkoxyaryl; cycloalkyl; (CY$_2$)$_n$-heteroaryl; and (CY$_2$)$_n$-alkyl; each of which except hydrogen and deuterium may be individually and independently substituted one or more times with XA; halogen; NY$_2$; CXXY; XCY$_3$; alkyl; hydrogen; deuterium; carboxylic acid; ether; amine; XX$_2$NY$_2$; =X; XCY$_2$X or any combinations thereof. In some embodiments, R$_3$ can be independently selected from a group consisting of hydrogen; deuterium; (CY$_2$)$_n$-aryl; (CY$_2$)$_n$-alkoxyaryl; alkenyl; alkylaryl; cycloalkyl; alkyldiaryl; and alkyl; each of which except hydrogen and deuterium may be individually and independently substituted one or more times with XA; halogen; NY$_2$; CXXY; XCY$_3$; alkyl; hydrogen; deuterium; carboxylic acid; ether; amine; XX$_2$NY$_2$; =X; XCY$_2$X or any combinations thereof. In some embodiments, R$_4$ can be independently selected from a group consisting of hydrogen; deuterium; $(CY_2)_n$-aryl; alkyl; cycloalkyl; and $(CY_2)_n$-alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_5$ can be independently selected from a group consisting of hydrogen; deuterium; $(CY_2)_n$-aryl; $(CY_2)_n$-alkyl; alkyl; and alkyldiaryl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_6$ can be independently selected from a group consisting of hydrogen; deuterium; alkyldiaryl; alkylaryl; and $(CY_2)_n$-alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_7$ can be independently selected from a group consisting of hydrogen; deuterium; alkyl; alkylaryl; $(CY_2)_n$-aryl; $(CY_2)_n$-alkyl; and alkyldiaryl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_8$ can be independently selected from a group consisting of hydrogen; deuterium; $(CY_2)_n$-heteroaryl; $(CY_2)_n$-aryl; alkenyl; $(CY_2)_n$-alkyl; alkyl; and alkyldiaryl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_9$ can be independently selected from a group consisting of hydrogen; deuterium; alkylaryl; $(CY_2)_n$-aryl; alkyldiaryl; and $(CY_2)_n$-alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_{10}$ can be independently selected from a group consisting of hydrogen; deuterium; $(CY_2)_n$-aryl; alkyl; $(CY_2)_n$-alkyl; and $(CY_2)_n$-heteroaryl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_{11}$ can be independently selected from a group consisting of hydrogen; deuterium; $C_{1-6}$ alkyl; $C_{2-6}$ alkenyl; $C_{2-6}$ alkynyl, $C_{3-8}$cycloalkyl; heteroaryl, cycloalkyl; $C_{1-6}$alkylheteroaryl; $C_{1-6}$alkylaryl; and alkylcycloalkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_{12}$ can be independently selected from a group consisting of a coupling group capable of coupling to a linker, a substrate, or a label; hydrogen; deuterium; $C_{1-6}$ alkyl; $C_{2-6}$ alkenyl; $C_{2-6}$ alkynyl, $C_{3-8}$cycloalkyl; heteroaryl, cycloalkyl; $C_{1-6}$alkylheteroaryl; $C_{1-6}$alkylaryl; and alkylcycloalkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_{13}$ can be individually and independently selected from a group consisting of hydrogen; deuterium; a halogen; ethyl; and methyl. In some embodiments, when $R_{13}$ can be not hydrogen each carbon denoted with an * can independent be R or S. In some embodiments, X can be independently selected from oxygen or sulfur. In some embodiments, Y can be independently selected from deuterium or hydrogen. In some embodiments, A can be hydrogen, deuterium, aryl, or heteroaryl. In some embodiments, n can be 1-10. In some embodiments, $R_3$ is not hydrogen or deuterium. In some embodiments, $R_4$ is not hydrogen or deuterium. In some embodiments, $R_5$ is not hydrogen or deuterium. In some embodiments, $R_6$ is not hydrogen or deuterium. In some embodiments, $R_7$ is not hydrogen or deuterium. In some embodiments, $R_8$ is not hydrogen or deuterium. In some embodiments, $R_9$ is not hydrogen or deuterium. In some embodiments, $R_{10}$ is not hydrogen or deuterium. In some embodiments, the peptoid or pharmaceutically acceptable salt thereof can be selected from a group comprising a formula:

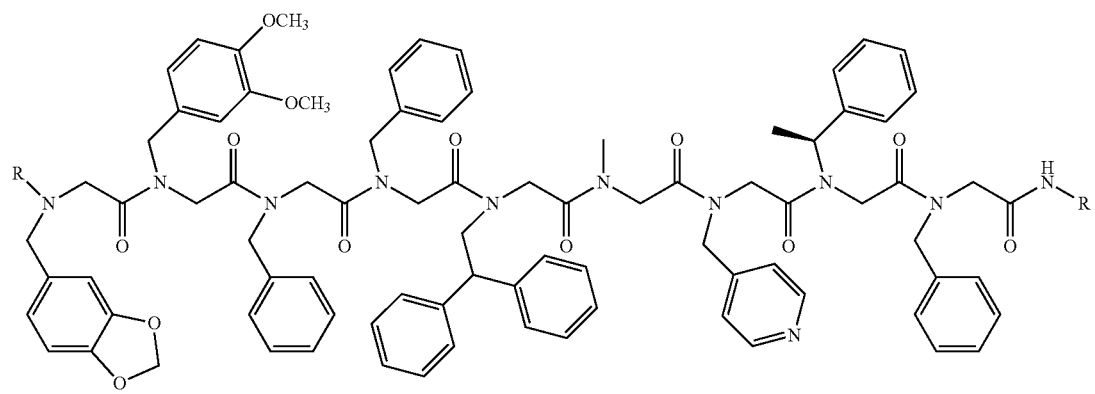

ErAD1

ErAD2
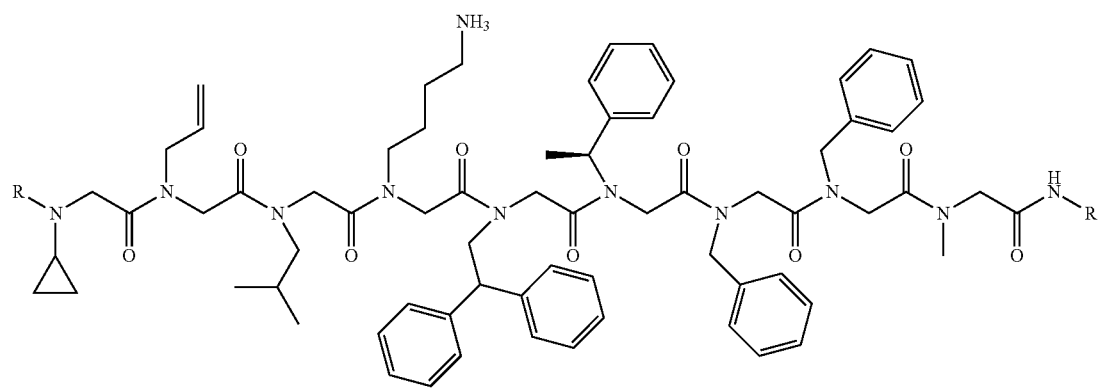
ErAD3
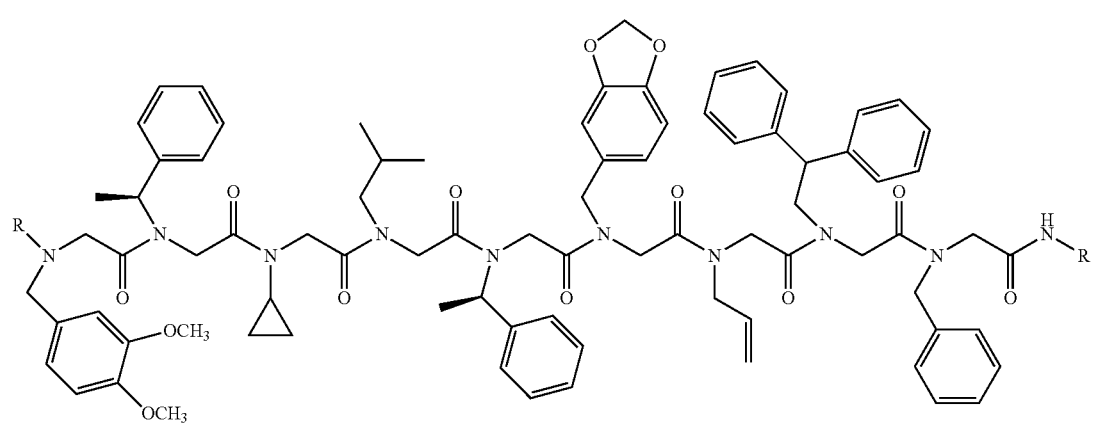
ErAD4
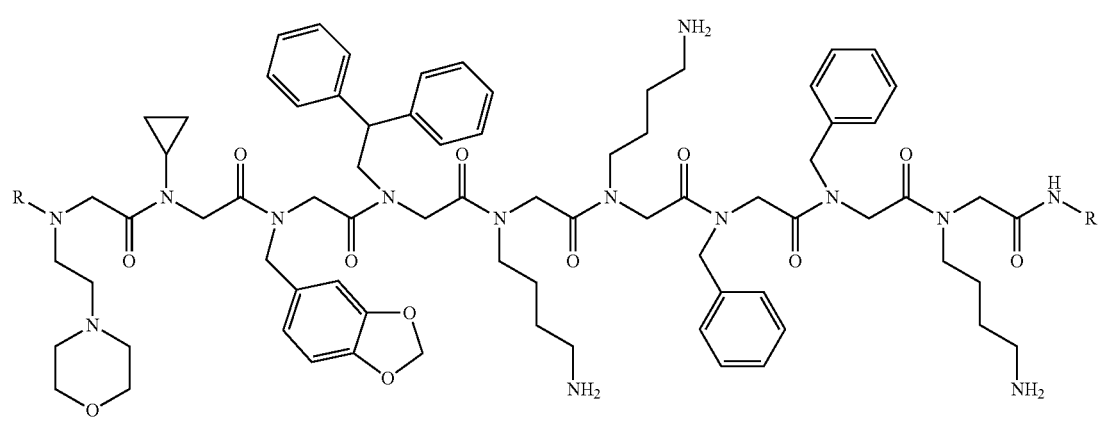
ErAD5
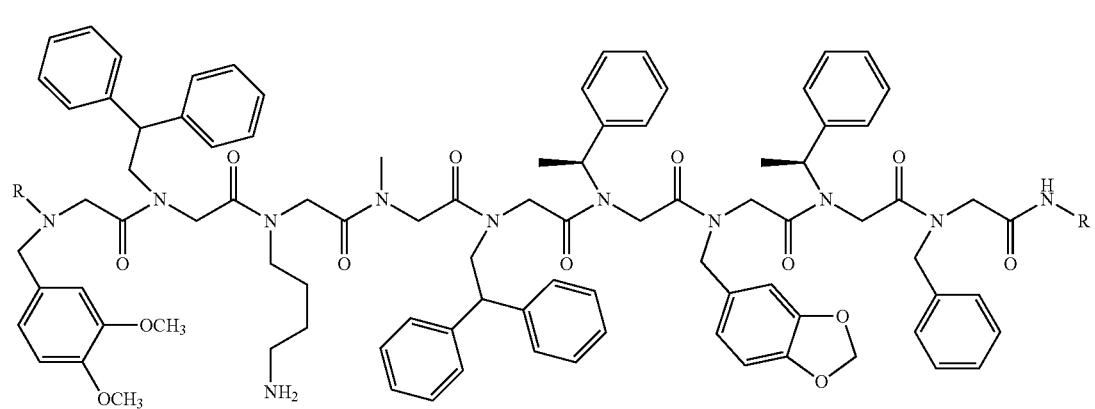

ErAD6
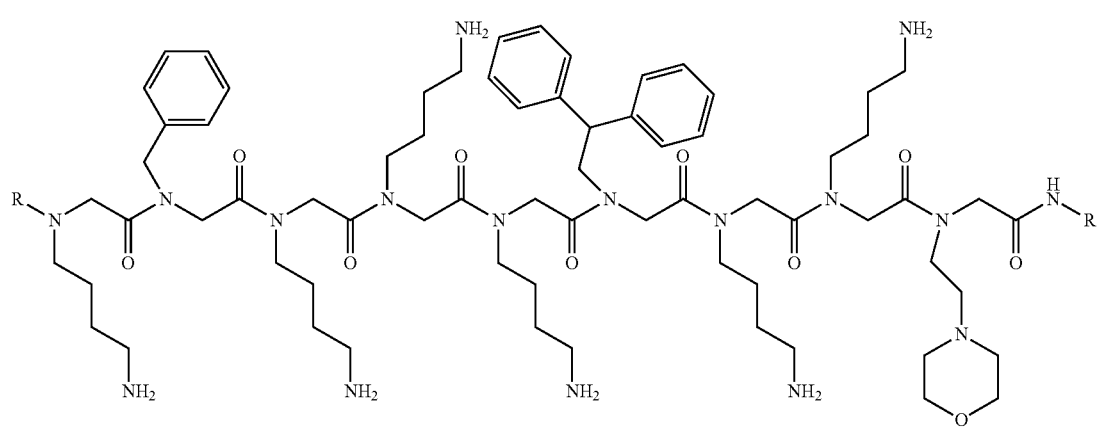
AAD1
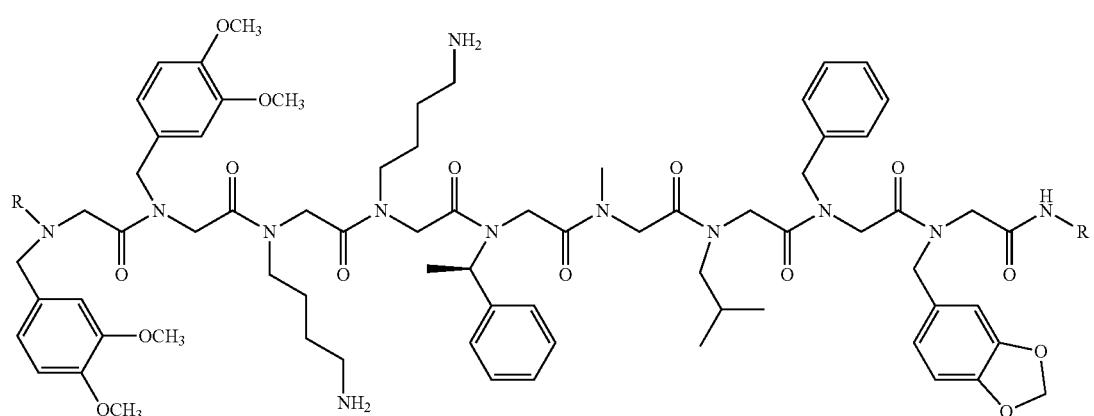
AAD2
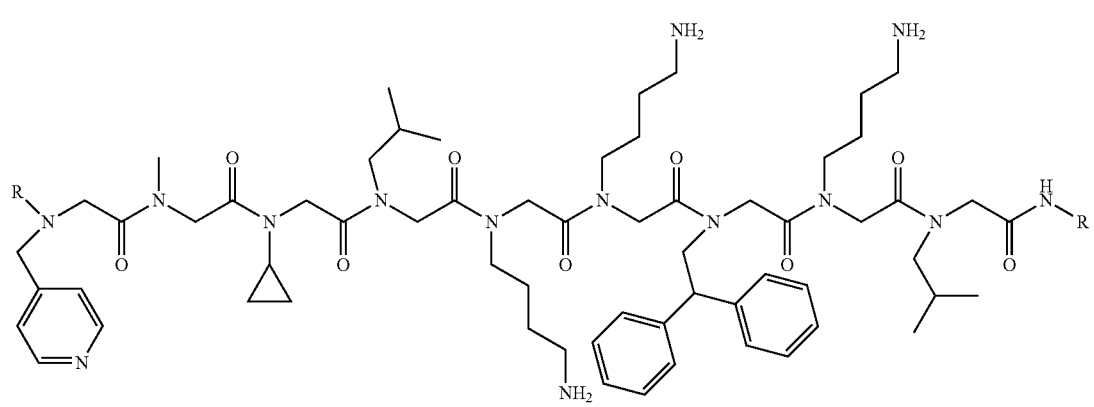
AAD3
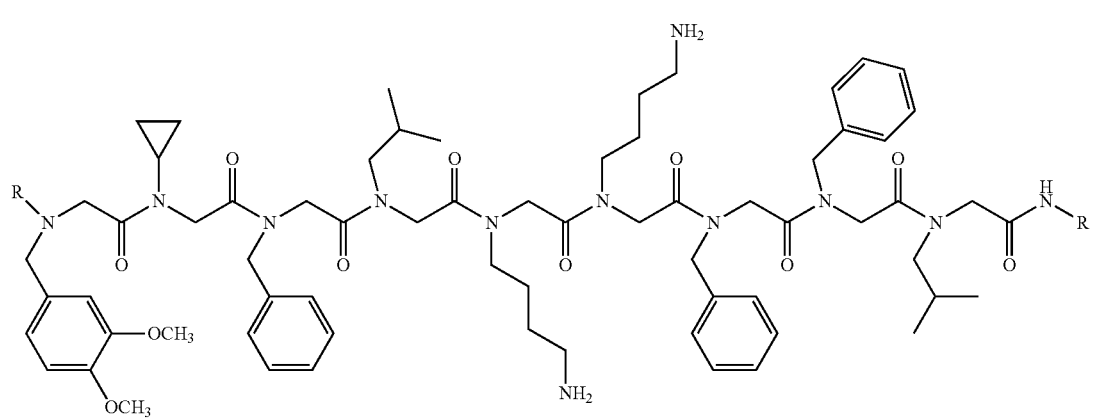

or any combination thereof. In some embodiments, R can be independently selected from a group consisting of a coupling group capable of coupling to a linker, a substrate, or a label; hydrogen; deuterium; $C_{1-6}$ alkyl; $C_{2-6}$ alkenyl; $C_{2-6}$ alkynyl, $C_{3-8}$cycloalkyl; heteroaryl, cycloalkyl; $C_{1-6}$alkylheteroaryl; $C_{1-6}$alkylaryl; and alkylcycloalkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof.

Disclosed herein are compositions. In some embodiments, the composition can comprise a peptoid or pharmaceutically acceptable salt thereof of having the formula:

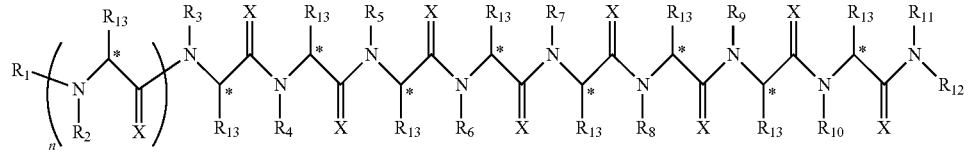

In some embodiments, $R_1$ can be independently selected from a group consisting of a coupling group capable of coupling to a linker, a substrate, or a label; hydrogen; deuterium; $C_{1-6}$ alkyl; $C_{2-6}$ alkenyl; $C_{2-6}$ alkynyl, $C_{3-8}$cycloalkyl; heteroaryl, cycloalkyl; $C_{1-6}$alkylheteroaryl; $C_{1-6}$alkylaryl; and alkylcycloalkyl, each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_2$ can be independently selected from a group consisting of hydrogen; deuterium; $(CY_2)_n$-aryl; $(CY_2)_n$-alkoxyaryl; cycloalkyl; $(CY_2)_n$-heteroaryl; and $(CY_2)_n$-alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_3$ can be independently selected from a group consisting of hydrogen; deuterium; $(CY_2)_n$-aryl; $(CY_2)_n$-alkoxyaryl; alkenyl; alkylaryl; cycloalkyl; alkyldiaryl; and alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_4$ can be independently selected from a group consisting of hydrogen; deuterium; $(CY_2)_n$-aryl; alkyl; cycloalkyl; and $(CY_2)_n$-alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_5$ can be independently selected from a group consisting of hydrogen; deuterium; $(CY_2)_n$-aryl; $(CY_2)_n$-alkyl; alkyl; and alkyldiaryl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_6$ can be independently selected from a group consisting of hydrogen; deuterium; alkyldiaryl; alkylaryl; and $(CY_2)_n$-alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_7$ can be independently selected from a group consisting of hydrogen; deuterium; alkyl; alkylaryl; $(CY_2)_n$-aryl; $(CY_2)_n$-alkyl; and alkyldiaryl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_8$ can be independently selected from a group consisting of hydrogen; deuterium; $(CY_2)_n$-heteroaryl; $(CY_2)_n$-aryl; alkenyl; $(CY_2)_n$-alkyl; alkyl; and alkyldiaryl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_9$ can be independently selected from a group consisting of hydrogen; deuterium; alkylaryl; $(CY_2)_n$-aryl; alkyldiaryl; and $(CY_2)_n$-alkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_{10}$ can be independently selected from a group consisting of hydrogen; deuterium; $(CY_2)_n$-aryl; alkyl; $(CY_2)_n$-alkyl; and $(CY_2)_n$-heteroaryl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_{11}$ can be independently selected from a group consisting of hydrogen; deuterium; $C_{1-6}$ alkyl; $C_{2-6}$ alkenyl; $C_{2-6}$ alkynyl, $C_{3-8}$cycloalkyl; heteroaryl, cycloalkyl; $C_{1-6}$alkylheteroaryl; $C_{1-6}$alkylaryl; and alkylcycloalkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_{12}$ can be independently selected from a group consisting of a coupling group capable of coupling to a linker, a substrate, or a label; hydrogen; deuterium; $C_{1-6}$ alkyl; $C_{2-6}$ alkenyl; $C_{2-6}$ alkynyl, $C_{3-8}$cycloalkyl; heteroaryl, cycloalkyl; $C_{1-6}$alkylheteroaryl; $C_{1-6}$alkylaryl; and alkylcycloalkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof. In some embodiments, $R_{13}$ can be individually and independently selected from a group consisting of hydrogen; deuterium; a halogen;

ethyl; and methyl. In some embodiments, when $R_{13}$ can be not hydrogen each carbon denoted with an * can independent be R or S. In some embodiments, X can be independently selected from oxygen or sulfur. In some embodiments, Y can be independently selected from deuterium or hydrogen. In some embodiments, A can be hydrogen, deuterium, aryl, or heteroaryl. In some embodiments, n can be 1-10. In some embodiments, $R_3$ is not hydrogen or deuterium. In some embodiments, $R_4$ is not hydrogen or deuterium. In some embodiments, $R_5$ is not hydrogen or deuterium. In some embodiments, $R_6$ is not hydrogen or deuterium. In some embodiments, $R_7$ is not hydrogen or deuterium. In some embodiments, $R_8$ is not hydrogen or deuterium. In some embodiments, $R_9$ is not hydrogen or deuterium. In some embodiments, $R_{10}$ is not hydrogen or deuterium. In some embodiments, the pharmaceutical composition can comprise a pharmaceutically acceptable carrier and a peptoid or pharmaceutically acceptable salt thereof. In some embodiments, the carrier can be a parenteral carrier, oral or topical carrier.

INCORPORATION BY REFERENCE

All publications, patents, and patent applications mentioned in this specification are herein incorporated by reference in their entirety for all purposes, to the same extent as if each individual publication, patent, or patent application is specifically and individually indicated to be incorporated by reference in their entireties.

BRIEF DESCRIPTION OF THE DRAWINGS

The novel features described herein are set forth with particularity in the appended claims. A better understanding of the features and advantages of the features described herein will be obtained by reference to the following detailed description that sets forth illustrative examples, in which the principles of the features described herein are utilized, and the accompanying drawings of which:

FIG. 5. Blind analysis of specific molecules binding to MCI subjects: depicts quantitation of fluorescence intensity of each molecule specific to MCI on the microarray that differentiates MCI subjects from normal controls.

FIG. 7. Blind analysis of specific molecules binding to AD subjects: depicts quantitation of fluorescence intensity of each molecule specific to AD on the microarray that differentiates AD subjects from normal controls.

FIG. 8. Quantitation of fluorescence intensity of each molecule specific to AD on the microarray that differentiates AD subjects from normal controls: depicts average intensity of serum sample responses to nine isolated specific molecules comparing 29 normal control subjects and 21 AD subjects. Bar at 20,000 differentiates between AD positive and AD negative.

FIG. 9. Alzheimer's disease specific molecules and their current drug response: depicts quantitation of fluorescence intensity of each molecule specific to AD on the microarray that differentiates AD subjects from normal controls. Further depicts average intensity of serum sample to nine isolated AD specific molecules compared their current drug response (circled).

FIG. 10. Building blocks: depicts building blocks used in the synthesis of the molecule library.

FIG. 11. Chemical Structures of six MCI specific molecules (ErAD1-6): depicts the chemical structures of six MCI specific molecules (ErAD1-6) that were extracted to differentiate MCI subjects from normal control.

FIG. 12. The Chemical Structures of three AD specific molecules (AAD1-3): depicts the chemical Structures of three AD specific molecules (AAD1-3) that were extracted to differentiate AD subjects from normal control.

FIG. 13. Purification of serum samples by AD specific molecules Serum from AD and normal control subjects were purified using three (ErAD1-3) molecules. The enriched serum samples were then hybridized to microarrays (right).

FIG. 14. Tuning signal-to-background conditions: depicts microarray scan images of molecules printed in serial dilution and incubated with serum.

FIG. 15. Tuning signal-to-background conditions: depicts layout of microarrays printed in serial dilution.

FIG. 16. Response intensity: depicts quantitation of fluorescence intensity of each molecule on a microarray that differentiates AD subjects from normal controls.

DETAILED DESCRIPTION OF THE DISCLOSURE

Figure 1A:
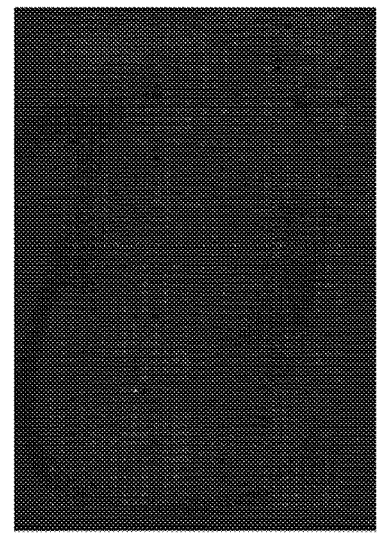
FIG. 1. Specificity: depicts an image showing a subset (1A) of molecules that bind to IgG, IgA, and IgM antibodies—and not to phosphorylated proteins (1B) or amyloid beta 42 peptide (1C). The fluorescence intensity of each molecule on a microarray is shown in the image FIG. 2. Molecules bind to Alzheimer's subjects but not to normal controls: depicts raw images of microarray scans that were hybridized with serum from normal control (2A) and Alzheimer's disease (2B) subjects. The fluorescence intensity of each molecule on microarray is shown in the image.

Several aspects are described below with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

Definitions

In this disclosure the term "about" or "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, and within 2-fold, of a value. Where particular values are described in the application and claims, unless otherwise stated the term "about" meaning within an acceptable error range for the particular value should be assumed.

The terms "attach", "bind", "couple", and "link" are used interchangeably and refer to covalent interactions (e.g., by chemically coupling), or non-covalent interactions (e.g., ionic interactions, hydrophobic interactions, hydrogen bonds, hybridization, etc.).

The terms "specific", "specifically", or specificity" refer to the preferential recognition, contact, and formation of a stable complex between a first molecule and a second molecule compared to that of the first molecule with any one of a plurality of other molecules (e.g., substantially less to no recognition, contact, or formation of a stable complex between the first molecule and any one of the plurality of other molecules).

The terms poly (N-substituted glycines), oligo (N-substituted) glycines, and poly NSGs are used interchangeably herein and are produced using the methodology of the present invention. Poly NSGs are not peptides, i.e., they are not composed of naturally-occurring amino acids linked in peptide bonds. However, they may be designed so as to have structural features (e.g., reactive sites) which are closely related to naturally occurring peptides and proteins, and as such are useful as potential therapeutic agents and/or as binding sites on assays. The poly NSGs disclosed herein can be designed so as to have a wide variety of side-chain substituents—including substituents normally found on natural amino acids and others not naturally occurring. For example, the invention makes it possible to synthesize compounds having side chains which resemble pharmacophores of known drugs, e.g., phenoxyphenyl or 2-adamantyl.

When used in the context of a chemical group, "hydrogen" means —H; "hydroxy" means —OH; "oxo" means =O; "halogen" means independently —F, —Cl, —Br or —I; "amino" means —NH$_2$.

For the structures provided herein, the following parenthetical subscripts further define the groups as follows: "(C$_8$)" defines the exact number (n) of carbon atoms in the group. For example, "(C$_{2-10}$)alkyl designates those alkyl groups having from 2 to 10 carbon atoms (e.g., 2, 3, 4, 5, 6, 7, 8, 9, or 10, or any range derivable therein (e.g., 3 to 10 carbon atoms).

The term "alkyl" when used without the "substituted" modifier refers to a non-aromatic monovalent group with a saturated carbon atom as the point of attachment, a linear or branched, cyclo, cyclic or acyclic structure, no carbon-carbon double or triple bonds, and no atoms other than carbon and hydrogen. The groups, —CH$_3$ (Me), —CH$_2$CH$_3$ (Et), —CH$_2$CH$_2$CH$_1$ (n-Pr), —CH(CH$_3$)$_2$ (iso-Pr), —CH(CH$_2$)$_2$ (cyclopropyl). —CH$_2$CH$_2$CH$_2$CH$_3$ (n-Bu), —CH(CH)CH$_2$CH$_3$ (sec-butyl), —CH$_2$CH(CH$_3$)$_2$(iso-butyl), —C(CH$_3$)$_3$ (tert-butyl), —CH$_2$C(CH$_3$)$_3$(neo-pentyl), cyclobutyl, cyclopentyl, cyclohexyl, and cyclohexylmethyl are non-limiting examples of alkyl groups. Substituted alkyl refers to a non-aromatic monovalent group with a saturated carbon atom as the point of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkyl groups: —CH$_2$OH, —CH$_2$Cl, —CH$_2$Br, —CH$_2$SH, —CF$_3$, —CH$_2$CN, —CH$_2$C(O)H, —CH$_2$C(O)OH, —CH$_2$C(O)OCH$_3$, —CH$_2$C(O)NH$_2$, —CH$_2$C(O)NHCH$_3$, —CH$_2$C(O)CH$_3$, —CH$_2$OCH$_3$, —CH$_2$OCH$_2$CF$_3$, —CH$_2$OC(O)CH$_3$, —CH$_2$NH$_2$, —CH$_2$NHCH$_3$, —CH$_2$N(CH$_3$)$_2$, —CH$_2$CH$_2$Cl, —CH$_2$CH$_2$OH, —CH$_2$CF$_3$, —CH$_2$CH$_2$OC(O)CH$_3$, —CH$_2$CH$_2$NHCO$_2$C(CH$_3$)$_3$, and —CH$_2$Si(CH$_3$)$_3$.

The term "alkenyl" when used without the "substituted" modifier refers to a monovalent group with a nonaromatic carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. Substituted alkenyl refers to a monovalent group with a nonaromatic carbon atom as the point of attachment, at least one nonaromatic carbon-carbon double bond, no carbon-carbon triple bonds, a linear or branched, cyclo, cyclic or acyclic structure, and at least one atom independently selected from the group consisting of N, O, F, Cl, Br, I, Si, P, and S. The groups, —CH=CHF, —CH=CHCl and —CH=CHBr, are non-limiting examples of substituted alkenyl groups.

The term "alkynyl" when used without the "substituted" modifier refers to a monovalent group with a nonaromatic carbon atom as the point of attachment, a linear or branched, cyclo, cyclic or acyclic structure, at least one carbon-carbon triple bond, and no atoms other than carbon and hydrogen. The groups, —C☉CH, —C≡CH$_3$, —C≡C$_6$CH$_5$ and —CH$_2$C≡CCH$_3$, are non-limiting examples of alkynyl groups. Substituted alkynyl refers to a monovalent group with a nonaromatic carbon atom as the point of attachment and at least one carbon-carbon triple bond, a linear or branched, cyclo, cyclic or acyclic structure, and at least one atom independently selected from the group consisting of N, O, F, Cl, Br, I, Si, P, and S. The group, —C≡CSi(CH$_3$)$_3$, is a non-limiting example of a substituted alkynyl group.

The term "aryl" when used without the "substituted" modifier refers to a monovalent group with an aromatic carbon atom as the point of attachment, said carbon atom forming part of one or more six-membered aromatic ring structure(s) wherein the ring atoms are all carbon, and wherein the monovalent group consists of no atoms other than carbon and hydrogen. Non-limiting examples of aryl groups include phenyl (Ph), methylphenyl, (dimethyl)phenyl, —$C_6H_4CH_2CH_3$ (ethylphenyl), —$C_6H_4CH_2CH_2CH_3$ (propylphenyl), —$C_6H_4CH(CH_3)_2$, —$C_6H_4CH(CH_2)_2$, —$C_6H_3(CH_3)CH_2CH_3$ (methylethylphenyl), —$C_6H_4CH=CH_2$ (vinylphenyl), —$CH_4CH=CHCH_3$, —$CH_4C\equiv CH$, —$C_6H_4C\equiv CCH_3$, naphthyl, and the monovalent group derived from biphenyl. Substituted aryl refers to a monovalent group with an aromatic carbon atom as the point of attachment, said carbon atom forming part of one or more six-membered aromatic ring structure(s) wherein the ring atoms are all carbon, and wherein the monovalent group further has at least one atom independently selected from the group consisting of N, O, F, Cl, Br, I, Si. P. and S. Non-limiting examples of substituted aryl groups include the groups: —$C_6H_4F$, —$CH_4Cl$, —$C_6H_4Br$, —$C_6H_4I$, —$C_6H_4OH$, —$C_6H_4OCH_3$, —$C_6H_4OCH_2CH_3$, —$C_6H_4OC(O)CH_3$, —$C_6H_4NH_2$, —$C_6H_4NHCH_3$, —$C_6H_4N(CH_3)_2$, —$C_6H_4CH_2OH$, —$C_6H_4CH_2OC(O)CH_3$, —$C_6H_4CH_2NH_2$, —$CH_4CF_3$, —$C_6H_4CN$, —$C_6H_4CHO$, —$C_6H_4CHO$, —$C_6H_4C(O)CH_3$, —$CH_4C(O)C_6H_5$, —$CH_4CO_2H$, —$C_6H_4CO_2CH_3$, —$C_6H_4CONH_2$, —$C_6H_4CONHCH_3$, and —$CH_4CON(CH_3)_2$.

The term "cycloalkyl" refers to a saturated alicyclic moiety having three or more carbon atoms (e.g., from three to six carbon atoms) and which may be optionally benzo-fused at any available position. Non-limiting examples of cycloalkyl groups include the group cyclopropyl, cyclobutyl, cyclopentyl, cyclohexyl, indanyl and tetrahydronaphthyl.

The term "heteroaryl" when used without the "substituted" modifier refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group consists of no atoms other than carbon, hydrogen, aromatic nitrogen, aromatic oxygen and aromatic sulfur. Non-limiting examples of heteraryl groups include acridinyl, furanyl, imidazoimidazolyl, imidazopyrazolyl, imidazopyridinyl, imidazopyrimidinyl, indolyl, indazolinyl, methylpyridyl, oxazolyl, phenylimidazolyl, pyridyl, pyrrolyl, pyrimidyl, pyrazinyl, quinolyl, quinazolyl, quinoxalinyl, tetrahydroquinolinyl, thienyl, triazinyl, pyrrolopyridinyl, pyrrolopyrimidinyl, pyrrolopyrazinyl, pyrrolotriazinyl, pyrroloimidazolyl, chromenyl (where the point of attachment is one of the aromatic atoms), and chromanyl (where the point of attachment is one of the aromatic atoms). Substituted heteroaryl refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group further has at least one atom independently selected from the group consisting of non-aromatic nitrogen, non-aromatic oxygen, non aromatic sulfur F, Cl, Br, I, Si, and P.

The term "alkoxy" when used without the "substituted" modifier refers to the group —OR, in which R is an alkyl, as that term is defined above. Non-limiting examples of alkoxy groups include: —$OCH_3$, —$OCH_2CH_3$, —$OCH_2CH_2CH_3$, —$OCH(CH_2)_2$, —$OCH(CH_2)$, —O-cyclopentyl, and —O— cyclohexyl. Substituted alkoxy" refers to the group —OR, in which R is a substituted alkyl, as that term is defined above. For example, —$OCH_2CF_3$ is a substituted alkoxy group.

"Effective amount," "Therapeutically effective amount" or "pharmaceutically effective amount" means that amount which, when administered to a subject or patient for treating a disease, is sufficient to effect such treatment for the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

Overview

Alzheimer's Disease (AD) is a progressive and fatal brain disease that affects as many as 5.3 million Americans. AD destroys brain cells, causing problems with memory, thinking and behavior. AD symptoms progressively worsen over time, and the disease is ultimately fatal. Today, AD is the sixth-leading cause of death in the United States and is the most common form of dementia, accounting for 50-70% of all dementia cases. While treatments for symptoms exist, there is no cure.

Diagnosing AD is an empirical process that involves several types of evaluations that can take many days to weeks to complete. Evaluations can include for example, taking a detailed medical history and physical examination. Standard laboratory tests can include blood, urine and CSF tests. Evaluations can further include neuropsychological testing, to assess memory, problem-solving, attention, vision-motor coordination and abstract thinking. Evaluations can also include tests for depression and brain-imaging scans to rule out brain tumors or blood clots in the brain as the reason for symptoms. In some instances, AD evaluation can comprise but is not limited to the TARC neuropsychology core battery, the NACC Uniform Dataset including digit span (WAIS-R, WAIS-III, WMS-R), Trail-Making Test, WMS Logical Memory and Visual Reproduction (WMS-R and WMS-III), Boston Naming Test (30- and 60-item versions), verbal fluency (FAS), Clock-Drawing Test, the American National Adult Reading Test (AMNART), the Geriatric Depression Scale (GDS-30), Mini-Mental State Examination (MMSE), and ratings on the Clinical Dementia Rating scale (CDR).

Currently, there is no single test that accurately diagnoses AD. A definitive diagnosis of AD is possible only by examining brain tissue after death.

Thus, there remains a need for diagnostic and/or treatment procedures for neurological diseases that are (i) accurate and objective, (ii) simple and reproducible, and (iii) useful in both early and late stage case.

The present invention relates to molecules, methods and kits for detecting biomarkers indicative of AD. In some instances, the molecules described herein are peptoids. The peptoids described herein can be synthesized as a library or plurality of libraries comprising peptoids. The library or plurality of libraries can be selected to screen for a target disease or condition, for example AD. Each library can be used to screen against a different disease or condition or the same library can be used to screen multiple disease states or conditions. Libraries can include those libraries that have a rich assortment of side chains on the mono-substituted amines that form any particular monomer in an oligomeric chain. This assortment of R groups on the amine starting material can be feature specific. In some embodiments, the peptoids are feature specific peptides. A molecule can be feature specific even if some of the chemical and/or physical features of any particular monomer such as functionality/solubility are not part of a desired feature or characteristic of the target oligomers. For plasma based screens or serum screens, for example, it can be desired that any particular ligand bound to a bead has solubility characteristics which facilitate interaction, in solution, with a ligand binding moiety and/or a biomarker such as an antibody. In some embodiments, a ligand can be a molecule. In some embodiments, a ligand binding moiety can be a biomarker. In some embodiments, a biomarker can be a peptide, a peptoid, a protein, a carbohydrate, a lipid, a lipoprotein, a receptor, a T cell receptor, a molecule with a molecular weight of 1000 Daltons or less, a molecule with a molecular weight of 1000 Daltons or more, a cell, an antibody or a fragment thereof. In addition, the size of the oligomer can be a feature that is considered when forming a library of ligands that can bind to a ligand-binding moiety and/or a biomarker for example, an antibody or protein.

In some embodiments, the library is a bead based library. Bead based library can comprise beads or similar support structures (i.e., polymeric resins) having bonded thereto (or to a linker on such resin) a ligand selected from the group of small molecules, peptides, peptoids, polysaccharides or any oligomer based compound including nucleic acids or modified nucleic acid moieties. In some embodiments, the bead based library can comprise peptoids. Oligomeric peptoids can be generated using, for example, a hybrid combination of a typical solid state peptide synthesis merged with a submonomer synthetic approach and comprise glycine or carbon substituted glycine-like moieties having a mono-substituted amide wherein the substituent on the amide nitrogen or α-carbon is selected from a wide range of moieties depending upon the monosubstituted amine or glycine a carbon substituent utilized in the synthesis. Peptoid libraries can generally be prepared as described in, for example, Kodadek and Reddy, Proceedings of the National Academy of Sciences, Sep. 6, 2005, volume 102, No. 36 or as described herein. Kodadek and Reddy is hereby incorporated in its entirety. As referenced above, the monosubstituted amine pool can be generally selected from a wide range of monomers. The size of the library can range from less than about 10, 100, 1000, 10,000, 100,000, 200.000 to about 150 million or greater beads having said number of distinct ligands per bead. Alternatively, and depending upon the size of the bead or support, each support or bead may have more than one ligand per bead/support and the ligand(s) may be the same ligand or distinct ligands.

In some embodiments, the library may not be pretreated prior to exposure to binding moieties and/or biomarkers. In some embodiments, the library can be pretreated. The library can be pretreated and exposed, under the right conditions and after exposure to a control plasma or serum sample to permit removal of non-selective ligands, biomarker containing sample for example a biological fluid such as plasma or serum which is screened for the presence or absence of disease-associated biomarkers or other target biomarkers such as antibodies or proteins or other markers such as cell surface proteins. The biomarker containing sample, blood samples or other biological fluid samples can be taken from subjects that may or may not have a particular disease and the results generated from the screen can be compared to results taken from a control healthy subject or control diseased subject.

The screening process can result in a significant number of high-affinity ligands for any particular disease-associated biomarker such as an antibody. The invention further comprises a process for generating high affinity ligands which are useful in either a diagnostic setting for such disease state and/or are useful as ligands in their own right—e.g., as therapeutic vaccines or as drugs which can target said disease associated antibodies located in a particular region of the body or body tissue. Such drugs can be linked to other moieties such as chemotherapeutic agents or other agents that generate or can generate a localized immune response to remove and/or degrade auto-antibodies.

Peptoids

Peptoids are oligomers having monomeric units of between 5 to 15 monomers linked covalently to form the oligomer. In some embodiments, the ligand or peptoid can be a 3-mer, a 4-mer, a 5-mer, a 6-mer, a 7-mer, an 8-mer, a 9-mer, a 10-mer, an 11-mer, a 12-mer, a 13-mer, a 14-mer, a 15-mer, a 16-mer or larger oligomer. The oligomer may have additional moieties linked to a terminal end of the oligomer to bond to a support or to a linker which links the oligomer to the support. Due to their N-substitution, peptoids are more cell permeable than peptides and are stable to proteases. In some embodiments, the ligand described herein can be a peptoid.

For the molecules disclosed herein, all chiral, diastereomeric, racemic form, epimeric form, and all geometric isomeric forms of a structure are intended, unless the specific stereochemistry or isomeric form is specifically indicated. Molecules can occur as racemates and racemic mixtures, single enantiomers, diastereomeric mixtures and individual diastereomers. In some embodiments, a single diastereomer is obtained. The chiral centers of the molecules of the present invention can have the S or the R configuration. A "stereoisomer" or "optical isomer" is an isomer of a given molecule in which the same atoms are bonded to the same other atoms, but where the configuration of those atoms in three dimensions differs. "Enantiomers" are stereoisomers of a given molecule that are mirror images of each other, like left and right hands. "Diastereomers" are stereoisomers of a given molecule that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center can be for example a carbon, phosphorus or sulfur atom, though it is also possible for other atoms to be stereocenters in organic and inorganic compounds. A molecule can have multiple stereocenters, giving it many stereoisomers. In molecules whose stereoisomerism is due to tetrahedral stereogenic centers (e.g., tetrahedral carbon), the total number of hypothetically possible stereoisomers will not exceed 2n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form. S form, or as a mixture of the R and S forms, including racemic and non-racemic mixtures. In some embodiments, a molecule can be least than about 1%, 5%, 10%, 15%, 20%, 25%, 30%, 35%, 40%, 50%, 60%, 80%, 90%, 95% of another stereoisomer(s).

Diseases

In some embodiments, the inventions disclosed herein may be used by one of skill in the art to discover disease associated biomarkers and for making diagnostic kits and/or devices comprising high-affinity ligands for such biomarkers. In some embodiments, the disease may comprise Alzheimer's disease, Parkinson's disease, and/or Cancer. In some embodiments, blood-based methods can represent one of a number of methods used to evaluate, diagnose and/or treat a disease or condition. In some embodiments, blood-based methods can represent the only method used to evaluate, diagnose and/or treat a disease or condition.

Diagnosing Alzheimer's Disease

When diagnosed, drugs proposed as therapeutic agents for AD generally fit into the broad categories of cholinesterase inhibitors, muscarinic agonists, anti-oxidants or anti-inflammatories. For example, the following may be used alone or in combination: Galantamine (Reminyl), tacrine (Cognex), selegiline, physostigmine, revistigmin, donepezil, (Aricept), rivastigmine (Exelon), metrifonate, milameline, xanomeline, saeluzole, acetyl-L-carnitine, idebenone, ENA-713, memric, quetiapine, neurestrol and neuromidal.

However, diagnosing Alzheimer's disease ("AD") may involve several types of evaluations and may take many days to weeks to complete. Evaluations may include taking a detailed medical history and physical examination. Standard laboratory tests including blood, urine and CSF tests may be used to help eliminate other possible conditions. Neuropsychological testing, using a variety of tools to assess memory, problem-solving, attention, vision-motor coordination and abstract thinking, may also be performed. Tests for depression may also be included. Brain-imaging scans may be included to rule out brain tumors or blood clots in the brain as the reason for symptoms. In sum, there exists no single test that accurately diagnoses AD, with a definitive diagnosis of Alzheimer's possible only by examining brain tissue after death.

Advanced neuroimaging and CSF techniques may also aid the diagnostic accuracy within the clinic based settings for detecting AD. However, blood-based biomarkers represent an approach for enhancing the utility of imaging and CSF-based modalities by serving as a generalized and/or specific screening tool. In some aspects, blood based methods may serve as the first step in a multistep diagnostic process as may be the case with many other pathologies, such as neurological diseases, cardiovascular diseases, infectious diseases, and cancer. In some aspects, following the first step, screen positives may be referred for neuroimaging or CSF assessment for confirmatory purposes (e.g. for diagnostics or enrollment into clinical trials). In another aspect, blood based methods may serve as a single test that accurately diagnoses AD.

There is a need for improved methods of discovering disease associated biomarkers and for making diagnostic kits comprising high-affinity ligands for such biomarkers. The present invention relates to a method of synthesizing feature specific ligands, screening such ligands, detecting molecules with high affinity to disease associated biomarkers, detecting biomarkers and for diagnosing disease and disease progression.

In accordance with the present invention, there is provided compositions comprising peptoid(s) that bind antibodies indicative of a neurodegenerative disease and methods of detecting antibodies in an antibody-containing sample comprising contacting an antibody-containing sample to a peptoid. In some embodiments, a support can be affixed thereto a peptoid. Ligand libraries can include for example Erad1, Erad2, Erad3, Erad4, Erad5, Erad6, AD1, AD2, or AD3.

In some embodiments, the inventions disclosed herein can be used by one of skill in the art to discover disease associated biomarkers and for making diagnostic kits comprising high-affinity ligands for such biomarkers. In some embodiments, the disease may comprise Parkinson's disease.

Parkinson's Disease

When diagnosed, drugs proposed as therapeutic agents for Parkinson's Disease (PD) alone or in combination include Levodopa, Sinemet (levodopa+Carbidopa), Stalevo (carbidopa+levodopa+entacapone), Symmetrel (amantadine hydrochloride), Anticholinergics (trihexyphenidyl, benztropine mesylate, procyclidine, etc), Selegiline, deprenyl (Eldepryl), dopamine agonist such as bromocriptine (Parlodel), pergolide (Permax), pramipexole (Mirapex) and ropinirole (Requip), COMT inhibitors such as tolcapone (Tasmar) and entacapone (Comtan). Surgery can also be an option for some patients after medications are no longer satisfactory.

PD is a degenerative disease of the brain (central nervous system) that often impairs motor skills, speech, and other functions. PD affects movement (motor symptoms), but other typical symptoms may include disorders of mood, behavior, thinking, and sensation (non-motor symptoms). Subject's individual symptoms may be quite dissimilar and progression of the disease is also distinctly individual. The symptoms of PD result from the loss (idiopathic or genetic, toxic or traumatic) of pigmented dopamine-secreting (dopaminergic) cells in the pars compacta region of the substantia nigra (literally "black substance"). These neurons project to the striatum and their loss leads to alterations in the activity of the neural circuits within the basal ganglia that regulate movement, in essence an inhibition of the direct pathway and excitation of the indirect pathway. When performing a neurologic examination to evaluate a subject with any movement disorder, the doctor may review the subject's medical history and perform a physical examination. In addition, a neurologic exam may be conducted to make a thorough evaluation of the nervous system, including observing aspects of the subject's movement, coordination and balance. Laboratory testing of the blood of subjects with the symptoms typical of Parkinson's rarely uncovers any abnormality. Electroencephalograms (EEG's) record some aspects of brain electrical activity, but they are not effective in spotting PD. The MRI and CAT scans of the brain produce remarkable and exquisite anatomic pictures, but the brains of people with PD disease appear normal even under this scrutiny because the changes associated with PD are microscopic and are not revealed by these scans. With no definitive diagnostic tests to provide specific answers, physicians base their diagnosis of PD on judgment. Thus, there remains a need for diagnostic procedures for both of these diseases and other neurological diseases that are (i) accurate and objective, (ii) simple and reproducible, and (iii) useful in both early and late stage case.

In some embodiments, the inventions disclosed herein can be used by one of skill in the art to discover molecules with high affinity to disease associated biomarkers, discover disease associated biomarkers and for making diagnostic kits and/or devices comprising high-affinity ligands for such biomarkers. In some embodiments, the disease may comprise autoimmune diseases.

Autoimmune Diseases

The present invention can also provide for the identification of ligands that can bind autoimmune T-cells and/or antibodies from a variety of autoimmune disease states or conditions. In certain aspects, disease states include, but are not limited to diseases such as acute disseminated encephalomyelitis (ADEM), acute necrotizing hemorrhagic leukoencephalitis, Addison's disease, agammaglobulinemia, allergic asthma, allergic rhinitis, alopecia areata, amyloidosis, ankylosing spondylitis, anti-GBM/anti-TBM nephritis, antiphospholipid syndrome (APS), autoimmune aplastic anemia, autoimmune dysautonomia, autoimmune hepatitius, autoimmune hyperlipidemia, autoimmune immunodeficiency, autoimmune inner ear disease (AIED), autoimmune myocarditis, autoimmune pancreatitis, autoimmune retinopathy, autoimmune thrombocytopenic purpura (ATP), autoimmune thyroid disease, axonal & neuronal neuropathies, Balo disease, Behcet's disease, bullous pemphigoid, cardiomyopathy, Castlemen disease, celiac sprue (non-tropical), Chagas disease, chronic fatigue syndrome, chronic inflammatory demyelinating polyneuropathy (CIDP), chronic recurrent multifocal ostomyelitis (CRMO), Churg-Strauss syndrome, cicatricial pemphigoid/benign mucosal pemphigoid, Crohn's disease, Cogan's syndrome, cold agglutinin disease, congenital heart block, coxsackie myocarditis, CREST disease, essential mixed cryoglobulinemia, demyelinating neuropathies, dermatomyositis, Devic's disease (neuromyelitis optica), discoid lupus, Dressler's syndrome, endometriosis, eosinophillic fasciitis, erythema nodosum, experimental allergic encephalomyelitis, Evan's syndrome, fibromyalgia, fibrosing alveolitis, giant cell arteritis (temporal arteritis), glomerulonephritis, Goodpasture's syndrome, Grave's disease, Guillain-Barre syndrome, Hashimoto's encephalitis, Hashimoto's thyroiditis, hemolytic anemia, Henock-Schoniein purpura, herpes gestationis, hypogammaglobulinemia, idiopathic thrombocytopenic purpura (ITP), IgA nephropathy, immunoregulatory lipoproteins, inclusion body myositis, insulin-dependent diabetes (type 1), interstitial cystitis, juvenile arthritis, juvenile diabetes, Kawasaki syndrome, Lambert-Eaton syndrome, leukocytoclastic vasculitis, lichen planus, lichen sclerosus, ligneous conjunctivitis, linear IgA disease (LAD). Lupus (SLE), Lyme disease, Meniere's disease, microscopic polyangitis, mixed connective tissue disease (MCTD), Mooren's ulcer, Mucha-Habermann disease, multiple sclerosis, myasthenia gravis, myositis, narcolepsy, neuromyelitis optica (Devic's), neutropenia, ocular cicatricial pemphigoid, optic neuritis, palindromic rheumatism. PANDAS (Pediatric Autoimmune Neuropsychiatric Disorders Associated with *Streptococcus*), paraneoplastic cerebellar degeneration, paroxysmal nocturnal hemoglobinuria (PNH), Parry Romberg syndrome, Parsonnage-Turner syndrome, pars plantis (peripheral uveitis), pemphigus, peripheral neuropathy, perivenous encephalomyelitis, pernicious anemia, POEMS syndrome, polyarteritis *nodosa*, type I, II & III autoimmune polyglandular syndromes, polmyalgia rheumatic, polymyositis, postmyocardial infarction syndrome, postpericardiotomy syndrome, progesterone dermatitis, primary biliary cirrhosis, primary sclerosing cholangitis, psoriasis, psoriatic arthritis, idiopathic pulmonary fibrosis, pyoderma gangrenosum, pure red cell aplasia, Raynaud's phenomena, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Slogren's syndrome, sperm and testicular autoimmunity, stiff person syndrome, subacute bacterial endocarditis (SBE), sympathetic ophthalmia, Takayasu's arteritis, temporal arteritis/giant cell arteries, thrombocytopenic purpura (TPP), Tolosa-Hunt syndrome, transverse myelitis, ulcerative colitis, undifferentiated connective tissue disease (UCTD), uveitis, vasculitis, vesiculobullous dermatosis, vitiligo or Wegener's granulomatosis or, chronic active hepatitis, primary biliary cirrhosis, cadilated cardiomyopathy, myocarditis, autoimmune polyendocrine syndrome type I (APS-I), cystic fibrosis vasculitides, acquired hypoparathyroidism, coronary artery disease, pemphigus foliaceus, pemphigus vulgaris, Rasmussen encephalitis, autoimmune gastritis, insulin hypoglycemic syndrome (Hirata disease), Type B insulin resistance, acanthosis, systemic lupus erythematosus (SLE), pernicious anemia, treatment-resistant Lyme arthritis, polyneuropathy, demyelinating diseases, atopic dermatitis, autoimmune hypothyroidism, vitiligo, thyroid associated ophthalmopathy, autoimmune coeliac disease, ACTH deficiency, dermatomyositis, Sjogren syndrome, systemic sclerosis, progressive systemic sclerosis, morphea, primary antiphospholipid syndrome, chronic idiopathic urticaria, connective tissue syndromes, necrotizing and crescentic glomerulonephritis (NCGN), systemic vasculitis, Raynaud syndrome, chronic liver disease, visceral leishmaniasis, autoimmune C deficiency, membrane proliferative glomerulonephritis (MPGN), prolonged coagulation time, immunodeficiency, atherosclerosis, neuronopathy, paraneoplastic pemphigus, paraneoplastic stiff man syndrome, paraneoplastic encephalomyelitis, subacute autonomic neuropathy, cancer-associated retinopathy, parancoplastic opsoclonus myoclonus ataxia, lower motor neuron syndrome and Lambert-Eaton myasthenic syndrome.

In some embodiments, the inventions disclosed herein may be used by one of skill in the art to discover disease associated biomarkers and for making diagnostic kits and/or devices comprising high-affinity ligands for such biomarkers. In some embodiments, the disease may comprise cancers.

Cancer

The present invention can also be useful in identifying and/or characterizing the presence or absence of biomarkers associated with cancer or pre-cancerous conditions. These cancers include but are not limited to, for example, Acute lymphoblastic leukemia, Acute myeloid leukemia, Adrenocortical carcinoma, AIDS-related cancers, AIDS-related lymphoma, Anal cancer, Appendix cancer, Astrocytoma, childhood cerebellar or cerebral. Basal cell carcinoma, Bile duct cancer, extrahepatic, Bladder cancer, Bone cancer, Osteosarcoma/Malignant fibrous histiocytoma, Brainstem glioma, Brain tumor. Brain tumor, cerebellar astrocytoma, Brain tumor, cerebral astrocytoma/malignant glioma, Brain tumor, ependymoma, Brain tumor, medulloblastoma, Brain tumor, supratentorial primitive neuroectodermal tumors, Brain tumor, visual pathway and hypothalamic glioma, Breast cancer, Bronchial adenomas/carcinoids, Burkitt lymphoma, Carcinoid tumor, childhood, Carcinoid tumor, gastrointestinal, Carcinoma of unknown primary, Central nervous system lymphoma, primary, Cerebellar astrocytoma, childhood, Cerebral astrocytoma/Malignant glioma, childhood, Cervical cancer, Childhood cancers, Chronic lymphocytic leukemia, Chronic myelogenous leukemia, Chronic myeloproliferative disorders, Colon Cancer, Cutaneous T-cell lymphoma. Desmoplastic small round cell tumor, Endometrial cancer. Ependymoma, Esophageal cancer, Ewing's sarcoma in the Ewing family of tumors, Extracranial germ cell tumor, Childhood, Extragonadal Germ cell tumor, Extrahepatic bile duct cancer, Eye Cancer, Intraocular melanoma, Eye Cancer, Retinoblastoma. Gallbladder cancer, Gastric (Stomach) cancer, Gastrointestinal Carcinoid Tumor, Gastrointestinal stromal tumor (GIST), Germ cell tumor: extracranial, extragonadal, or ovarian. Gestational trophoblastic tumor, Glioma of the brain stem, Glioma, Childhood Cerebral Astrocytoma, Glioma, Childhood Visual Pathway and Hypothalamic, Gastric carcinoid, Hairy cell leukemia. Head and neck cancer, Heart cancer, Hepatocellular (liver) cancer. Hodgkin lymphoma, Hypopharyngeal cancer, Hypothalamic and visual pathway glioma, childhood, Intraocular Melanoma, Islet Cell Carcinoma (Endocrine Pancreas), Kaposi sarcoma, Kidney cancer (renal cell cancer), Laryngeal Cancer, Leukemias, Leukemia, acute lymphoblastic (also called acute lymphocytic leukemia), Leukemia, acute myeloid (also called acute myelogenous leukemia), Leukemia, chronic lymphocytic (also called chronic lymphocytic leukemia), Leukemia, chronic myelogenous (also called chronic myeloid leukemia), Leukemia, hairy cell, Lip and Oral Cavity Cancer, Liver Cancer (Primary), Lung Cancer, Non-Small Cell, Lung Cancer, Small Cell, Lymphomas, Lymphoma, AIDS-related, Lymphoma, Burkitt, Lymphoma, cutaneous T-Cell. Lymphoma, Hodgkin, Lymphomas, Non-Hodgkin (an old classification of all lymphomas except Hodgkin's), Lymphoma, Primary Central Nervous System, Marcus Whittle, Deadly Disease, Macroglobulinemia, Waldenström, Malignant Fibrous Histiocytoma of Bone/Osteosarcoma. Medulloblastoma. Childhood, Melanoma, Melanoma, Intraocular (Eye), Merkel Cell Carcinoma, Mesothelioma, Adult Malignant, Mesothelioma, Childhood, Metastatic Squamous Neck Cancer with Occult Primary, Mouth Cancer, Multiple Endocrine Neoplasia Syndrome, Childhood, Multiple Myeloma/Plasma Cell Neoplasm. Mycosis Fungoides, Myelodysplastic Syndromes, Myelodysplastic/Myeloproliferative Diseases, Myelogenous Leukemia. Chronic, Myeloid Leukemia, Adult Acute, Myeloid Leukemia, Childhood Acute, Myeloma. Multiple (Cancer of the Bone-Marrow), Myeloproliferative Disorders, Chronic, Nasal cavity and paranasal sinus cancer, Nasopharyngeal carcinoma, Neuroblastoma, Non-Hodgkin lymphoma, Non-small cell lung cancer, Oral Cancer, Oropharyngeal cancer, Osteosarcoma/malignant fibrous histiocytoma of bone, Ovarian cancer, Ovarian epithelial cancer (Surface epithelial-stromal tumor), Ovarian germ cell tumor, Ovarian low malignant potential tumor, Pancreatic cancer, Pancreatic cancer, islet cell, Paranasal sinus and nasal cavity cancer, Parathyroid cancer, Penile cancer, Pharyngeal cancer, Pheochromocytoma. Pineal astrocytoma, Pineal germinoma, Pineoblastoma and supratentorial primitive neuroectodermal tumors, childhood, Pituitary adenoma. Plasma cell neoplasia/Multiple myeloma, Pleuropulmonary blastoma, Primary central nervous system lymphoma, Prostate cancer, Rectal cancer, Renal cell carcinoma (kidney cancer). Renal pelvis and ureter, transitional cell cancer, Retinoblastoma, Rhabdomyosarcoma, childhood, Salivary gland cancer, Sarcoma, Ewing family of tumors, Sarcoma, Kaposi, Sarcoma, soft tissue, Sarcoma uterine, Sezary syndrome, Skin cancer (nonmelanoma), Skin cancer (melanoma), Skin carcinoma. Merkel cell, Small cell lung cancer, Small intestine cancer, Soft tissue sarcoma, Squamous cell carcinoma-see Skin cancer (nonmelanoma). Squamous neck cancer with occult primary, metastatic. Stomach cancer, Supratentorial primitive neuroectodermal tumor, childhood, T-Cell lymphoma, cutaneous-see Mycosis Fungoides and Sezary syndrome, Testicular cancer, Throat cancer, Thymoma, childhood, Thymoma and Thymic carcinoma, Thyroid cancer, Thyroid cancer, childhood. Transitional cell cancer of the renal pelvis and ureter, Trophoblastic tumor, gestational, Unknown primary site, carcinoma of, adult, Unknown primary site, cancer of, childhood, Ureter and renal pelvis, transitional cell cancer, Urethral cancer. Uterine cancer, endometrial, Uterine sarcoma. Vaginal cancer, Visual pathway and hypothalamic glioma, childhood, Vulvar cancer, Waldenström macroglobulinemia, Wilms tumor (kidney cancer), childhood.

Other Diseases

The present invention can also be useful in screening for biomarkers associated with any other disease or condition. Such diseases and conditions range from the neurological diseases, autoimmune diseases and cancers identified above as well as any other disease or condition that has a biomarker such as an antibody or other characterizing protein or biomolecule associated with the disease or progression of the disease. These diseases and conditions specifically include inflammatory disease, infectious disease, cardiovascular disease and metabolic disease. Specific infectious diseases include, but is not limited to AIDS, anthrax, botulism, brucellosis, chancroid, chlamydial infection, cholera, coccidioidomycosis, cryptosporidiosis, cyclosporiasis, dipheheria, ehrlichiosis, arboviral encephalitis, enterohemorrhagic *Escherichia coli*, giardiasis, gonorrhea, dengue fever, haemophilus influenza, Hansen's disease (Leprosy), hantavirus pulmonary syndrome, hemolytic uremic syndrome, hepatitis A, hepatitis B, hepatitis C, human immunodeficiency virus, legionellosis, listeriosis, lyme disease, malaria, measles. Meningococcal disease, mumps, pertussis (whooping cough), plague, paralytic poliomyelitis, psittacosis, Q fever, rabies, rocky mountain spotted fever, rubella, congenital rubella syndrome (SARS), shigellosis, smallpox, streptococcal disease (invasive group A), streptococcal toxic shock syndrome, *Streptococcus pneumonia*, syphilis, tetanus, toxic shock syndrome, trichinosis, tuberculosis, tularemia, typhoid fever, vancomycin intermediate resistant *staphylocossus aureus*, varicella, yellow fever, variant Creutzfeldt-Jakob disease (vCJD), Ebola hemorrhagic fever, Echinococcosis, Hendra virus infection, human monkeypox, influenza A, H5N1, lassa fever, Margurg hemorrhagic fever, Nipah virus. O'nyong fever, Rift valley fever, Venezuelan equine encephalitis and West Nile virus.

Antibody

In some embodiments, a peptoid described herein can bind a disease-associated antibody. An antibody, also known as an immunoglobulin (Ig), is a large, Y-shape protein produced by plasma cells that can be used by the immune system of an animal to identify and neutralize pathogens, for example bacteria and viruses. Antibody recognizes a unique molecule of the harmful agent, called an antigen, via the variable region. Each tip of the "Y" of an antibody contains a paratope (analogous to a lock) that is specific for one particular epitope (similarly analogous to a key) on an antigen, allowing these two structures to bind together with precision. Using this binding mechanism, an antibody can tag a microbe or an infected cell for attack by other parts of the immune system, or can neutralize its target directly (for example, by blocking a part of a microbe that is essential for its invasion and survival). The ability of an antibody to communicate with the other components of the immune system is mediated via its Fc region (located at the base of the "Y"), which contains a conserved glycosylation site involved in these interactions. The production of antibodies is the main function of the humoral immune system.

The adaptive immune system is known to react specifically to many different disease states, in part through the amplification of particular antibodies that recognize disease-specific antigens. Thus, it is possible to devise diagnostic tests for many different diseases based on the measurement of the levels and/or presence of disease specific antibodies in biological fluids such as serum, tissues or any biological fluid described herein. The current invention recites design and synthesis of ligands, and ligand libraries wherein the ligands or ligand libraries can be differentially screened for ligands binding disease specific biomarkers, for example antibodies. In some embodiments the ligands can be molecules having an affinity to IgA, IgM, IgE, IgD, IgG antibodies and or fragments thereof. In some instances, the ligand can have an affinity to two or more of IgA, IgM, IgE, IgD, IgG antibodies and or fragments thereof. In some embodiments, IgG antibody can include, for example, IgG1, IgG2, IgG3, IgG4, and the IgA can include, for example, IgA1 or IgA2.

In some aspects, the molecules can have a binding affinity of at least $10^{-5}$M ($K_D$) for a molecule. In some embodiments, at least 1% to 100% of a plurality of molecules described herein can have a binding affinity of at least $10^{-5}$M ($K_D$) for an antibody. At least one of the molecules described herein can have a binding affinity of at least $10^{-5}$M ($K_D$), such as at least $10^{-5}$M, $10^{-4}$M, $10^{-7}$M, $10^{-8}$ M, $10^{-9}$M, $10^{-10}$M, $10^{-11}$ M, $10^{-12}$M, $10^{-13}$ M, $10^{-14}$ M, $10^{-15}$M, or $10^{-16}$M, for its target. At least 1% of the ligands described herein or of the ligand library described herein can be monospecific. For example, at least 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% of the ligands in the library can be monospecific and at least one of the ligands in the library can have a binding affinity of at least at least $10^{-5}$M, $10^{-6}$M, $10^{-7}$M, $10^{-8}$M, $10^{-9}$M, $10^{-10}$ M, $10^{-11}$M, $10^{-12}$M, $10^{-13}$M, $10^{-14}$M, $10^{-15}$M, or $10^{-16}$ M for an antibody. In some embodiments, a ligand can have different binding affinity for a first target and a second target. In some embodiments, a ligand can have the binding affinity for a first target and a second target. In some embodiments, the target can be an antibody.

Combinatorial Library

The term "combinatorial library" or "library" refers to a library in which the individual molecules are either systematic or random combinations of a limited set of basic elements, the properties of each ligand being dependent on the choice and location of the elements incorporated into it. In some embodiments, the ligands of the library can be screened simultaneously. The ligands of a combinatorial library can be oligomers or polymers of some kind, in which the variation occurs through the choice of monomeric building block at one or more positions of the oligomer or polymer, and possibly in terms of the connecting linkage, or the length of the oligomer or polymer. Ligands of the library can be nonoligomeric ligands with a standard core structure, with the variation being introduced by the choice of substituents at particular variable sites on the core structure. Ligands of the library may be nonoligomeric molecules assembled like a jigsaw puzzle, but wherein each piece has both one or more variable moieties (contributing to library diversity) and one or more constant moieties (providing the functionalities for coupling the piece in question to other pieces). In some embodiments, ligand building blocks can be at least partially randomly combined into a large number of different compounds, which are then simultaneously screened for binding (or other) activity against one or more targets. In some embodiments, the building blocks are not randomly combined. In some embodiments, the combinatorial library described herein may contain less than about $10^1$, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, or $10^{20}$ different molecules. In some embodiments, the combinatorial library described herein may contain at least about $10^1$, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, or at least $10^{20}$ different molecules.

Combinatorial Libraries of Peptoids May be Prepared as Follows

Peptoids can be synthesized via techniques known in the art. In some aspects, the synthesis can be performed using combinatorial methods for solution phase synthesis. In some embodiments, the synthesis can be performed using combinatorial methods for solid phase synthesis. In some embodiments, the synthesis can be performed using combinatorial methods for a combination of solution phase and solid phase synthesis techniques. *Comprehensive Biomaterials* (2011), vol. 2, pp. 53-76 is hereby incorporated by reference in its entirety. In some embodiments, peptoid synthesis can be automated. In some embodiments, peptoids can be synthesis via parallel synthesis. In some embodiments, peptoids can be synthesized via split pool (split/mix) synthesis. In some embodiments, peptoids can be synthesized via spot synthesis. In some embodiments, peptoids can be synthesized using a microwave assisted synthesis protocol. "*Combinatorial Chemistry*", *Chemical and Engineering News*, Feb. 24, 1997, p. 43; Thompson et al., *Chem. Rev.* (1996) 96:555); Fodor et al., *Science* 251 (1991) 767; U.S. Pat. No. 5,143,854: WO 93/09668 are hereby incorporated by reference.

Peptoids having a cysteine or methionine monomeric amino acid attached to a support or a linker on a support or resin or bead can be prepared by first adding a protected amino acid to a support or linker on a support. Following addition of said amino acid (or any amino acid desired which can serve a functional or other purpose in the oligomer or a diagnostic having said oligomer), remaining monomers can be added using standard peptide chemistry or using sub-monomers of bromoacetic acid (or α-substituted bromoacetic acid or similar reactant) and a monosubstituted amine wherein the amine is substituted with an R group. The R group may be selected from any known peptoid substituent including those described in, for example, U.S. Pat. Publication Nos. 2010/0303805 or 2010/0303835, those described in Zuckermann and various Kodadek publications and those described herein. U.S. Pat. Publication Nos. 2010/0303805 and 2010/0303835 are hereby incorporated by reference in their entirety.

In detail, the process to make each peptoid generally can involve (1) preparation of an amino acid reactant on a support (including an optional linker on a support): (2) reaction of the amino acid moiety on said support with an acyl halide such as bromoacetic acid or chloroacetic acid to form a halogenated derivative (3) reaction of the halogenated derivative with a monosubstitued amine to form an amide and (4) repeat of steps (2) and (3) to form a peptoid. Methionine or cysteine containing peptoids can be made in the large libraries. In some embodiments, A PEG linker can be on a bead or resin. In some embodiments, the PEG linker can be a short linker of less than about 10 monomeric units. In some embodiments, the PEG linker can be a long linker of more than about 10 monomeric units.

The conditions used to perform each step in the oligomer building process can utilize solvents such as DMF or acetonitrile or dichloromethane. Trifluoroacetic acid can be utilized for cleavage purposes and piperidine or other suitable base can be used as a base in the reaction between a bromo derivative and an amine. Various protecting groups can be utilized in the preparation of the amino acid reactant. In some embodiments, diaminobutane can be utilized as the first amine submonomer in the chain adjacent to the cysteine residue at the C-terminus of the peptoid. In the first step of the process, the selected beads or resins (in gram or milligram quantities) can be swollen in a suitable solvent such as DMF. If the beads are "protected" with a protecting group on the reactive amine on said bead, a base solution such as piperidine can be repeatedly added with subsequent washing with DMF to deprotect the bead. Once the bead is deprotected or if a bead such as a TentaGel® bead is initially utilized, it can be reacted with a suitable amino acid such as cysteine or methionine (protected with Fmoc or other suitable protecting group on the nitrogen and protected with Trt (triphenylmethyl) on the sulfur and in sufficient molar quantities to react with each bead) in a suitable solvent such as DMF. HBTU (tetramethyluronium hexafluorophosphate (coupling reagent) and 4-methylmorpholine (base) along with the protected amino acid can be added to the bead solution in a beaker (or tube or flask) and shaken at room temperature to form the Fmoc/Trt protected amino acid on the resin (or on a linker on the resin). The beads can then be washed multiple times in a solvent such as DMF. The Fmoc group can be then deprotected using a suitable reagent which permits reaction of the amine on the amino acid with another reactant such as another protected amino acid or a submonomer such as bromoacetic acid and an activating agent e.g. DIC (3-isopropylcarbodiimide) in a suitable solvent under heat for example, microwave with stirring. The resultant beads can be washed multiple times and then treated with a desired monomeric amine in a suitable solvent under heat. The resultant beads can be washed multiple times and then treated repeatedly with bromoacetic acid and the amine of choice to build the oligomer and oligomeric library. The peptoids may be cleaved from the beads using triflouroacetic acid.

In some embodiments, peptoids having cysteine adjacent to a monomer having a 1-yl-n-butylamine can include building a peptoid having two amino acids on the C-terminus followed by a process that further includes adding any of the monomers built in a submonomer process wherein the second amino acid is lysine. This can further include the selection of any monomer or submonomer to make α-substituted bromoacetic acid submonomers wherein the carbon substituents may be selected from typical amino acid side chains to form, after reaction of the reactants, α-substituted peptoids wherein an R group is found on either or both of the carbon on the peptoid chain or the nitrogen on the peptoid chain.

Combinatorial libraries of small molecules may be obtained commercially or prepared using methods known in the art. See for example, Eichler et al., 1995; Cho et al., 1999; LePlae et al., 2002; Ostergaard and Holm, 1997; Yang et al., 1999). In addition, U.S. Pat. No. 6,344,334 and publications Gallop et al., (1994), Gordon et al., (1994) Thompson and Ellman (1996) are also sources of such molecules and libraries, each of which are hereby incorporated by reference in their entirety.

Combinatorial libraries of peptides can be obtained commercially or prepared using methods known in the art. See, for example, Stewart and Young (1984): Tam et al. (1983); Merrifield (1986); and Barany and Merrifield (1979), each of which are hereby incorporated by reference in their entirety.

Combinatorial libraries of nucleic acids including RNA or DNA can be obtained commercially or prepared using methods known in the art. Combinatorial libraries of oligosaccharides may be obtained commercially or prepared using methods known in the art.

In each instance, the "ligands" can be added to a support, support resins or beads to form libraries, under the conditions described herein. The libraries can be screened for biomarkers in a sample, for example a biomarker containing sample, for example biological fluid. In some embodiments, the ligands can be a peptoid. In some embodiments, a ligand can by synthesize, in part, from submonomers, which can be selected from any known monomeric amine and from any known acetic acid halide or substituted acetic acid halide. For example, Table 1 provides a range of R groups on a monosubstituted amine that may be selected:

TABLE 1

Side chain modifications for peptoids

Amine Side Chain,
NH2R
n-Bu1
—CH2CH2—CH(Ph)2
—CH2Ph
—CH2CH2OH
—OH

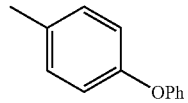

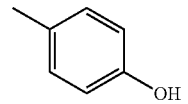

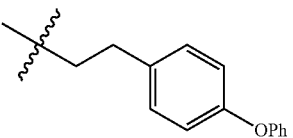 [SMILES: *CCc1ccc(Oc2ccccc2)cc1]

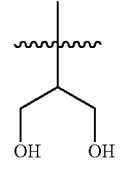

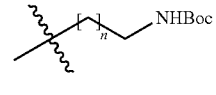

n = 0-4

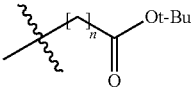

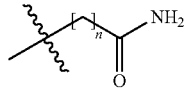

TABLE 1-continued
Side chain modifications for peptoids
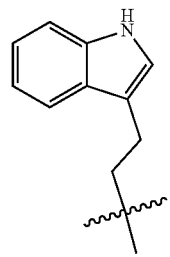 [SMILES: *CCc1c[nH]c2ccccc12]
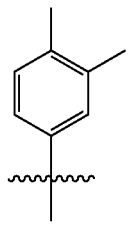 [SMILES: *c1ccc(C)c(C)c1]
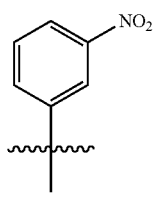 [SMILES: *c1cccc([N+](=O)[O-])c1]
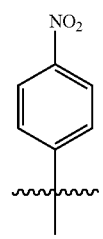
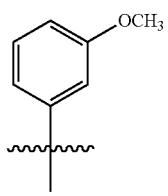 [SMILES: *c1cccc(OC)c1]
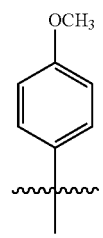
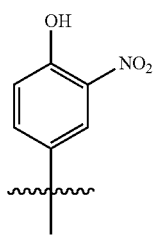
TABLE 1-continued
Side chain modifications for peptoids
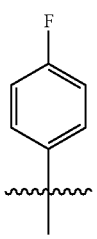
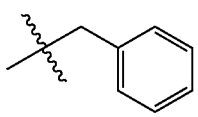 [SMILES: *Cc1ccccc1]
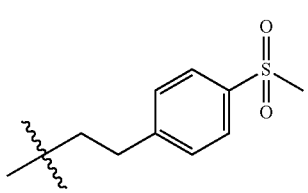 [SMILES: *CCc1ccc(S(C)(=O)=O)cc1]
-nPr
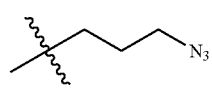 [SMILES: *CCCN=[N+]=[N-]]
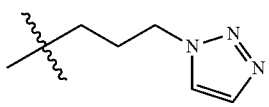 [SMILES: *CCCn1ccnn1]
—CH2CH2CH2OMe
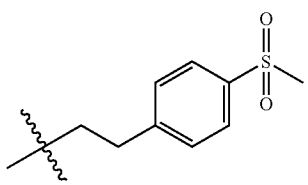 [SMILES: *CCc1ccc(S(C)(=O)=O)cc1]
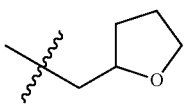 [SMILES: *CC1CCCO1]
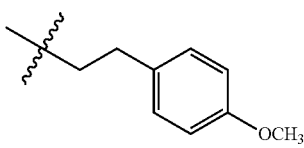 [SMILES: *CCc1ccc(OC)cc1]
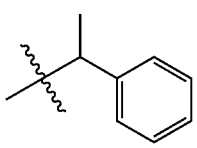 [SMILES: *C(C)c1ccccc1]

TABLE 1-continued
Side chain modifications for peptoids
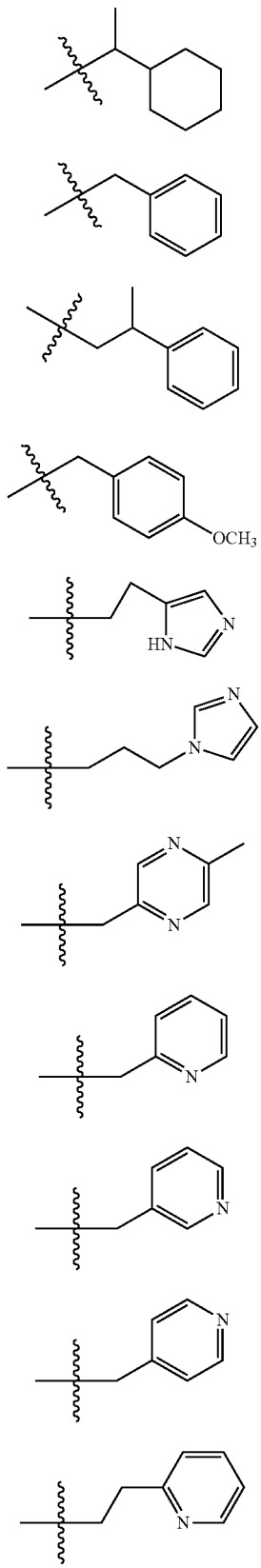
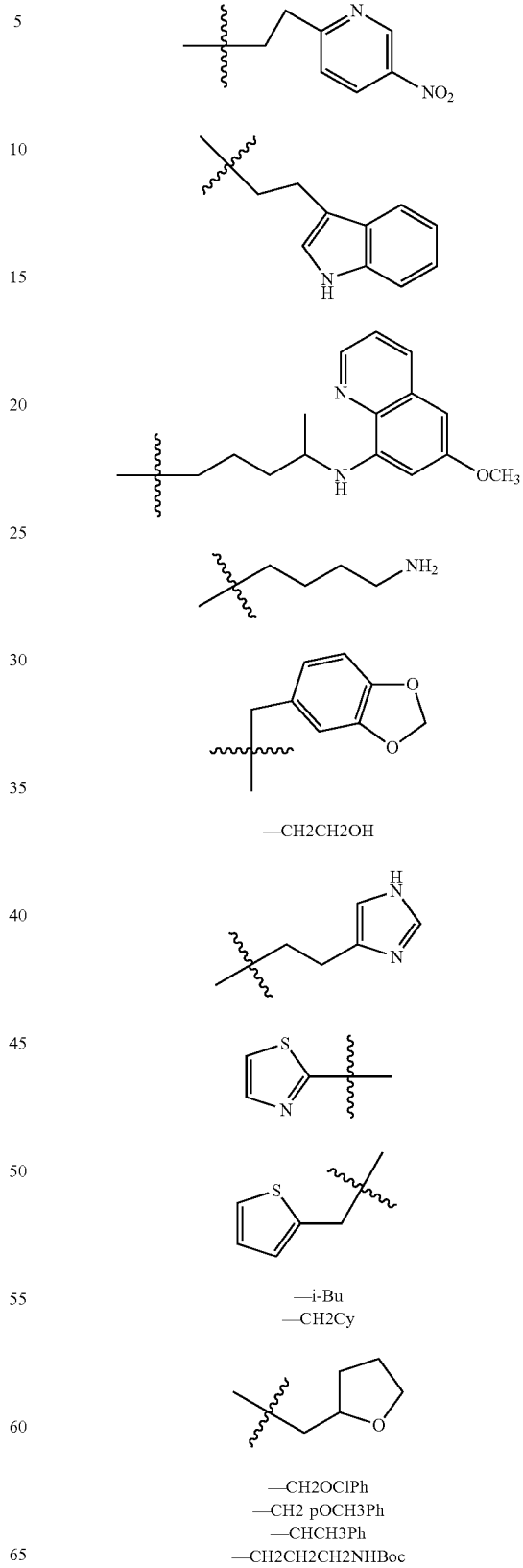
—CH2CH2OH
—i-Bu
—CH2Cy
—CH2OClPh
—CH2 pOCH3Ph
—CHCH3Ph
—CH2CH2CH2NHBoc TABLE 1-continued
Side chain modifications for peptoids
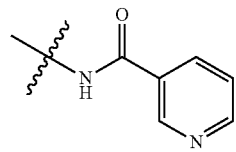 [SMILES: *NC(=O)c1cccnc1]
—CH2CH2OMe
—CH2CH2CH2OH
—CH(CH3)CH2OH
—CH2CHOHCH2OH
—CH2CH(OH)Ph
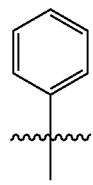 [SMILES: *c1ccccc1]
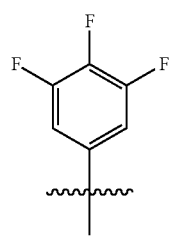
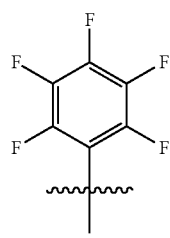 [SMILES: *c1c(F)c(F)c(F)c(F)c1F]
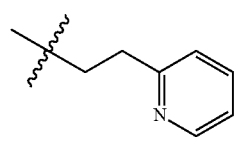 [SMILES: *CCc1ccccn1]
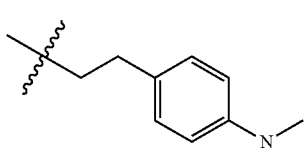
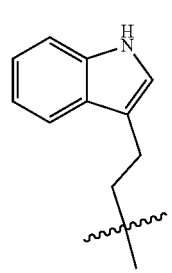 [SMILES: *CCc1c[nH]c2ccccc12]
TABLE 1-continued
Side chain modifications for peptoids
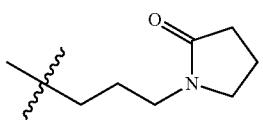 [SMILES: *CCCN1CCCC1=O]
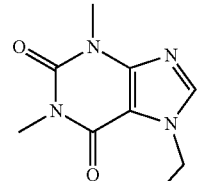
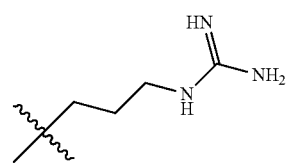 [SMILES: *CCCNC(=N)N]
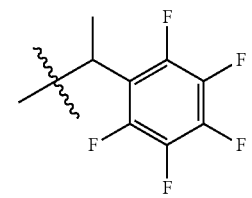 [SMILES: *C(C)c1c(F)c(F)c(F)c(F)c1F]
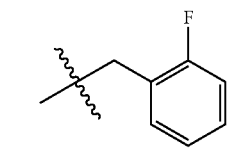 [SMILES: *Cc1ccccc1F]
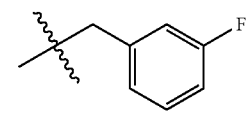 [SMILES: *Cc1cccc(F)c1]
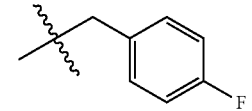 [SMILES: *Cc1ccc(F)cc1]
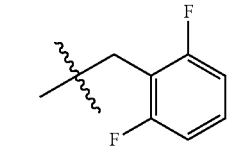 [SMILES: *Cc1c(F)cccc1F]
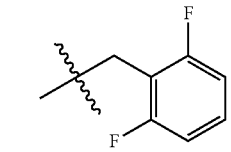 [SMILES: *Cc1c(F)cccc1F]

TABLE 1-continued
Side chain modifications for peptoids
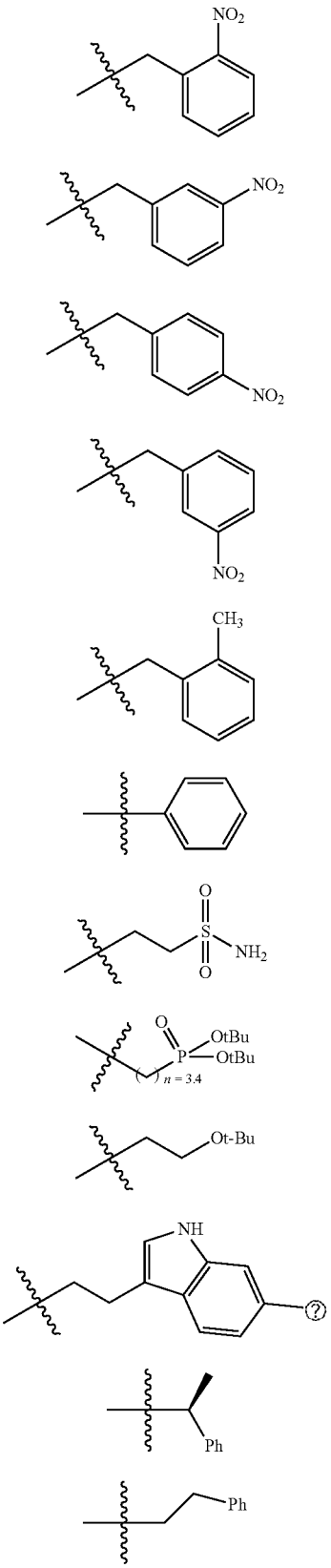
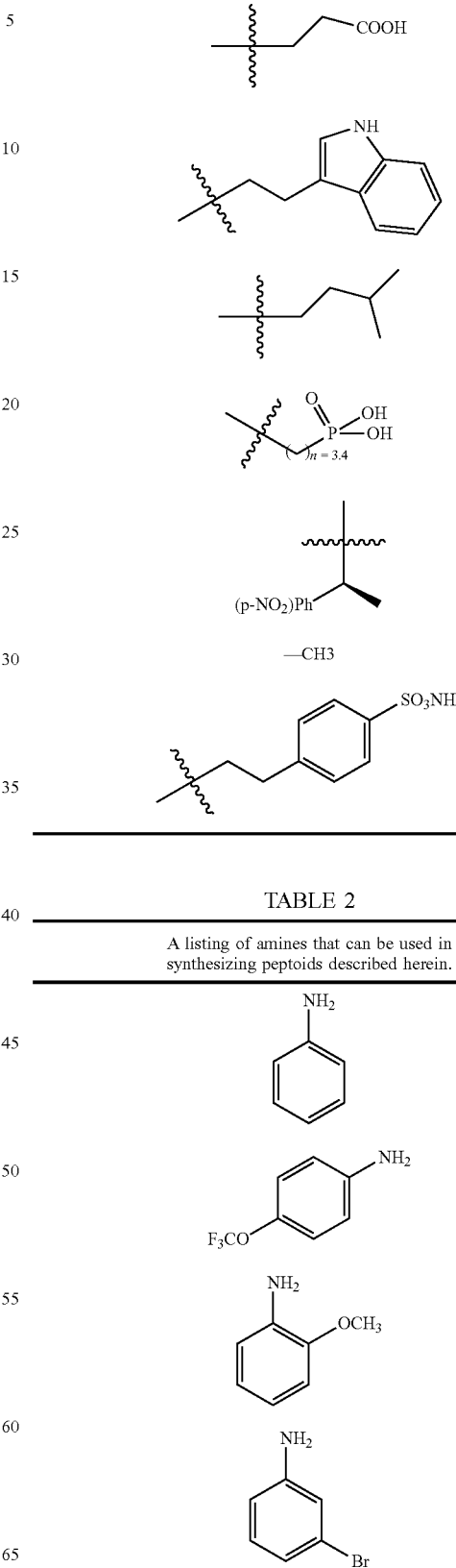
TABLE 2
A listing of amines that can be used in synthesizing peptoids described herein.

TABLE 2-continued
A listing of amines that can be used in synthesizing peptoids described herein.
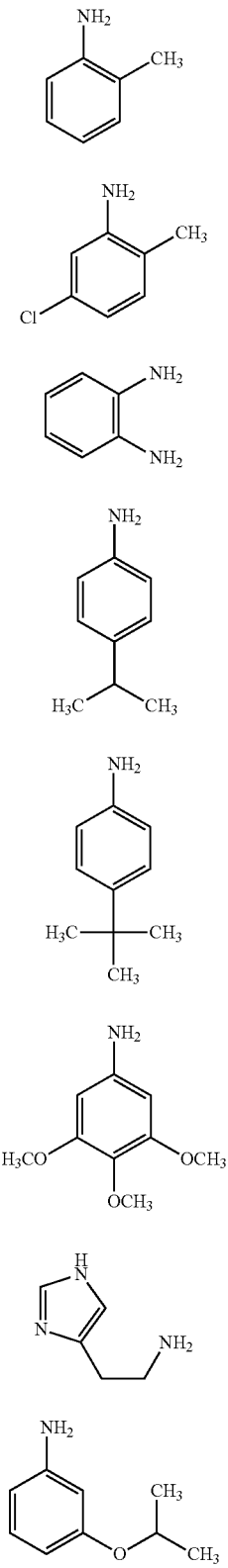
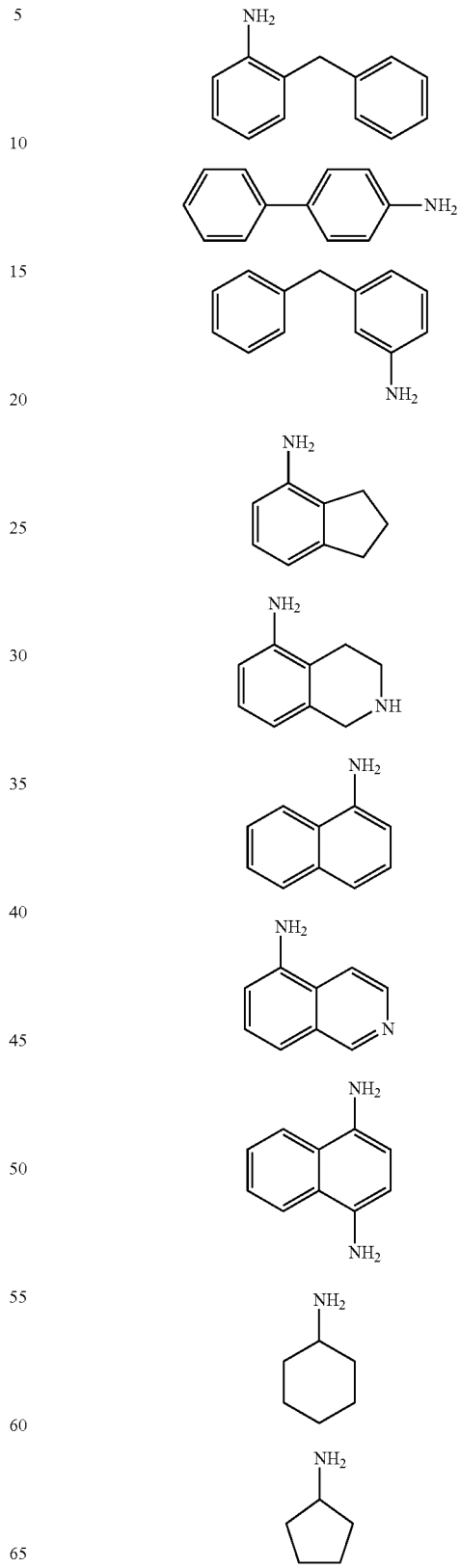

TABLE 2-continued
A listing of amines that can be used in synthesizing peptoids described herein.
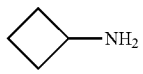
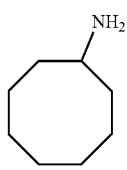
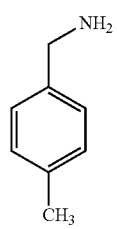
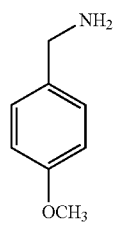
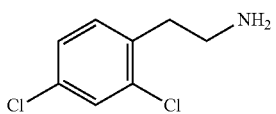 [SMILES: NCCc1ccc(Cl)cc1Cl]
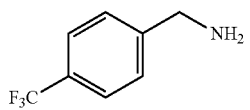 [SMILES: NCc1ccc(C(F)(F)F)cc1]
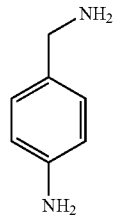
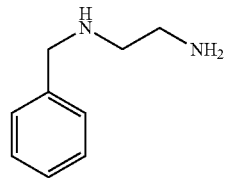 [SMILES: NCCNCc1ccccc1]
TABLE 2-continued
A listing of amines that can be used in synthesizing peptoids described herein.
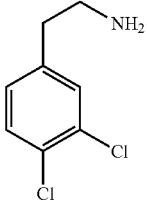 [SMILES: NCCc1ccc(Cl)c(Cl)c1]
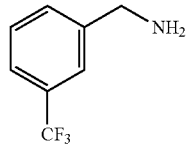 [SMILES: NCc1cccc(C(F)(F)F)c1]
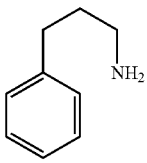
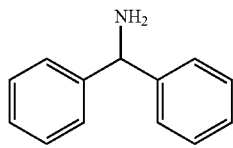 [SMILES: NC(c1ccccc1)c1ccccc1]
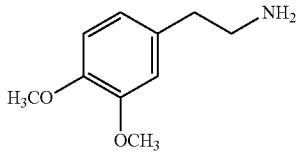 [SMILES: COc1ccc(CCN)cc1OC]
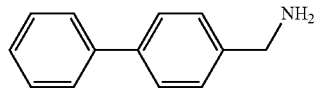 [SMILES: NCc1ccc(-c2ccccc2)cc1]
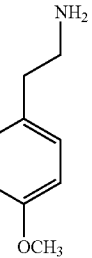
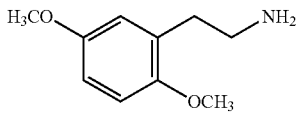
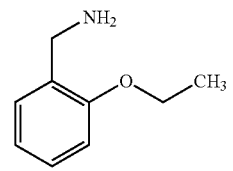

TABLE 2-continued
A listing of amines that can be used in
synthesizing peptoids described herein.
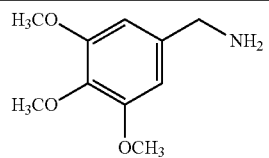
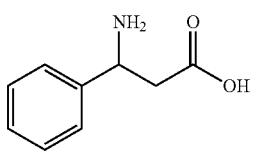 [SMILES: NC(CC(=O)O)c1ccccc1]
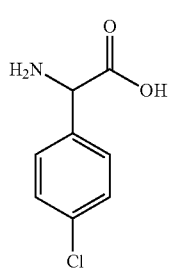
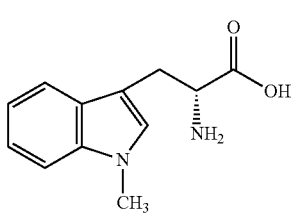 [SMILES: Cn1cc(C[C@@H](N)C(=O)O)c2ccccc21]
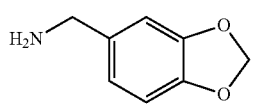
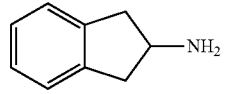
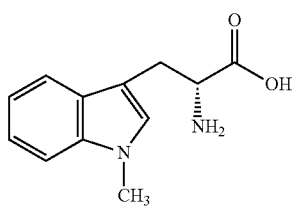 [SMILES: Cn1cc(C[C@@H](N)C(=O)O)c2ccccc21]
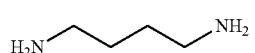
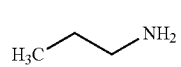
CH3OOCH2CH2NH2
TABLE 2-continued
A listing of amines that can be used in
synthesizing peptoids described herein.
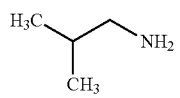
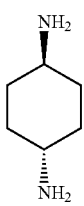
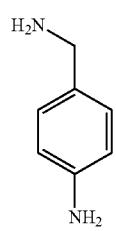
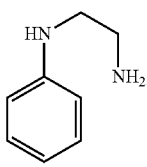
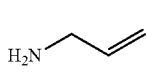
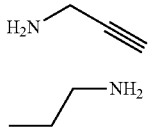
CF3CH2NH2
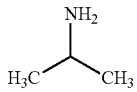
CH3(CH2)4CH2NH2
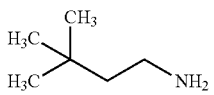
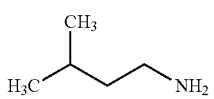
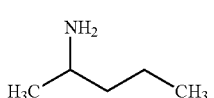
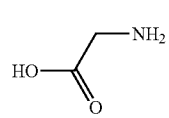

TABLE 2-continued
A listing of amines that can be used in synthesizing peptoids described herein.
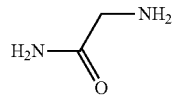
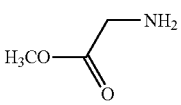
Any amino acid
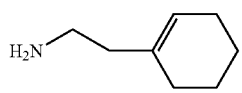
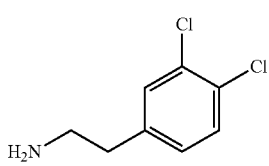 [SMILES: NCCc1ccc(Cl)c(Cl)c1]
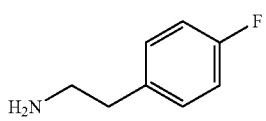
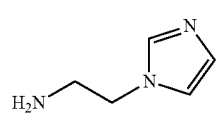
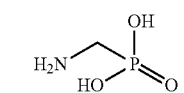
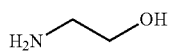
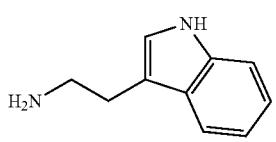
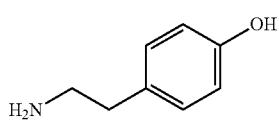
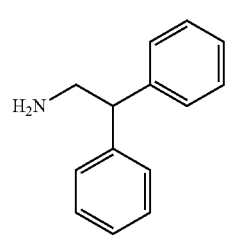 [SMILES: NCC(c1ccccc1)c1ccccc1]
TABLE 2-continued
A listing of amines that can be used in synthesizing peptoids described herein.
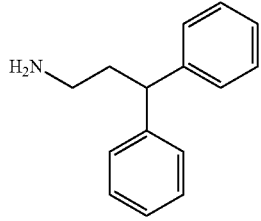 [SMILES: NCCC(c1ccccc1)c1ccccc1]
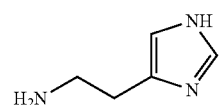
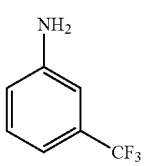
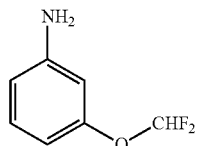
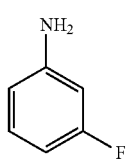
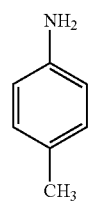
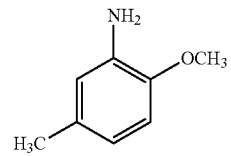
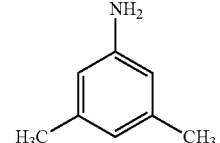
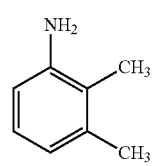

TABLE 2-continued
A listing of amines that can be used in synthesizing peptoids described herein.
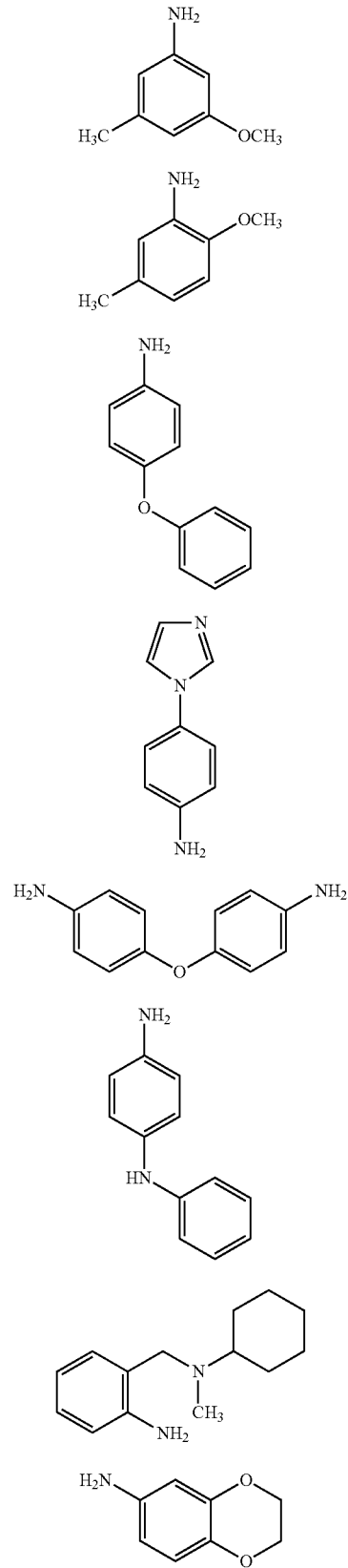
TABLE 2-continued
A listing of amines that can be used in synthesizing peptoids described herein.
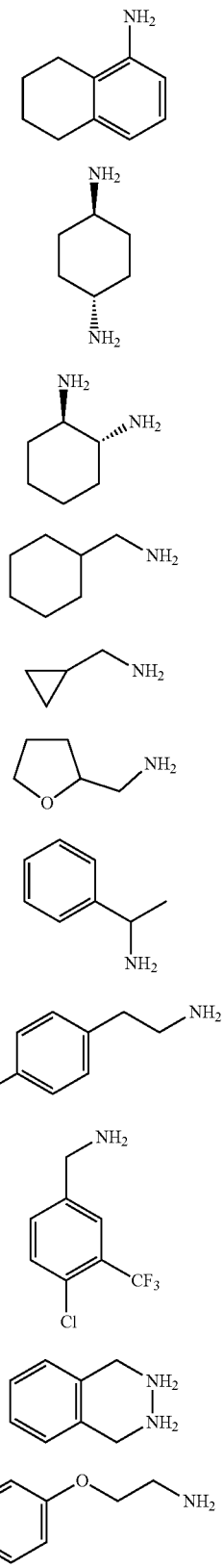

TABLE 2-continued
A listing of amines that can be used in synthesizing peptoids described herein.
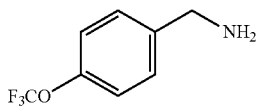
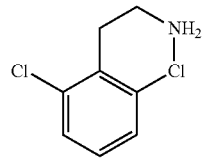
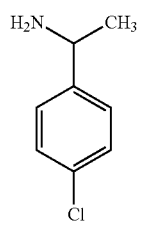
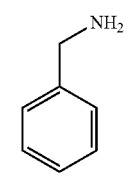
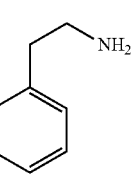
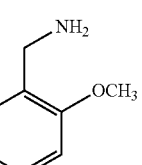
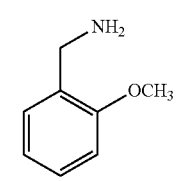
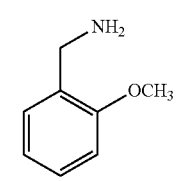
TABLE 2-continued
A listing of amines that can be used in synthesizing peptoids described herein.
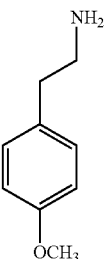
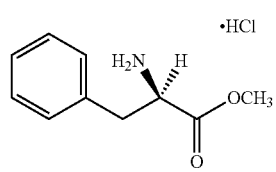 [SMILES: Cl ; COC(=O)[C@H](N)Cc1ccccc1]
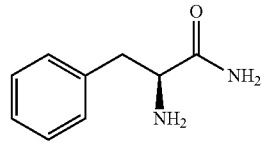 [SMILES: NC(=O)[C@@H](N)Cc1ccccc1]
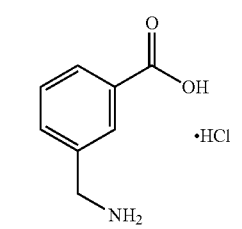 [SMILES: NCc1cccc(C(=O)O)c1 ; Cl]
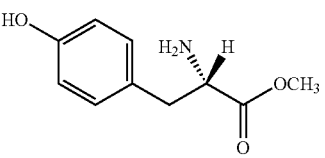 [SMILES: COC(=O)[C@@H](N)Cc1ccc(O)cc1]
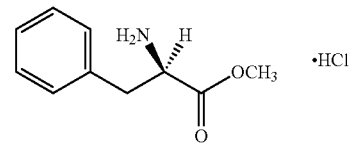 [SMILES: COC(=O)[C@H](N)Cc1ccccc1 ; Cl]
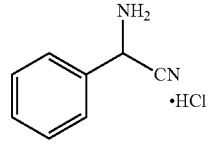
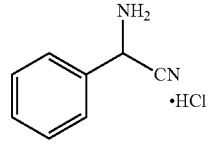

TABLE 2-continued

A listing of amines that can be used in synthesizing peptoids described herein.

TABLE 2-continued

A listing of amines that can be used in synthesizing peptoids described herein.

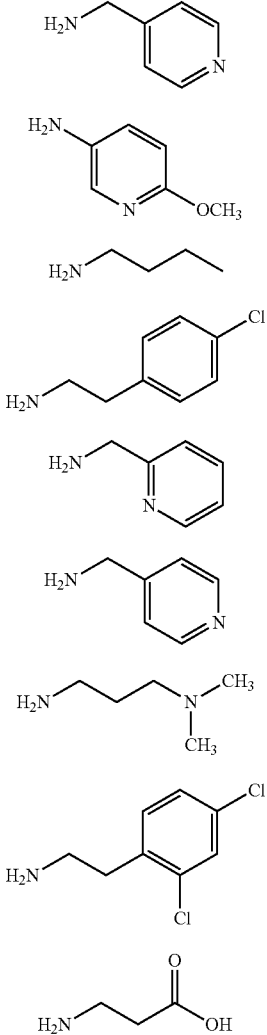

Peptoids disclosed herein may employ modified, non-natural and/or unusual amino acids. Non-natural residues include, but are not limited to 2-Aminoadipic acid, N-Ethylasparagine, 3-Aminoadipic acid, Hydroxylysine, beta-alanine, allo-Hydroxylysine propionic acid, 2-Aminobutyric acid, 3-Hydroxyproline, 4-Aminobutyric acid, 4-Hydroxyproline piperidinic acid, 6-Aminocaproic acid, Isodesmosine, 2-Aminoheptanoic acid, allo-Isoleucine, 2-Aminoisobutyric acid, N-Methylglycine, 3-Aminoisobutyric acid, N-Methylisolcucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, and N-Ethylglycine. Peptoid residues such as 2-methoxyethylamine ethanolamine, fufurylamine can be incorporated using conventional submonomer chemistry. In some embodiments, mononomers and/or submonombers for the purposes of the invention may further comprise benzylamine, methylamine, allylamine, isobutylamine, 4-(Aminomethyl)pyridine, 4-(2-Aminoethyl)morpholine, 3,4-Dimethoxybenzylamine, 2,2-Diphenylethylamine, piperonylamine, R-(+)-α-Methylbenzylamine, Cyclopropylamine, 1,4-diaminobutane, Glycine, 2-Aminoethanol) and or those listed in table 2.

Molecules described herein can include R groups on either the amine side chain or the alpha carbon and can be independently selected from the group of hydrogen; alkyl: allyl; methyl; ethyl; n-propyl; isopropyl; n-butyl; isobutyl; n-butylamine; sec-butyl: tert-butyl; pentyl; hexyl; isopentyl; aryl; hetero aryl; furanyl: indolyl; thiophenyl; thiazolyl; imidazolyl; isoxazoyl; oxazoyl; piperonyl; pyrazoyl; pyrrolyl; pyrazinyl: pyridyl: pyrimidyl: pyrimidinyl; purinyl; cinnolinyl: benzofuranyl; benzothienyl; benzotriazolyl; benzoxazolyl; quinoline; isoxazolyl: isoquinoline cycloalkyl; alkenyl; cycloalkenyl: phenyl; pyridyl; methoxyethyl; (R)-methylbenzyl; $C_{0-6}$ alkylaryl; $C_{0-6}$ alkylheteroaryl; $C_{1-6}$ alkyl substituted with a group selected from OH, SH, a halogen, $OR^{15}$, $COOR^{15}$, $NR^{15}$ (wherein $R^{15}$ is selected from the group consisting of H or $C_{1-6}$alkyl or $C_{1-6}$ alkynl) or $R^{16}$ (wherein $R^{16}$ is selected from the group consisting of H or $C_{1-6}$ alkynl); $OC_{1-6}$ alkyl; $C_{2-6}$ alkenyl: $C_{2-6}$ alkynyl: $C_{2-6}$ alkenyl: and $C_{2-6}$ alkynyl-including one or more chemical group described in Tables 1 and 2 below.

In some embodiments, molecules can include R groups independently selected from hydrogen; $C_{1-6}$ alkyl; $C_{2-4}$ alkenyl; $C_3$-$C_8$cycloalkyl; $C_1$-$C_6$alkylheteroaryl; $C_1$-$C_6$alkylaryl: wherein any one of said alkyl or alkenyl groups may be optionally substituted with OH, a halogen, $NH_2$ or COOH; wherein any one of said aryl or heteroaryl groups may be optionally substituted with OH, halogen, $OCH_3$, $SO_2NH_2$ or $OCH_2O$ Support The choice of a suitable support will be routine to the skilled artisan. In some embodiments, important criteria may include that the reactivity of the support not interfere with the reactions required to prepare the library. In some embodiments, the support can be insoluble. In some embodiments, the support can be a polymeric support. In some embodiments, insoluble polymeric supports can include functionalized polymers based on polystyrene, polystyrene/divinylbenzene copolymers, and the like. It will be understood that the polymeric support may be coated, grafted or otherwise bonded to other solid supports. In another embodiment, the support may be provided by reversibly soluble polymers. Such supports can include functionalized polymers based on polyvinyl alcohol and/or polyethylene glycol (PEG). A soluble support can be made insoluble (e.g., may be made to precipitate) by addition of a suitable inert nonsolvent.

A number of reactive groups can be used for coupling such as Carboxylic acid (—COOH), Hydrazide (—CONHNH$_2$), Primary aliphatic amine (—RNH$_2$), Aldehyde (—CHO), Aromatic amine (—ArCH$_2$Cl), Hydroxyl (—OH), Chloromethyl (vinyl benzyl chloride) (—ArCH$_2$Cl), Thiol (—SH), Amide (—CONH$_2$), and Epoxy (—COC—).

In certain aspects, a peptoid as described herein can comprise a terminal functional group, at either the carboxy or amino terminus. In some instances, the functional group can be capable of being coupled to a support, a linker moiety, a label, substrate or other moieties. In some embodiments, a terminal cysteine residue can be coupled to a peptoid and can provide a sulfhydryl group for further coupling the peptoid to a substrate. In some embodiments, the carboxy terminus can comprise an NH$_2$, OH, or other chemical group that can be further reacted with a substrate (directly or indirectly) or a linker, or a label, or other moiety. For example, a wide variety of labels may be used, including directly detectable labels such as dyes, such as luminescers and fluorescers (e.g. rhodamine, lanthanide-based dyes, etc.) and indirectly detectable labels such as enzymes and haptens, including digoxigenin, biotin, etc. Examples of additional labels can include, but are not limited to, Glutathione-S-transferase (GST), Maltose binding protein (MBP), Green Fluorescent Protein (GFP), AviTag, Calmodulin-tag, polyglutamate tag, FLAG-tag, HA-tag, His tag, Myc-tag, S-tag, SBP-tag, Softag 1, Strep-tag, TC tag, V5 tag, Xpress tag, Isopeptag, SpyTag or a combination thereof.

A wide variety of linkers can be used. The linker component in its simplest form can be a bond between the peptoid and a second moiety, such as a substrate or other entity. More generally, the linker can provide a mono- or multi-molecular skeleton covalently or non-covalently linking one or more peptoid to one or more substrates or moieties. Thus, linking of a peptoid described herein to a desired substrate or moiety can be achieved by covalent or non-covalent means, usually involving interaction with one or more functional groups located on the peptoid and/or substrate or second entity. Examples of chemically reactive functional groups which may be employed for this purpose can include but is not limited to amino, hydroxyl, sulfhydroxyl, carboxyl and carbonyl groups, as well as carbohydrate groups, vicinal diols, thioethers, 2-aminoalcohols, 2-aminothiols, guanidinyl, imidazolyl and phenolic groups.

Supports can be made of any suitable material. In some embodiments, materials utilized to make such supports can include without limitation, for example, glass, plastic, ceramic or polymeric resins or beads. Supports can also include materials such as nickel, brass, steel or other metals or mixtures of metals. In some embodiments, a support can be covered partially or fully with a substrate. The substrate can be planar or a particle and can comprise a solid or porous material. The substrate may be either organic or inorganic, biological or non-biological, or any combination of these materials. The substrate can transparent or translucent. The substrate or portions thereof can be flat and firm or semi-firm. Numerous materials are suitable for use as a substrate. The substrate can comprise silicon, silica, glass, or a polymer. For instance, the substrate can comprise a material selected from a group consisting of silicon, silica, quartz, glass, controlled pore glass, carbon, alumina, titanium dioxide, germanium, silicon nitride, zeolites, and gallium arsenide. Many metals such as gold, platinum, aluminum, copper, titanium, and their alloys can also be used for substrates of the array. In addition, many ceramics and polymers can also be used as substrates. Polymers which can be used as substrates include, but are not limited to, the following: polystyrene; poly(tetra)fluorethylene; (poly)vinylidenedifluoride; polycarbonate; polymethylmethacrylate; polyvinylethylene; polyethyleneimine; poly(etherether)ketone; polyoxymethylene (POM); polyvinylphenol; polylactides; polymethacrylimide (PMI); polyalkenesulfone (PAS); polyhydroxyethylmethacrylate; polydimethylsiloxane; polyacrylamide; polyimide; co-block-polymers; and Eupergit® Photoresists, polymerized Langmuir-Blodgett films, and LIGA structures.

A substrate may be modified with one or more different layers of compounds or coatings that serve to modify the properties of the surface in a desirable manner. For example, a substrate may further comprise a coating material on the whole or a portion of the surface of the substrate. In some embodiments, a coating material enhances the affinity of the ligand, and a binding moiety contained in the sample, or another moiety (e.g., a functional group) for the substrate. For example, the coating material can be nitrocellulose, silane, thiol, disulfide, or a polymer. When the material is a thiol, the substrate may comprise a gold-coated surface and/or the thiol comprises hydrophobic and hydrophilic moieties. When the coating material is a silane, the substrate can comprise glass and the silane may present terminal moieties including, for example, hydroxyl, carboxyl, phosphate, glycidoxy, sulfonate, isocyanato, thiol, or amino groups. In an alternative embodiment, the coating material may be a derivatized monolayer or multilayer having covalently bonded linker moieties. For example, the monolayer coating may have thiol (e.g., a thioalkyl selected from the group consisting of a thioalkyl acid (e.g., 16-mercaptohexadecanoic acid), thioalkyl alcohol, thioalkyl amine, and halogen containing thioalkyl compound), disulfide or silane groups that produce a chemical or physicochemical bonding to the substrate. The attachment of the monolayer to the substrate may also be achieved by non-covalent interactions or by covalent reactions.

After attachment to a substrate, the coating can comprise at least one functional group. Examples of functional groups on the monolayer coating include, but are not limited to, carboxyl, isocyanate, halogen, amine or hydroxyl groups. In one embodiment, these reactive functional groups on the coating may be activated by standard chemical techniques to corresponding activated functional groups on the monolayer coating (e.g., conversion of carboxyl groups to anhydrides or acid halides, etc.). Exemplary activated functional groups of the coating on the substrate for covalent coupling to terminal amino groups include anhydrides, N-hydroxysuccinimide esters or other common activated esters or acid halides, Exemplary activated functional groups of the coating on the substrate include anhydride derivatives for coupling with a terminal hydroxyl group; hydrazine derivatives for coupling onto oxidized sugar residues of the linker compound; or maleimide derivatives for covalent attachment to thiol groups of the linker compound. To produce a derivatized coating, at least one terminal carboxyl group on the coating can be activated to an anhydride group and then reacted, for example, with a linker compound. Alternatively, the functional groups on the coating may be reacted with a linker having activated functional groups (e.g., N-hydroxysuccinimide esters, acid halides, anhydrides, and isocyanates) for covalent coupling to reactive amino groups on the coating.

A substrate can contain a linker (e.g., to indirectly couple a moiety to the substrate). The terminal functional groups for reacting with functional groups on an activated coating include halogen, amino, hydroxyl, or thiol groups. In some instances, a terminal functional group can be selected from the group of a carboxylic acid, halogen, amine, thiol, alkene, acrylate, anhydride, ester, acid halide, isocyanate, hydrazine, maleimide and hydroxyl group.

In some embodiments, the support can be associated with a brush polymer. In some aspects, the support can be associated with a bottle brush polymer. In some embodiments the bottle brush polymer or the brush polymer can be deposited onto a substrate. In some embodiments, bottle-brush polymers can be different from polymer brushes in that in a polymer brush, the polymer is reacted to only one surface of a substrate, while in a bottle brush polymer, the polymer is grafted on all sides of the polymer backbone, thus producing a morphology that appears to be bottle-brush like in appearance. In one embodiment, the backbone polymer can be one that comprises a strained ring along the chain backbone. In another embodiment, the backbone polymer can be a polyacetal, a polyacrylic, a polycarbonate, a polystyrene, a polyester, a polyamide, a polyamideimide, a polyarylate, a polyarylsulfone, a polyethersulfone, a polyphenylene sulfide, a polyvinyl chloride, a polysulfone, a polyimide, a polyetherimide, a polytetrafluoroethylene, a polyetherketone, a polyether etherketone, a polyether ketone ketone, a polybenzoxazole, a polyoxadiazole, a polybenzothiazinophenothiazine, a polybenzothiazole, a polypyrazinoquinoxaline, a polypyromellitimide, a polyquinoxaline, a polybenzimidazole, a polyoxindole, a polyoxoisoindoline, a polydioxoisoindoline, a polytriazine, a polypyridazine, a polypiperazine, a polypyridine, a polypiperidine, a polytriazole, a polypyrazole, a polypyrrolidine, a polycarborane, a polyoxabicyclononane, a polvdibenzofuran, a polyphthalide, a polyanhydride, a polyvinyl ether, a polyvinyl thioether, a polyvinyl alcohol, a polyvinyl ketone, a polyvinyl halide, a polyvinyl nitrile, a polyvinyl ester, a polysulfonate, a polynorbornene, a polysulfide, a polythiocster, a polysulfonamide, a polyurea, a polyphosphazene, a polysilazane, a polyurethane, or the like, or a combination including at least one of the foregoing polymers.

A surface of a solid support can be coated with a functional group and a peptoid can be attached to the solid support through the functional group. For example, a solid support can be coated with a first functional group and a peptoid comprising a second functional group can be attached to the solid support by reacting the first functional group with the second functional group. For example, a surface of a solid support can be coated with an antibody, an antibody fragment, glutathione, calmodulin, biotin, streptavidin, streptactin, amylose, an anion-exchange resin such as Mono-Q, FlAsH and ReAsH biarsenical compounds, pilin-C protein, SpyCatcher protein or a metal chelate. In some instances, the metal chelate can include but is not limited to nickel, cobalt, zinc, mercury, cupper or iron chelate. In some embodiments, the solid support can be coated entirely. In some embodiments, the solid support can be coated partially.

In some embodiments, the support can be magnetic. In some instances, a magnetic solid support can comprises magnetite, maghemitite, FePt, SrFe, iron, cobalt, nickel, chromium dioxide, ferrites, or mixtures thereof. In some instances, a support can be nonmagnetic.

Supports can also be conditioned to have linkers and/or other means to bind to or connect to or react with a ligand or active group on a ligand. Such groups are also described in U.S. Pat. Pub. No. 2007/0003954, and are also described herein. U.S. Pat. Pub. No. 2007/0003954 is hereby incorporated by reference in its entirety. In some embodiments, the support can be a resin or a bead. In the present invention, the number of resins or beads having individual ligands bonded thereto or to a linker and then to said support can range from less than about 1, 10, 100, 1000, 100,000 to greater than about 150 million.

In some embodiments, the resin can be a TentaGel® resin. TentaGel® resins are grafted copolymers consisting of a low crosslinked polystyrene matrix on which poly (ethylene glycol) (PEG or POE) is grafted. There are several types of TentaGel® resins available showing tailored properties dependent on their application. In some embodiments the solid support can be TentaGel® S Resins. In some embodiments the solid support can be TentaGel® PAP Resins. In some embodiments the solid support can be TentaGel® N Resins. In some embodiments the solid support can be TentaGel® R. In some embodiments the solid support can be TentaGel® HL. In some embodiments the solid support can be TentaGel® MB. In some embodiments the solid support can be TentaGel® J. In some embodiments the solid support can be TentaGel® M. In some embodiments the solid support can be TentaGel® B. In addition to TentaGel® beads, other resins and/or particles can be utilized. For example, lightly cross-linked polystyrene resins or polyamide resins can be utilized. In certain aspects, the support may be a bead, a plate, a dipstick, a filter, a membrane a pin, or a well. In some embodiments, the beads used herein can be at least about 1 m. In some embodiments, the beads used herein can be at least about 1, 5, 10, 35, 50, 90, 100, 130, 150, 200, 300, 500, 750, or at least about 1000 μm. In some embodiments, the beads used herein can be greater than about 500, 700, 800, 900, 1000 μm.

In some embodiments, the support can be a leuminex bead. Luminex's xMAP®, including flow cytometry, microspheres, lasers, digital signal processing and traditional chemistry. Featuring a flexible, open-architecture design, xMAP®) technology can be configured to perform a wide variety of bioassays quickly, cost-effectively and accurately. Luminex color-codes microspheres into 100 distinct sets. Each bead set can be coated with a peptoid according to the present invention, thereby allowing the capture and detection of specific antibodies from samples. Within the Luminex compact analyzer, lasers excite the internal dyes that identify each microsphere particle, and also any reporter dye captured during the assay. Many readings are made on each bead set, further validating the results. In this way, xMAP technology allows multiplexing of unique assays within a single sample, both rapidly and precisely, xMAP technology has been adopted across many segments of the life sciences, including protein expression profiling, molecular and immunodiagnostics, HLA testing, and biodefense/environmental.

In some embodiments, split synthesis method can yield beads each of which comprises multiple copies of a single peptoid sequence.

In some instances, a support can be an array. In some embodiment a solid support can comprise an array. In some embodiments, an array of the invention can comprise an ordered spatial arrangement.

Samples

In some embodiments, the one or more molecules and/or libraries disclosed herein can be screened with a sample. In some embodiments, the sample can be an antibody containing sample. In some embodiments, the sample can be a biomarker containing sample. In some embodiments, a biomarker containing sample can be a biological fluid. In some embodiments, an antibody containing sample can be a biological fluid. In some embodiments, the sample can be a biological fluid. The biological fluids prepared for analysis in the process described herein include or can include a host of potential biomarkers including markers expressed on cells (non-adherent cells, including T-cells or other immune effector cells), microorganisms, proteins, peptides, lipids, polysaccharides, small molecules, organic molecules, inorganic molecules, biological molecules and including any detectable or reactable moiety in such complex milieu. In some embodiments, such biomarker can be antibodies and, in particular, are antibodies generated as a result of a disease or condition. In some embodiments, body fluids such as serum, plasma, saliva or other fluids or samples derived from a subject or animal or organism can be the source of such biomarkers. In some embodiments, the sample can be blood, serum, saliva or CSF. In some embodiments, the sample can be for example, sputum, bone marrow, synovial fluid, aqueous humor, amniotic fluid, cerumen, breast milk, broncheoalveolar lavage fluid, semen, prostatic fluid, Cowper's fluid, pre-ejaculatory fluid, female ejaculate, sweat, tears, cyst fluid, pleural fluid, peritoneal fluid, pericardial fluid, lymph, chyme, chyle, bile, interstitial fluid, menses, pus, sebum, vaginal secretion, mucosal secretion, stool water, pancreatic juice, lavage fluid from sinus cavities, bronchopulmonary aspirate, blastocyl cavity fluid, or umbilical cord blood.

In some embodiments, washing or eluting steps and other conditioning means are utilized following exposure of sample to the ligand library and/or ligand(s) or kits derived from such library. Aqueous solutions can be utilized including buffered solutions such as HEPES buffer, Tris buffer or phosphate buffered saline. Supports can also be treated with energy absorbing materials to facilitate desorption or ionization. In some embodiments, chemical means can also be utilized to decouple or remove ligand-ligand binding moiety complexes from supports.

Equipment

In some embodiments, ligands of the present invention may be prepared using standard solid phase technology on commercially available equipment (such as Advanced Chemtech multiple organic synthesizers). In some aspects, a starting material or later reactant may be attached to the solid phase, through a linking unit, or directly and subsequently used in the synthesis of desired ligands. The choice of linkage will depend upon the reactivity of the molecules and the solid support units and the stability of these linkages. Direct attachment to the solid support via a linker molecule may be useful if it is desired not to detach the library member from the solid support. For example, for direct on-bead analysis of biological activity, a stronger interaction between the library member and the solid support may be desirable. Alternatively, the use of a linking reagent may be useful if more facile cleavage of the inventive library members from the solid support is desired.

Automation

In some embodiments, the combinational synthesis process described herein may be automated. In regard to automation of the present methods, a variety of instrumentation may be used to allow for the facile and efficient preparation of ligand libraries of the present invention, and methods of assaying members of such libraries. In general, automation, as used in reference to the synthesis and preparation of the ligand libraries, involves having instrumentation complete one or more of the operative steps that must be repeated a multitude of times because a library instead of a single ligand is being prepared. Examples of automation include, without limitation, having instrumentation complete the addition of reagents, the mixing and reaction of them, filtering of reaction mixtures, washing of solids with solvents, removal and addition of solvents, and the like. Automation can be applied to any steps in a reaction scheme, including those to prepare, purify and assay ligands for use in the present invention.

A range of automation is possible. For example, the synthesis of the ligand libraries may be wholly automated or only partially automated. If wholly automated, the library can be prepared by the instrumentation without any human intervention after initiating the synthetic process, other than refilling reagent bottles or monitoring or programming the instrumentation as necessary. Although synthesis of a ligand library may be wholly automated, it may be necessary for there to be human intervention for purification, identification, or the like of the library members.

In some embodiments, the combinational synthesis process described herein may be partially automated. Partial automation of the synthesis of a ligand library may involve some robotic assistance with the physical steps of the reaction schema that gives rise to the library, such as mixing, stirring, filtering and the like, but still requires some human intervention other than just refilling reagent bottles or monitoring or programming the instrumentation. This type of robotic automation can be distinguished from assistance provided by convention organic synthetic and biological techniques because in partial automation, instrumentation still completes one or more of the steps of any schema that is required to be completed a multitude of times because a library of ligands is being prepared.

Characterization of the Library Members

In addition to building and/or using such libraries, it can be necessary or desired to characterize, purify and/or synthesize or re-synthesize any such ligand. Such methods are known in the art and include the entire gamut of purification methods such as HPLC via chromatographic means or purification methods via chemical means, characterization methods such as mass spec or NMR or combinations of any of these methods. Such methods are further described in, for example, US Pat. Publication 2007/0003954, which is hereby incorporated by reference in its entirety Characterization of the library members can be performed using standard analytical techniques, such as mass spectrometry, Nuclear Magnetic Resonance Spectroscopy, including 195Pt and 1H NMR, chromatography (e.g., liquid etc.) and infra-red spectroscopy. One of ordinary skill in the art will realize that the selection of a particular analytical technique will depend upon whether the inventive library members are in the solution phase or on the solid phase. In addition to such characterization, the library member may be synthesized separately to allow for more ready identification.

In other embodiments, the ligand library may be synthesized in solution, and by the use of deconvolution techniques, the identity of particular members can be determined.

The use of solid phase techniques in the present invention can also include the use of a specific encoding technique. Specific encoding techniques have been reviewed by Czarnik in *Current Opinion in Chemical Biology* (1997) 1:60. One of ordinary skill in the art will also realize that if smaller solid phase libraries are generated in specific reaction wells, such as 96 well plates, or on plastic pins, the reaction history of these library members may also be identified by their spatial coordinates in the particular plate, and thus are spatially encoded. In other embodiments, an encoding technique involves the use of a particular "identifying agent" attached to the solid support, which enables the determination of the structure of a specific library member without reference to its spatial coordinates. Examples of such encoding techniques include, but are not limited to, spatial encoding techniques, graphical encoding techniques, including the "tea bag" method, chemical encoding methods, and spectrophotometric encoding methods. One of ordinary skill in the art will realize that the particular encoding method to be used in the present invention can be selected based upon the number of library members desired, and the reaction chemistry employed.

Screening

In some embodiments, the synthesized ligand libraries of the invention can be screened. For screening, the library of ligands can be present in different formats, such as in liquid solution, such as in tubes, microtiter-plates, or on a solid support, such as on filters, glass slides, silicon surfaces, beads or a customized chemical microarray.

The libraries can be used directly in biological fluid, under the appropriate experimental conditions, to screen biomarkers and without the need or requirement to transfer such peptoids or ligands to a microarray before screening the biological fluid. In addition, the ligand libraries may also be used to screen for cell based receptors that specifically relate to a particular cell surface marker. In some embodiments, the ligands of the present invention can be used for monitoring disease progression comprising the steps of screening a subject's biological sample at time point 1 followed by screening said subject's biological sample at time point 2 or any subsequent time to follow and/or monitor the presence or absence of the disease associated biomarker in said subject at any point in time using a kit or instrument or device having at least one ligand.

In one aspect, the present invention provides methods of screening synthesized ligands to discover biomarkers, as well as methods of designing such biomarkers. Biomarkers of the invention and other structurally related molecules, and complexes containing the same, can be identified and developed as set forth below and otherwise using techniques and methods known to those of skill in the art. The biomarkers of the invention may be employed to detect disease states. In some embodiments, the disease state can be Alzheimer's disease states or other neurological conditions disease states. The biomarkers of the invention may be employed to develop and or identify potential molecules, for instance, to treat, ameliorate, or retard the progression of a disease, for example AD or other neurological conditions.

In one aspect, the present invention is directed towards a biomarker that interacts with a disease related epitope. In some aspects, the disease related epitope is an AD related epitope. In another aspect, the present invention is directed towards small synthetic ligand that mimics the shape or some other feature of a native protein antigen sufficiently well to bind to the antibody combining sites or the antigen binding pockets of T cell receptors with high affinity and specificity.

In still another aspect, the present invention is directed toward a biomarker that is a fragment (or homolog of such fragment or mimetic of such fragment) of an epitope. In some embodiments, the biomarker can be a fragment of an AD related epitope. Biomarkers of any of the above-described epitopes may be used alone or in complementary approaches to develop and or identify potential molecules to treat, ameliorate, or retard the progression of a disease, for example AD or other neurological conditions.

In general, in some embodiments, to screen combinatorial peptoid libraries, one, tens, hundreds, thousands, tens of thousands to millions of peptoid bearing beads can be prepared and then mixed with a biomarker containing sample such as a biological sample. The initial biological sample can be a control sample and a subsequent biological sample treated with a ligand library that has removed the control hits can then be treated and/or screened against a diseased biological sample. The ligands/beads that interact with at least one disease associated biomarker are then detected, identified and isolated and/or characterized. In some embodiments, a TentaGel® screening protocol is used which comprises (1) bead preparation, (2) screening of biological fluid and (3) detection of hits.

In detail, in some embodiments, the ligands of the invention can be screened. In some embodiments, screening can comprise a process for screening a biomarker containing sample, for example a biological fluid for disease associated biomarkers comprising the steps of screening a biological control sample and a biological diseased sample with at least one ligand library and finding disease associated biomarkers using such a screen. In some embodiments, a library may comprise one molecule. In some embodiment, a library may comprise one or more molecule. In some embodiments, screening can comprise a process for screening a biological sample for the presence of a disease-associated biomarker, which comprises exposing said sample to one or a plurality of ligand wherein at least one ligand detectably binds to the disease associated biomarker. In some embodiments, the method of screening a biological sample for disease associated biomarkers comprises the steps of (1) exposing a ligand library to a control sample to identify and remove any non-specific ligand hits and (2) exposing the remaining ligand library to a diseased sample to identify any ligands which bind to a disease associated biomarker in the diseased sample. In some embodiments, the process for screening a biological sample for a disease associated biomarker can comprise (1) pre-treating a ligand library with a suitable solvent to form a treated ligand library: (2) exposing the treated ligand library to a normal control biological sample having control sample ligand binding moieties: (3) exposing the treated ligand library from the control sample to a Dynabead screen (for example, iron tagged anti-IgG antibody) and removing the hits; (4) washing the remaining ligand library and exposing said library to an normal control biological sample having any remaining control sample ligand binding moieties using quantam dot labeled secondary antibody (for example, anti IgG antibodies) and removing the hits; (5) washing the remaining ligand library and exposing said library to a biological sample from a subject having a disease: (6) exposing the treated ligand library from the diseased sample to a Dynabead screen and removing the hits; (7) washing the remaining ligand library and exposing said library to the biological sample from a subject having a disease; (8) adding quantam dot labeled secondary antibodies to the washed ligand library and identifying the disease-associated ligand binding moieties bound to a ligand on the ligand library and, optionally, after washing the Dynabeads from step (6), repeating step (8) using the Dynabead hits from step (6) and identifying the Dynabead Qdot hits. In some embodiments, TentaGel® beads (having embedded PEG linkers) are utilized in the preparation of the ligand library. In some embodiments, beads and/or particles having different and/or optional linkers may also be utilized along with alternative detecting means. Beads can also be selected from, for example, Luminex beads. In some embodiments, the Dynabead steps are not utilized except as initial validation steps to confirm the Qdot hits.

In some embodiments, any or all of the separated hits from the step or steps identified above may be further characterized, chemically identified and synthesized as the same moiety or as a modified version thereof. In some embodiments, characterization relates to taking the ligands of the ligand library and sequencing the particular ligand bound to the biomarker. In some embodiments, the ligand can be a peptoid. In some embodiments, the peptoid can be sequenced to identify and/or confirm or reconfirm the identity of the peptoid. In some embodiment, the peptoid can be further utilized in a diagnostic kit or as the basis for a therapeutic drug or vaccine candidate depending upon the particular disease or condition. In some embodiments, the ligands of the currently invention can be sequenced, identified and then resynthesized or synthesized in a larger scale using a bead or support based synthetic method to produce the identified/sequenced ligand.

In general, in some embodiments, to screen peptide libraries, tens of thousands to millions of peptide bearing beads are prepared and then mixed with a biological sample following the processes described herein. The beads that interact with disease associated biomarkers can then be identified and isolated for compound structure determination. For example, library screening using streptavidin (SA)

as probe protein, labeled with a red fluorescent dye and using the COPAS BIO-BEAD flow sorting equipment to separate fluorescent from nonfluorescent beads may be performed. See Marani et al., *J. Comb. Chem.*, 2009, 11 (1), pp 146-150. The red dyes which may be used are for example ATTO 590 and Texas Red. After incubating the library with the SA-red fluorescent dye conjugate, positive beads caused by peptide-SA interaction are obtained. The beads can be analyzed by matrix-assisted laser desorption ionization time-of-flight mass spectrometry (MALDI-TOF MS). Thus, peptide libraries may be used in a manner that is analogous to the process described herein with peptoids wherein initial control biological fluid samples are used to remove any ligand/bead hits from the starting compound library and wherein the remaining members of the library are used to then screen for any hits in a diseased biological fluid sample. These hits are the putative hits which are then carried forward in any diagnostic kits.

Computational Evaluation of Potential Biomarkers

In one aspect, the method of biomarker screening may generally include computationally evaluating the potential of a ligand of the present invention (or portions thereof) to associate with any disease related epitopes or portions thereof. In one aspect, the method of biomarker screening may generally include computationally evaluating the potential of a ligand of the present invention (or portions thereof) to associate any disease epitopes or portions thereof, for example AD related epitopes or portions thereof. For example, this method may include the steps of (a) employing computational means to perform a fitting operation between the ligand and an AD related epitope or protein region: and (b) analyzing the results of said fitting operation to quantify the association between the molecule and the epitope.

In many screening programs which test libraries of ligands and natural extracts, high throughput assays can be desirable in order to maximize the number of ligands surveyed in a given period of time. Assays can be performed in cell-free systems.

The screening methods disclosed herein can be accomplished by using a variety of assay formats. In light of the present disclosure, those not expressly described herein will nevertheless be known and comprehended by one of ordinary skill in the art. Assay formats which approximate such conditions as formation of protein complexes or protein-nucleic acid complexes, and enzymatic activity may be generated in many different forms, as those skilled in the art will appreciate based on the present description and include but are not limited to assays based on cell-free systems, e.g. purified proteins or cell lysates, as well as cell-based assays which utilize intact cells. Assaying binding resulting from a given target: ligand interaction may be accomplished in any vessel suitable for containing the reactants. Examples include microtitre plates, test tubes, and micro-centrifuge tubes. Any of the assays may be provided in kit format and may be automated. Many of the following particularized assays rely on general principles, such as blockage or prevention of fusion, that may apply to other particular assays.

Detection Methods

Detection methods for detecting ligand-binding moiety or ligand-biomarker complexes can include photometric and non-photometric means. In some embodiments, such methods process includes a method to detect and measure absorbance, fluorescence, refractive index, polarization or light scattering. These include direct and/or indirect means to measure such parameters. Methods involving fluorescence include fluorescent tagging in immunological methods such as ELISA or sandwich assay. Methods involving refractive index include surface Plasmon resonance (SPR), grating coupled methods (e.g. sensors uniform grating couplers, wavelength-interrogated optical sensors (WIOS) and chirped grating couplers), resonant minor and interferometric techniques. Methods involving polarization include ellipsometry. Light scattering methods may also be used. Other means for tagging and/or separating and/or detecting can also include magnetic means. Magnetic resonance imaging, gas phase ion spectrometry, MRI may all be used.

Non-photometric methods of detection include, without limitation, magnetic resonance imaging, gas phase ion spectrometry, atomic force microscopy and multipolar coupled resonance spectroscopy. Magnetic resonance imaging (MRI) is based on the principles of nuclear magnetic resonance (NMR), a spectroscopic technique used by scientists to obtain microscopic chemical and physical information about molecules. Gas phase ion spectrometers include mass spectrometers, ion mobility spectrometers and total ion current measuring devices.

Mass spectrometers measure a parameter which can be translated into mass-to-charge ratios of ions. Generally ions of interest bear a single charge, and mass-to-charge ratios are often simply referred to as mass. Mass spectrometers include an inlet system, an ionization source, an ion optic assembly, a mass analyzer, and a detector. Several different ionization sources have been used for desorbing and ionizing analytes from the surface of a support or biochip in a mass spectrometer. Such methodologies include laser desorption/ionization (MALDI, SELDI), fast atom bombardment, plasma desorption, and secondary ion mass spectrometers. In such mass spectrometers the inlet system comprises a support interface capable of engaging the support and positioning it in interrogatable relationship with the ionization source and concurrently in communication with the mass spectrometer. e.g., the ion optic assembly, the mass analyzer and the detector. Solid supports for use in bioassays that have a generally planar surface for the capture of targets and adapted for facile use as supports with detection instruments are generally referred to as biochips.

Analysis of the data generated typically involves quantification of a signal due to the detected biomarker versus a control or reference. The data can be analyzed by any suitable means. Computers and computer programs may be utilized to generate and analyze the data. Beads and/or other supports may be computer coded or coded for identification purposes. Data analysis includes analysis of signal strength under the particular conditions of the assay or detection method. Ligands, ligand binding moieties, biomarkers or reference moieties and/or secondary detection moieties may be labeled or radio-labeled or tagged with a detectable moiety. One of ordinary skill in the art can assess the difference and/or distinction between samples that have disease associated biomarkers versus those control or healthy subject samples that do not contain such biomarkers. One of ordinary skill in the art can also determine, pursuant to the methods described herein, the presence of false positives or other hits that are or may be found in control samples to account for and/or remove such hits and one of ordinary skill in the art, pursuant to the methods described herein, can continue the process of determining or finding disease associated biomarkers in subject samples having any disease or condition. The detection of such hits, in all cases, can be accomplished by means for detecting the binding of a ligand-binding moiety or a biomarker such as a disease associated biomarker or other marker to ligands in a ligand library such as those described herein.

Biomarkers associated with the diseases and/or conditions recited herein will vary depending upon the particular stage of the disease and/or condition of the particular subject or animal or other organism assessed. The ligands, which are the putative hits recited herein, are expected to, in most cases, mimic the natural antigen that initiates the immune response and/or formation of antibodies or immune cells in the first instance. In some embodiments, present invention and screening process claimed and recited herein does not require knowledge of either the particular antigen or the antibody generated in response to the antigen. The ligands, however, may be useful in their own right as vaccines or drug candidates in addition to being useful in the screens and diagnostic methods recited herein.

Binding Assays

Screens can be conducted by screening for ligands described herein that are capable of binding to disease related antibodies. Binding assays can also be useful, e.g., for identifying disease related antibodies that interact with the ligands described herein. For example, antibodies or other molecules that bind ligands of the invention can be identified in binding assays. Binding assays can involve, but are not limited to, use of isolated polypeptides, crude extracts, or cell-based assays. In some embodiments the assays described herein can be used to a) identify subjects whose serum antibody profile puts them at risk of developing or having a disease; (b) identify subjects whose symptoms are such that they may or may not be suffering from disease (i.e., provide a definitive diagnosis of a disease); (c) assess the impact of an disease therapy; and (d) monitor disease progression.

Binding assays can involve contacting a ligand with one or more test agents (antibody) and allowing sufficient time for the molecule and test agents to form a binding complex. Any binding complexes formed can be detected using any of a number of established analytical techniques. Binding assays include, but are not limited to, methods that measure co-precipitation or co-migration on non-denaturing SDS-polyacrylamide gels, co-migration on Western blots, enzyme linked immunosorbent assay (ELISA), radioimmunoassay (RIA), immunoradiometric assay, fluoroimmunoassay, chemiluminescent assay, bioluminescent assay, FACS, FRET. The steps of various useful immunodetection methods have been described in the scientific literature, such as, e.g., Doolittle and Ben-Zeev (1999), Gulbis and Galand (1993), De Jager et al. (1993), and Nakamura et al. (1987). (see, e.g., Bennet, J. P. and Yamamura, H. I. (1985) "Neurotransmitter, Hormone or Drug Receptor Binding Methods," in Neurotransmitter Receptor Binding (Yamamura, H. L, et al, eds.), pp. 61-89. Other binding assays involve the use of mass spectrometry or NMR techniques to identify ligands bound the antibody or displacement of labeled substrates. The antibodies used in these assays can be naturally expressed, cloned or synthesized. [108] In addition, mammalian or yeast two-hybrid approaches (see, e.g., Bartel, P. L. et. al. Methods Enzymol, 254:241 (1995)) can be used to identify polypeptides or other molecules that interact or bind to the polypeptide when expressed together in a host cell. U.S. Pat. Nos. 3,817,837, 3,850,752, 3,939, 350, 3,996,345, 4,277,437, 4,275,149 and 4,366,241 are hereby incorporated by reference in its entirety.

ELISAs

Immunoassays, in their most simple and direct sense, are binding assays. Certain immunoassays finding particular use in the present invention are various types of enzyme linked immunosorbent assays (ELISAs) and radioimmunoassays (RIA) known in the art. In one exemplary ELISA, the ligands of the invention are immobilized onto a selected surface, such as a well in a polystyrene microtiter plate. Then, a test composition suspected of containing the antibody is added to the wells. After binding and washing to remove non-specifically bound complexes, the bound antibody may be detected. Detection may be achieved by the addition of another ligand linked to a detectable label. This type of assay is analogous to a simple "sandwich ELISA" except that binding of the labeled agent is direct at the Fab portion of the bound antibody. Detection may also be achieved by the addition of a labeled antibody that binds any bound antibody, e.g., that recognizes the Fc portion of the bound antibody. Optionally, this antibody is not labeled, and is followed by the addition of a second antibody that has binding affinity for the first antibody, with the second antibody being linked to a detectable label.

In another exemplary ELISA, the samples suspected of containing the antibodies are immobilized onto a well surface and then contacted with labeled ligands of the present invention. After binding and washing to remove non-specifically bound immune complexes, the bound labeled ligands are detected. Alternatively, the ligands are not labeled and can be detected against an artificial antibody (non-sample) that is selected for specific binding the ligand of choice, this second would be linked to a detectable label, thereby permitting detection.

Irrespective of the format employed, ELISAs have certain features in common, such as coating, incubating and binding, washing to remove non-specifically bound species, and detecting the bound immune complexes. These are described below.

In coating a plate with either ligand or antibody, one can generally incubate the wells of the plate with a solution of the ligand or antibody, either overnight or for a specified period of hours. In certain aspects, the plate can be blocked using a bacterial lysate, such as an *E. coli* lysate (See Example 1). The wells of the plate can then be washed to remove incompletely adsorbed material. Any remaining available surfaces of the wells can then be coated with a non-specific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface. Alternatively, because of the simple and predictable chemistry of the ligands, they can be attached to the support by means of a specific chemical reaction.

In ELISAs, it is probably more customary to use a secondary or tertiary detection means rather than a direct procedure. Thus, after binding of a ligand or antibody to the well, coating with a non-reactive material to reduce background, and washing to remove unbound material, the immobilizing surface can be contacted with the biological sample or ligand to be tested under conditions effective to allow immune complex formation. Detection of the immune complex then requires a labeled secondary binding ligand or antibody, or a secondary binding ligand or antibody in conjunction with a labeled tertiary antibody (with specificity either for the Fc region of the antibody or the ligand).

Under conditions effective to allow immune complex (antigen/antibody) formation means that the conditions can include diluting the antigens and/or antibodies with solutions such as BSA, bovine gamma globulin (BGG) or phosphate buffered saline (PBS)/Tween. These added agents can assist in the reduction of nonspecific background.

The suitable conditions can also mean that the incubation is at a temperature or for a period of time sufficient to allow effective binding. Incubation steps can be from about 1 to 2 to 4 to 6 to 24 to about 48 hours or so, at temperatures on the order of about 20° C. to about 37° C. In some embodiments, about 21° C., 22° C., 23° C., 24° C., 25° C. 26° C., 27° C., 28° C., 29° C., 30° C., 31° C., 32, ° C., 33° C., 34° C. 35° C., 36° C., or about 37° C. or may be overnight at about 2° C., 3° C., 4° C. 5° C., 6° C., 7° C. or so.

Following incubation steps in an ELISA, the contacted surface can be washed so as to remove non-complexed material. In some embodiments, the washing procedure includes washing with a solution such as PBS/Tween, or borate buffer. Following the formation of specific immune complexes between the test sample and the originally bound material, and subsequent washing, the occurrence of even minute amounts of immune complexes may be determined.

Detection may utilize an enzyme that can generate color development upon incubating with an appropriate chromogenic substrate. Thus, for example, one can desire to contact or incubate the first and second immune complex with a urease, glucose oxidase, alkaline phosphatase or hydrogen peroxidase-conjugated antibody or ligand for a period of time and under conditions that favor the development of further immune complex formation (e.g., incubation for about 1, 2, 3, 4, 5, 6, 7, 8, 9, or about 10 hours at room temperature in a PBS-containing solution such as PBS-Tween).

After incubation with the labeled antibody or peptoid, and subsequent to washing to remove unbound material, the amount of label can be quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label.

Quantification can be achieved by measuring the degree of color generated, e.g., using a visible spectra spectrophotometer.

Förster Resonance Energy Transfer (FRET)

FRET is a phenomenon in which the excited-state energy in one molecule (called the donor) is transferred to another molecule by a radiationless coupling. This mechanism was first correctly described by Forster, and differs from other types of energy transfer, such as electron sharing (Dexter) or trivial transfer (emission of a photon from the donor and reabsorption by the acceptor). The Dexter mechanism requires the two molecules to be in physical contact, while trivial transfer is a very low probability. In contrast, the Forster mechanism exhibits a high probability when the two molecules are within the Forster radius, which is defined for any given pair of fluorophores.

The overall FRET efficiency depends on the Förster radius, and is determined by several factors and is directly related to the amount of overlap between the absorption spectra of the acceptor molecule and the emission spectra of the donor molecule. The amount of FRET also depends on the alignment of the donor and acceptor molecules, although most biological systems are not rigidly aligned. The FRET efficiency is also affected by the ability of the acceptor molecule to absorb light, as indicated by its molar extinction coefficient, and the overall stability of the excited state of the donor molecule, as indicated by the probability that absorption will lead to fluorescence (quantum yield) and the lifetime of the excited state.

FRET between two different fluorophores can be assayed by several methods, looking at the change in color of the fluorescence, measuring the fluorescence lifetime of the donor, examining the changes upon photo bleaching either the donor or acceptor, or by measuring the fluorescence polarization of the acceptor. Regardless of the approach, most of these assays share common features of the instrumentation.

The types of microscopes used to measure FRET can be suitably selected depending on the purpose. In some embodiments, where frequent observations are necessary for monitoring a time course of the changing, conventional incident-light fluorescent microscope can be used. In some embodiments, where resolution is to be increased as in the case where detailed intercellular localization is to be monitored, confocal laser microscope can be used. As a microscope system, an inverted microscope can be used for most live cell measurements in view of keeping the physiological state of cell and preventing contamination. When an upright microscope is used, a water immersion lens can be used in the case of using lens of high power.

The filter set can be suitably selected depending on the fluorescent wave length of the fluorescent protein. For the observation of GFP, a filter with excitation light of about 470-490 nm and fluorescent light of about 500-520 nm can be used. For the observation of YFP, a filter with excitation light of about 490-510 nm and fluorescent light of about 520-550 nm can be used. For the observation of CFP, it is preferred to use a filter with excitation light of about 425 nm and fluorescent light of about 460-500 nm. Moreover, when time course observation is carried out in living cells by using a fluorescent microscope, the cells can be photographed in a short period, and therefore a high sensitive cooled CCD camera can be used. By using a cooled CCD camera, thermal noise can be decreased by cooling CCD, and weak fluorescent image can be clearly acquired by exposure of short period. Confocal microscopes can also be used for live cell imaging, as long as care is taken to minimize the exposure times.

In a similar manner, any ligand may be screened on the beads or supports using the processes described herein. These ligands include, in addition to peptoids or peptides, nucleic acid oligomers, polysaccharides, small molecules and/or any combination thereof which can be built into libraries and, under the conditions recited herein, used to screen biological fluid.

In some embodiments, detecting may comprise radio immunoassay ("RIA"), fluorescence immunoassay ("FIA"), enzyme-linked immunosorbent assay ("ELISA"), Western blot, flow cytometry, Forster resonance energy transfer ("FRET"), or surface plasmon resonance.

Linkers

In some embodiments, the molecules described herein can comprise a linker. In some embodiments, the linker can be the group that joins the molecule to the support (resin bead). In some embodiments, a linker joins the molecule to the resin bead. In some embodiments, the linkers herein can be carboxylic acid linkers. In some embodiments, the linkers herein can be Carboxamide Linkers. In some embodiments, the linkers herein can be Alcohol Linkers. In some embodiments, the linkers herein can be Carbamates and Amines Linker. In some embodiments, the linkers herein can be Traceless Linkers.

Carboxylic Acid Linkers

The first linking group used for peptide synthesis bears the name of the father of solid phase synthesis. Merrifield resin is cross-linked polystyrene functionalized with a chloromethyl group. The carbonyl group is attached by the nucleophilic displacement of the chloride with a cesium carboxylate salt in DMF. Cleavage to regenerate the carboxylic acid is usually achieved by hydrogen fluoride.

The second class of linker used for carboxylic acid is the Wang linker. This linker is generally attached to cross-linked polystyrene, TentaGel® and polyacrylamide to form Wang resin. It was designed for the synthesis of peptide carboxylic acids using the Fmoc-protection strategy, and due to the activated benzyl alcohol design, the carboxylic acid product can be cleaved with TFA. A more acid-labile form of the Wang resin has been developed. The SASRIN resin has the same structure as the Wang linker but with the addition of a methoxy group to stabilize the carbonium ion formed during acid catalyzed cleavage.

Carboxamide Linkers

The rink linker is generally preferred for generating primary carboxamide on solid phase. In the present invention, this linker is utilized when manufacturing or resynthesizing the hits or putative hits from the primary screen of the invention. In such cases, cysteine is the first monomer reacted with the rink linker and then the process involves either subsequent monomer addition to build the oligomer or subsequent submonomer chemistry to build the oligomer. The greater acid sensitivity in the rink linker is a consequence of the two additional electron donating methoxy groups. In the generation of primary carboxamide, the starting material is attached to the linker as a carboxylic acid and after synthetic modification is cleaved from the resin with TFA.

Alcohol Linkers

A hydroxyl linker based on the tetrahydropyranyl (THP) protecting group has been developed by Thompson and Ellmann. All type of alcohols readily add to dihydropyran and the resulting THP protecting group is stable to strong base, but easily cleaved with acid. This linker is attached to a Merrifield resin. The trityl group is a good acid-labile protecting group for a lot of heteroatoms. The trityl group has been used to anchor alcohols in the synthesis of a library of β-mercaptoketones.

Carbamates and Amines Linker

Carbamates linker has been used for the synthesis of a combinatorial library of 576 polyamines prepared in the search of inhibitors of trypanosomal parasitic infections. Two linkers were investigated. One based on hydroxymethylbenzoic acid 1, and the other one, an electron-donating group has been added 2. The last one allowed cleavage by TFA while the first one could be cleaved with strong acidic conditions.

A very useful linker has been recently developed for the generation of tertiary amine. (Tertiary amines are commonly used in drug molecules.) Primary and secondary amines are introduced to the linker by Michael addition. The amine may be alkylated to gives a resin-bound quaternary ammonium ion. In mildly basic condition, Hoffmann elimination occurs to give a tertiary amines of high purity.

Traceless Linkers

In some case, the starting materials are loaded onto the resin in one form, such as carboxylic acid, and cleaved in another form; a carboxamide for example. This is perfectly acceptable if the target compound requires the released function. (Peptides invariably contain a carboxylic acid or carboxamide.) However, the growth in interest in combinatorial libraries of low molecular weight non-peptides has elicited a need in new types of linker. These linkers show non-specific function after cleavage. Traceless linkers are so called because an examination of the final compound reveals no trace of the point of linkage to the solid phase.

Characterizing Bounded Antibody

Certain embodiments include methods and compositions for characterizing antibodies and the antigenic determinants recognized by the antibodies characteristic of a particular disease. For purposes of this specification and the accompanying claims the terms "epitope" and "antigenic determinant" are used interchangeably to refer to a site on an antigen to which B and/or T cells respond or recognize. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols (1996). Antibodies that recognize the same epitope can be identified in a simple immunoassay showing the ability of one antibody to block the binding of another antibody to a target antigen.

T cells recognize continuous epitopes of about nine amino acids for CD8 cells or about 13-15 amino acids for CD4 cells. T cells that recognize the epitope can be identified by in vitro assays that measure antigen-dependent proliferation, as determined by H-thymidine incorporation by primed T cells in response to an epitope (Burke et al., 1994), by antigen-dependent killing (cytotoxic T lymphocyte assay, Tigges et al., 1996) or by cytokine secretion.

As used herein and in the claims, the terms "antibody" or "immunoglobulin" are used interchangeably and refer to any of several classes of structurally related proteins that function as part of the immune response of an animal or recipient, which proteins include IgG, IgD, IgE, IgA, IgM, IgY, IgW and related proteins.

Under normal physiological conditions antibodies are found in plasma and other body fluids and in the membrane of certain cells and are produced by lymphocytes of the type denoted B cells or their functional equivalent. Antibodies of the IgG class are made up of four polypeptide chains linked together by disulfide bonds. The four chains of intact IgG molecules are two identical heavy chains referred to as H-chains and two identical light chains referred to as L-chains.

IgD is an antibody isotype that makes up about 1% of proteins in the plasma membranes of mature B-lymphocytes where it is usually coexpressed with another IgM. IgD is also produced in a secreted form that is found in very small amounts in blood serum, representing about 0.25% of immunoglobulins in serum.

IgE is a member of the immunoglobulin family that mediates allergic responses such as asthma, food allergies, type 1 hypersensitivity and the familiar sinus inflammation suffered on a widespread basis. IgE is secreted by, and expressed on the surface of B-cells or B-lymphocytes. IgE binds to B-cells (as well as to monocytes, eosinophils and platelets) through its Fc region to a low affinity IgE receptor, known as FcεRII. Upon exposure of a mammal to an allergen, B-cells bearing a surface-bound IgE antibody specific for the antigen are activated and developed into IgE-secreting plasma cells. The resulting allergen-specific IgE then circulates through the bloodstream and becomes bound to the surface of mast cells in tissues and basophils in the blood, through the high affinity receptor also known as FεRI. The mast cells and basophils thereby become sensitized for the allergen. Subsequent exposure to the allergen causes a cross linking of the basophilic and mast cellular FεRI which results in a release of histamine, leukotrienes and platelet activating factors, eosinophil and neutrophil chemotactic factors and the cytokines IL-3, IL-4, IL-5 and GM-CSF which are responsible for clinical hypersensitivity and anaphylaxis.

IgA is an antibody that plays a critical role in mucosal immunity. More IgA is produced in mucosal linings than all other types of antibody combined; between about three and about five grams are secreted into the intestinal lumen each day. This accumulates up to about 15% of the total immunoglobulin produced in the entire body. IgA has two subclasses (IgA and IgA2) and can exist in a dimeric form called secretory IgA (sIgA). In its secretory form, IgA is the main immunoglobulin found in mucous secretions, including tears, saliva, sweat, colostrum and secretions from the genitourinary tract, gastrointestinal tract, prostate and respiratory epithelium. It is also found in small amounts in blood. The secretory component of sIgA protects the immunoglobulin from being degraded by proteolytic enzymes, thus sIgA can survive in the harsh gastrointestinal tract environment and provide protection against microbes that multiply in body secretions. sIgA can also inhibit inflammatory effects of other immunoglobulins. IgA is a poor activator of the complement system, and opsonises only weakly. Its heavy chains are of the type α.

IgM is a basic antibody that is produced by B cells. IgM is the physically largest antibody in the human circulatory system. It is the first antibody to appear in response to initial exposure to an antigen. The spleen, where plasmablasts responsible for antibody production reside, is the major site of specific IgM production. IgM forms polymers where multiple immunoglobulins are covalently linked together with disulfide bonds, mostly as a pentamer but also as a hexamer. IgM has a molecular mass of approximately 970 kDa (in its pentamer form). Because each monomer has two antigen binding sites, a pentameric IgM has 10 binding sites. Typically, however, IgM cannot bind 10 antigens at the same time because the large size of most antigens hinders binding to nearby sites. The J chain is found in pentameric IgM but not in the hexameric form, perhaps due to space constraints in the hexameric complex. Pentameric IgM can also be made in the absence of J chain. At present, it is still uncertain what fraction of normal pentamer contains J chain, and to this extent it is also uncertain whether a J chain-containing pentamer contains one or more than one J chain. Although hexameric IgM without J chain has higher efficiency of complement fixation than pentameric IgM with J chain. Because IgM is a large molecule, it cannot diffuse well, and is found in the interstitium in very low quantities. IgM is primarily found in serum; however, because of the J chain, it is also important as a secretory immunoglobulin. Due to its polymeric nature, IgM possesses high avidity, and is particularly effective at complement activation. By itself, IgM is an ineffective opsonin; however it contributes greatly to opsonization by activating complement and causing C3b to bind to the antigen.

IgY is a type of immunoglobulin which is the major antibody in bird, reptile, and lungfish blood. It is also found in high concentrations in chicken egg yolk. As with the other immunoglobulins, IgY is a class of proteins which are formed by the immune system in reaction to certain foreign substances, and specifically recognize them.

The antibody can be bound to a solid support substrate or conjugated with a detectable moiety or be both bound and conjugated as is well known in the art. For a general discussion of conjugation of fluorescent or enzymatic moieties see Johnstone et al. (1982). The binding of antibodies to a solid support substrate is also well known in the art (Harlow et al., 1988; Borrebaeck, 1992).

Once an antigen or antibody indicative of a disease is identified, recombinant techniques can be used to produce both the antigen and/or variants of the identified antibody, including monoclonal antibodies. For instance, single chain antibodies (SCAs) are genetically engineered proteins designed to expand on the therapeutic and diagnostic applications possible with monoclonal antibodies. SCAs have the binding specificity and affinity of monoclonal antibodies and, in their native form, are about one-fifth to one-sixth of the size of a monoclonal antibody, typically giving them very short half-lives. SCAs offer some benefits compared to most monoclonal antibodies, including their ability to be directly fused with a polypeptide that may be used for detection (e.g., luciferase or fluorescent proteins). In addition to these benefits, fully-human SCAs can be isolated directly from human SCA libraries without the need for costly and time consuming "humanization" procedures.

Single-chain recombinant antibodies (scFvs) consist of the antibody VL and VH domains linked by a designed flexible peptide tether (Atwell et al., 1999). Compared to intact IgGs, scFvs have the advantages of smaller size and structural simplicity with comparable antigen-binding affinities, and they can be more stable than the analogous 2-chain Fab fragments (Colcher et al., 1998; Adams and Schier, 1999). The variable regions from the heavy and light chains (VH and VL) are both approximately 110 amino acids long. They can be linked by a 15 amino acid linker or longer with a sequence, for example, which has sufficient flexibility to allow the two domains to assemble a functional antigen binding pocket. In specific embodiments, addition of various signal sequences allows the scFv to be targeted to different organelles within the cell, or to be secreted. Addition of the light chain constant region (Ck) allows dimerization via disulfide bonds, giving increased stability and avidity. Thus, for a single chain Fv (scFv) SCA, although the two domains of the Fv fragment are coded for by separate genes, it has been proven possible to make a synthetic linker that enables them to be made as a single protein chain scFv (Bird et al., 1988; Huston et al., 1988) by recombinant methods. Furthermore, they are frequently used due to their ease of isolation from phage display libraries and their ability to recognize conserved antigens (for review, see Adams and Schier, 1999). Thus, in some aspects of the invention, an antibody may be an SCA that is isolated from a phage display library rather that generated by the more traditional antibody production techniques described above.

Methods of producing or isolating polyclonal antibodies are known to those of skill in the art. Typically, polyclonal antibodies can be prepared by taking a source containing antibodies of interest and fractionating the source to enrich for antibodies with a reactivity of interest, e.g., peptoid binding. See, e.g., Harlow and Lane (1988) Antibodies: A Laboratory Manual, CSH press, NY.

Briefly, an example of isolating antibodies that bind particular ligands can include, but is not limited to obtaining a sample comprising such antibodies: ammonium sulfate precipitating the antibodies from the sample: and isolating the antibodies by immunoaffinity purification using standard techniques and one or more ligands as an affinity reagent. The affinity resin used can be an activated CH-Sepharose coupled to ligands(s) having a structure described herein. The antibody precipitate can be loaded onto the column and washed with PBS or another appropriate buffer or washing solution. The precipitate can then be eluted and collected.

The concentration of the antibody obtained can be determined using a total protein colorimetric determination (Bio-Rad).

It is not intended that the present invention be limited to the use of this particular protocol for the production and purification of antibodies, as numerous protocols are available and known to those in the art (See, e.g., Sambrook et al. (eds.), Molecular Cloning, Cold Spring Harbor Laboratory Press [1989]; Harlow and Lane (eds.), Antibodies: A Laboratory Manual, Cold Spring Harbor Laboratory Press [1988]: and Ausubel et al. (eds.), Current Protocols in Molecular Biology. Ch. 11, John Wiley & Sons, Inc., New York [1994]). The only criterion for antibody production methods finding use with the invention is that sufficiently purified antibody preparations be produced.

Kits and Diagnostic Tools

Any molecule described herein may be further utilized in diagnostic kits either in a clinical or laboratory setting. These kits can range from simple point of care diagnostic assays to complex and multiplex instruments or probes. The support systems and packaging surrounding the core support/ligand system can be selected from current commercial kits. The kits can typically be accompanied by all suitable reagents and instructions to use the kits to screen for and/or diagnosis the particular disease or condition the kit is designed for. Any such kit or method can comprise at least one ligand that has been identified pursuant to the screening method recited herein. The ligands may be selected based upon their affinity for a disease associated biomarker for one particular disease state or a group or battery of diseases or conditions. In some embodiments, the ligands are peptoid. The kits can also contain instructions for the physicians diagnosing a particular disease or condition and specific labeling for the particular kit and disease state or condition. It is also envisioned that the particular processes and methods and materials disclosed herein may be utilized in a clinical and laboratory setting under the supervision of a skilled operator. The kits and/or instruments or equipment can comprise ligands such as peptoids that are specific for disease associated antibodies and/or cells. The kit may comprise a complete diagnostic kit and or screening kit. The kit may comprise components or sub-components containing or comprising the diagnostic ligands, antibodies discovered and characterized through such ligands or native antigens that are discovered and purified and/or characterized as a result of interaction with and discovery from the autoantibody. Such antibodies and purified antigens comprise part of the present invention.

In diagnostic kits or other kits having ligands of the invention, the support systems can be broadened to virtually any support system including microarrays or any other known diagnostic platforms. In these cases, it can be necessary to ensure that such kits or other support systems with the ligands also have or are adapted to have a detector or detection methods to permit detection of ligands having ligand binding moieties attached to such ligands. In some embodiments, for example, the detection can be ELISA or other methods which involve the use of labeled secondary antibodies.

In some embodiments detection can be a combination screen in which B-cells, T-cells or other cells which produce or cause the production of such antibodies are screened against a library of ligands to find high affinity ligands for such B-cells or T-cells pursuant to the methods disclosed in patent application Ser. No. 12/789,711 wherein said ligands are highly selective for B-cells producing such autoantibodies and/or T-cells which help stimulate the production of such antibody producing cells yet not selective for healthy cells or cells not associated with such autoimmune disorders.

The ligands used in any one of the processes or methods described herein may be bound to a support, such as a bead, a chip, a filter, a dipstick, microarray, a membrane, a polymer matrix or a well. The contacting step, in the case of the screening of T-cells when used in combination with the use of autoantibody screens may comprise bringing said support into contact with said first and second T cell populations at the same time. The T cell population may comprise CD4 T cells. The subjects may be human or animal.

Immunodetection Kits

In still further embodiments, the present invention concerns detection kits for use with the methods described above. Ligands according to the present invention can be included in the kit. The immunodetection kits can thus comprise, in a suitable container, one or more ligands that bind antibodies for a disease such as Alzheimer's Disease, Parkinson's Disease, or both, optionally linked to a detection reagent and/or a support.

In certain embodiments where the ligand is pre-bound to a solid support, the support can be provided and includes a column matrix, bead, stick or well of a microtitre plate. The immunodetection reagents of the kit may take any one of a variety of forms, including those detectable labels that are associated with or linked to the given peptoid or secondary antibody. Exemplary secondary antibodies are those having binding affinity for the sample antibodies.

The container can generally include at least one vial, test tube, flask, bottle, syringe or other container, into which the ligand may be placed, or in some embodiments, suitably aliquot. The kits of the present invention can also include a means for containing the ligand, antibody, and any other reagent containers in close confinement for commercial sale. Such containers may include injection or blow-molded plastic containers into which the desired vials are retained.

In some embodiments the kit can comprise methods for employing ligands described herein. A kit and/or method for detecting, evidencing, and/or categorizing at least one disease state disclosed. The steps taken can include obtaining a sample from a subject, e.g., a human, and conducting a ligand binding analysis on the sample using reagents or array substrate supplied in a kit format. As a result, at least one antibody indicative of a disease state is isolated from or identified in a sample. Antibodies binding the ligand described here are related to at least a risk of disease development or to the existence of a particular disease state.

In addition, various kits are contemplated for use by the present invention. One such kit can provide for determining the presence of the disease specific antibody, including one or more antibodies related to Alzheimer's disease and/or Parkinson's disease. At least one ligand can be incorporated into the kit that is capable of specifically binding with a disease specific antibody. In certain aspects reagents for determining binding between the ligand and an antibody can also be included. The ligands described herein may be immobilized on a solid support or substrate, and include at least one detection reagent to determine if an antibody is bound to the ligand. The sample utilized for any of the kits may be a fractionated or unfractionated body fluid or a tissue sample. Non-limiting examples of such fluids are blood, blood products, urine, saliva, cerebrospinal fluid, and lymph.

Further contemplated is a kit for diagnosing, determining risk-assessment, and identifying therapeutic avenues related to a disease state, such as a neurodegenerative disease state.

This kit can include at least one ligand capable of specifically binding an antibody indicative of a disease state. Reagents for determining binding between the ligand and the antibody can also be included.

The disease specific antibodies that are analyzed according to the method of the invention can be released into the circulation and may be present in the blood or in any blood product, for example plasma, or serum, and dilutions and preparations thereof, as well as other body fluids, e.g. cerebrospinal fluid (CSF), saliva, urine, lymph, and the like. Any suitable direct or indirect assay method may be used to determine the level of antibodies measured. The assays may be competitive assays, sandwich assays, and the labels may be selected from the group of well-known labels such as radioimmunoassay, fluorescent, or chemiluminescence immunoassay or immunoPCR technology.

Diagnostic Methods

The data generated as a result of the screening may then be analyzed after to find or not find statistically significant results or correlations with known or underlying data about any particular subject or group of subjects. The present invention comprises a method of screening for the presence of a disease or condition comprising (1) screening a biomarker containing sample from a subject with at least one molecule of the invention; (2) screening a control biomarker containing sample under the same conditions using said at least one molecule and (3) comparing the healthy control data versus the subject data to determine the presence or absence of a disease associated biomarker. A group of subjects or subject samples having or suspected of having a disease may be screened against a kit or diagnostic probe having at least one molecule of the invention and the data generated with respect to each subject may be utilized on a case by case basis to confirm or validate a disease state or condition or lack thereof. Such data generated herein may be used in combination with the total information known about that particular subject to assess the subject's condition and to provide guidance to the medical practitioner providing treatment options. The information generated as a result of any such screen may be used in the clinical trial setting to assess individual subjects that are taking drug therapy. The present invention thus includes a method of assessing clinical trial progression comprising use of a screen performed according to the methods described herein. In some embodiments, the present invention relates to a method of screening for or diagnosing an early disease state comprising use of a screen or molecule claimed herein to detect a disease associated biomarker. The invention is particular useful in the context of early cancer intervention wherein detection of such biomarkers is expected to occur well before aggressive progression of the disease. In another context, early intervention in cardiovascular disease and/or metabolic disease as well as neurological disease is expected to save lives and prevent or be useful for preventing further development of such diseases without early medical intervention or treatment.

In yet another embodiment, there is provided a method of treating a subject suspected of having a disease comprising (a) contacting an antibody-containing sample from said subject with one or more ligands (b) detecting antibodies bound to said ligand; and (c) making a treatment decision based on the result of step (b). The method may further comprise obtaining said sample from a subject. The method may also further comprise making a diagnosis of a disease for a subject from which said sample was obtained if antibody binding to the ligand is greater than that observed for control non-diseased subjects. The method may also further comprise making a treatment decision for said subject. The sample may be contacted with more than one ligands of formulas recited herein. The sample may be contacted with a multiplex platform for the purposes of diagnosing multiple disease states or conditions. The support may be a bead, a plate, a dipstick, a filter, a membrane a pin, or a well. The sample may be blood, serum, saliva or CSF. Detecting may comprise RIA, FIA, ELISA, Western blot, flow cytometry, FRET, or surface plasmon resonance.

A further embodiment is directed to an antibody composition isolated from a biomarker containing sample that is indicative of a disease. In certain embodiments the antibody can be isolated by contacting a sample having such antibodies with a ligand that specifically binds antibodies indicative or associated with a disease. The antibodies can be removed, isolated, or purified from other non-antibody and non-disease specific components. The antibodies can then be washed and/or disassociated from the ligand.

Single Biomarker

In some embodiments, the biomarkers and/or molecules of the invention can be used in diagnostic tests to assess the disease status of a subject. Non limiting examples follow below. Alzheimer's disease status in a subject, e.g., to diagnose Alzheimer's disease. The phrase "Alzheimer's disease status" includes distinguishing, inter alia, Alzheimer's disease v. non-Alzheimers disease and, in particular, Alzheimer's disease v. non-Alzheimer's disease normal or Alzheimer's disease v. non-Alzheimer's disease dementia. Based on this status, further procedures may be indicated, including additional diagnostic tests or therapeutic procedures or regimens.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of actual positives who test as positive. Negative predictive value is the percentage of actual negatives that test as negative.

The biomarkers and/or molecules of this invention may show a statistical difference in different Alzheimer's disease statuses of at least $p \leq 0.05$, $p \leq 10^{-2}$, $p\, 10^{-3}$, $p \leq 10^{-4}$ or $p \leq 10^{-5}$. Diagnostic tests that use these biomarkers and/or molecules alone or in combination may show a sensitivity and specificity of at least 60%, at least 65%, at least 70%, at least 75%, at least 80%, at least 85%, at least 90%, at least 95%, at least 98% and about 100%.

In some embodiments, the method involves, first, measuring the selected biomarker in a subject sample using the methods described herein, second, comparing the measurement with a diagnostic amount or cut-off that distinguishes a positive disease status from a negative disease status, for example Alzheimer's disease status from a negative Alzheimer's disease status. In some embodiments, in vitro techniques for detection of a biomarker illustratively include enzyme linked immunosorbent assays (ELISAs), radioimmuno assay, radioassay, western blot, Southern blot, northern blot, immunoprecipitation, immunofluorescence, mass spectrometry, RT-PCR, PCR, liquid chromatography, high performance liquid chromatography, enzyme activity assay, cellular assay, positron emission tomography, mass spectroscopy, combinations thereof, or other technique known in the art. Furthermore, in vivo techniques for detection of a biomarker cam include introducing a labeled agent that specifically binds the biomarker in a biological sample or test subject. For example, the agent can be labeled with a radioactive marker whose presence and location in a biological sample or test subject can be detected by standard imaging techniques.

The diagnostic amount represents a measured amount of a biomarker above which or below which a subject is classified as having a particular disease status, for example Alzheimer's disease status. For example, if the biomarker is up-regulated compared to normal during Alzheimer's disease, then a measured amount above the diagnostic cutoff provides a diagnosis of Alzheimer's disease. Alternatively, if the biomarker is down-regulated during Alzheimer's disease, then a measured amount below the diagnostic cutoff provides a diagnosis of Alzheimer's disease.

Similarly, if the biomarker is up-regulated compared to normal during non-Alzheimer's dementia, then a measured amount above the diagnostic cutoff provides a diagnosis of non-Alzheimer's dementia. Alternatively, if the biomarker is down-regulated during non-Alzheimer's dementia compared to Alzheimer's disease, then a measured amount below the diagnostic cutoff provides a diagnosis of non-Alzheimer's dementia (i.e., a negative diagnosis of Alzheimer's disease).

As is well understood in the art, by adjusting the particular diagnostic cut-off used in an assay, one can increase sensitivity or specificity of the diagnostic assay depending on the preference of the diagnostician. The particular diagnostic cut-off can be determined, for example, by measuring the amount of the biomarker in a statistically significant number of samples from subjects with the different Alzheimer's disease statuses, as was done here, and drawing the cut-off to suit the diagnostician's desired levels of specificity and sensitivity.

Method of Making

Methods of making the molecules described herein are provided in the Examples. The molecules may be synthesized using conventional chemical technologies available to those skilled in the art. Salts of the molecules described herein are also provided. In some embodiments, the salts are pharmaceutically acceptable. Acceptable salts of the compounds include, but are not limited to hydrochloride, hydrobromide, hydroiodide, nitrate, sulfate, bisulfate, phosphate, acid phosphate.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxy ethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, /chlorobenzenesulfonic acid, phenyl-substituted alkanoic acids, propionic acid, -toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolaminc, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in Handbook of Pharmaceutical Salts: Properties, and Use (2002).

The molecules described herein can be used to make pharmaceutical compositions. Pharmaceutical compositions comprising the peptoids described herein and a pharmaceutically acceptable carrier are provided. A pharmaceutically acceptable carrier is any carrier suitable for in vivo administration. Examples of pharmaceutically acceptable carriers suitable for use in the composition include, but are not limited to, water, buffered solutions, glucose solutions, oil-based or bacterial culture fluids. Additional components of the compositions may suitably include, for example, excipients such as stabilizers, preservatives, diluents, emulsifiers and lubricants. Examples of pharmaceutically acceptable carriers or diluents include stabilizers such as carbohydrates (e.g., sorbitol, mannitol, starch, sucrose, glucose, dextran), proteins such as albumin or casein, protein-containing agents such as bovine serum or skimmed milk and buffers (e.g., phosphate buffer). Especially when such stabilizers are added to the compositions, the composition is suitable for freeze-drying or spray-drying. The composition can also be emulsified.

The compositions described herein may be administered by any means known to those skilled in the art, including, but not limited to, oral, topical, intranasal, intraperitoneal, parenteral, intravenous, intramuscular, subcutaneous, intrathecal, transcutaneous, nasopharyngeal, or via transmucosal absorption. Thus the compositions may be formulated as an ingestible, injectable, topical or suppository formulation. The compositions may also be delivered with in a liposomal or time-release vehicle. In some instances, the compositions described herein can be administered such that they are delivered or are able to cross the blood-brain barrier. In some embodiments, administration of the compositions described herein to a subject can elicit beneficial effects in a dose-dependent manner. The composition can be administered as a single dose or as divided doses. In some embodiments, the compositions described herein can be administered at a first time point and a second time point. In some embodiments, a composition can be administered such that a first administration is administered before the other with a difference in administration time of 1 hour, 2 hours, 4 hours, 8 hours, 12 hours, 16 hours, 20 hours, 1 day, 2 days, 4 days, 7 days, 2 weeks, 4 weeks, 2 months, 3 months, 4 months, 5 months, 6 months, 7 months, 8 months, 9 months, 10 months, 11 months, 1 year or more.

It will be appreciated that the specific dosage administered in any given case will be adjusted in accordance with the composition or compositions being administered, the disease to be treated or inhibited, the condition of the subject, and other relevant medical factors that may modify the activity of the composition or the response of the subject, as is well known by those skilled in the art. For example, the specific dose for a particular subject can depend on age, body weight, general state of health, diet, the timing and mode of administration, the rate of excretion, medications used in combination and the severity of the particular disorder to which the therapy is applied. Dosages for a given patient can be determined using conventional considerations, e.g., by customary comparison of the differential activities of the composition of the invention and of a known agent, such as by means of an appropriate conventional pharmacological or prophylactic protocol. Suitable effective dosage amounts for administering the compositions can be determined by those of skill in the art, but typically range from about 1 microgram to about 100.000 micrograms per kilogram of body weight weekly, although they are typically about 1,000 micrograms or less per kilogram of body weight weekly. In some embodiments, the effective dosage amount ranges from about 10 to about 10,000 micrograms per kilogram of body weight weekly. In another embodiment, the effective dosage amount ranges from about 50 to about 5,000 micrograms per kilogram of body weight weekly. In another embodiment, the effective dosage amount ranges from about 75 to about 1,000 micrograms per kilogram of body weight weekly. The effective dosage amounts described herein refer to total amounts administered, that is, if more than one composition is administered, the effective dosage amounts correspond to the total amount administered.

The maximal dosage for a subject is the highest dosage that does not cause undesirable or intolerable side effects. The number of variables in regard to an individual prophylactic or treatment regimen is large, and a considerable range of doses is expected. The route of administration will also impact the dosage requirements. It is anticipated that dosages of the composition will inhibit progression of the condition by at least 10%, 20%, 30%, 40%, 50%, 60%, 70%, 80%, 90% or 100% compared to pre-treatment symptoms or progression of the disease if left untreated. It is specifically contemplated that pharmaceutical preparations and compositions may palliate or alleviate symptoms of the disease without providing a cure, or, in some embodiments, may be used to stop progression of the disease or disorder and in some cases may even reverse progression.

Combinations of Markers

While individual biomarkers are useful diagnostic biomarkers, it has been found that a combination of biomarkers can provide greater predictive value of a particular status than single biomarkers alone. Specifically, the detection of a plurality of biomarkers in a sample can increase the sensitivity and/or specificity of the test. In some embodiments, a plurality of biomarkers is used in a diagnostic test described herein. In some embodiments, a plurality of molecules with an affinity to biomarkers indicative of a disease can be used to diagnose a disease.

Determining Risk of Developing Disease

In some embodiments, this invention provides methods for determining the risk of developing a disease, for example Alzheimer's disease in a subject. Biomarker amounts or patterns are characteristic of various risk states, e.g., high, medium or low. The risk of developing Alzheimer's disease can be determined by measuring the relevant biomarker or biomarkers and then either submitting them to a classification algorithm or comparing them with a reference amount and/or pattern of biomarkers that is associated with the particular risk level.

Determining State of Disease

In some embodiments, this invention provides methods for determining the stage of a disease, for example, Alzheimers disease in a subject. Each stage of the disease has a characteristic amount of a biomarker or relative amounts of a set of biomarkers (a pattern). The stage of a disease can be determined by measuring the relevant biomarker or biomarkers and then either submitting them to a classification algorithm or comparing them with a reference amount and/or pattern of biomarkers that is associated with the particular stage.

Determining Course (Progression/Remission) of Disease

In one embodiment, this invention provides methods for determining the course of a disease in a subject, for example, Alzheimer's disease in a subject. Disease course refers to changes in disease status over time, including disease progression (worsening) and disease regression (improvement). Over time, the amounts or relative amounts (e.g., the pattern) of the biomarkers changes. For example, the concentrations of biomarkers may increase/decrease in samples from Alzheimer's subjects. Therefore, the trend of these markers, either increased or decreased over time toward diseased or non-diseased indicates the course of the disease. Accordingly, this method involves measuring one or more biomarkers in a subject at least two different time points, e.g., a first time and a second time, and comparing the change in amounts, if any. The course of disease can be determined based on these comparisons. Similarly, this method can be useful for determining the response to treatment. If a treatment is effective, then the biomarkers will trend toward normal, while if treatment is ineffective, the biomarkers will trend toward disease indications.

Subject Management

In certain embodiments of the methods of qualifying a disease for example, Alzheimer's disease status, the methods further comprise managing subject treatment based on the status. Such management can include the actions of the physician or clinician subsequent to determining Alzheimer's disease status. For example, if a physician makes a diagnosis of Alzheimer's disease, then a certain regime of treatment, such as prescription or administration of cholinesterase inhibitors, antiglutamatergic therapy or antioxidants, might follow. Alternatively, a diagnosis of non-Alzheimer's disease or non-Alzheimer's disease dementia might be followed with further testing to determine a specific dementia that might the subject might be suffering from. Also, if the diagnostic test gives an inconclusive result on Alzheimer's disease status, further tests may be called for.

Communication Results

Additional embodiments of the invention relate to the communication of assay results or diagnoses or both to technicians, physicians or subjects, for example. In certain embodiments, computers will be used to communicate assay results or diagnoses or both to interested parties, e.g., physicians and their subjects. In some embodiments, the assays can be performed or the assay results analyzed in a country or jurisdiction which differs from the country or jurisdiction to which the results or diagnoses are communicated. In some embodiments of the invention, a diagnosis based on the presence or absence in a test subject of any biomarker identified by the invention may be communicated to the subject as soon as possible after the diagnosis is obtained. The diagnosis may be communicated to the subject by the subject's treating physician. Alternatively, the diagnosis may be sent to a test subject by email or communicated to the subject by phone. A computer may be used to communicate the diagnosis by email or phone. In certain embodiments, the message containing results of a diagnostic test maybe generated and delivered automatically to the subject using a combination of computer hardware and software which will be familiar to artisans skilled in telecommunications. One example of a healthcare-oriented communications system is described in U.S. Pat. No. 6,283, 761; however, the present invention is not limited to methods which utilize this particular communications system. In certain embodiments of the methods of the invention, all or some of the method steps, including the assaying of samples, diagnosing of diseases, and communicating of assay results or diagnoses, may be carried out in diverse (e.g., foreign) jurisdictions.

EXAMPLES

Example 1. Peptoid Library Synthesis

A Peptoid library was prepared on Polystyrene macrobeads (500-560 µm; substitution: 0.4-0.7 mmol/g, Rapp) by solid-phase split and pool synthesis, yielding a one-bead one-compound library. Polystyrene macrobeads (500-560 µm; substitution: 0.4-0.7 mmol/g, Rapp Polymere) were swollen in 12 mL of dimethylformamide (DMF) at room temperature for 4 hours. The beads were then equally distributed into 14 fritted syringes and then treated twice with 20% (v/v) piperidine in DMF at room temperature with shaking (250 r.p.m.) for 12 min (2×2 ml) in an incubator shaker. The fritted syringe reaction vessels were drained and washed, repeated four times prior to followed amino acid coupling cycle with DMF (4×2 ml). To couple the Cysteine, 2 ml of 220 mM Fmoc-Cys(Trt)-OH solution was added to the beads followed by 2 ml of 220 mM solution of O-(benzotriazol-1-yl)-N,N,N',N'-tetramethyluronium hexafluorophosphate (HBTU) and 1-hydroxybenzotriazole (HOBT) in DMF containing 440 mM N-methyl morpholine (NMM). The syringes were shaken at room temperature for 90 minutes. The syringes were then drained and washed with DMF (4×2 ml). The beads were treated two times with 20% piperidine in DMF for 12 min (2×2 ml) then washed with DMF. Peptoid synthesis was carried out in each of the reaction vessels according to the submonomer addition method. Peptoid monomer addition was carried out in a two-step process. In step 1, acylation was carried out using chloroacetic acid and di-isopropylcarbodiimide (DIC). A 1 ml solution of 1.8 M chloroacetic acid in anhydrous DMF and 1 ml solution of 1.8M DIC in anhydrous DMF were added to the resin and mixed for 12 min at 36° C. during the acylation step of the submonomer cycle. After washing the resin with 2 mL of DMF four times a 1.8 M solution of the 1,4-diaminobutane (2 mL) in N-methylpyrrolidinone (NMP) to each of fourteen reaction vessels. This displacement reaction was carried out for 90 minutes at 36° C. with periodic bubbling mixing. Following displacement the resin was washed four times with 2 mL of DMF. In step 2, the acylation was carried out using chloroacetic acid and di-isopropylcarbodiimide (DIC). A 1 ml solution of 1.8 M chloroacetic acid in anhydrous DMF and 1 ml solution of 1.8M DIC in anhydrous DMF were added to the resin and mixed for 12 min at 36° C. in an incubator shaker. The resin was washed with 2 mL of DMF for four times and the resin-bound bromine was then displaced with one of the fourteen (Benzylamine, Methylamine, Allylamine, Isobutulamine, 4-(Aminomethyl)pyridine, 4-(2-Aminoethyl)morpholine, 3,4-Dimethoxybenzylamine, 2,2-Diphenylethylamine, Piperonylamine, R-(+)-α-Methylbenzylamine, Cyclopropylamine, 1,4-Diaminobutane, Glycine, 2-Aminoethanol) amine sub-monomers chosen for the library synthesis by adding a 1.8 M solution of the amine (2 mL) in N-methylpyrrolidinone (NMP) to each of the fourteen reaction vessels. FIG. 10. The resin was then combined from each of the reaction vessels into a mixing vessel and then equally redistributed back into the fourteen reaction vessels. Peptoid couplings proceeded as described above for the eight remaining couplings. Following the final peptoid residue coupling the resin was not combined. The resulting library consisted of fourteen sub-libraries with the identity of the final residue from each reaction vessel known. After library synthesis, the beads were washed with dichloromethane (4×12 ml) and with absolute ethanol (4×12 ml).

Example 2. Quality Control

All synthesis products of example 1 were checked for quality using Thermo LTQ FT mass spectrometer (Fourier Transform Ion Cyclotron Mass Spectrometer coupled to a Linear Ion Trap) produced by Thermo Scientific (formerly Finnigan), 2 beads were isolated, cleaved (as described below) and analyzed using MS and MS/MS.

Example 3. On-Bead Library Screening

The peptoid library of example 1 was screened by placing the library in a fritted syringe, washing the library three times with PBST and then adding 1:300 dilution of Alzheimer's disease serum in PBST and incubating the mixture for 3 hours at room temperature on the incubator shaker. Unbound serum was then removed and the beads were washed four times with PBST. The secondary antibody Alexa Fluor® 647 AffiniPure Goat Anti-Human IgA+IgG+ IgM (H+L) at 1:250 dilution in PBST was added to the reaction vessel and incubated for 90 minutes at room temperature. The polystyrene macrobeads were then washed with PBST (4×4 ml) and screened under a microscope. The isolated beads were then manually sorted into 384-well polypropylene plates, one bead per well. To cleave the library beads 40 µl of a cleavage cocktail consisting of 48% TFA, 48% dichloroethane, 2% tri-isopropylsilane and 2% water was added to each well. The plates were sealed and incubated at room temperature for 8 h, after which the cleavage cocktail was allowed to evaporate in a fume hood. The peptoids were dissolved in 100 µl of acetonitrile/water (1:1) and transferred quantitatively into a duplicate set of 384-well polypropylene plates. Solvent was evaporated and the residue in each well was dissolved in 20 µl dimethylsulfoxide (DMSO).

Example 4. Mass Spectrometer Analysis

ESI MS and tandem MS/MS analysis of samples were performed using a Thermo LTQ FT mass spectrometer (Fourier Transform Ion Cyclotron Mass Spectrometer coupled to a Linear Ion Trap) produced by Thermo Scientific (formerly Finnigan). Samples were infused into the ESI source using syringe pump with 5 uL/min flow rate and analyzed in positive ion mode. Source parameters used were source Voltage 3.0 kV, capillary Voltage 48V, tube Lens Voltage 250V and CID (collision-induced dissociation) energy 26%. The software Xcalibur (version 2.0.7) that controls the instrument is used for the data analysis.

Example 5. Printing and Analysis of Glass Slides

Compounds were diluted in the polypropylene 384 plates (catalog ID: MMP384) to a final concentration of 75 uM, 50% DMSO and 50% PBS to enable a visual inspection and confirmation of the printed dry spots prior to using the slides. Fresh frozen vacuum packed maleimide slides (Microsurfaces MAL_02 high density type) were used to print the compounds. The slides were printed 24 microarrays/slide, with robotic microarrayer using Arrayit 946MP3 microarray printing pin(s) with the chamber of the microarrayer set to 50% humidity, stringent wash/dry settings for microarray printing pins between small molecules, spot spacing such that small molecule spots on slides cannot merge together and at least 2 technical replicates per small molecule. Small molecules are tracked in source plates using excel and txt files. The spot map (GAL file) is created using microarray robot sample tracking software and txt files of source plate information. After printing is completed, slides were left to dry overnight. To confirm that all printed spots were dry, observation under a microscope used small salt PBS crystals for each spot executed in the print run. Next day, slides were washed 2 times for 1 minute in freshly made 1% (v/v) solution of 2-mercaptoethanol in DMF to remove unbound small molecules from the surface of the slides using microarray wash tubes (Arrayit catalog ID: MWT). Then reacted in 1% (v/v) solution of 2-mercaptoethanol in DMF for 1 hour. The slides were then washed 1× in DMF followed by 3× times 10 seconds in iso-propanol. The slides were washed 3×10 seconds PBST and right into 1 hour Arrayit Blockit Plus (casein based) blocking buffer for 1 hour in Microarray Reaction tray catalog ID: MRT. After 1 hour, slides were washed 3×10 seconds in PBST followed by very short rinse in ddH2O. Immediately proceeded to dry in Arrayit Microarray centrifuge (catalog ID: MHC) for 20 seconds and now the slide is ready to load into the AHC4×24 hybridization cassette. While slides are blocking, gasket from the AHC4×24 hybridization cassette was also soaked in 1X Protein Microarray Reaction Buffer Plus to be sure serum proteins cannot attach nor absorb into the rubber gasket of the hyb cassette. Prior to loading gasket onto the hardware of the cassette, the buffer was taken out, and dried by squeezing it dry inside a Microarray Cleanroom wipe (catalog ID: MCW). The gasket was loaded into the hyb cassette hardware and then the slides into the base of Arrayit Hybridization Cassette AHC4×24. Gasket seals were confirmed to be straight against glass to avoid the possibility of leaking from microarray to microarray (observed by dark lines made by the gasket against the glass).

Example 6. Serum Reaction

Serum samples were diluted 1 to 600 in 1X Arrayit Protein Microarray Reaction Buffer Plus (PMRBP) in polypropylene 96 well plate, and mixed well by pipetting up and down 10 times during transfer from serum tubes to plates containing reaction buffer. Using a multichannel pipette, 100 µl of mixed serum/reaction buffer samples from 96-well plate were transferred to corresponding reaction tool. The samples were incubated for 1 hour at 37° C., 500 RPM, 2 mm orbit, using Arrayit Hybridization Station Catalog ID: MMHS2. The wells were washed with PBST buffer 6 times, expelling buffer completely each time, then added secondary antibody Alexa Fluor® 647 AffiniPure Goat Anti-Human IgA+IgG+IgM (H+L) at 1:4000 dilution in 1X Arrayit PMRBP. Slides were incubated for 1 hour at 37° C., 500 RPM, MMHS2. The slides were washed with PBST buffer 6 times, expelling buffer completely each time and scanned at 50, 35, 25, 15 PMT with laser low using Arrayit Innoscan 710AL. The gal file was opened over the image, performed spot finding work, saved work file to preserve how the spots were found. The txt files were generated and saved for all scans by slide number and block number. Background subtracted median signals were used for further analysis.

Example 7. Tuning Signal-to-Background Conditions (FIG. 14 and FIG. 15)

A step in screening the fabricated peptoids was to determine the appropriate concentrations of peptoids, serum, and secondary antibodies to differentiate a signal from background or excessive saturation in the tests. The peptoids were printed at 1.25 mM, 625 µM, 300 µM, 150 µM, and 75 µM concentration. The serum samples were diluted 1:600, 1:1200 and 1:2400 in 1× Arrayit Protein Microarray Reaction Buffer Plus (PMRBP) and applied to the printed glass slides. Slides were washed then secondary antibody added (Alexa Fluor® 647 AffiniPure Goat Anti-Human IgA+IgG+IgM (H+L)). The secondary antibodies were diluted 1:2000 and 1:4000 in 1X Arrayit PMRBP and added to the slides. The slides were washed and scanned using Arrayit Innoscan 710AL. FIG. 14 data are displayed as the scanned raw images of all individual blocks. At the serum concentration of 1:600 dilution, peptoid concentration of 75 uM, and secondary antibody dilution of 1:4000 fold the peptoids bound specifically to the antibodies. Saturation or high background signal occurred at all other conditions. The matched control did not bind to the peptoids, demonstrating the specificity of interaction between the antibodies and the feature specific peptoids. These concentration conditions were used for all subsequent peptoid library screening and validation. FIG. 15, a schematic representation of the FSM printed on glass slides at different concentrations.

Example 8. Extraction of AD Biomarkers

The peptoids synthesized according to the invention can provide a general subset of approximately 100,000 feature specific molecules (FSMs). The FSMs can then be subjected to a series of filters or differentiating conditions to stepwise eliminate peptoids that do not meet the required functionality.

Figure 1B:
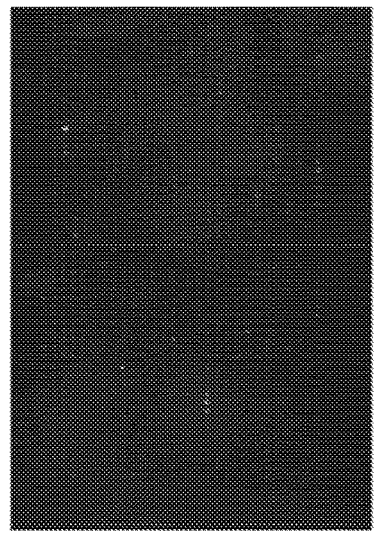
Figure 1C:
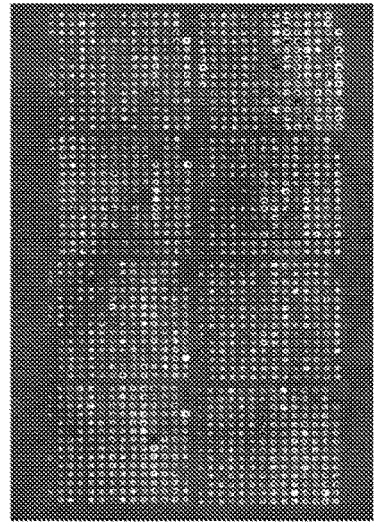

Filter #1: General binding to antibodies: The first step in the extraction phase of the protocol was to differentiate a subset of FSMs that bind only to the IgA, IgM and IgG antibodies from peptoids that bind promiscuously to other proteins. To determine the antibody specific binding, the appropriate concentration of Alzheimer's disease serum (1:600 dilution) was added. After incubation and washing, the serum antibodies bound by peptoid was quantified by adding Alexa Fluor® 647 AffiniPure Goat Anti-Human IgA+IgG+IgM (H+L) at 1:4000 dilution in 1X Arrayit PMRBP. In another parallel experiment a matched labeled anti-phospho antibody and anti-peptide antibody was used (FIG. 1.) This step of the experiment also demonstrated that the screening conditions developed above were also sufficient for the validation of specific binding. As shown in FIG. 1, a subset of the FSM peptoid molecules synthesized can be isolated by Filter #1 because they specifically bind to IgA, IgM and IgG antibodies but not to other protein targets (in this case phosphorylated proteins and amyloid beta 42 peptide). This refined subset of 1,536 peptoids that survived Filter #1 can be termed a "Focused Library" of peptoids that can be subjected to further filtering for more specific functionality.

Figure 2A:
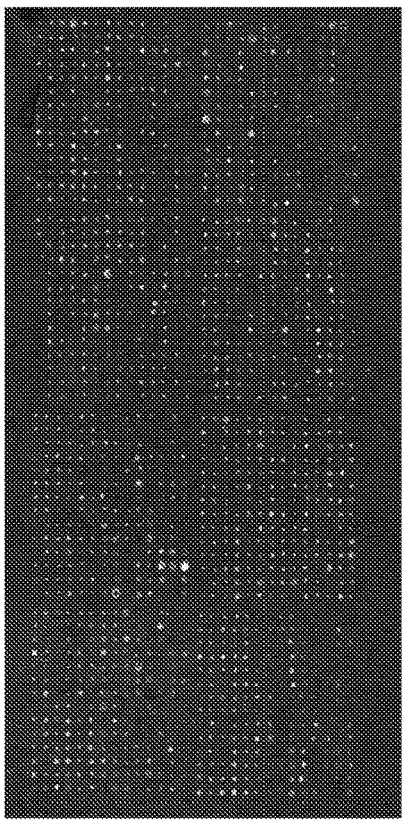
Figure 2B:
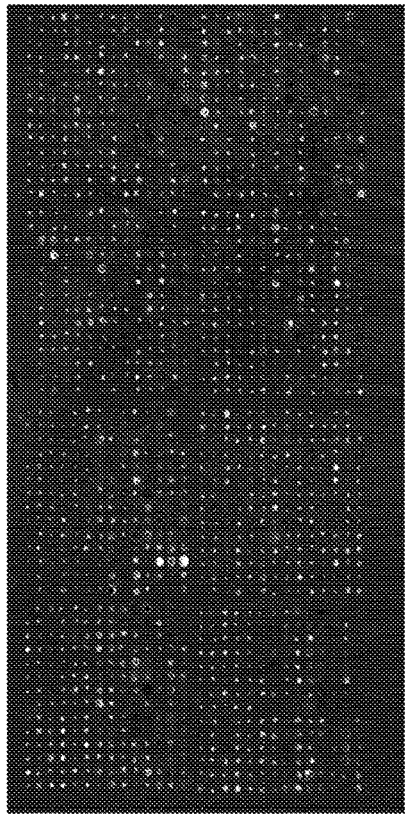

Filter #2: Specific binding to AD antibodies: The second step in the extraction phase of the protocol was to further differentiate peptoids within the Focused Library subset that bind to AD related antibodies (if any) from those binding to other antibodies. The Focused Library peptoids were exposed to serum samples in which known AD subjects and normal control subjects were included to isolate any binding that correlates only to AD subjects. FIG. 2, shows that the results of the 1,536 peptoids of the Focused Library subjected to Normal Control (left) and to a known Alzheimer's subject (right). Both subject populations show extensive response to the Focused Library peptoids designed and filtered to respond to IgG, IgM, and IgA. However, when the overlapping data was subtracted out, nine (9) of the peptoids show elevated specificity and sensitivity for antibodies correlating to AD subjects. In FIG. 16, the nine peptoids show clear differentiation in response to AD subjects in contrast to normal control subjects. Repeated comparisons of known AD subjects and Normal Control subjects demonstrated similar outcomes.

Example 9. Results

Nine peptoids were isolated that show high correlation with Alzheimer's disease subjects. A double blind analysis on fifty blood samples was then performed to provide an initial validation that the nine peptoids could identify AD positive and AD negative samples. FIG. 8 shows the average intensity of the peptoids for 50 blood samples randomly selected from a cohort of 126. An arbitrary value of 20,000 was set as the hurdle to determine AD positive from AD negative samples. Post-analysis sorting of Normal Control and AD subjects shows 5 false positives among the 29 Normal Control subjects and three false negatives among the 21 AD subjects which leads to sensitivity (85.72%) and specificity (82.76%).

Example 10. Validation of Specific Molecules Binding to MCI and AD Subjects (FIG. 3)

Figure 3A:
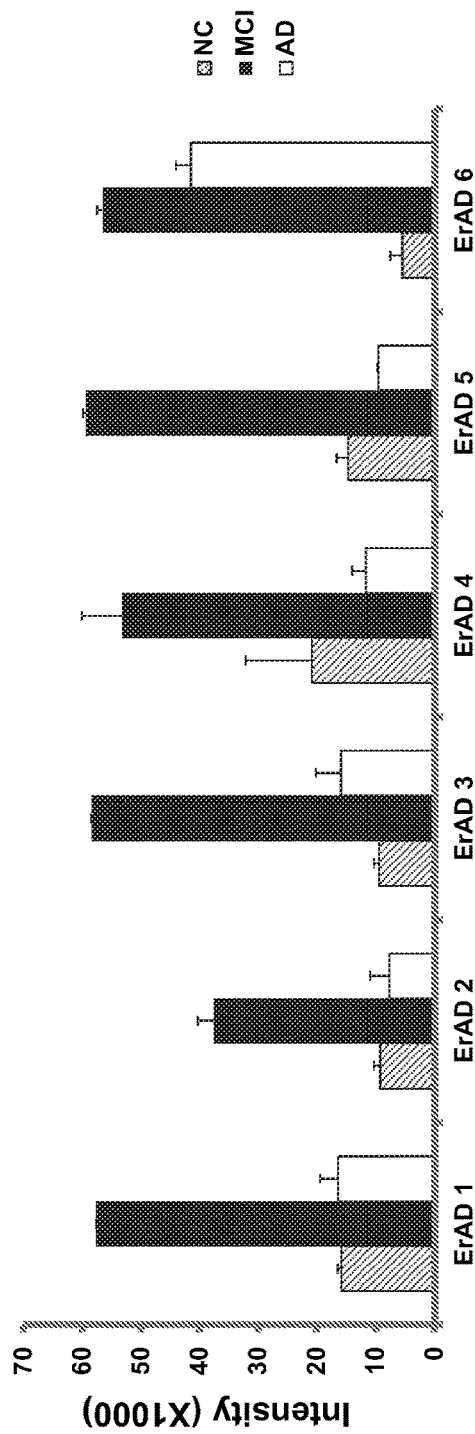
FIG. 3. Disease specific molecules: depicts quantitation of fluorescence intensity of each molecule incubated with either mild cognitive impairment (MCI) serum (3A) and AD (3B) serum samples on microarray.
Figure 3B:
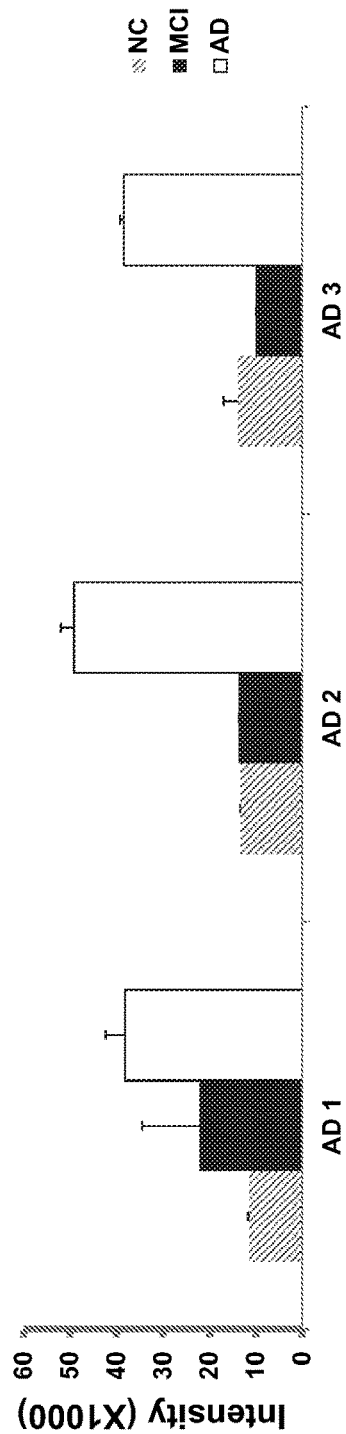

Serum samples (1:600 dilution) from MCI, AD and normal control subjects were incubated with microarrays printed with specific molecules. Slides were washed then added secondary antibody Alexa Fluor® 647 AffiniPure Goat Anti-Human IgA+IgG+IgM (H+L) at 1:4000 dilution in 1X Arrayit PMRBP. The slides were then washed and scanned using Arrayit Innoscan 710AL. The background subtracted median signals were used for analysis. In FIG. 3, the signal intensities were graphed against ErAD1-6 (FIG. 3A) and AAD1-3 (FIG. 3B). The data shows a correlation between signal intensities and the disease diagnosis. Error bars represent the median+standard deviation.

Figure 4A:
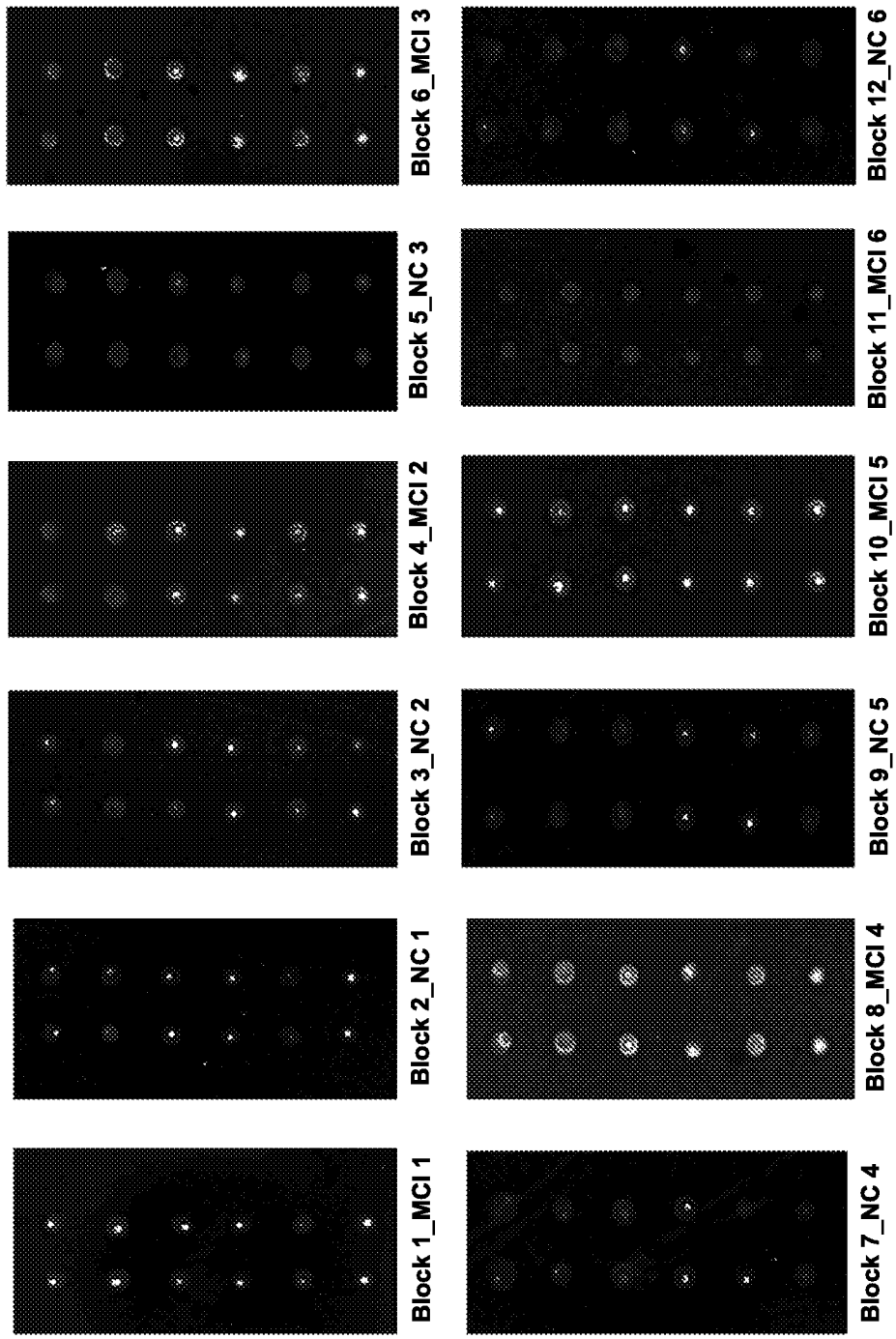
FIG. 4. Blind analysis of specific molecules binding to MCI subjects: (4A) depicts raw images of microarrays printed with 6 molecules specific to MCI subjects and incubated with corresponding serum samples followed by labeled secondary antibody. The fluorescence intensity of each spot on microarray is shown in image. (4B) depicts raw images of microarrays printed with 6 molecules specific to MCI subjects and incubated with corresponding serum samples followed by labeled secondary antibody. The fluorescence intensity of each spot on microarray is shown.
Figure 4B:
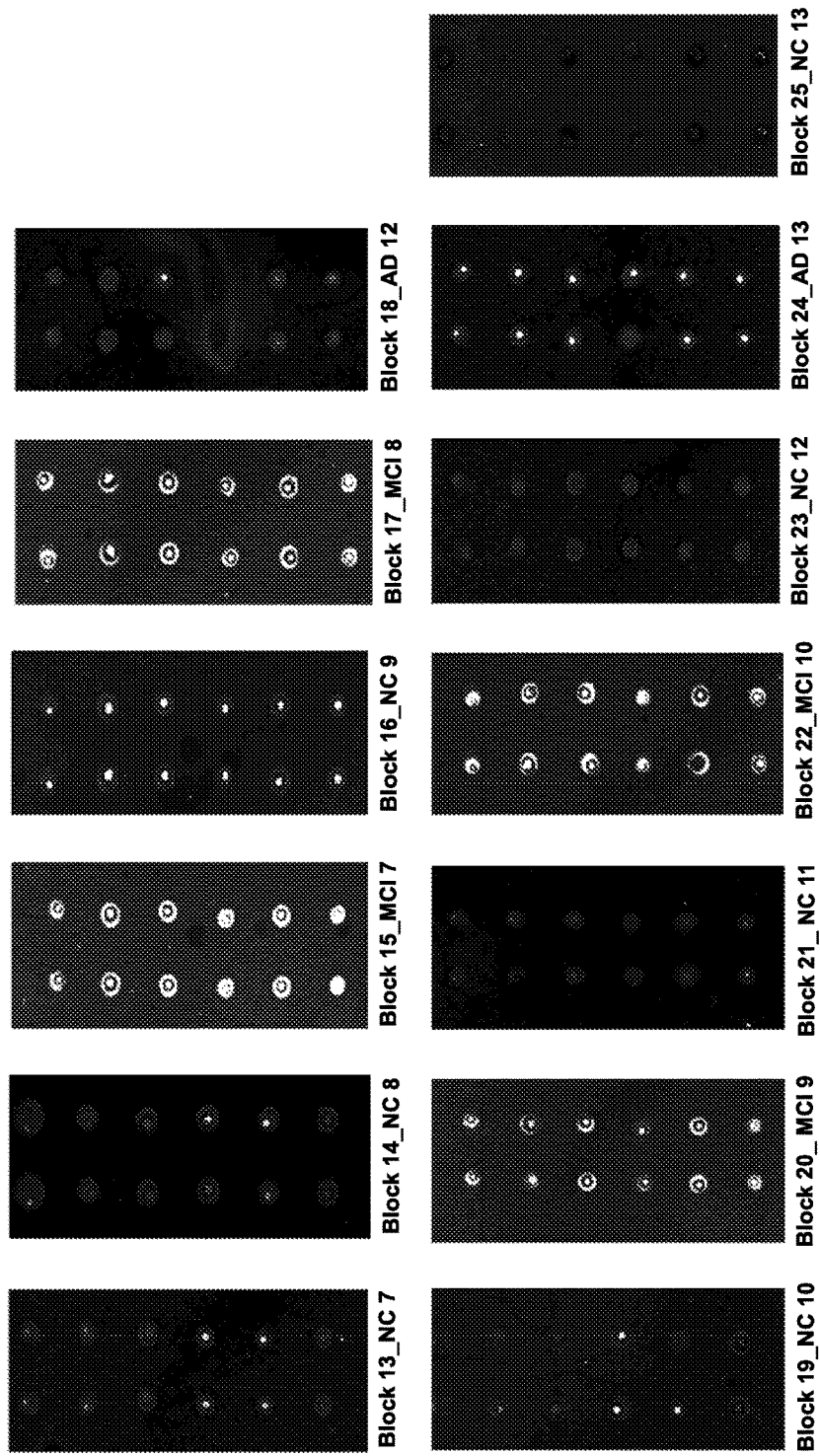

Example 11. Blind Analysis of Specific Molecules Binding to MCI Subjects (FIG. 4)

Serum samples (1:600 dilution) from MCI and normal control total of 25 subjects were incubated with microarrays printed with specific molecules ErAD1-6 in duplicate. Slides were washed then added secondary antibody Alexa Fluor® 647 AffiniPure Goat Anti-Human IgA+IgG+IgM (H+L) at 1:4000 dilution in 1X Arrayit PMRBP. After a brief wash slides were then scanned using Arrayit Innoscan 710AL. FIG. 4. shows the scanned raw images of 25 individual blocks.

Example 12. Blind Analysis of Specific Molecules Binding to MCI Subjects (FIG. 5)

The background subtracted median fluorescence signals from 25 blind subjects were used for analysis. In FIG. 5 the signal intensities were graphed against disease diagnosis for all ErAD1-6. Error bars represent the median+standard deviation. The data shows a correlation between signal intensities and the MCI state.

Figure 6A:
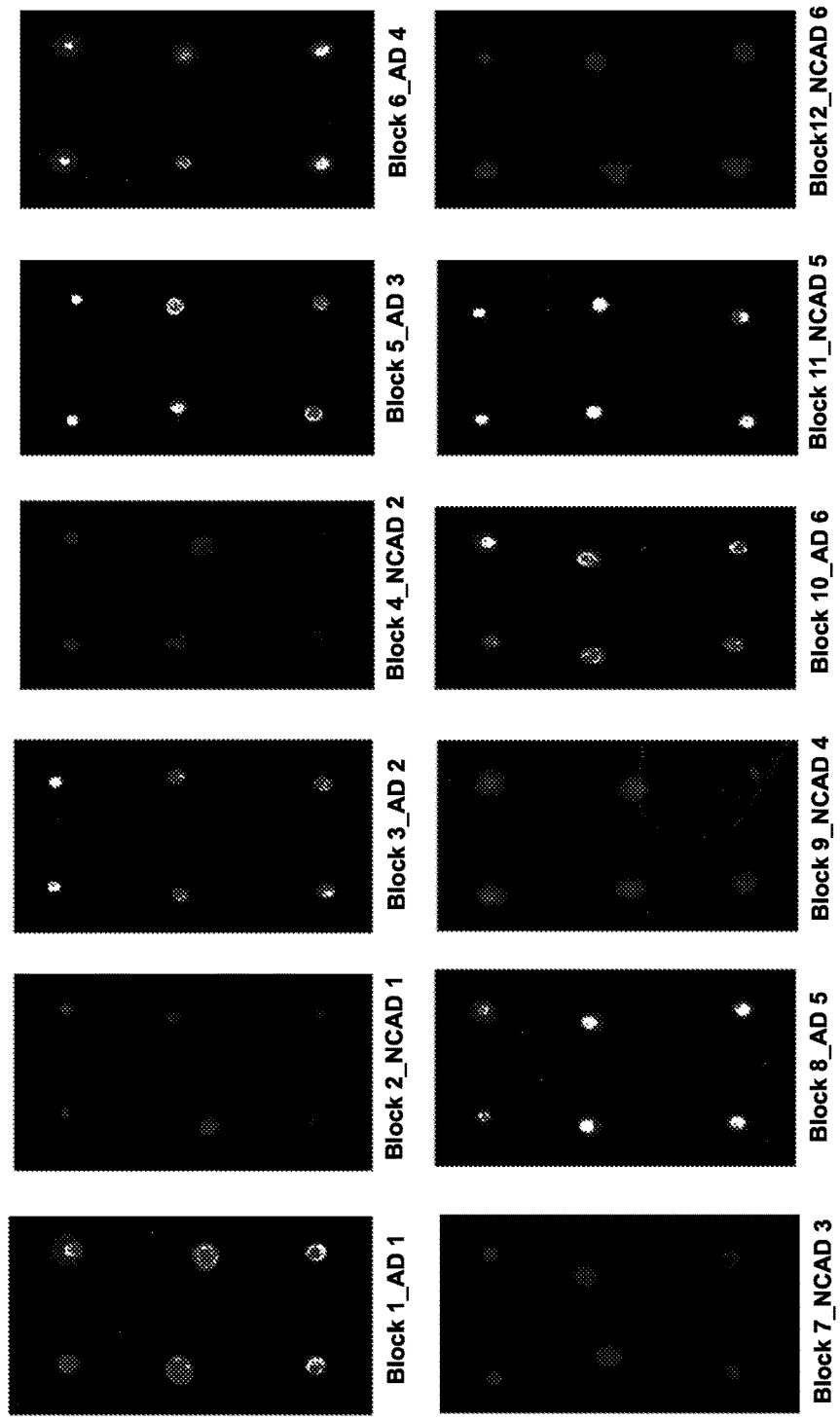
FIG. 6. Blind analysis of specific molecules binding to AD subjects: (6A) depicts raw images of microarrays printed with 3 molecules (in duplicate) specific to AD subjects and incubated with corresponding serum samples followed by labeled secondary antibody. The fluorescence intensity of each spot on microarray is shown in image. (6B) depicts raw images of microarrays printed with 3 molecules (in duplicate) specific to AD subjects and incubated with corresponding serum samples followed by labeled secondary antibody. The fluorescence intensity of each spot on microarray is shown in image.
Figure 6B:
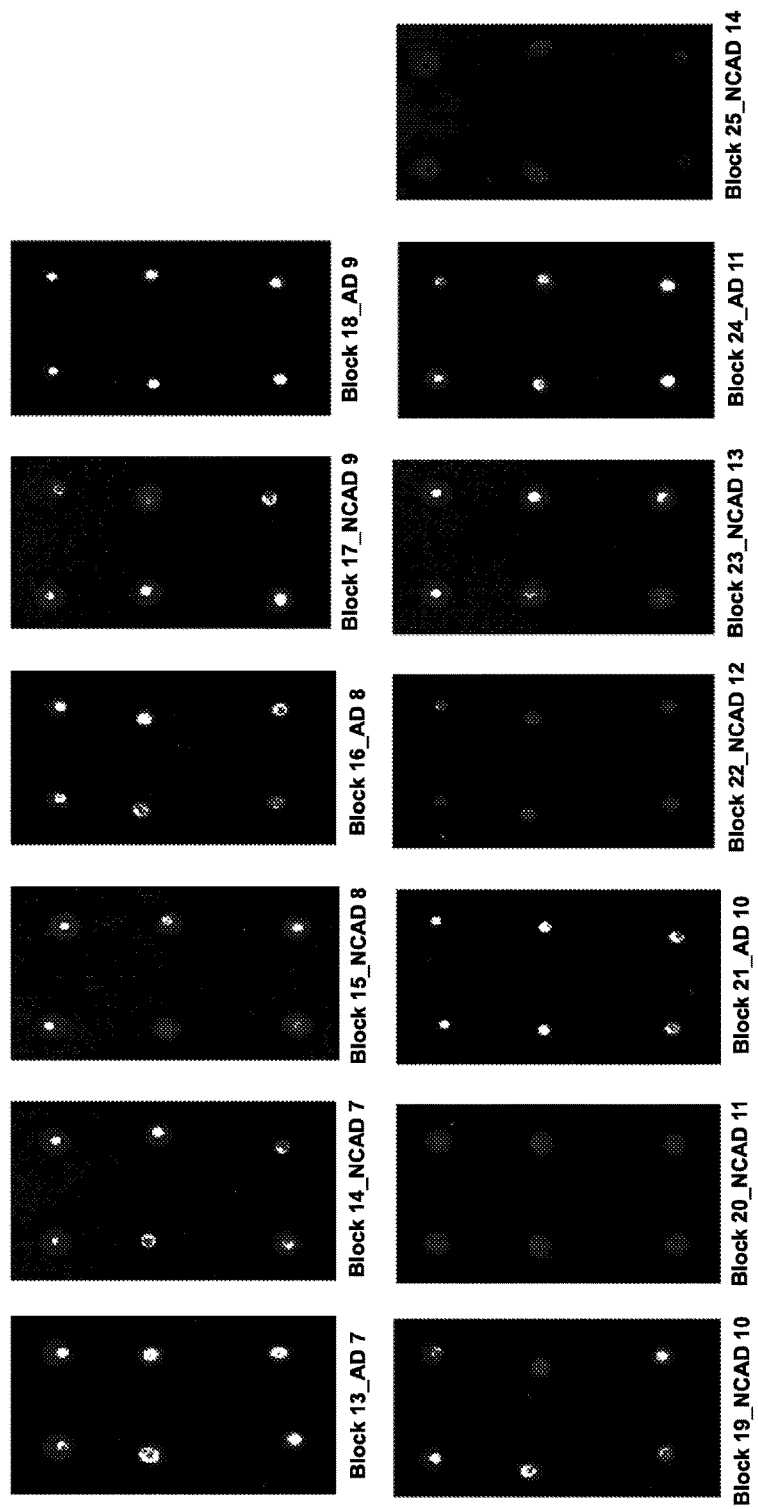

Example 13. Blind Analysis of Specific Molecules Binding to AD Subjects (FIG. 6)

Serum samples (1:600 dilution) from AD and normal control total of 25 subjects were incubated with microarrays printed with all 3 specific molecules AAD1-3 in duplicate. Slides were washed then added secondary antibody Alexa Fluor® 647 AffiniPure Goat Anti-Human IgA+IgG+IgM (H+L) at 1:4000 dilution in 1X Arrayit PMRBP. The slides were washed and scanned using Arrayit Innoscan 710AL. FIG. 6 shows the scanned raw images of all 25 individual blocks.

Example 14. Blind Analysis of Specific Molecules Binding to AD Subjects (FIG. 7)

The background subtracted median fluorescence signals from 25 blind AD and normal control subjects were used for analysis. In FIG. 7 the signal intensities were graphed against disease diagnosis for all three molecules (AAD1-3). Error bars represent the median+standard deviation. The data shows a correlation between signal intensities and the AD disease state.

Example 15. FIG. 8. Quantitation of Fluorescence Intensity of Each Molecule Specific to AD on the Microarray that Differentiates AD Subjects from Normal Controls (FIG. 8)

The background subtracted median fluorescence signals from a total of 50 different MCI, AD and normal control subjects were used for analysis. In FIG. 8 the average signal intensities were graphed against disease diagnosis for all nine molecules (ErAD1-6 and AAD1-3). The data shows correlation between signal intensities and the disease diagnosis Example 16. Alzheimer's Disease Specific Molecules and their Current Drug Response (FIG. 9)

The background subtracted median fluorescence signals from individual MCI, AD and normal control subjects were used for analysis. In FIG. 9 the signal intensities were graphed against disease diagnosis for all nine molecules (ErAD1-6 and AAD1-3) and their drug response. The data shows correlation between signal intensities and the drug response. The nine molecules showed distinctive patterns within subsets of subjects. These subset patterns can distinguish between various stages of AD. The subset patterns could also help differentiate particular drug responders from non-responders for clinical trials.

Example 17. Purification of Serum Samples by AD Specific Molecules (FIG. 13)

Serum samples (1:600 dilution) from AD and normal control subjects were column purified and incubated with microarrays printed with specific molecules ErAD1-3. Slides were washed then added secondary antibody Alexa Fluor® 647 AffiniPure Goat Anti-Human IgA+IgG+IgM (H+L) at 1:4000 dilution in 1X Arrayit PMRBP. The slides were washed and scanned using Arrayit Innoscan 710AL. The background subtracted median signals were used for analysis. In FIG. 13 the signal intensities were graphed against ErAD1-3. The data shows higher signal intensities after column purification.

Example 18. Response Intensity of the Nine Isolated Molecules for an Alzheimer's Disease (AD) Subject and for a Normal Control (NC) Subject (FIG. 16)

Nine molecules were printed at 75 µM concentration and incubated with pooled AD, MCI and normal control serum samples at 1:600 dilution. Slides were washed then added secondary antibody Alexa Fluor® 647 AffiniPure Goat Anti-Human IgA+IgG+IgM (H+L) at 1:4000 dilution in 1X Arrayit PMRBP. The slides were washed and scanned using Arrayit Innoscan 710AL. The background subtracted median signals were used for analysis. In FIG. 16 the signal intensities were graphed against nine individual molecules.

Disclosed herein are methods, materials, compositions, kits, and components that can be used for, can be used in conjunction with, can be used in preparation for, or are products of methods and compositions disclosed herein. It is understood that when combinations, subsets, interactions, groups, etc. of these materials are disclosed and while specific reference of each various individual and collective combinations and permutation of these molecules and compounds cannot be explicitly disclosed, each is specifically contemplated and described herein. It is understood that in some embodiments, the kits disclosed herein may comprise instructions to combine and or use the contents of said kits.

While some embodiments described herein have been shown and described herein, such embodiments are provided by way of example only. Numerous variations, changes, and substitutions will now occur to those skilled in the art without departing from the disclosure provided herein. It should be understood that various alternatives to the embodiments described herein can be employed in practicing the methods described herein.

What is claimed is:

1. A peptoid or pharmaceutically acceptable salt thereof comprising a formula:

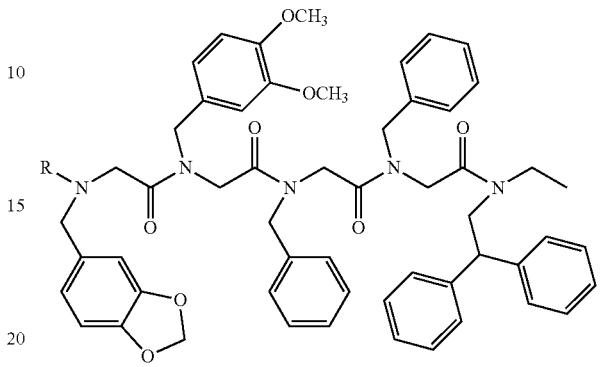

ErAD1

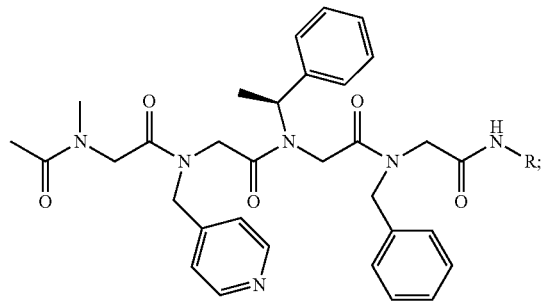

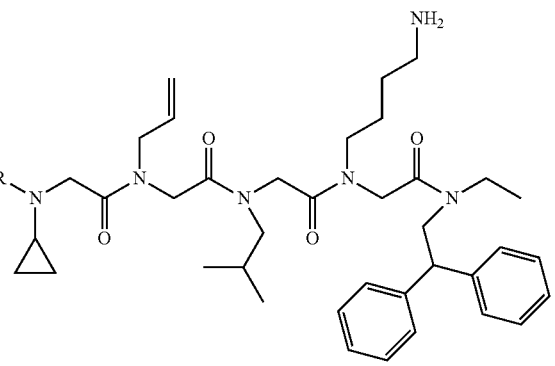

ErAD2

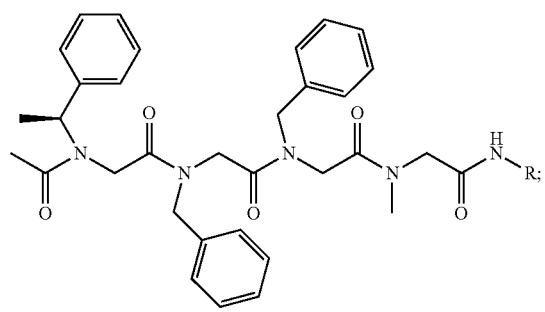

ErAD3
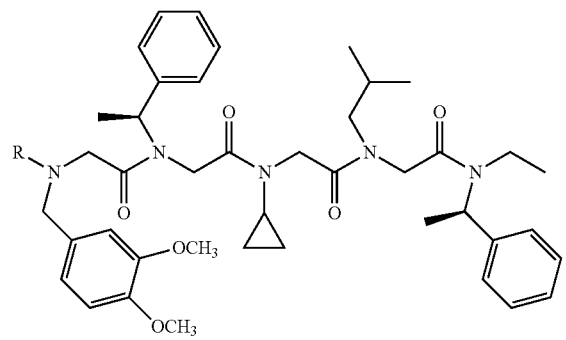
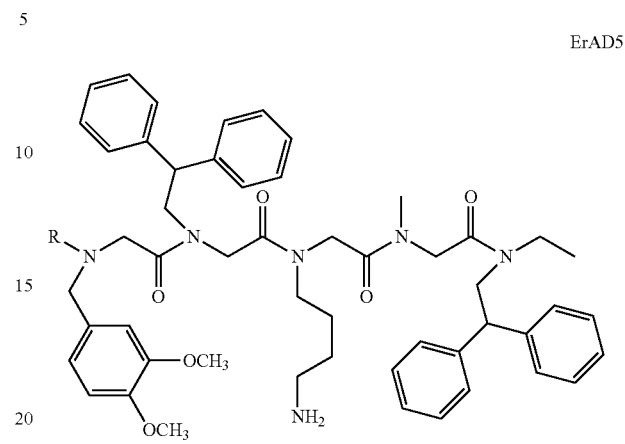
ErAD5
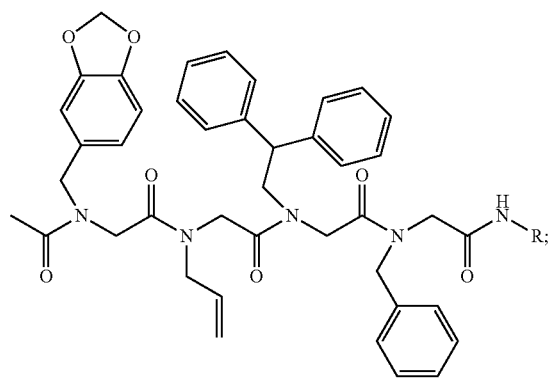
ErAD4
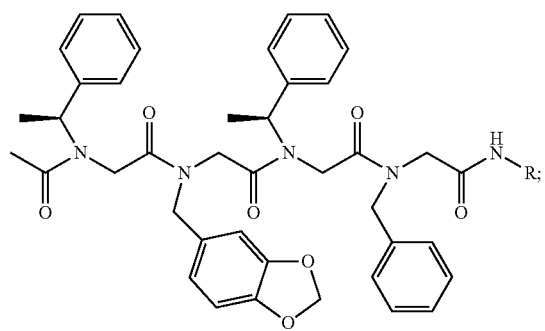
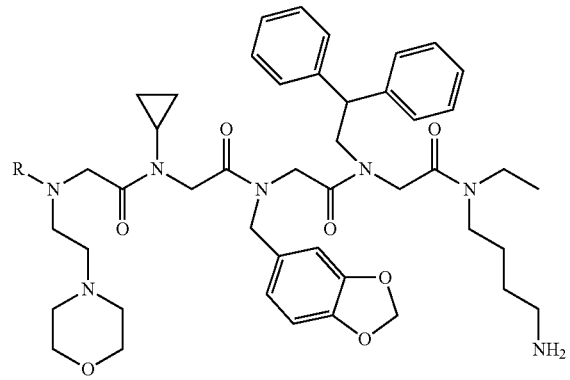
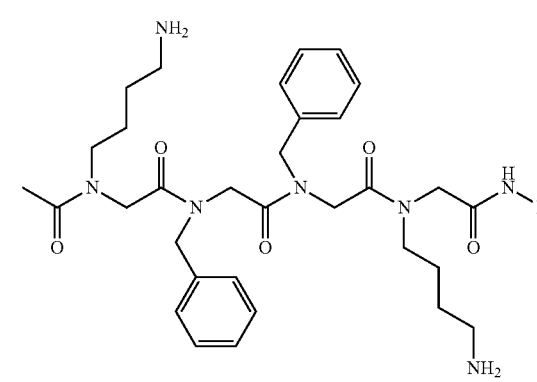
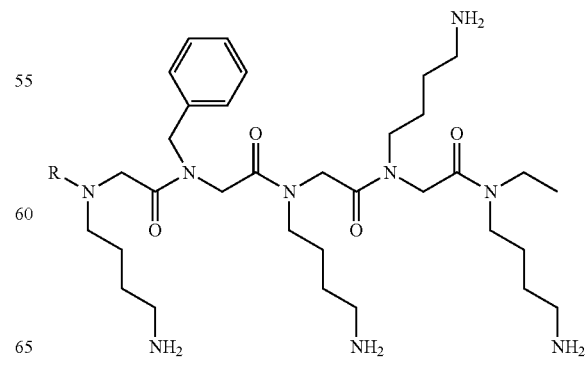
ErAD6

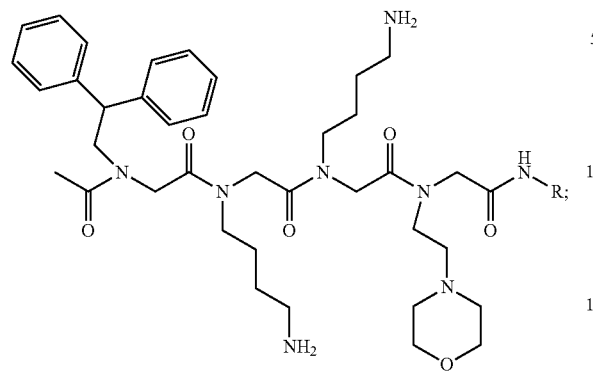

AAD1

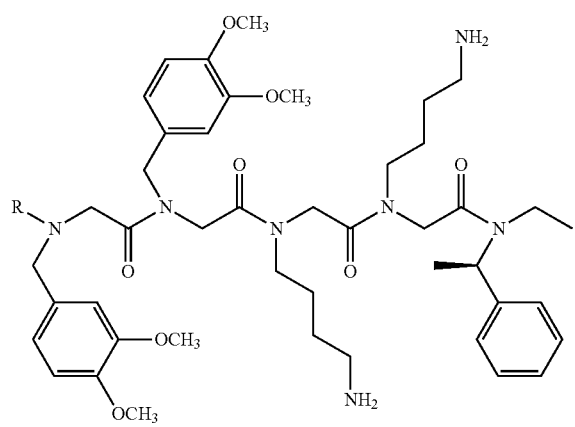

AAD2

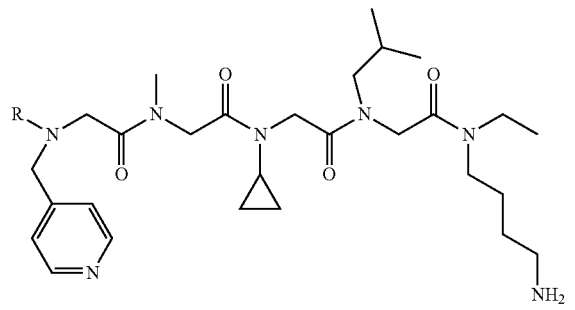

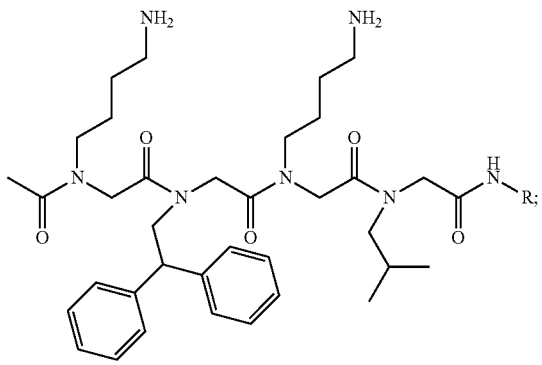

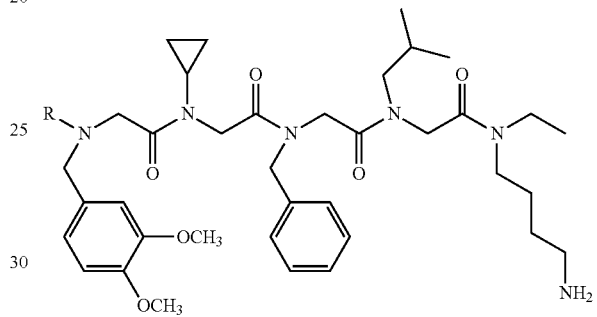

AAD3

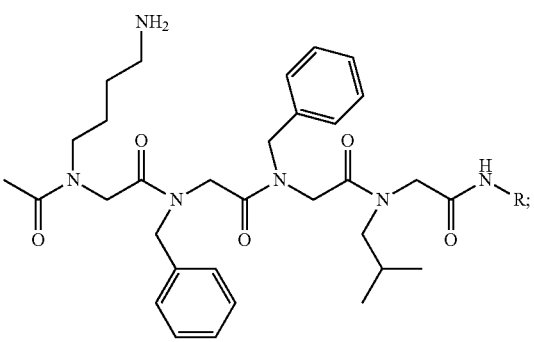

or any combination thereof, wherein R is independently selected from a group consisting of a coupling group that couples to a linker, a substrate, or a label; hydrogen; deuterium; $C_{1-6}$ alkyl; $C_{2-6}$ alkenyl; $C_{2-6}$ alkynyl, $C_{3-8}$cycloalkyl; heteroaryl, cycloalkyl; $C_{1-6}$alkylheteroaryl; $C_{1-6}$ alkylaryl; and alkylcycloalkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof, wherein X is independently selected from oxygen or sulfur; Y is independently selected from deuterium or hydrogen; A is hydrogen, deuterium, aryl, or heteroaryl.

2. The peptoid or pharmaceutically acceptable salt thereof of claim 1, comprising a structure
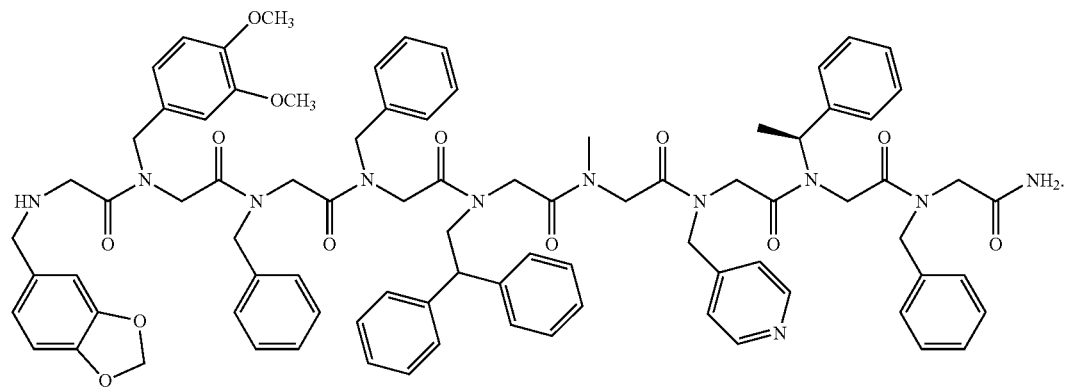 [SMILES: COc1ccc(CN(CC(=O)N(CC(=O)N(CC(=O)N(CC(=O)N(C)CC(=O)N(CC(=O)N(CC(=O)N(CC(N)=O)Cc2ccccc2)[C@@H](C)c2ccccc2)Cc2ccncc2)CC(c2ccccc2)c2ccccc2)Cc2ccccc2)Cc2ccccc2)C(=O)CNCc2ccc3c(c2)OCO3)cc1OC]
3. The peptoid or pharmaceutically acceptable salt thereof of claim 1, comprising a structure
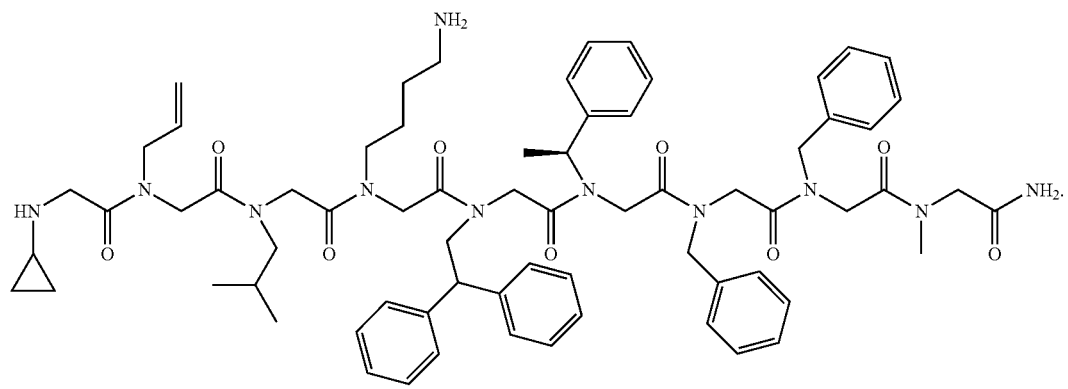 [SMILES: C=CCN(CC(=O)N(CC(=O)N(CCCCN)CC(=O)N(CC(=O)N(CC(=O)N(CC(=O)N(CC(=O)N(C)CC(N)=O)Cc1ccccc1)Cc1ccccc1)[C@@H](C)c1ccccc1)CC(c1ccccc1)c1ccccc1)CC(C)C)C(=O)CNC1CC1]
45
4. The peptoid or pharmaceutically acceptable salt thereof of claim 1, comprising a structure
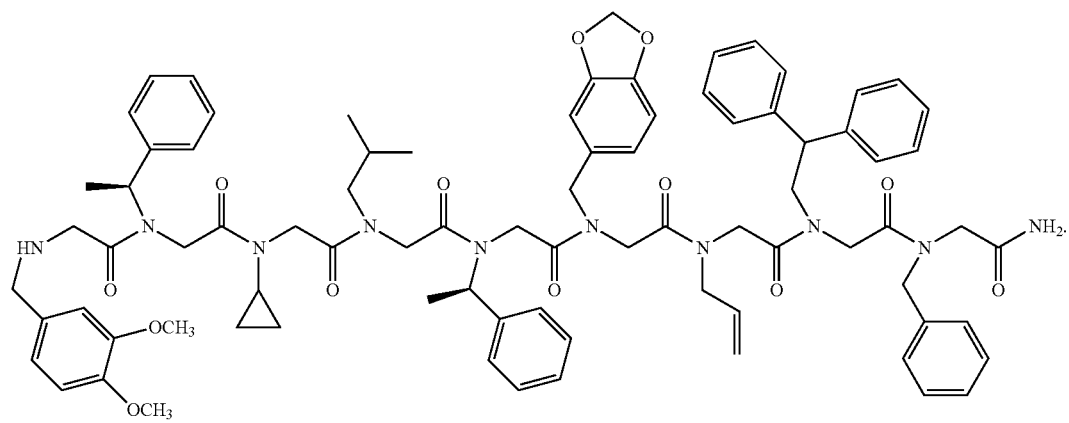 [SMILES: C=CCN(CC(=O)N(CC(=O)N(CC(N)=O)Cc1ccccc1)CC(c1ccccc1)c1ccccc1)C(=O)CN(Cc1ccc2c(c1)OCO2)C(=O)CN(C(=O)CN(CC(C)C)C(=O)CN(C(=O)CN(C(=O)CNCc1ccc(OC)c(OC)c1)[C@@H](C)c1ccccc1)C1CC1)[C@H](C)c1ccccc1]

5. The peptoid or pharmaceutically acceptable salt thereof of claim 1, comprising a structure
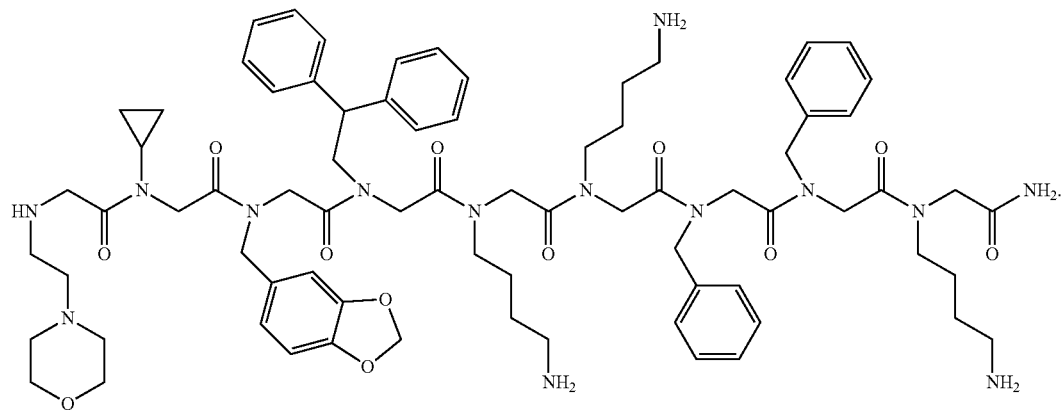 [SMILES: NCCCCN(CC(N)=O)C(=O)CN(Cc1ccccc1)C(=O)CN(Cc1ccccc1)C(=O)CN(CCCCN)C(=O)CN(CCCCN)C(=O)CN(CC(c1ccccc1)c1ccccc1)C(=O)CN(Cc1ccc2c(c1)OCO2)C(=O)CN(C(=O)CNCCN1CCOCC1)C1CC1]
6. The peptoid or pharmaceutically acceptable salt thereof of claim 1, comprising a structure
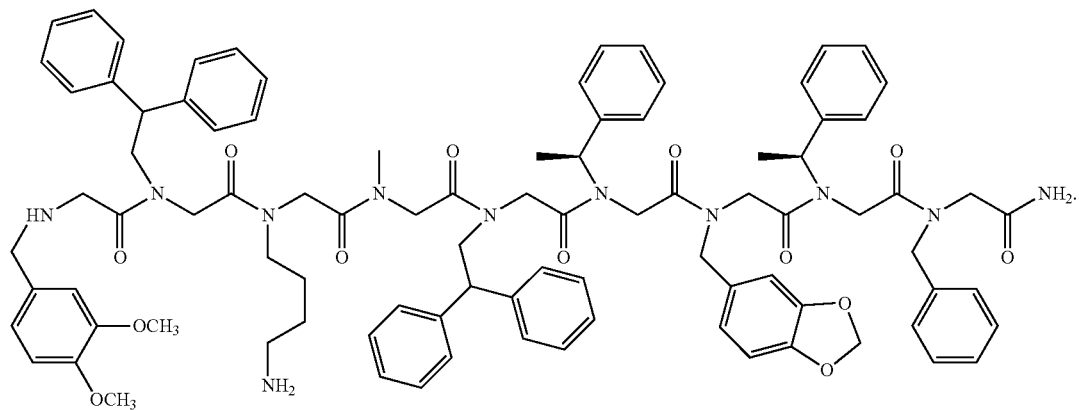 [SMILES: COc1ccc(CNCC(=O)N(CC(=O)N(CCCCN)CC(=O)N(C)CC(=O)N(CC(=O)N(CC(=O)N(CC(=O)N(CC(=O)N(CC(N)=O)Cc2ccccc2)[C@@H](C)c2ccccc2)Cc2ccc3c(c2)OCO3)[C@@H](C)c2ccccc2)CC(c2ccccc2)c2ccccc2)CC(c2ccccc2)c2ccccc2)cc1OC]
7. The peptoid or pharmaceutically acceptable salt thereof of claim 1, comprising a structure
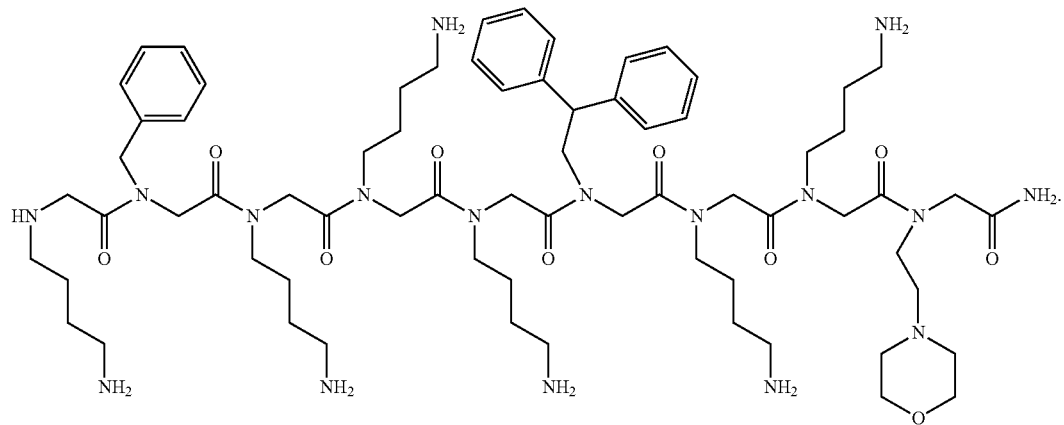 [SMILES: NCCCCNCC(=O)N(CC(=O)N(CCCCN)CC(=O)N(CCCCN)CC(=O)N(CCCCN)CC(=O)N(CC(=O)N(CCCCN)CC(=O)N(CCCCN)CC(=O)N(CCN1CCOCC1)CC(N)=O)CC(c1ccccc1)c1ccccc1)Cc1ccccc1]

8. The peptoid or pharmaceutically acceptable salt thereof of claim 1, comprising a structure
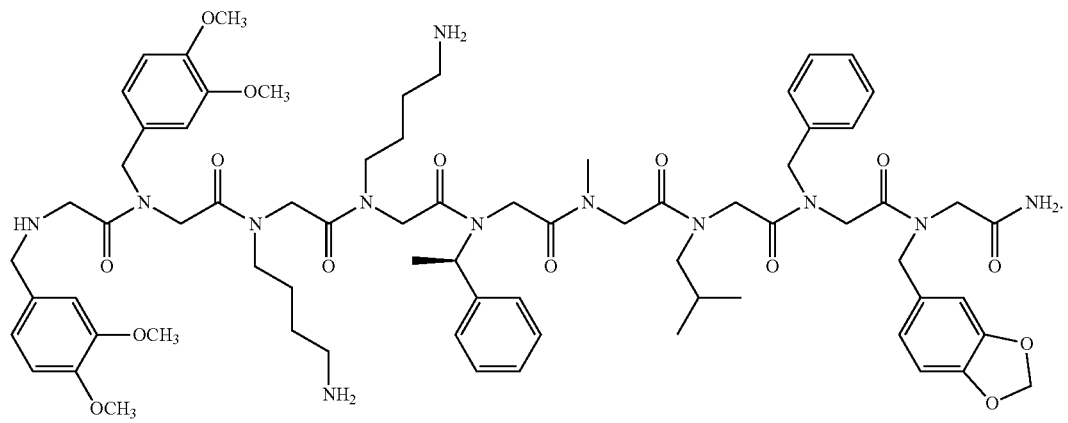 [SMILES: COc1ccc(CNCC(=O)N(CC(=O)N(CCCCN)CC(=O)N(CCCCN)CC(=O)N(CC(=O)N(C)CC(=O)N(CC(=O)N(CC(=O)N(CC(N)=O)Cc2ccc3c(c2)OCO3)Cc2ccccc2)CC(C)C)[C@H](C)c2ccccc2)Cc2ccc(OC)c(OC)c2)cc1OC]
9. The peptoid or pharmaceutically acceptable salt thereof of claim 1, comprising a structure
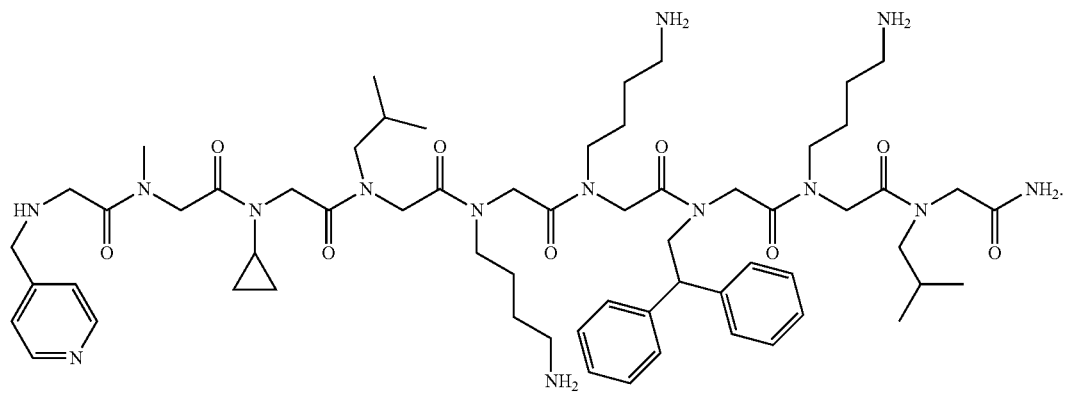 [SMILES: CC(C)CN(CC(N)=O)C(=O)CN(CCCCN)C(=O)CN(CC(c1ccccc1)c1ccccc1)C(=O)CN(CCCCN)C(=O)CN(CCCCN)C(=O)CN(CC(C)C)C(=O)CN(C(=O)CN(C)C(=O)CNCc1ccncc1)C1CC1]
10. The peptoid or pharmaceutically acceptable salt thereof of claim 1, comprising a structure
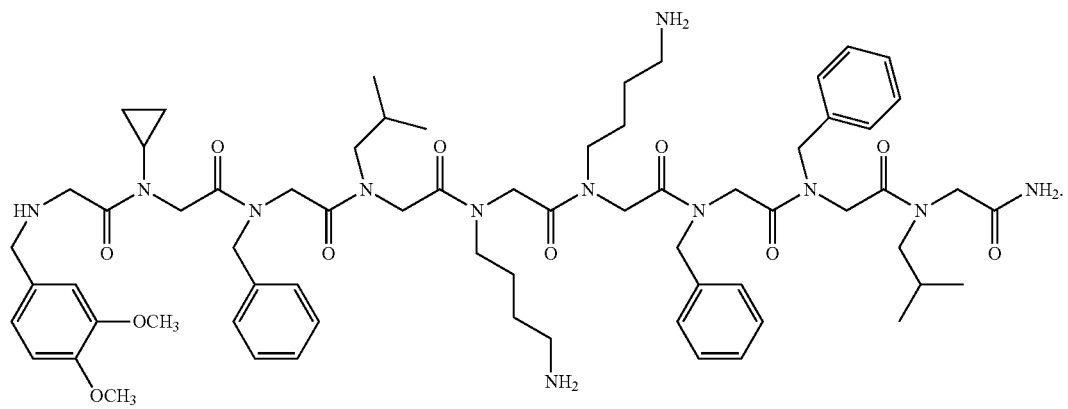 [SMILES: COc1ccc(CNCC(=O)N(CC(=O)N(CC(=O)N(CC(=O)N(CCCCN)CC(=O)N(CCCCN)CC(=O)N(CC(=O)N(CC(=O)N(CC(N)=O)CC(C)C)Cc2ccccc2)Cc2ccccc2)CC(C)C)Cc2ccccc2)C2CC2)cc1OC]

11. A method comprising;
  a. contacting a sample with one or more peptoid or pharmaceutically acceptable salt thereof, wherein said one or more peptoid or pharmaceutically acceptable salt thereof comprises a formula:
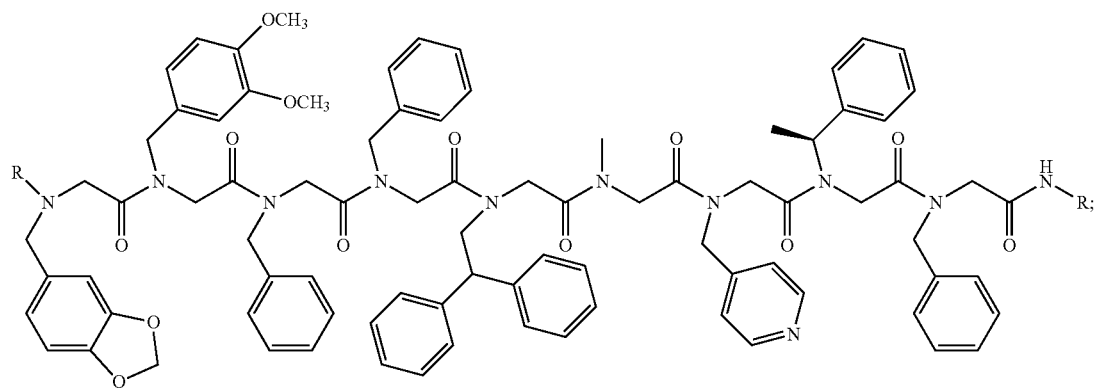
ErAD1
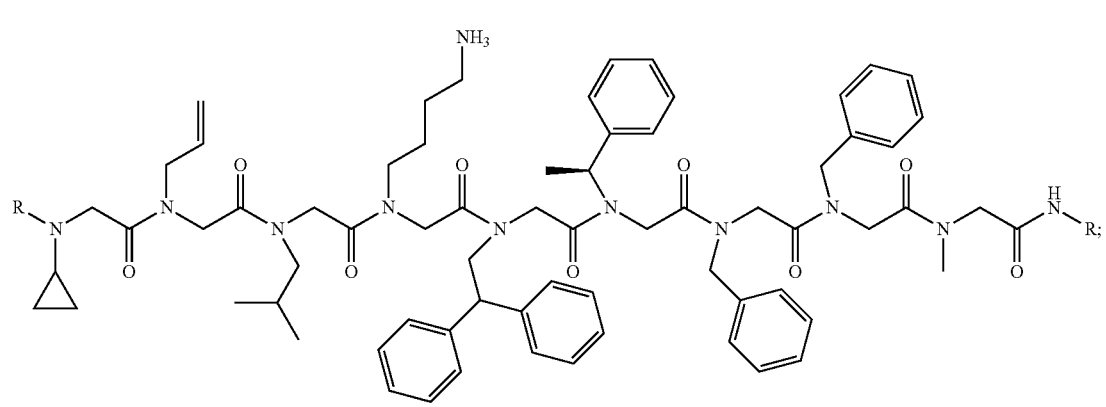
ErAD2
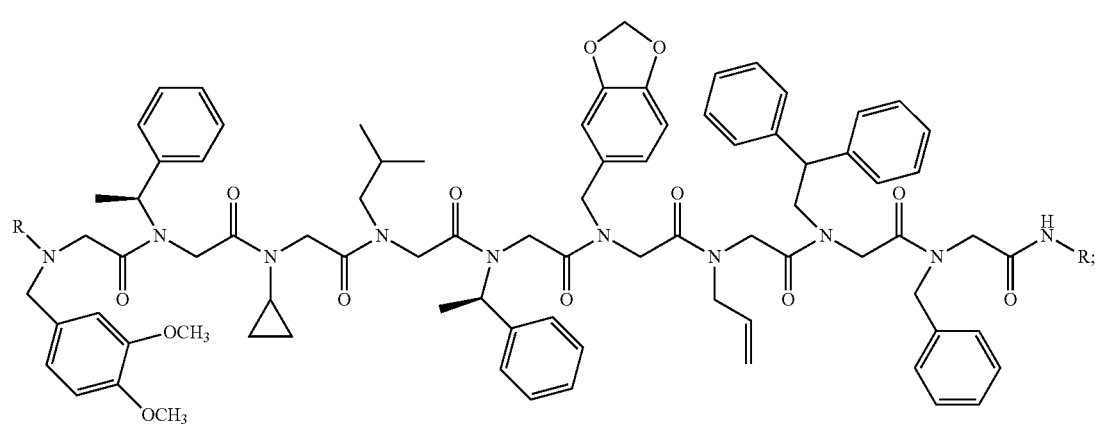
ErAD3

ErAD4
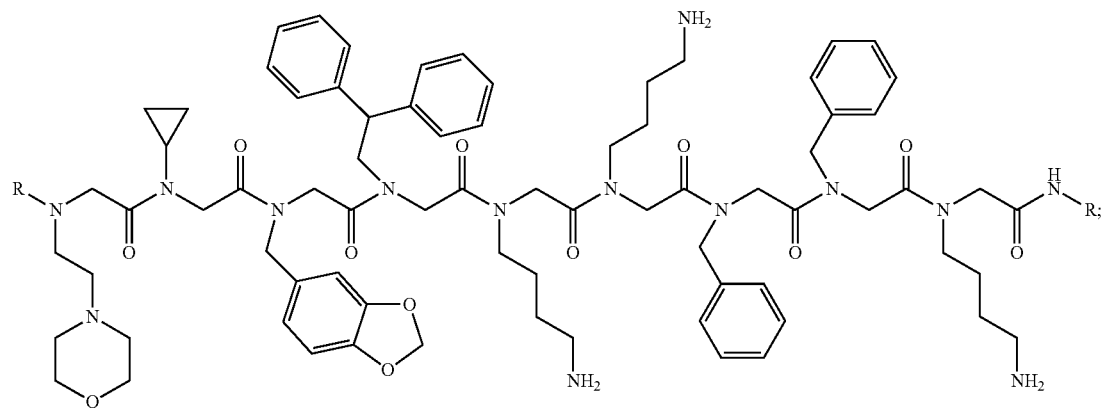
ErAD5
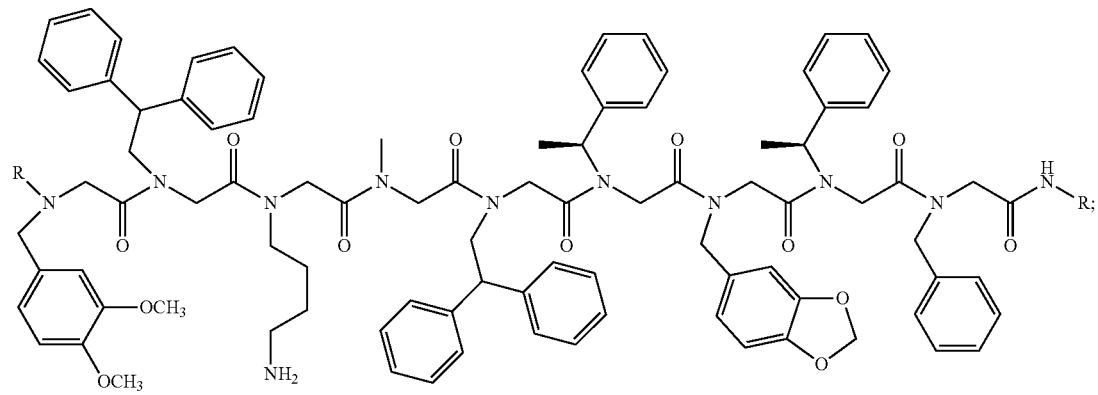
ErAD6
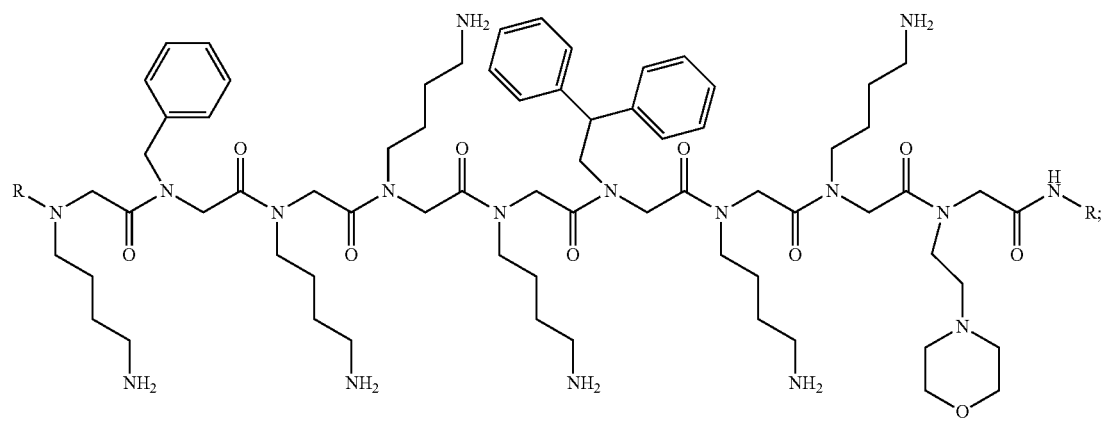
AAD1
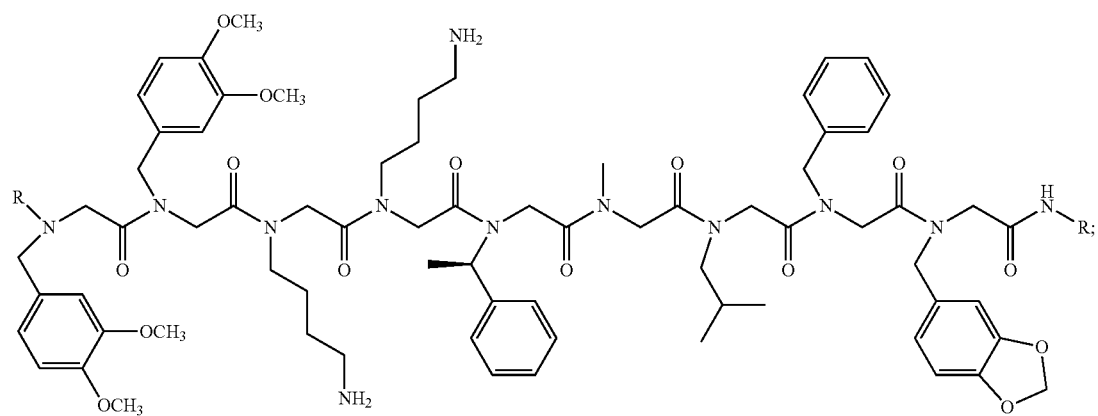

-continued

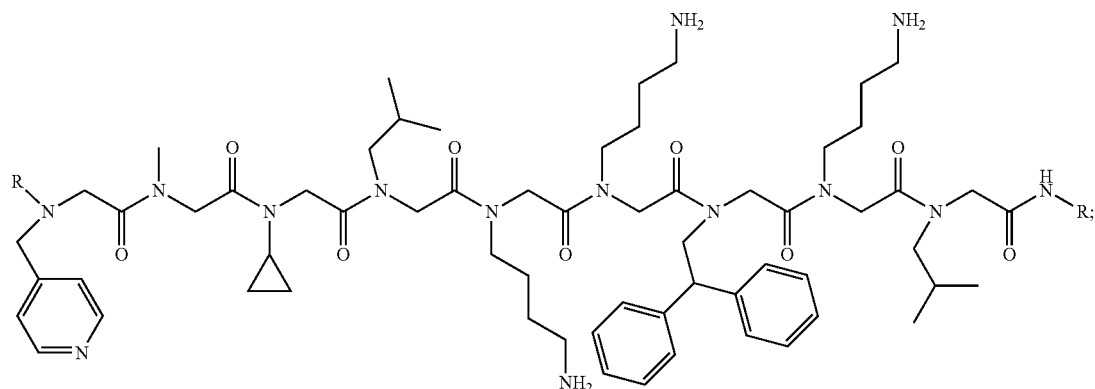

AAD2

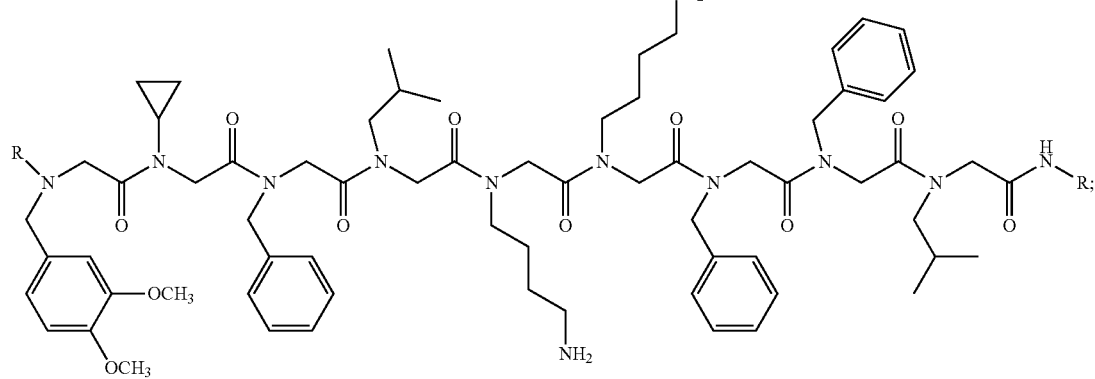

AAD3 or any combination thereof, wherein R is independently selected from a group consisting of a coupling group capable of coupling to a linker, a substrate, or a label; hydrogen; deuterium; $C_{1-6}$ alkyl; $C_{2-6}$ alkenyl; $C_{2-6}$ alkynyl, $C_{3-8}$cycloalkyl; heteroaryl, cycloalkyl; $C_{1-6}$alkylheteroaryl; $C_{1-6}$alkylaryl; and alkylcycloalkyl; each of which except hydrogen and deuterium may be individually and independently substituted one or more times with XA; halogen; $NY_2$; $CXXY$; $XCY_3$; alkyl; hydrogen; deuterium; carboxylic acid; ether; amine; $XX_2NY_2$; $=X$; $XCY_2X$ or any combinations thereof, wherein X is independently selected from oxygen or sulfur; Y is independently selected from deuterium or hydrogen; A is hydrogen, deuterium, aryl, or heteroaryl; and b. detecting whether or not a molecule is bound to said one or more peptoid or pharmaceutically acceptable salt thereof.

12. A method comprising:
a. contacting a sample with a non-random peptoid library, wherein said non-random peptoid library comprises one or more peptoid or pharmaceutically acceptable salt thereof having an affinity to an antibody, wherein said antibody comprises an IgA or a fragment thereof, or an IgM or a fragment thereof wherein said one or more peptoid or pharmaceutically acceptable salt thereof comprises a formula:

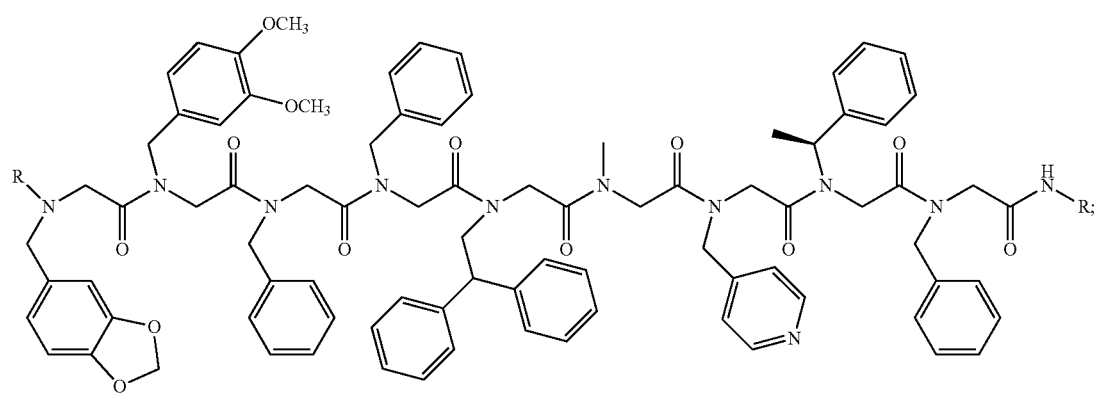

ErAD1

ErAD2
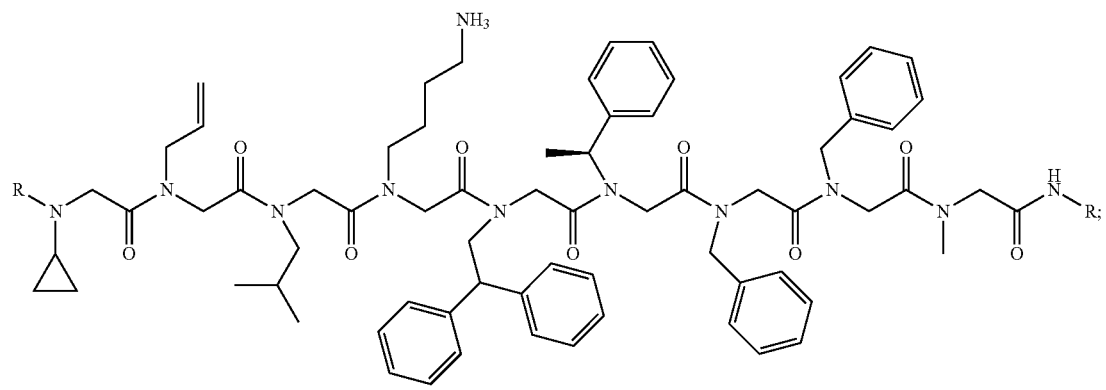
ErAD3
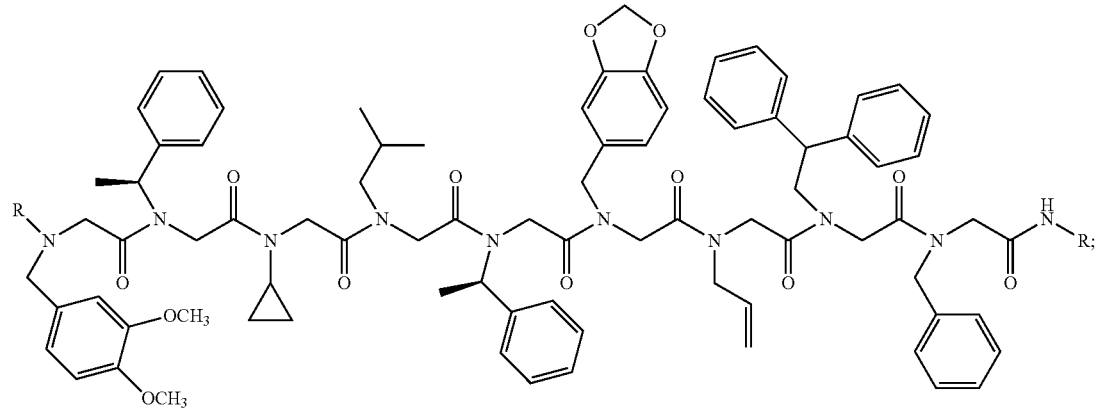
ErAD4
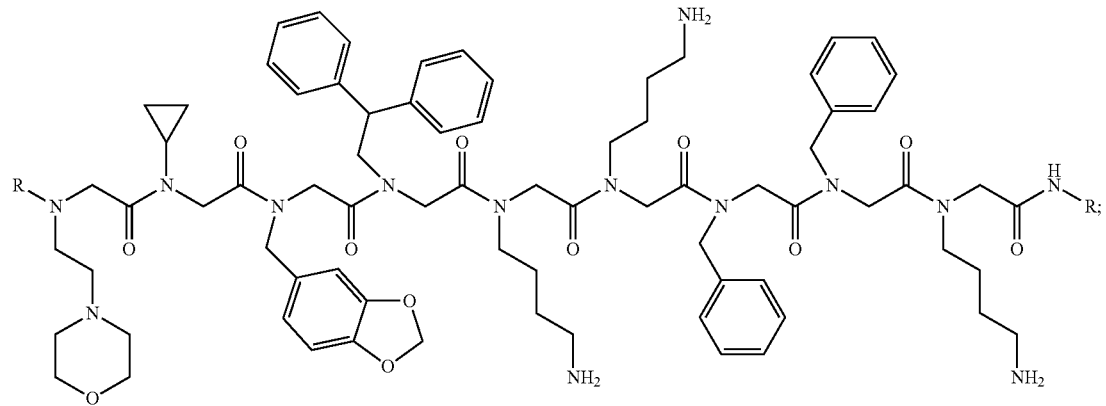
ErAD5
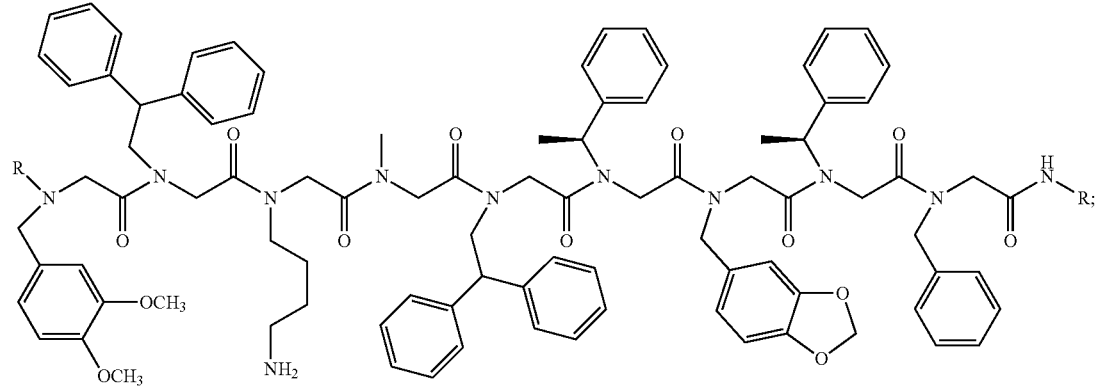

-continued
ErAD6
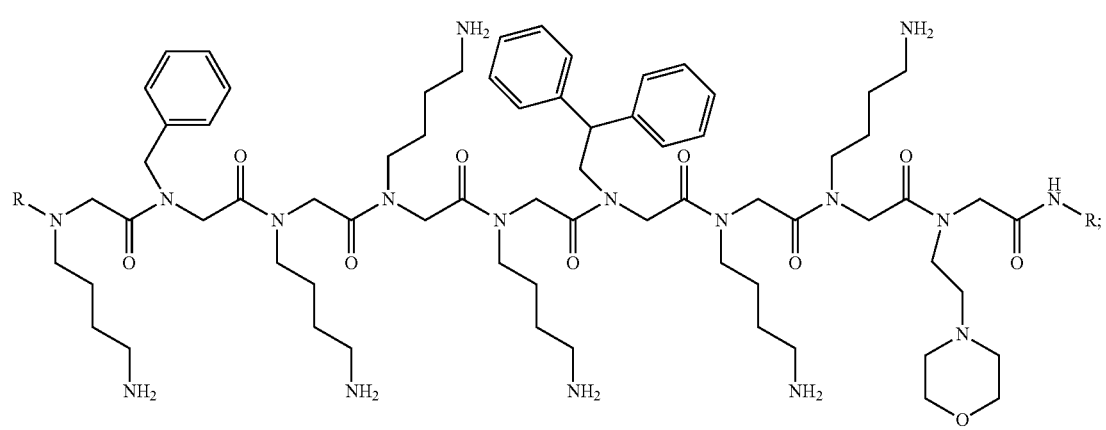
AAD1
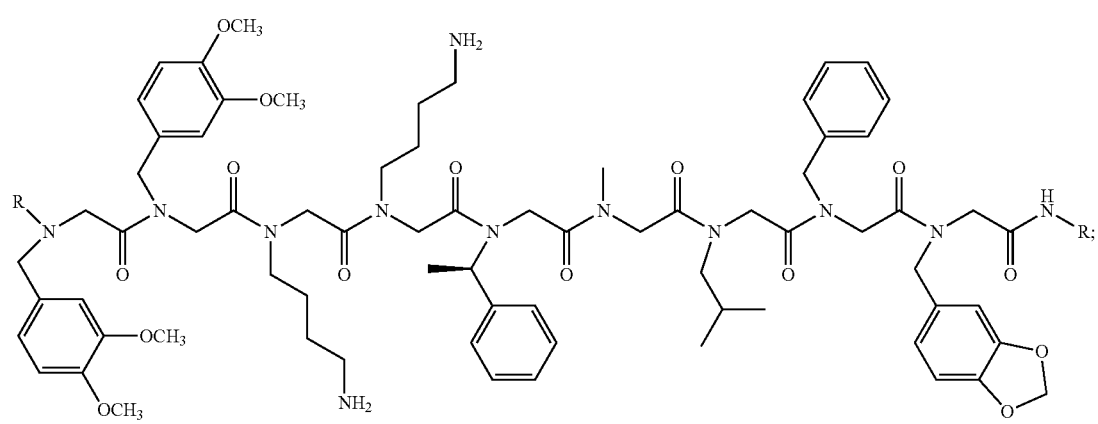
AAD2
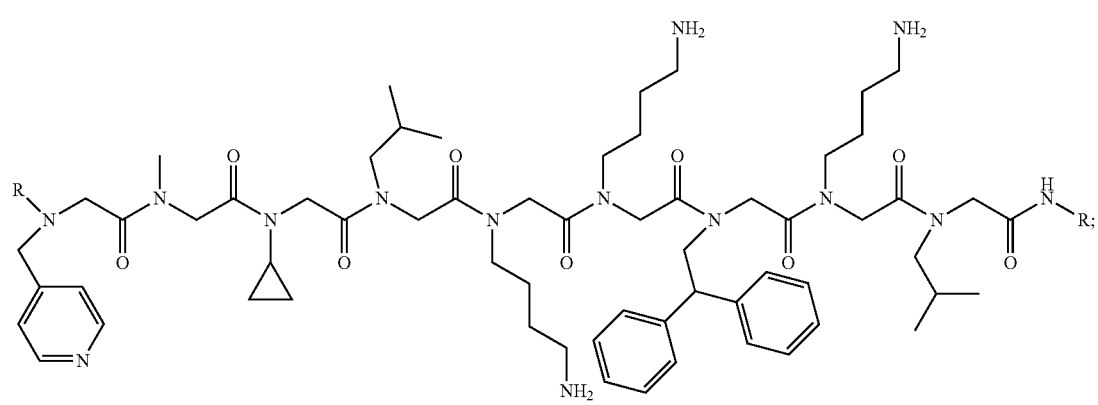
AAD3
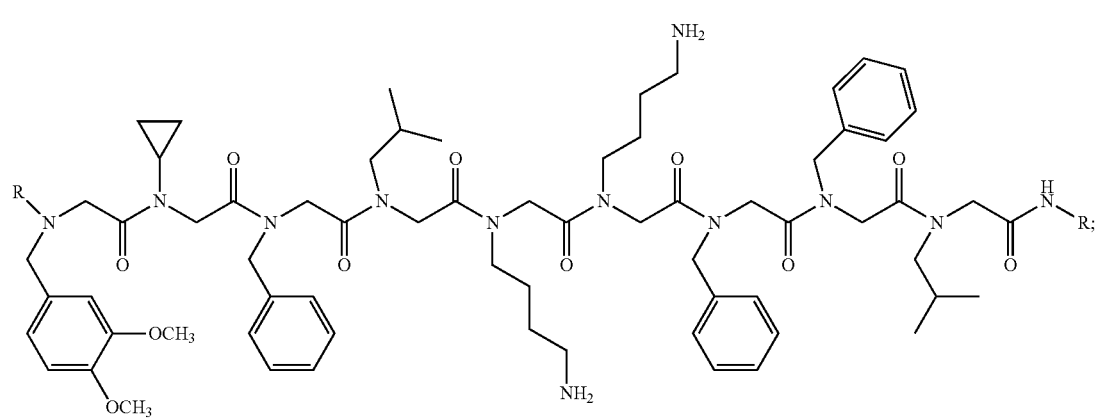

or any combination thereof, wherein R is independently selected from a group consisting of a coupling group capable of coupling to a linker, a substrate, or a label; hydrogen; deuterium; $C_{1-6}$ alkyl; $C_{2-6}$ alkenyl; $C_{2-6}$ alkynyl, $C_{3-8}$cycloalkyl; heteroaryl, cycloalkyl; $C_{1-6}$alkylheteroaryl; $C_{1-6}$alkylaryl; and alkylcycloalkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof, wherein X is independently selected from oxygen or sulfur; Y is independently selected from deuterium or hydrogen; A is hydrogen, deuterium, aryl, or heteroaryl; and b. detecting whether said antibody is bound to said one or more peptoid or pharmaceutically acceptable salt thereof.

13. A method of screening for a biomarker comprising:
a. contacting a control sample with a support having one or more peptoid or pharmaceutically acceptable salt thereof associated with said support, wherein said one or more peptoid or pharmaceutically acceptable salt thereof comprises a formula:

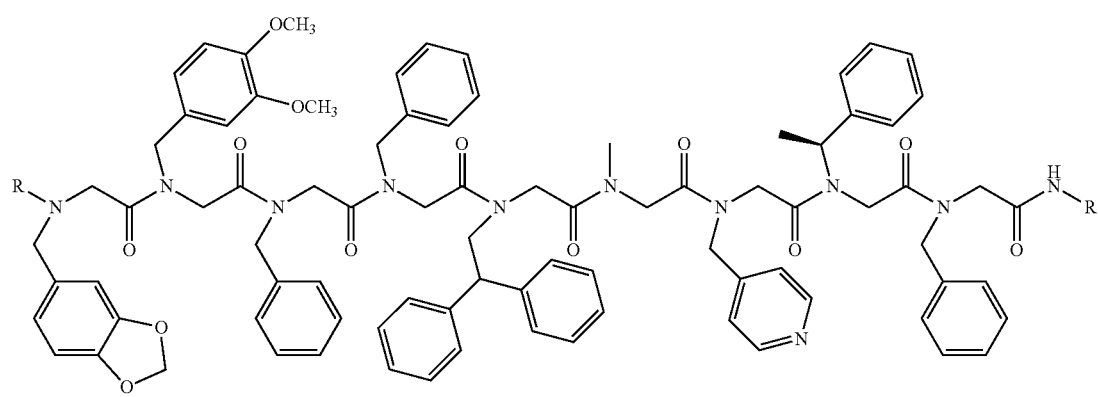

ErAD1

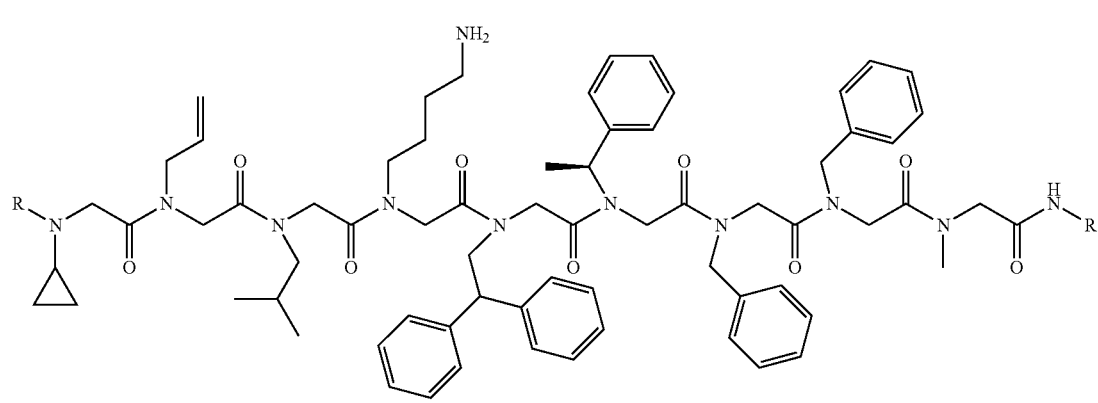

ErAD2

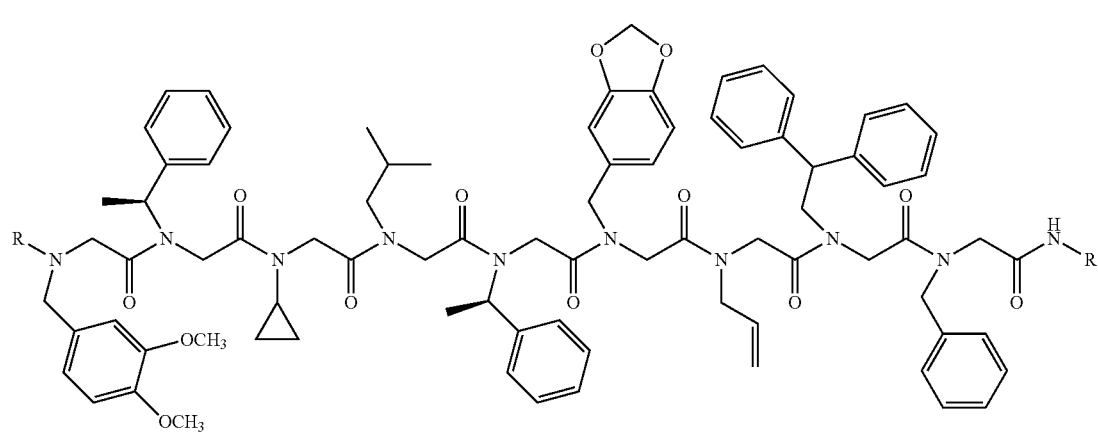

ErAD3

-continued
ErAD4
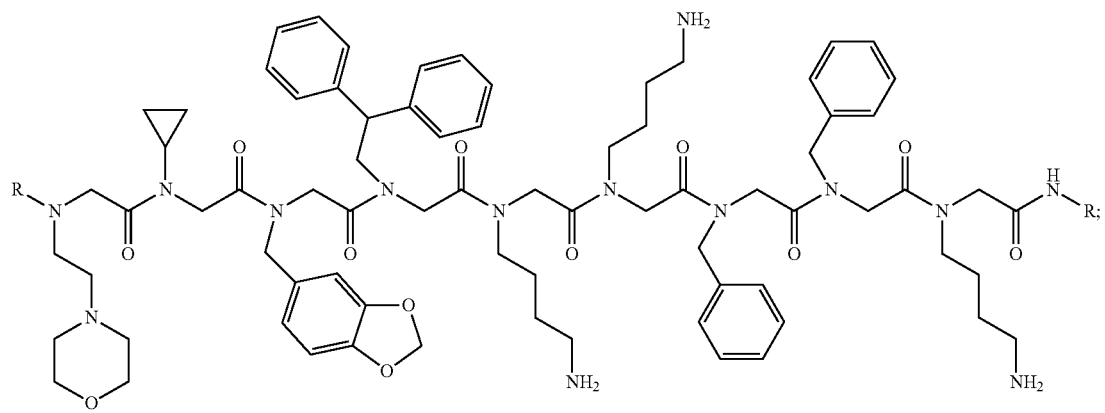
ErAD5
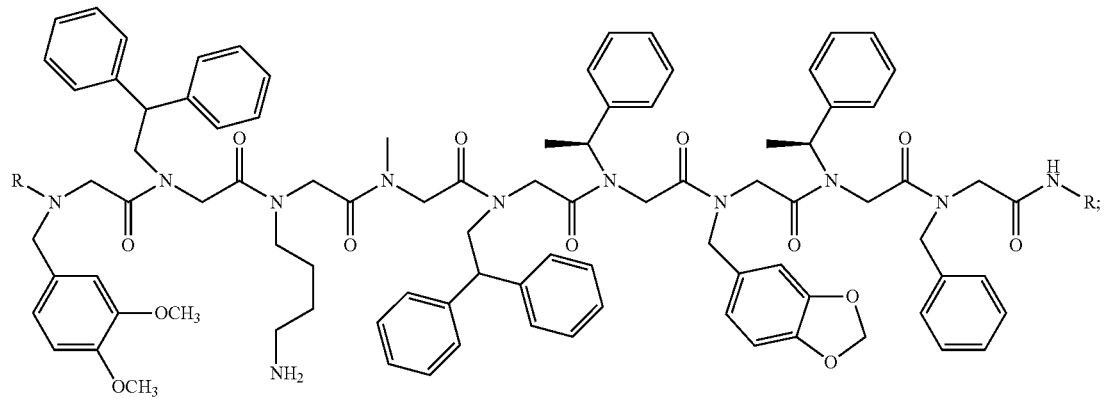
ErAD6
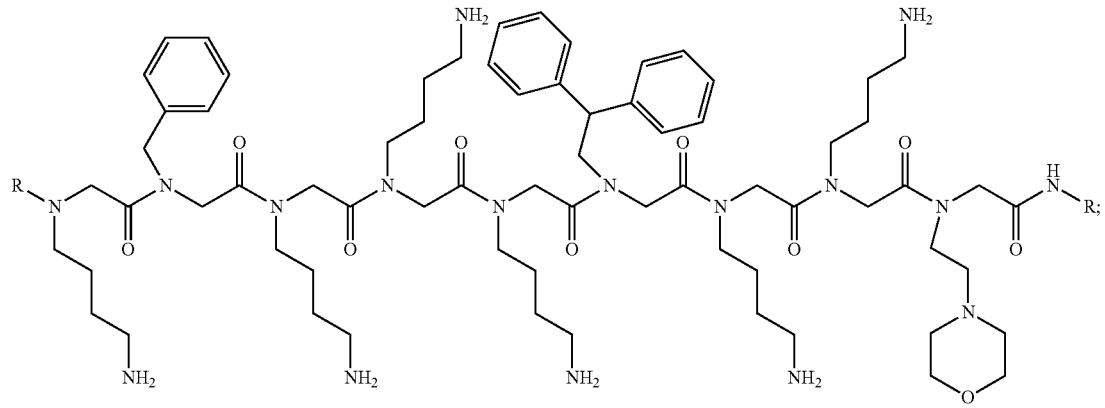
AAD1
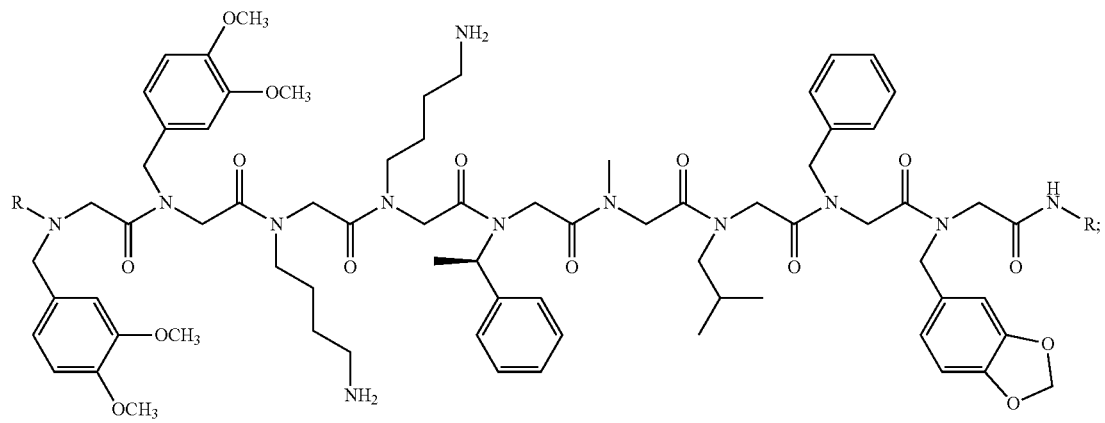

-continued

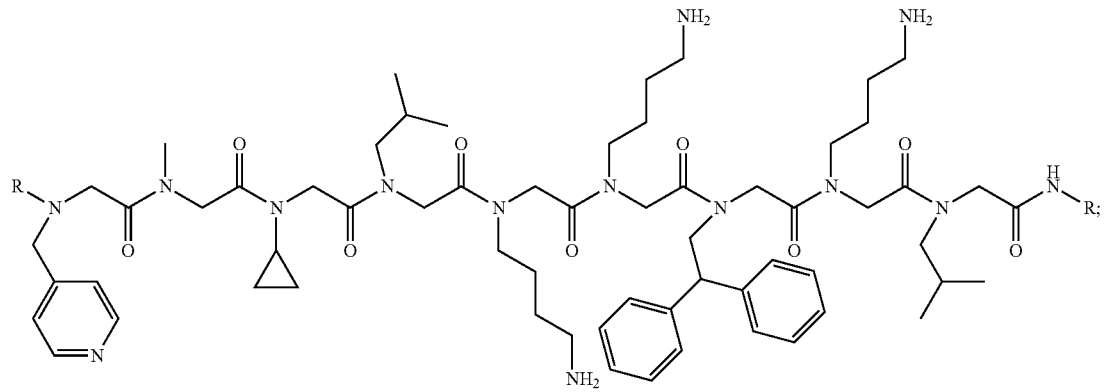
AAD2

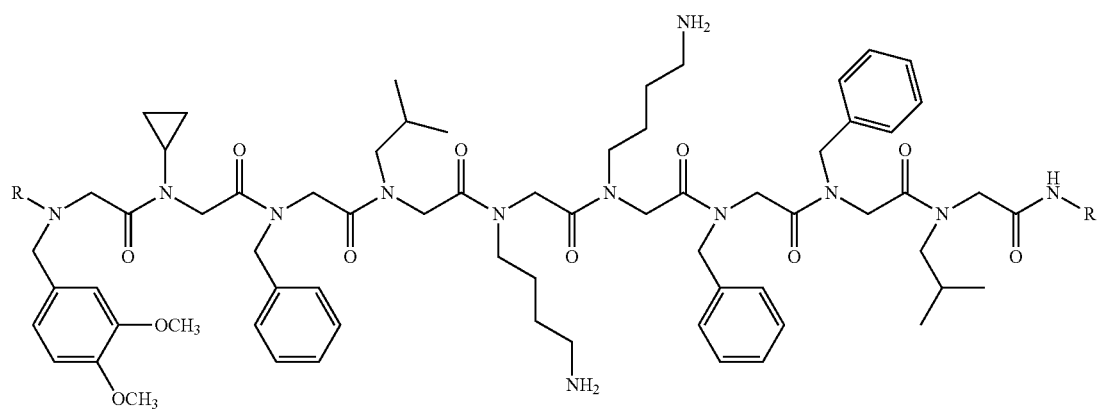
AAD3 or any combination thereof, wherein R is independently selected from a group consisting of a coupling group capable of coupling to a linker, a substrate, or a label; hydrogen; deuterium; $C_{1-6}$ alkyl; $C_{2-6}$ alkenyl; $C_{2-6}$ alkynyl, $C_{3-8}$cycloalkyl; heteroaryl, cycloalkyl; $C_{1-6}$alkylheteroaryl; $C_{1-6}$alkylaryl; and alkylcycloalkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof, wherein X is independently selected from oxygen or sulfur; Y is independently selected from deuterium or hydrogen; A is hydrogen, deuterium, aryl, or heteroaryl;

b. contacting said support with a disease sample; and
c. detecting said biomarker wherein said biomarker is bound to said one or more peptoid or pharmaceutically acceptable salt thereof and said biomarker is not present in said control sample or said one or more peptoid or pharmaceutically acceptable salt thereof does not bind to said biomarker in said control sample.

14. A method comprising:
a. contacting one or more peptoid or pharmaceutically acceptable salt thereof with a support having at least one biomarker associated with said support, wherein said one or more peptoid or pharmaceutically acceptable salt thereof comprises a formula:

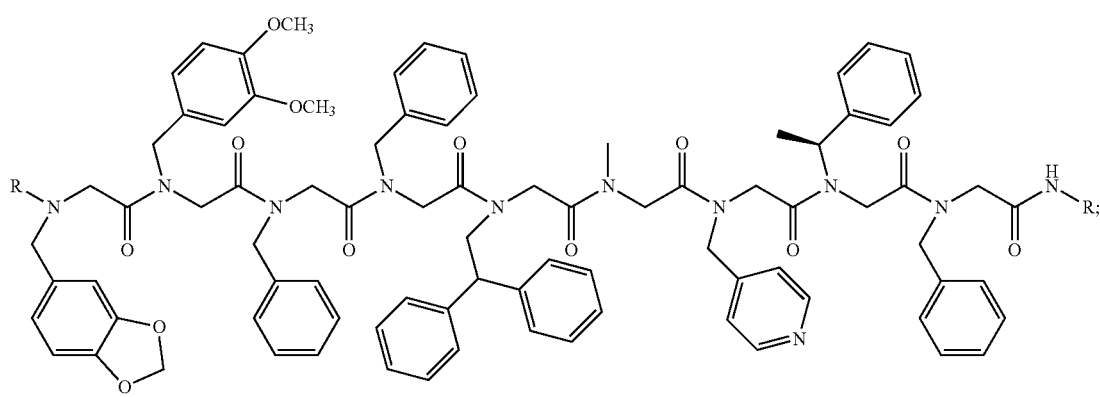
ErAD1

ErAD2
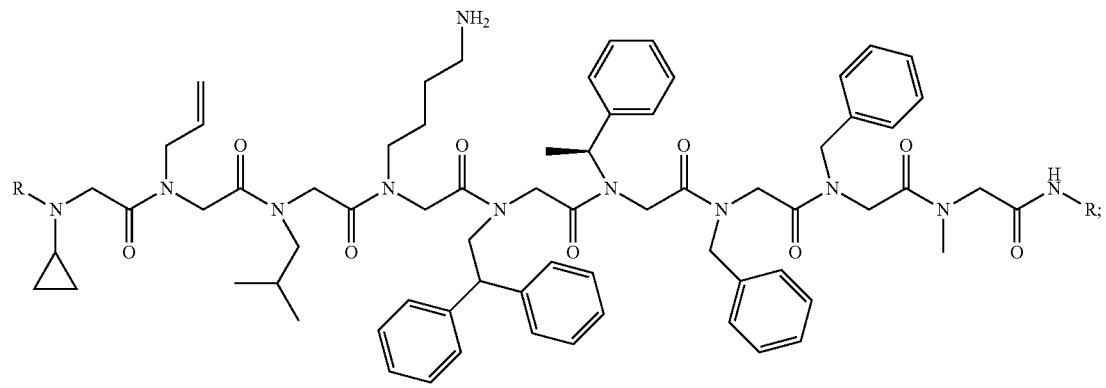
ErAD3
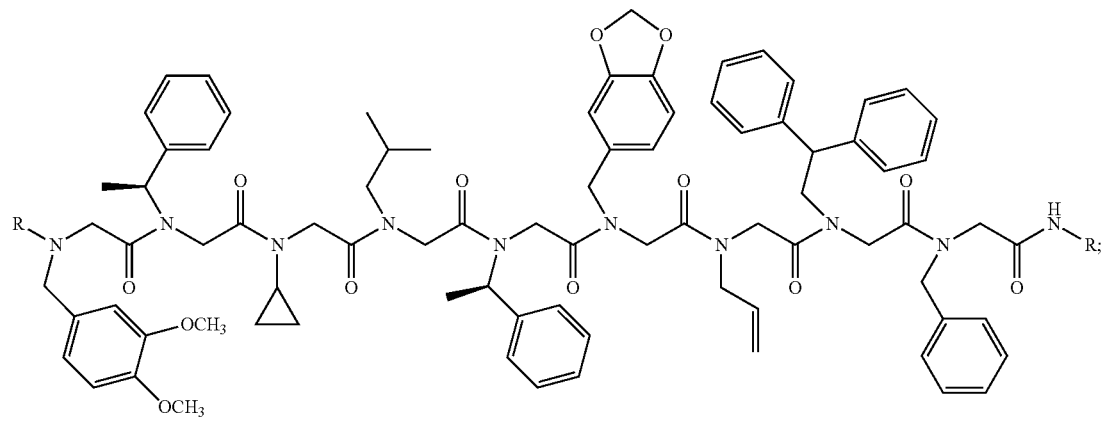
ErAD4
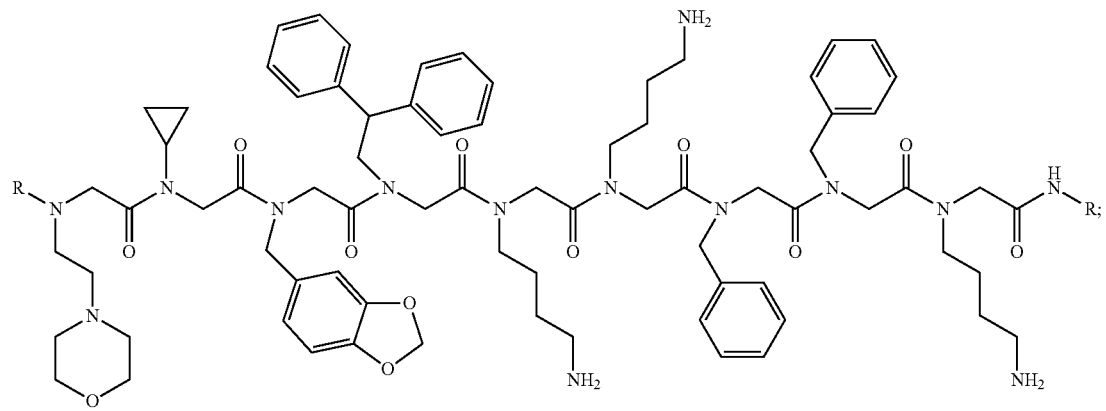
ErAD5
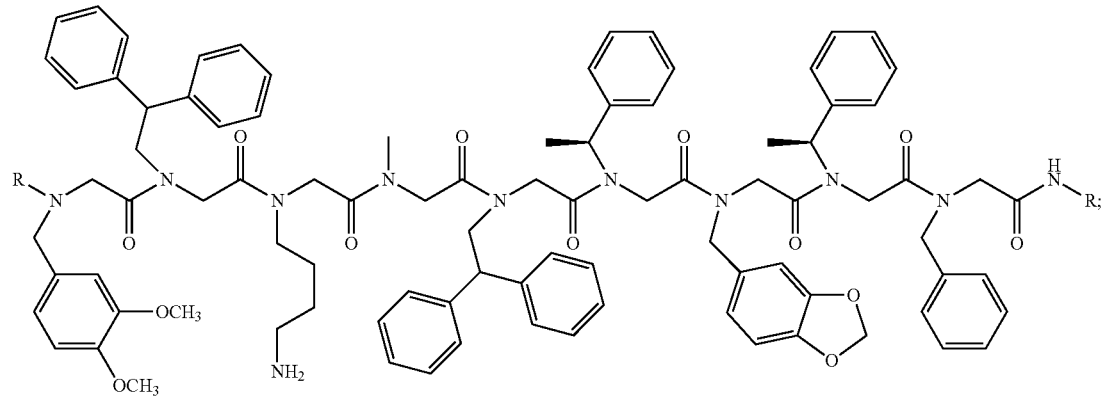

-continued
ErAD6
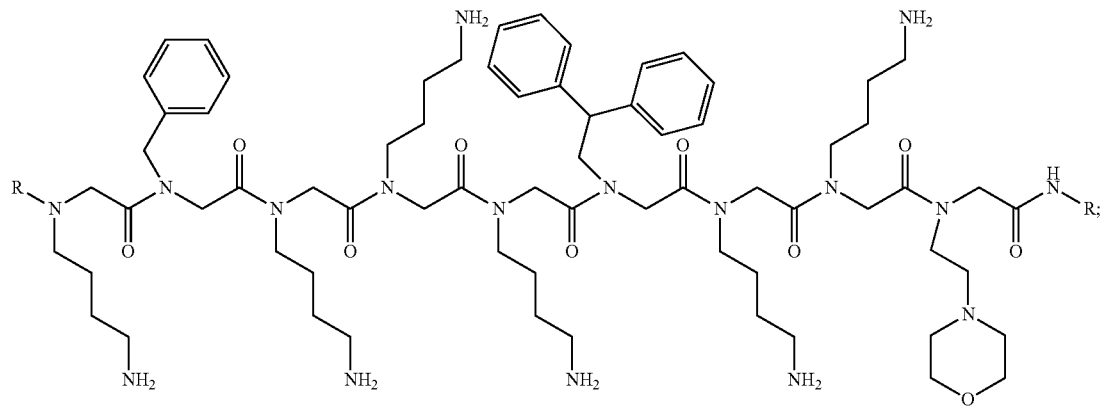
AAD1
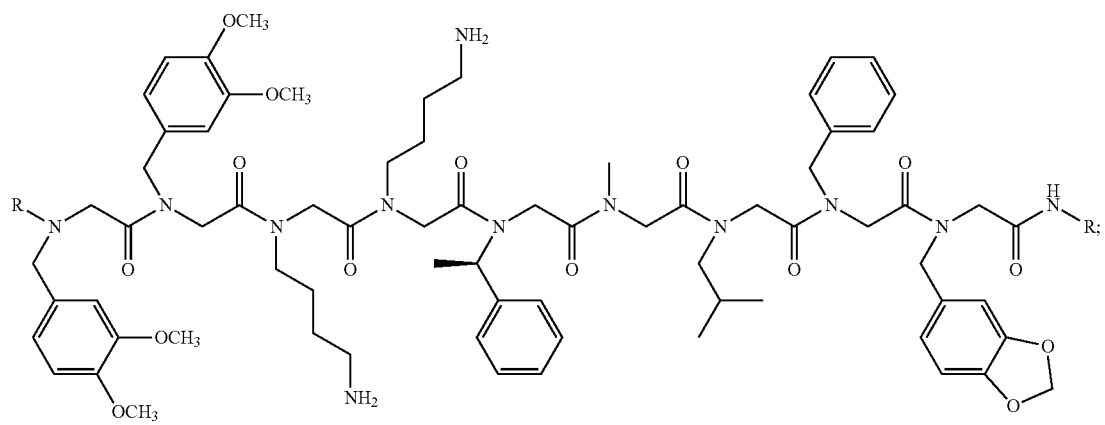
AAD2
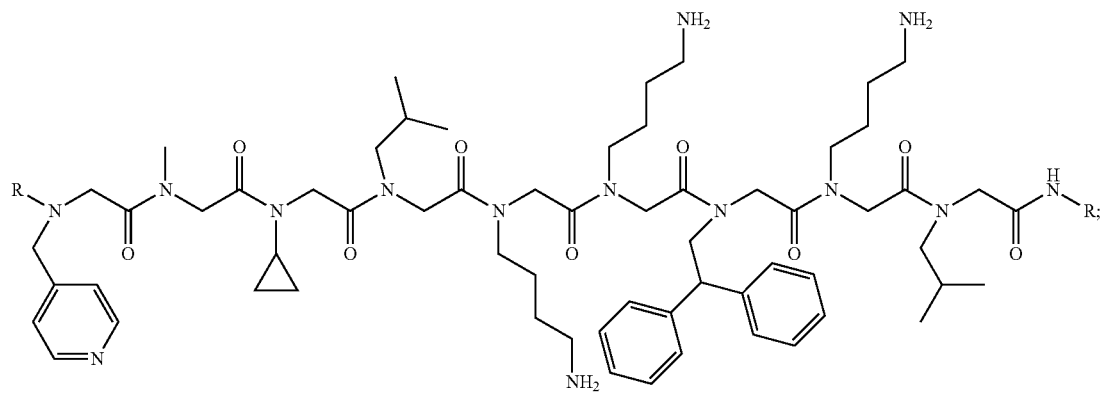
AAD3
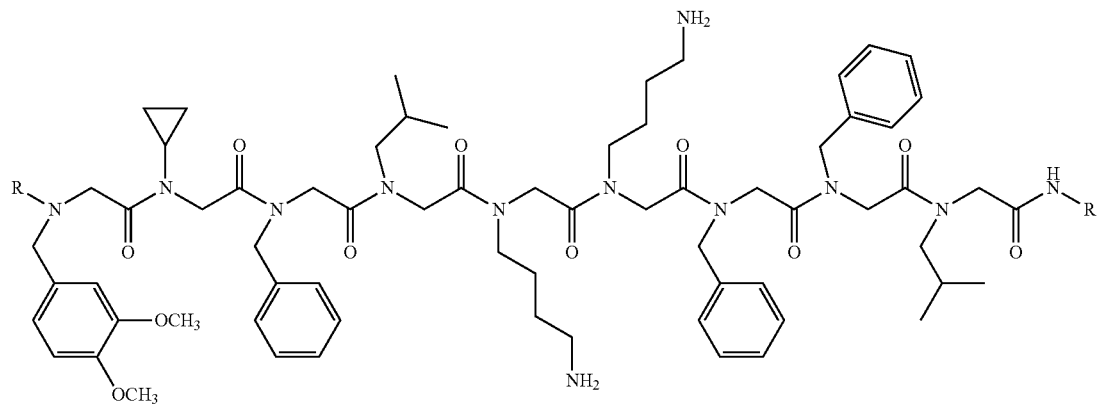

or any combination thereof, wherein R is independently selected from a group consisting of a coupling group capable of coupling to a linker, a substrate, or a label; hydrogen; deuterium; $C_{1-6}$ alkyl; $C_{2-6}$ alkenyl; $C_{2-6}$ alkynyl, $C_{3-8}$cycloalkyl; heteroaryl, cycloalkyl; $C_{1-6}$alkylheteroaryl; $C_{1-6}$alkylaryl; and alkylcycloalkyl; each of which except hydrogen and deuterium may be individually and independently substituted one or more times with XA; halogen; $NY_2$; CXXY; $XCY_3$; alkyl; hydrogen; deuterium; carboxylic acid; ether; amine; $XX_2NY_2$; =X; $XCY_2X$ or any combinations thereof, wherein X is independently selected from oxygen or sulfur; Y is independently selected from deuterium or hydrogen; A is hydrogen, deuterium, aryl, or heteroaryl; and b. detecting said biomarker having said one or more peptoid or pharmaceutically acceptable salt thereof bound thereto.

\* \* \* \* \*